US009957513B2

(12) United States Patent
Nielsen et al.

(10) Patent No.: US 9,957,513 B2
(45) **Date of Patent: *May 1, 2018**

(54) ENGINEERING OF HYDROCARBON METABOLISM IN YEAST

(71) Applicant: BIOPETROLIA AB, Gothenburg (SE)

(72) Inventors: Jens Nielsen, Gothenburg (SE); Verena Siewers, Gothenburg (SE); Paulo Alexandre Goncalves Teixeira, Vastra Frolunda (SE); Yongjin Zhou, Gothenburg (SE); Nicolaas A. A. Buijs, Hisings backa (SE); Florian David, Gothenburg (SE)

(73) Assignee: BIOPETROLIA AB, Gothenburg (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/682,002

(22) Filed: Aug. 21, 2017

(65) Prior Publication Data

US 2018/0030460 A1 Feb. 1, 2018

Related U.S. Application Data

(63) Continuation of application No. 15/029,818, filed as application No. PCT/SE2014/051229 on Oct. 17, 2014, now Pat. No. 9,777,283.

(60) Provisional application No. 61/893,125, filed on Oct. 18, 2013.

(51) Int. Cl.

| | |
|---|---|
| ***C12N 1/14*** | (2006.01) |
| ***C12N 15/81*** | (2006.01) |
| ***C12P 7/04*** | (2006.01) |
| ***C12N 9/02*** | (2006.01) |
| ***C12P 5/02*** | (2006.01) |
| ***C12N 9/10*** | (2006.01) |
| ***C12N 9/88*** | (2006.01) |

(52) U.S. Cl.

CPC ........... *C12N 15/81* (2013.01); *C12N 9/0008* (2013.01); *C12N 9/0042* (2013.01); *C12N 9/0069* (2013.01); *C12N 9/0095* (2013.01); *C12N 9/1029* (2013.01); *C12N 9/88* (2013.01); *C12P 5/02* (2013.01); *C12P 5/026* (2013.01); *C12P 7/04* (2013.01); *C12Y 102/01042* (2013.01)

(58) Field of Classification Search

CPC .............................. C12N 15/81; C12N 9/0008
USPC .............................................. 435/166, 254.2
See application file for complete search history.

(56) References Cited

U.S. PATENT DOCUMENTS

| | | | | |
|---|---|---|---|---|
| 9,777,283 | B2 * | 10/2017 | Nielsen .................. | C12N 15/81 |
| 2011/0201072 | A1 | 8/2011 | Bastian et al. | |
| 2013/0224818 | A1 | 8/2013 | Howard et al. | |
| 2014/0127765 | A1 | 5/2014 | Osterhout et al. | |
| 2014/0186915 | A1 | 7/2014 | Mori | |

FOREIGN PATENT DOCUMENTS

| | | |
|---|---|---|
| WO | WO 2011062987 | 5/2011 |
| WO | WO 2011127409 | 10/2011 |

OTHER PUBLICATIONS

Andre, C. et al. "Fusing catalase to an alkane-producing enzyme maintains enzymatic activity by converting the inhibitory byproduct H2O2 to the cosubstrate O2", *PNAS*, Feb. 19, 2013, vol. 110 No. 6, pp. 3191-3196.
International Preliminary Report and Patentability and Written Opinion corresponding to International Application No. PCT/SE2014/051229; dated Jan. 21, 2016, 6 pages.
International Search Report corresponding to International Application No. PCT/SE2014/051229; dated Jan. 21, 2015; 6 pages.
Iwama, R. et al. "Identification and characterization of fatty aldehyde dehydrogenase genes involved in n-alkane metabolism of Yarrowia lipolytica", 26th International Conference of Yeast Genetics and Molecular Biology in Yeast; vol. 30 Issue S1, S229.
Nakahara, K. et al. "The Sjogren-Larsson Syndrome Gene Encodes a Hexadecenal Dehydrogenase of the Sphingosine 1-Phosphate Degradation Pathway", *Molecular Cell*, 2012, vol. 46, pp. 461-471.
Schirmer, A. et al. "Microbial Biosynthesis of Alkanes", *Science*, 2010, vol. 329, pp. 559-562.
Zhang, F. et al. "Metabolic engineering of microbial pathways for advanced biofuels production", *Current Opinion in Biotechnology*, 2011, vol. 22, pp. 775-783.
Bernard, A., et al, "Reconstitution of Plane Alkane Biosynthesis in Yeast Demonstrates That *Arabidopsis* Eceriferum1 and Eceriferum3 Are Core Components of a Very-Long-Chain Alkane Synthesis Complex", *The Plant Cell*, vol. 24: pp. 3106-3118, Jul. 2012.

* cited by examiner

*Primary Examiner* — Tekchand Saidha
(74) *Attorney, Agent, or Firm* — Myers Bigel, P.A.

(57) ABSTRACT

The present invention relates to the development of genetically engineered yeasts that can produce hydrocarbons in a controllable and economic fashion. More specifically the invention relates to the production of liquid alkanes and alkenes that can be used for liquid transportation fuels, specialty chemicals, or feed stock for further chemical conversion.

14 Claims, 16 Drawing Sheets pRBye: ERG10, fadA, fadB, tdTER, tesA
pRBee: yqeF, fadA, fadB, tdTER, tesA

ENGINEERING OF HYDROCARBON METABOLISM IN YEAST

STATEMENT OF PRIORITY

This application is a continuation of U.S. patent application Ser. No. 15/029,818, filed on Apr. 15, 2016, which is a 35 U.S.C. § 371 national phase application of International Application Serial No. PCT/SE2014/051229, filed Oct. 17, 2014, which claims the benefit, under 35 U.S.C. § 119 (a) of U.S. Application Ser. No. 61/893,125, filed Oct. 18, 2013, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 9737-41_ST25.txt, 127,549 bytes in size, generated Apr. 14, 2016 and filed via EFS-Web, is provided in lieu of a paper copy. This Sequence Listing is hereby incorporated herein by reference into the specification for its disclosures.

FIELD OF THE INVENTION

The present invention relates to the development of genetically engineered yeasts that can produce hydrocarbons in a controllable and economic fashion. More specifically the invention relates to the production of, for instance liquid alkanes and alkenes, that can be used for liquid transportation fuels, specialty chemicals, or feed stock for further chemical conversion.

DESCRIPTION OF THE RELATED ART

Increased petroleum prices along with concerns about carbon dioxide emission and the lack of sustainability of fossil fuels have been strongly motivating the development and production of biofuels. As about 80% of mineral oils are being used for liquid transportation fuels, there is particular focus on developing alternative biotech processes to replace these.

Currently, the dominating biofuel is ethanol. This is produced in very large quantities, particularly in Brazil from sugar cane and in the USA from corn, but there are also several key initiatives on establishing so-called second-generation bioethanol production, where cellulosic biomass is used as the feedstock. The production of advanced biofuels to be used as gasoline does not solve a major problem associated with ensuring provision of jetfuels and fuels for maritime and heavy duty road transportation, both of which require high-density fuels—generally known as diesel-fuels.

Currently, biodiesel is produced from vegetable oils, but this biodiesel production is problematic since it competes against use of these oils in the food sector. Furthermore, the yield of oil per hectare is very low compared with that of sugar cane or other sugar crops. This type of biodiesel consists mainly of fatty acid alkyl esters (FAAEs). Recently, initiatives have been started to produce FAAEs in microorganisms such as the bacterium *Escherichia coli* and the yeast *Saccharomyces cerevisiae* with sugars as substrate, which would allow for higher per hectare yields resulting in a lower environmental impact. A disadvantage of FAAEs is that they contain oxygen, which leads to a lower energy density compared to pure hydrocarbon molecules.

SUMMARY OF THE INVENTION

A primary object of the present invention is to provide a genetically engineered yeast that can produce hydrocarbons, including but not limited to alkanes and alkenes, in a controllable and economic fashion.

An aspect of the embodiments relates to a yeast lacking a gene encoding hexadecanal dehydrogenase (HFD1) or comprising a disrupted gene encoding HFD1. The yeast also comprises at least one heterologous gene encoding an enzyme involved in a pathway of producing hydrocarbons.

Another aspect of the embodiments relates to a method for producing hydrocarbons. The method comprises culturing a yeast lacking a gene encoding hexadecenal dehydrogenase (HFD1) or comprising a disrupted gene encoding HFD1 in culture conditions suitable for production of the hydrocarbons from the yeast. The method also comprises collecting the hydrocarbons from the culture medium in which the yeast is cultured and/or from the yeast.

A further aspect of the embodiments relates to use of a yeast lacking a gene encoding hexadecenal dehydrogenase (HFD1) or comprising a disrupted gene encoding HFD1 for the production of hydrocarbons. In one embodiment, *Saccharomyces cerevisiae* was metabolically engineered to synthesize medium-chain alkanes. The inventors identified and demonstrated the importance of eliminating hexadecenal dehydrogenase Hfd1 in combination with heterologous expression of one or more enzymes, and/or biosynthetic and/or metabolic pathways, in enabling biosynthesis of the former compounds in yeast. The requirement of HFD1 deletion further illustrates a key difference between yeast and bacteria, in which the main competing enzymes are fatty aldehyde reductases and fatty alcohol dehydrogenases that convert the fatty aldehyde intermediate reversibly into a fatty alcohol.

The fatty acid derivatives (e.g., alkanes, alkenes, fatty alcohols) produced by the recombinant yeast of this invention are liquid (e.g., carbon chains with 5-17 carbon atoms). Such liquid alkanes and/or alkenes can be used, for example, as liquid transportation fuels. These and other aspects of the invention are set forth in more detail in the description of the invention below.

*tus* fatty aldehyde deformylating oxygenase (FADO), and/or *E. coli* ferredoxin/ferredoxin reductase (F/FNR). The error bars represent the standard deviation of three biological replicates.

Figure 3:
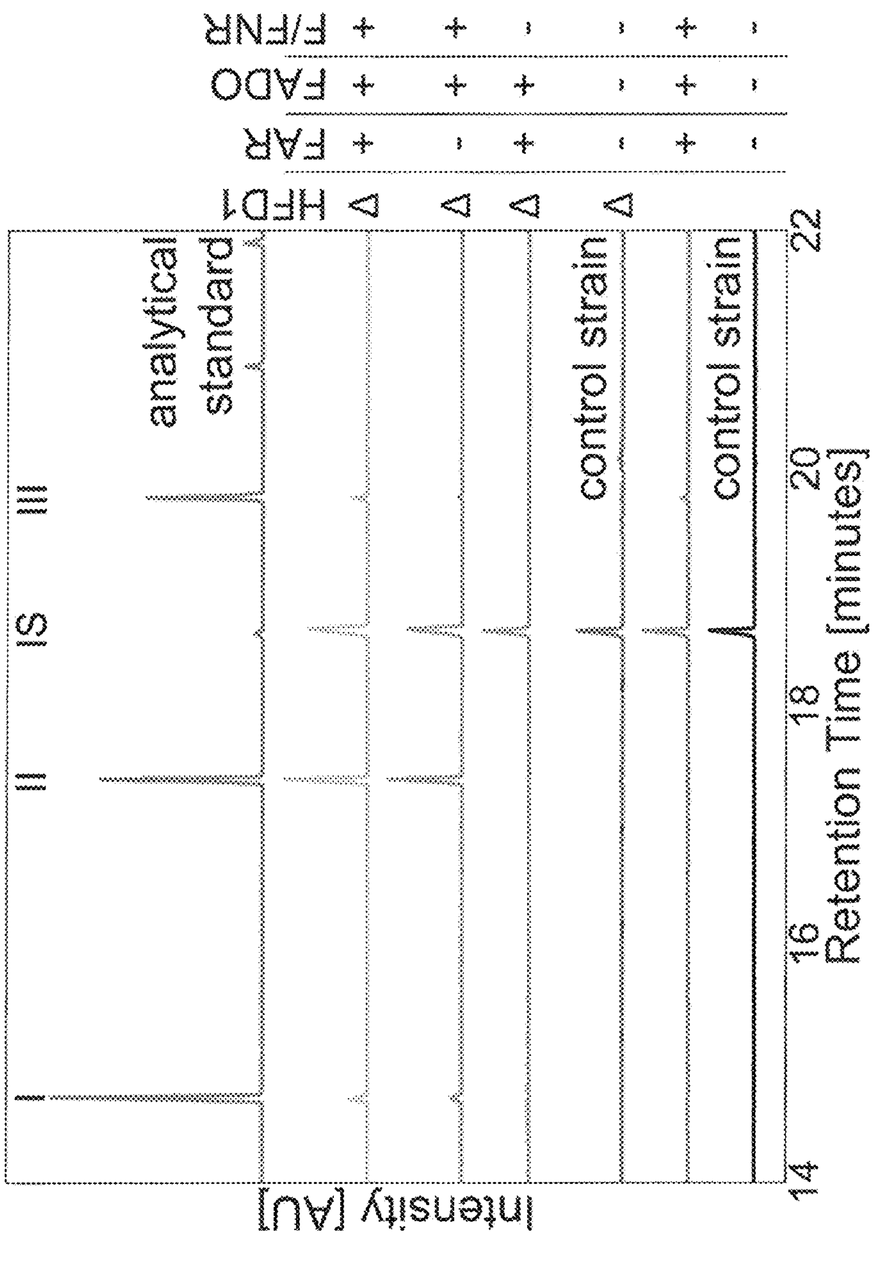

FIG. 3 shows alkane biosynthesis. Gas chromatograms of shake flask cultures incubated for 48 hours in glucose minimal medium. The lines represent *S. cerevisiae* CEN.PK113-11C strains that express *S. elongatus* FAR and FADO as well as the *E. coli* reduction system consisting of Fdx (F) and Fpr (FNR). The *S. cerevisiae* strains carrying an empty vector pYX212 (black and brown traces) are shown as a control. A C7-C30 alkane analytical standard (purple trace) was used as a reference. The peaks highlighted by the blue bars labeled with I, II, IS, and III represent tridecane (C13), pentadecane (C15), hexadecane (C16; internal standard), and heptadecane (C17), respectively. The shown spectra are for the m/z values 184, 212, and 240. The mass spectra for the labeled peaks in comparison with a NIST library standard.

Figure 4:
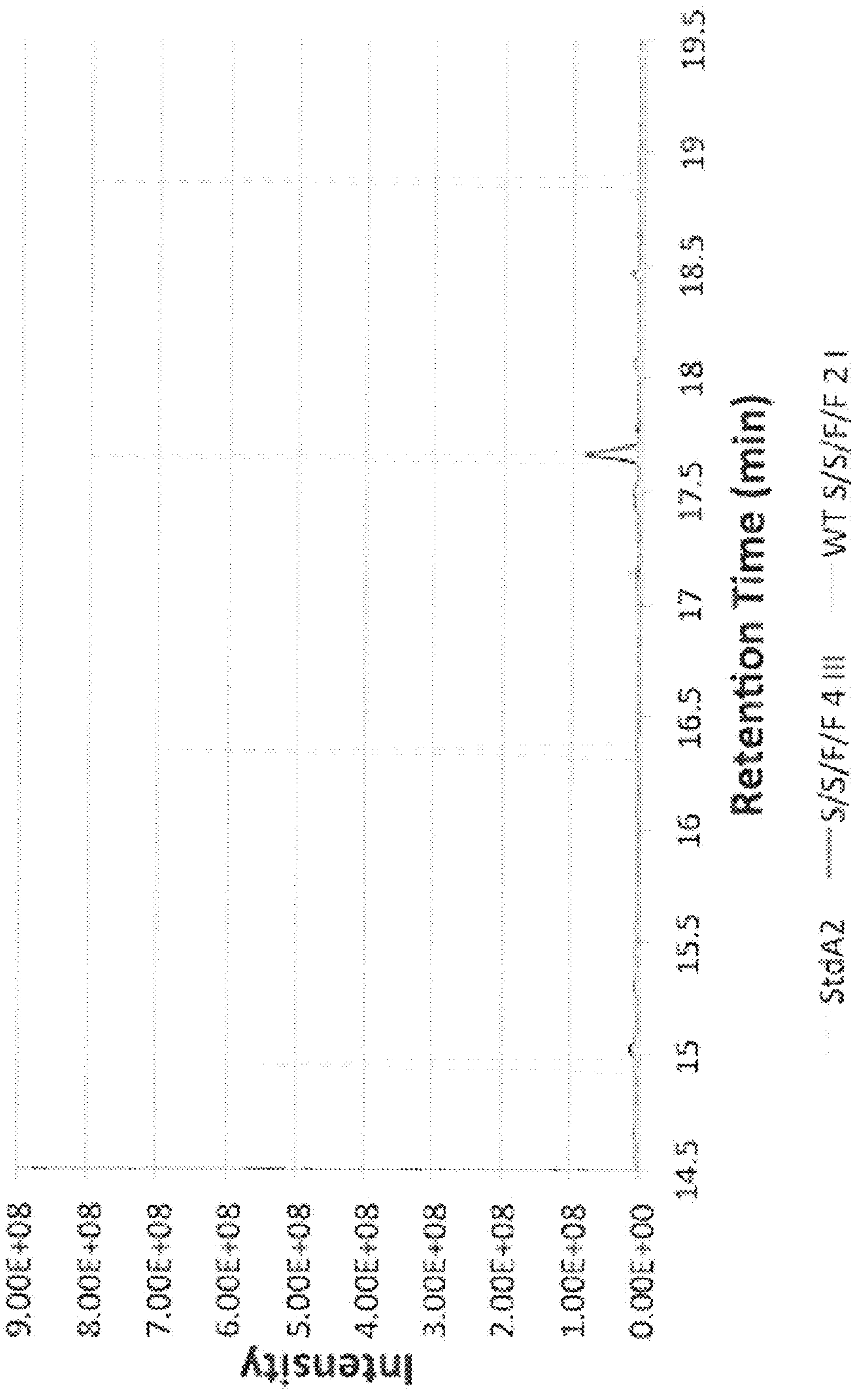

FIG. 4 shows gas chromatography spectrum of intracellular alkanes and alkenes produced in a *Saccharomyces cerevisiae* BY4741 wt strain carrying the plasmids KB02 and pAlkane0 (WT S/S/F/F 2 I) and the strain BY4741 6550 (hfd1Δstrain, S/S/F/F 4 III) carrying the same plasmids. The four dashed peaks represent the alkane standard that was analyzed under the same conditions; the peak at 17.6 minutes is a pentadecane peak. This spectrum illustrates the requirement of the HFD1 deletion for fatty acid derivatives produced via a fatty aldehyde intermediate pathway.

Figure 5:
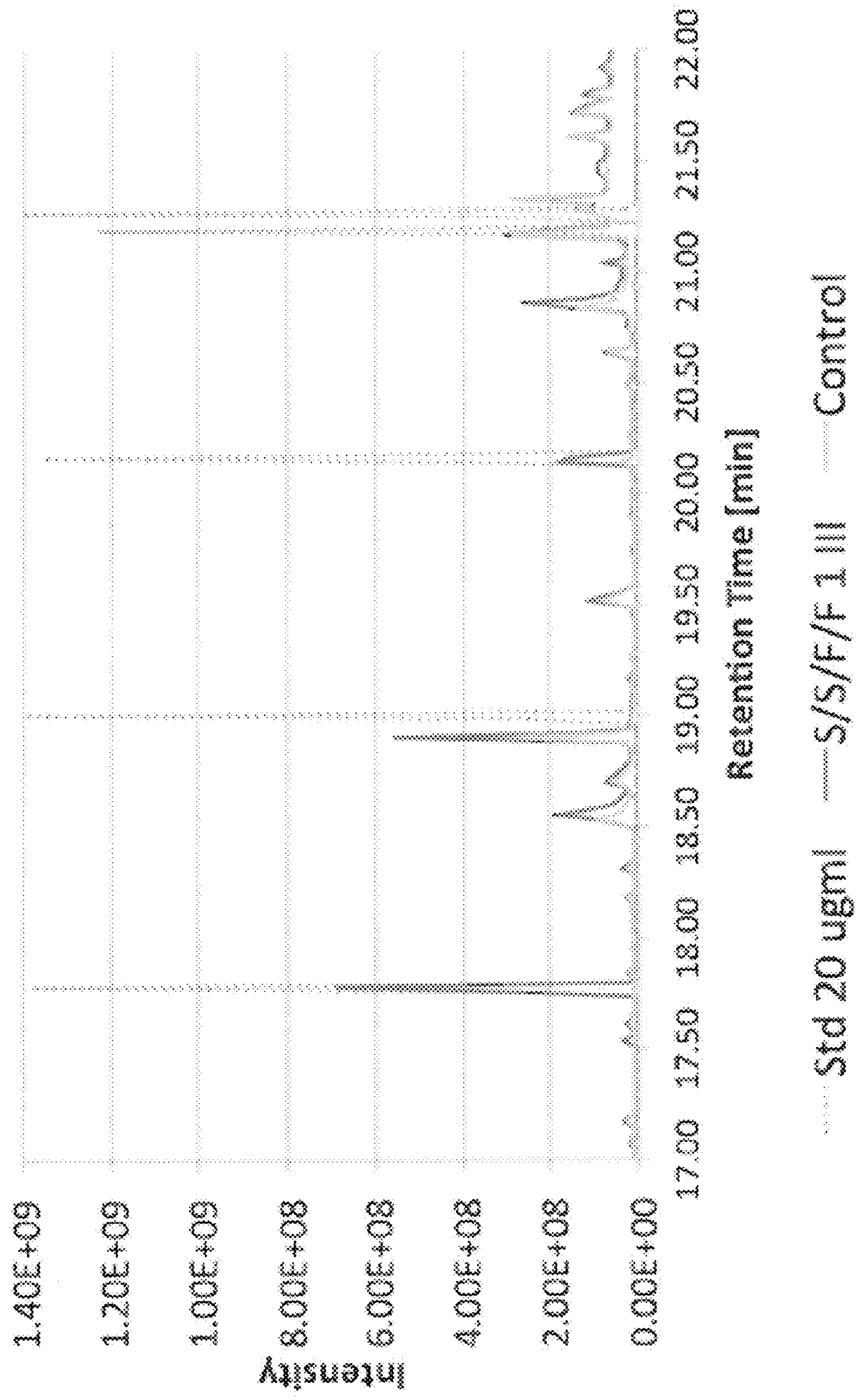

FIG. 5 shows gas chromatography spectrum of intracellular alkanes and alkenes produced in a *Saccharomyces cerevisiae* BY4741 6550 strain carrying the plasmids KB02 and pAlkane0 (S/S/F/F 1 III) and the control strain BY4741 6550 (hfd1Δ strain) carrying the empty plasmids pIYC04 and pSPGM1 (control). The five dashed peaks represent the alkane standard that was analyzed under the same conditions; the peak at 17.6 and 20.1 minutes are a pentadecane and a heptadecane peak, the peak (4th) after 21 minutes represents the internal standard 1-octadecene. This spectrum illustrates that introduction of a cyanobacterial alka/ene biosynthesis pathway and deletion of HFD1 enables yeast to produce hydrocarbons.

Figure 6:
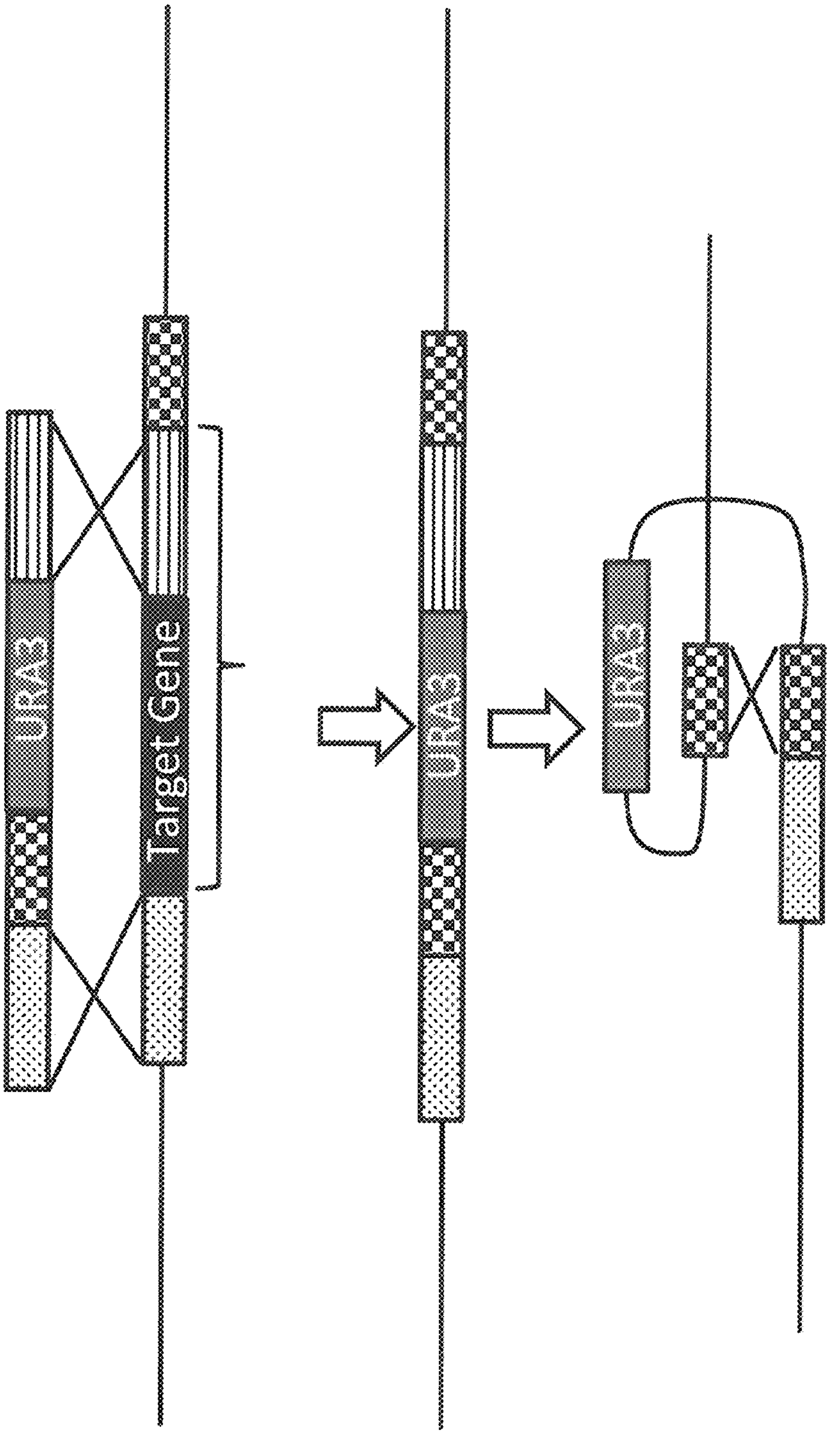

FIG. 6 describes direct repeat-mediated marker removal.

Figure 7:
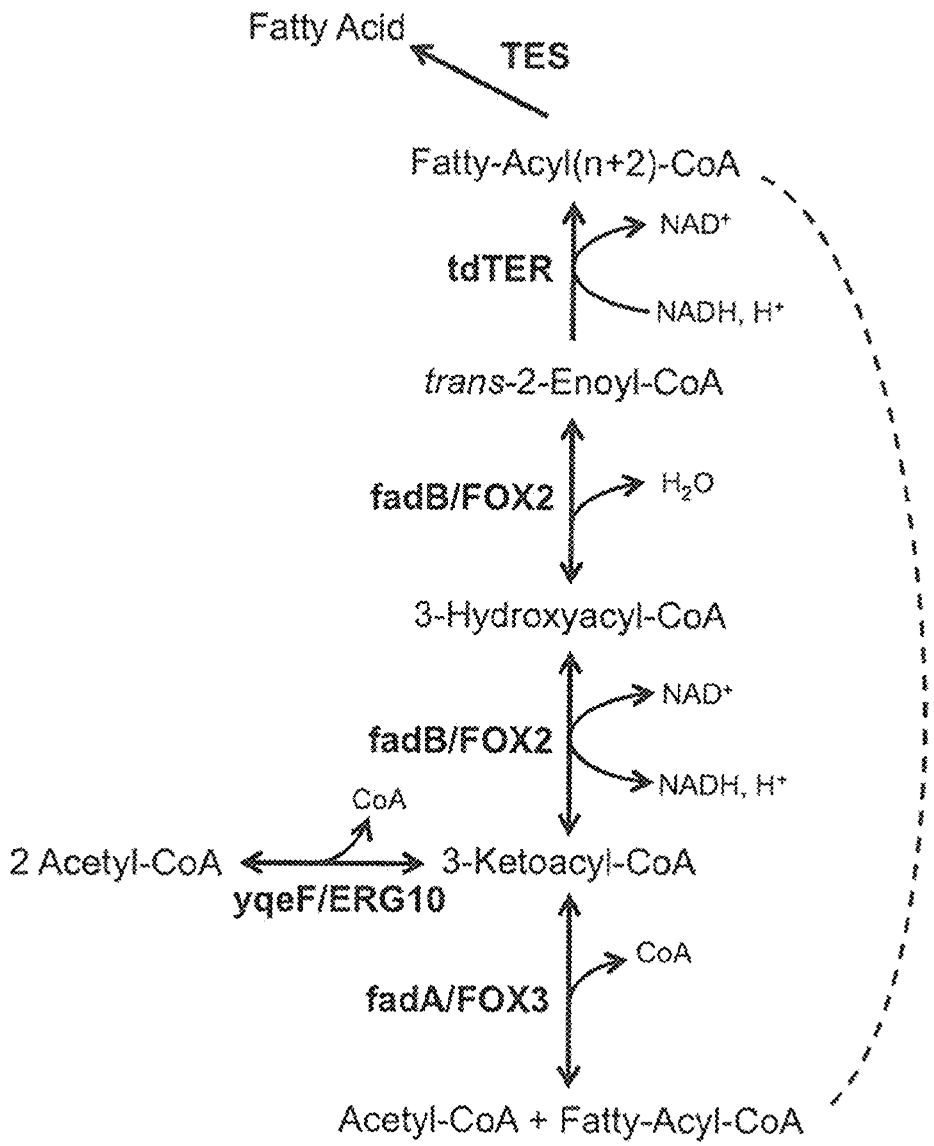

FIG. 7 describes the pathway for the biosynthesis of free fatty acids in yeast cells from cytosolic acetyl-CoA that may result from overexpression of the specified bacterial or yeast genes in the cytosol of a yeast cell.

Figure 8:
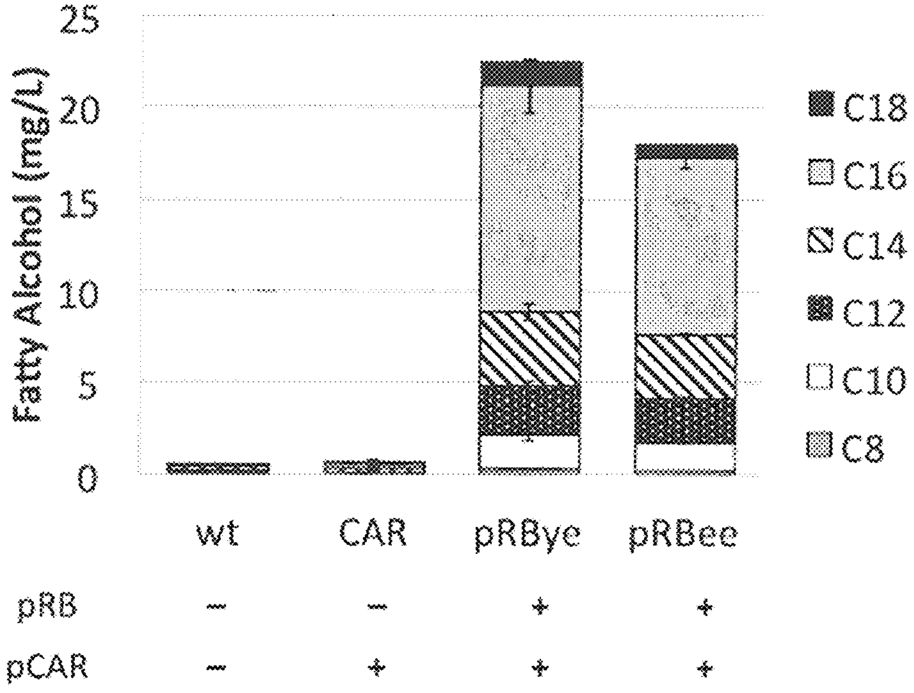

FIG. 8 shows the change in produced fatty alcohol profile when a fatty-acid producing pathway composed of an acetyl-CoA C-acetyltransferase, a 3-ketoacyl-CoA thiolase, a 3-hydroxyacyl-CoA dehydrogenase and enoyl-CoA hydratase multifunctional enzyme, a trans-enoyl-CoA reductase and a thioesterase is overexpressed in *S. cerevisiae* cytoplasm.

Figure 9:
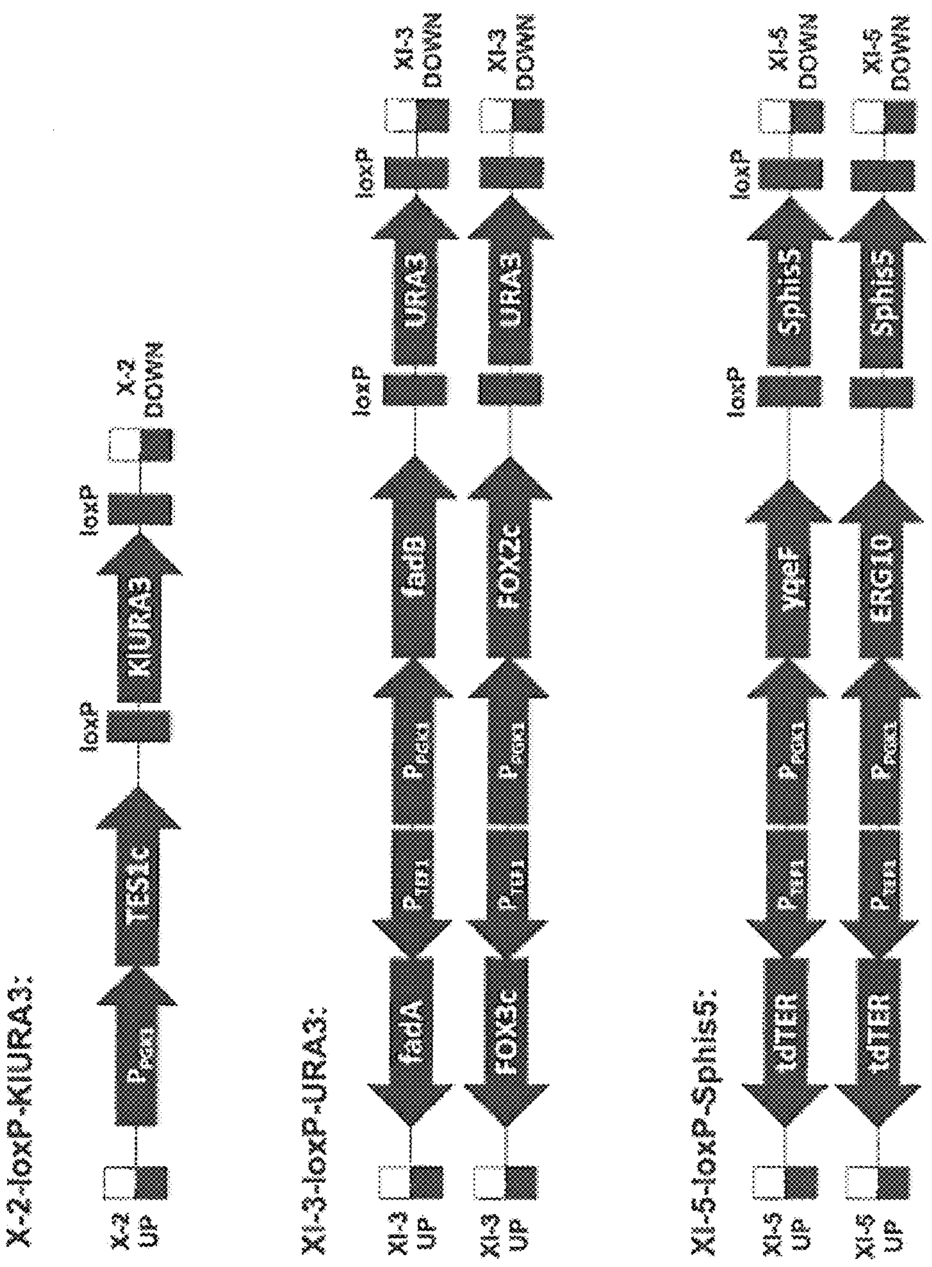

FIG. 9 describes constructs for integration into *S. cerevisiae* strain CEN.PK 113-11C for cytosolic overexpression of the medium-chain fatty acid biosynthesis pathway.

Figure 10:
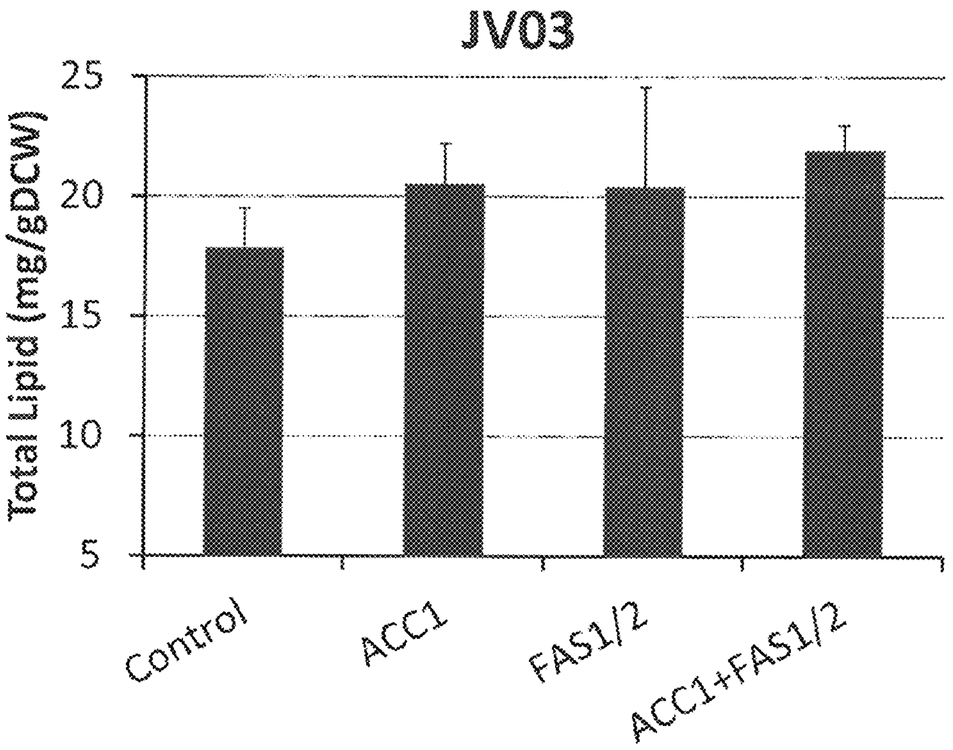

FIG. 10 shows overexpression of *Rhodosporidium toruloides* ACC1, FAS1+FAS2, and ACC1+FAS1+FAS2 in a storage lipid free *Saccharomyces cerevisiae*. Cells were cultivated and total lipids were measured as described by Khoomrung et al (2012).

Figure 11:
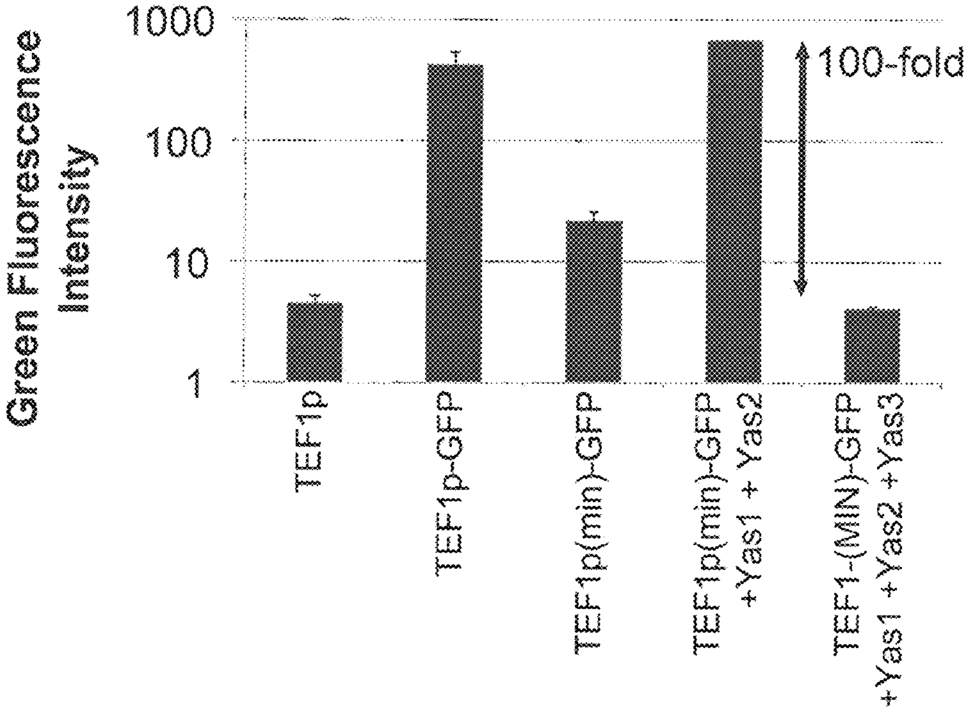

FIG. 11 shows an alkane sensor system, where ARE binding sites were fused to a minimal TEF promoter; by expressing the different components of the sensor system a dynamical range of 100-fold was achieved.

Figure 12A:
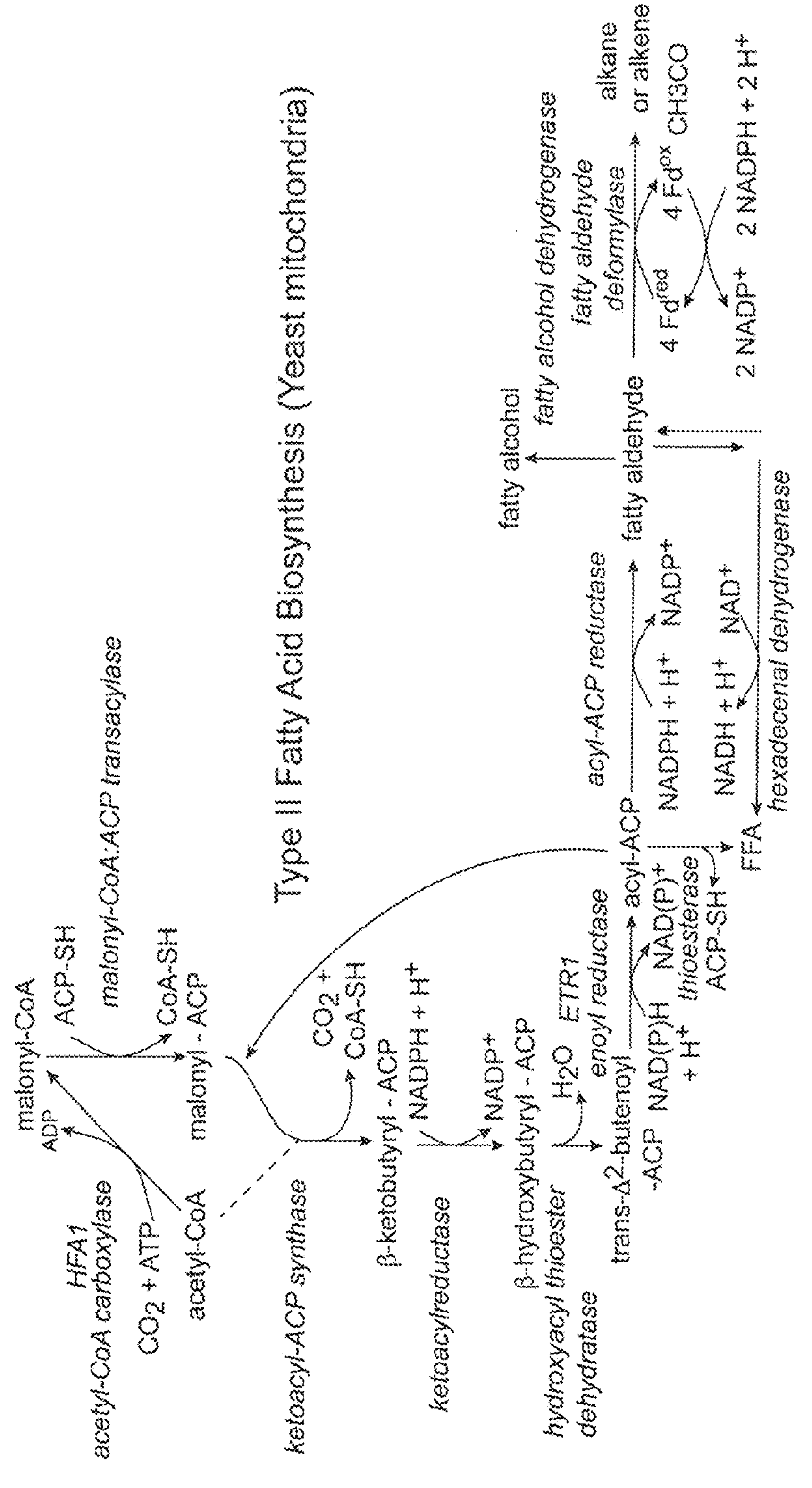
Figure 12B:
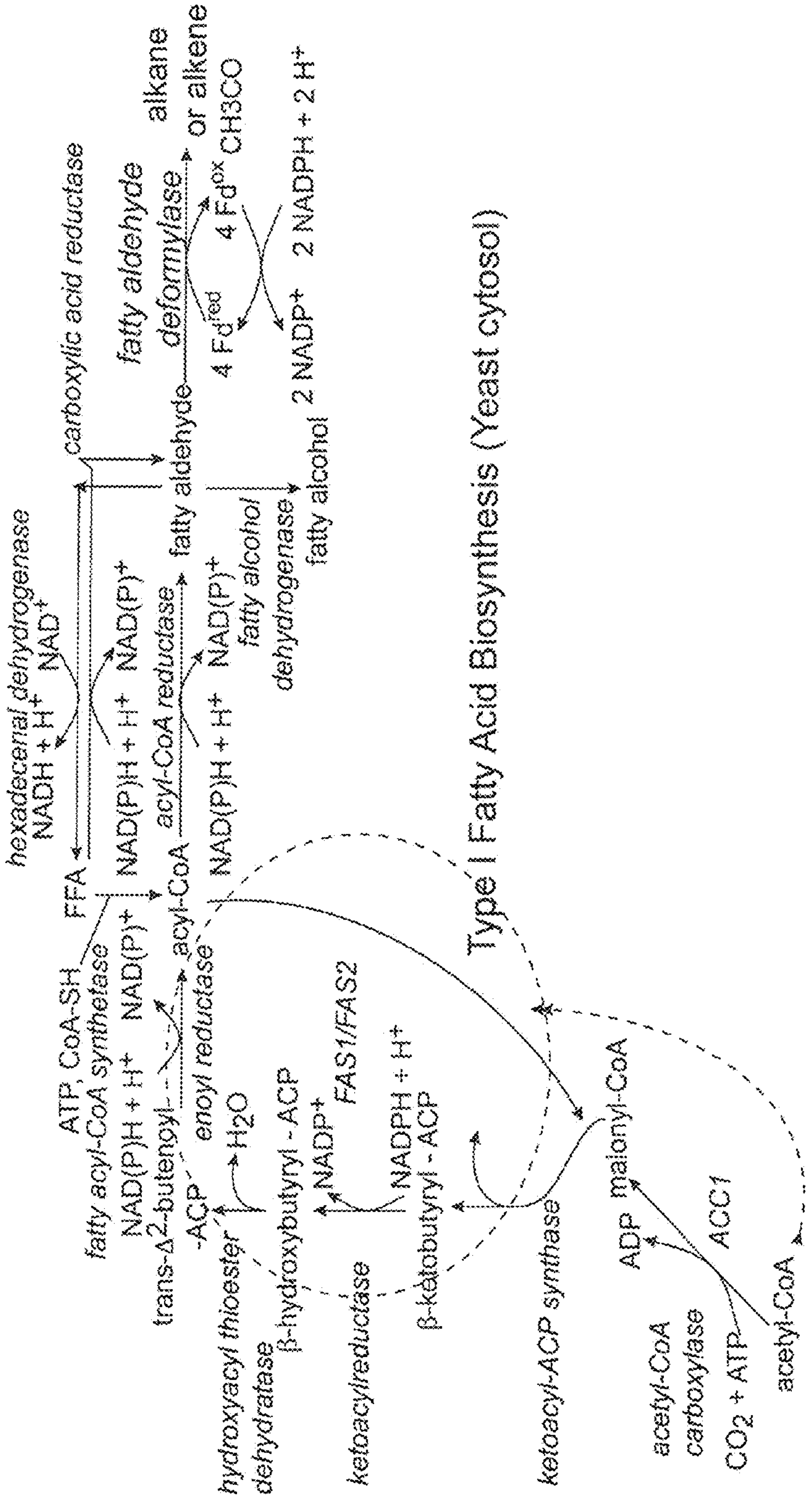

FIGS. 12A-12B show an overview of cytosolic and mitochondrial fatty acid biosynthesis and alkane, alkene, and fatty alcohol biosynthesis using fatty acid derivatives as substrate. Note: cytosolic acyl-CoA does not exist in this form during the fatty acid biosynthetic process but is released as such upon termination of it.

Figure 13:
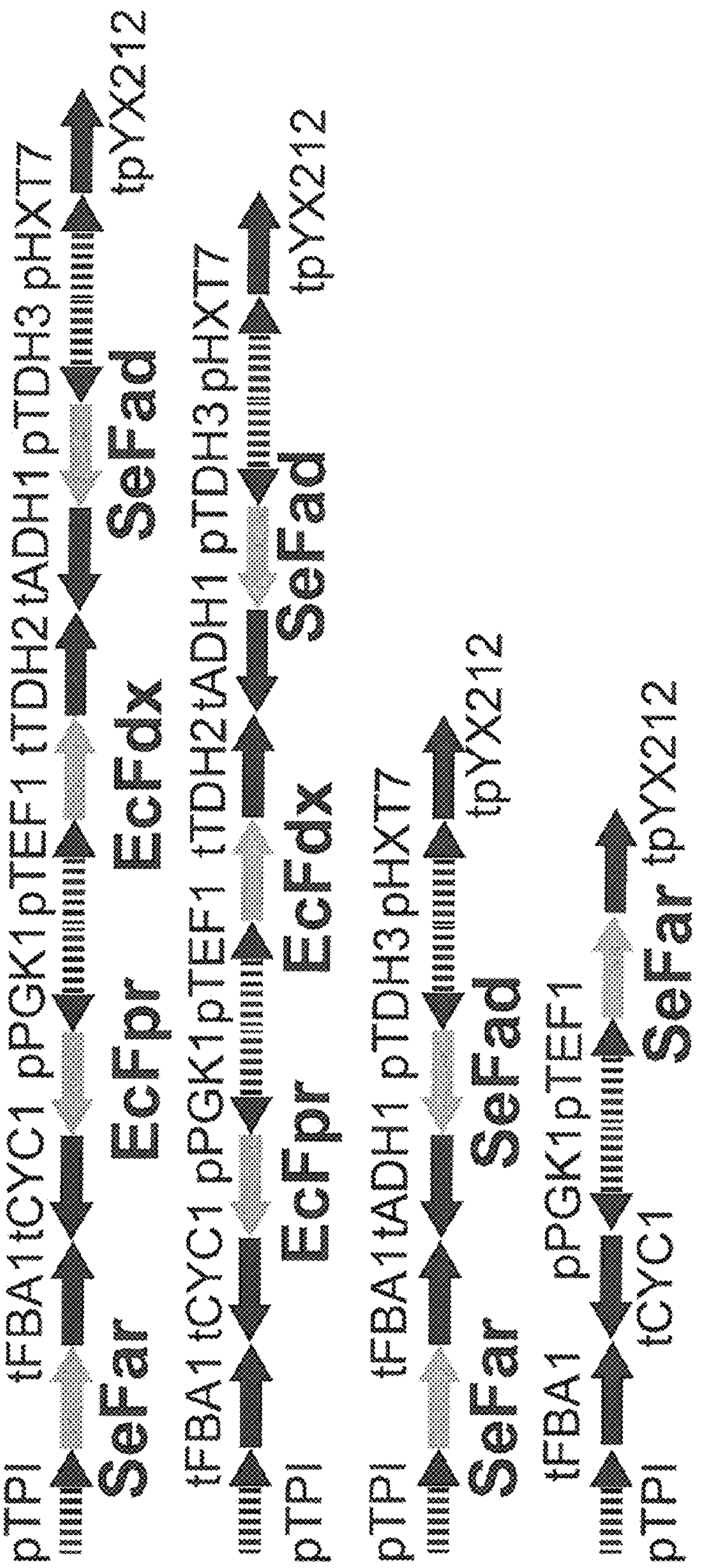

FIG. 13 shows the DNA pathway assembly constructs used to construct pAlkane1, pAlkane7, pAlkane8, and pFAR. *Synechoccocus elongatus* fatty acyl-ACP/CoA reductase (SeFar) and *S. elongatus* fatty aldehyde deformylating oxygenase (SeFad) were synthesized and codon-optimized. *Escherichia coli* ferredoxin (EcFdx) and *E. coli* ferredoxin NADP+ reductase (SeFpr) were amplified from *E. coli* DH5α. The promoter pTPI and the terminator tpYX212 are homologous to the respective promoter and terminator on the pYX212 plasmid. All four plasmids were constructed using the modular pathway engineering strategy (Zhou et al., 2012).

Figure 14:
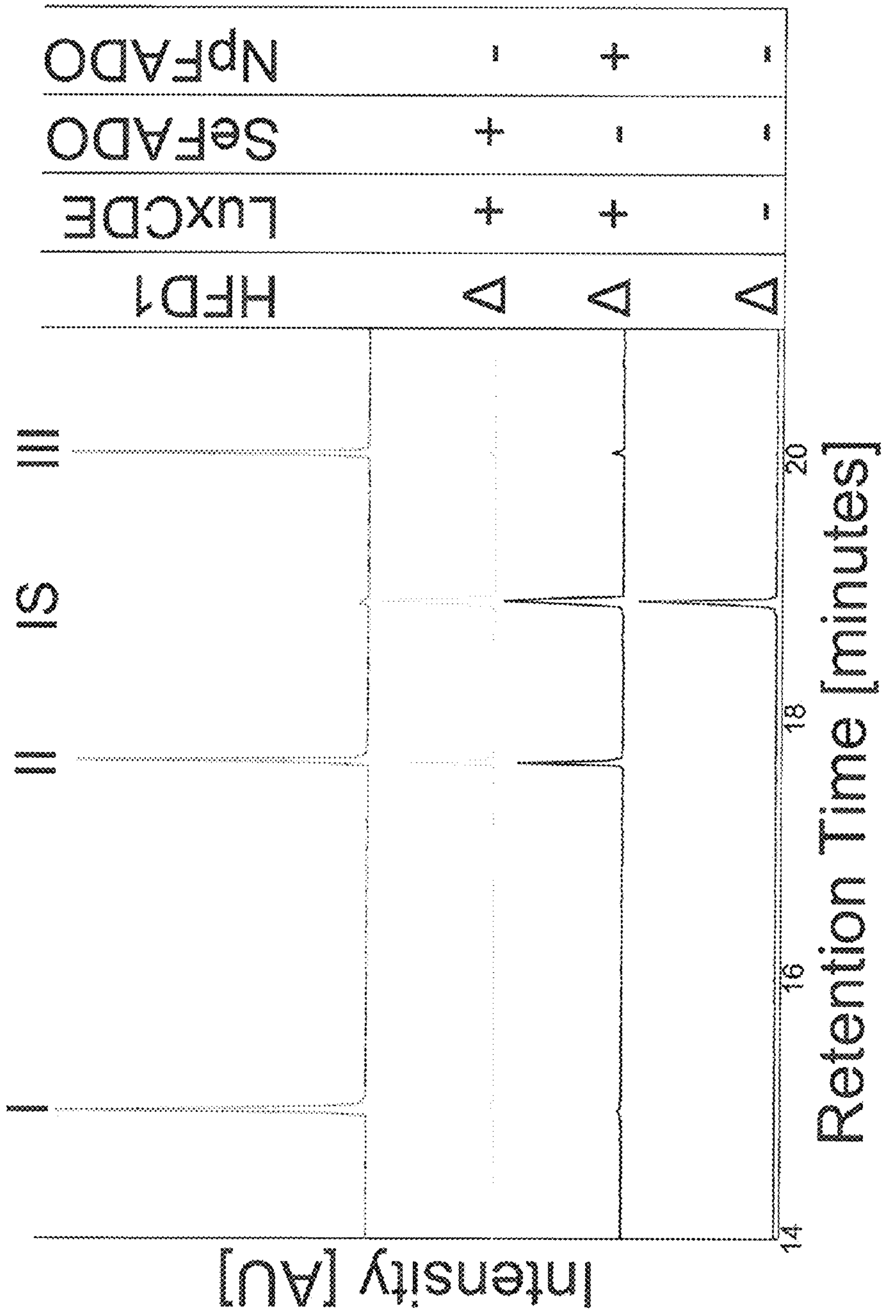

FIG. 14 shows alkane biosynthesis. Gas chromatograms of shake flask cultures incubated for 48 hours in glucose minimal medium. The lines represent *S. cerevisiae* CEN.PK113-11C strain carrying deletion of the HFD1 gene and which express *Photorhabdus luminescens* LuxC, LuxD, and LuxE; and either a *S. elongatus* or a *N. punctiforme* FADO. The *S. cerevisiae* strains carrying an empty vector pYX212 (bottom trace) are shown as a control. A C7-C30 alkane analytical standard (top trace) was used as a reference. The peaks highlighted by the blue bars labeled with I, II, IS, and III represent tridecane (C13), pentadecane (C15), hexadecane (C16; internal standard), and heptadecane (C17), respectively. The shown spectra are for the m/z values 184, 212, and 240. The mass spectra for the labeled peaks in comparison with a NIST library standard.

Figure 15:
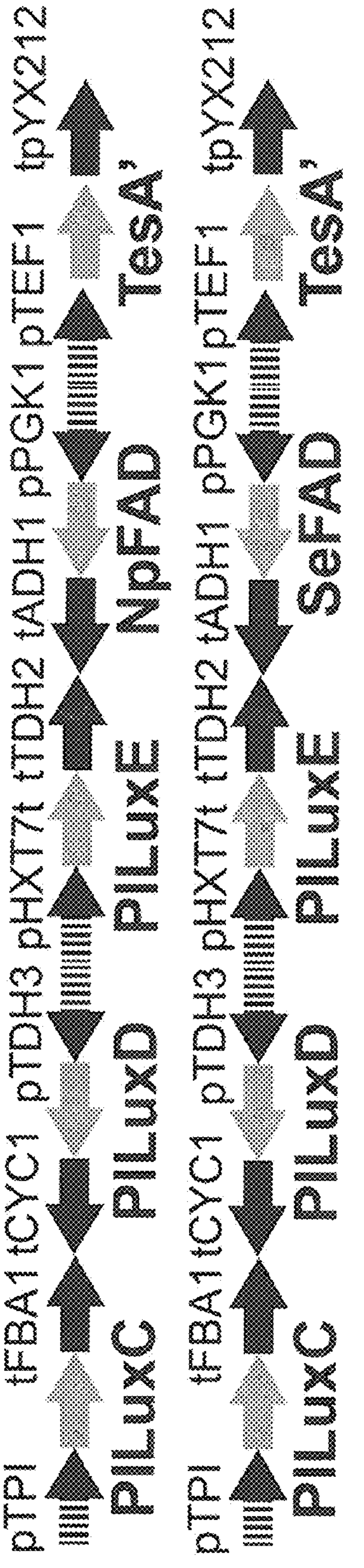

FIG. 15 shows the DNA pathway assembly constructs used to construct pAlkane1, pAlkane7, and pAlkane8. *Synechoccocus elongatus* fatty acyl-ACP/CoA reductase (SeFar) and *S. elongatus* fatty aldehyde deformylating oxygenase (SeFad) were synthesized and codon-optimized. *Escherichia coli* ferredoxin (EcFdx) and *E. coli* ferredoxin NADP+ reductase (SeFpr) were amplified from *E. coli* DH5α. The promoter pTPI and the terminator tpYX212 are homologous to the respective promoter and terminator on the pYX212 plasmid. All four plasmids were constructed using using the modular pathway engineering strategy (Zhou et al., 2012).

DETAILED DESCRIPTION OF THE INVENTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

An alternative type of diesel fuel can include terpene derived hydrocarbons. Since terpene derived diesels need chemical finishing due to the unsaturated nature of the primary fermentation products, an ideal biofuel would comprise saturated alkanes, which are also the main component of petrodiesels. Biosynthetically they are derived from fatty acids, which are constructed from the building block acetyl-CoA.

Biosynthetic pathways leading to alkane formation have however only been elucidated very recently, mainly in plants and bacteria. The"n−1 pathway" from cyanobacteria, is a two-step process, in which activated fatty acids are first reduced to fatty aldehydes and then decarbonylated to form alkanes. This pathway was transferred to *E. coli* and the resultant recombinant bacterium has been used in a fermentation process developed by a US-based company LS9.

The present invention provides a further industrial organism, yeast, that produces fatty acid derivatives (e.g., alkanes, alkenes, fatty alcohols and the like). Using today's methods, production of such fatty acid derivatives has not been efficient in yeast, since the yields are too low and it has not been possible to obtain short/medium chain fatty acid derivatives. However, the present inventors surprisingly discovered that deleting a hexadecenal dehydrogenase gene, HFD1, in yeast led to the blocking of the conversion of fatty aldehyde to fatty acid, thereby resulting in the production of, for example, alkanes, alkenes and fatty alcohols. Due to its adaptability to fermentation conditions, such as low pH, yeast provides an ideal industrial microorganism for the production of these fatty acid derivatives.

The HDF1 gene in yeast has so far only been studied in the context of Sjögren-Larssons disease, but has never been associated with production of fatty acid derivatives as in the present invention. Hexadecenal dehydrogenase Hfd1 (encoded by HFD1) competes for substrate with the heterologous fatty aldehyde decarbonylases leading to an ATP consuming futile cycle. By the discovery of the present inventors that a knock-out of this gene in yeast, alone or in combination with the integration of one or more heterologous nucleotide sequences and/or biosynthetic pathways, can alter the products of fatty acid biosynthesis and metabolism, the inventors have provided a solution to the utilization of different fatty acid biosynthetic machineries in the cytosol and in the mitochondria, respectively for the synthesis of medium and long chain fatty acids, and their subsequent conversion into alkanes, alkenes and/or fatty alcohols.

Figure 1:
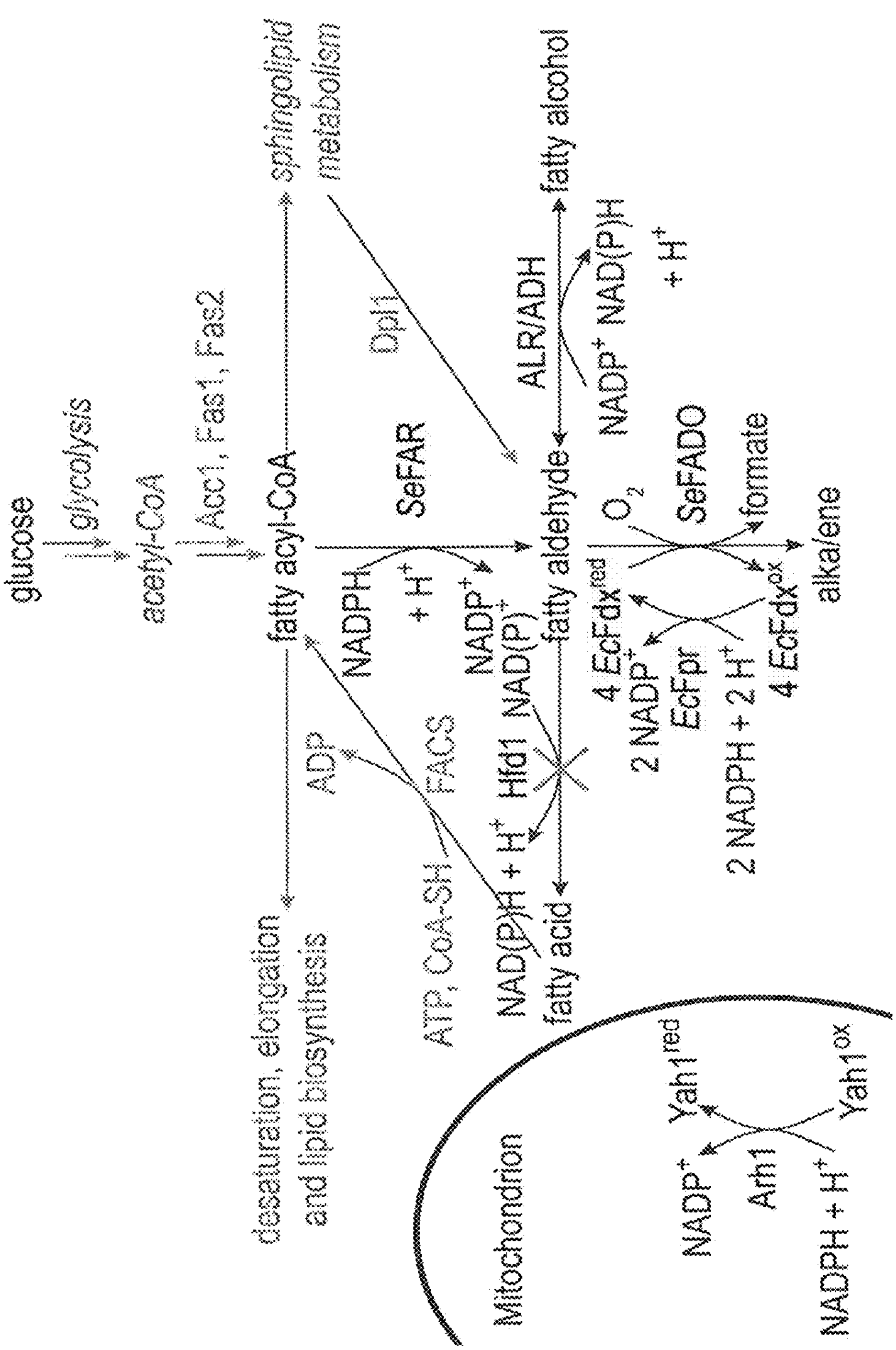
FIG. 1 shows the alkane biosynthetic pathway and fatty aldehyde metabolism in *Saccharomyces cerevisiae*. A heterologous alkane biosynthetic pathway, consisting of a *S. elongatus* fatty acyl-CoA/ACP reductase (SeFAR; encoded by orf1594) and a *S. elongatus* fatty aldehyde deformylating oxygenase (SeFADO; encoded by orf1593), was introduced in the yeast *S. cerevisiae*. This pathway intersects with endogenous metabolism of fatty aldehydes by promiscuous aldehyde reductase (ALR) and fatty alcohol dehydrogenases (ADH) and the hexadecenal dehydrogenase Hfd1 (encoded by HFD1/YMR110C), which catalyzes the last step in the sphingolipid breakdown pathway. The *E. coli* ferredoxin (EcFdx)/ferredoxin reductase (EcFpr) system was introduced to provide the cofactor required for the FADO enzyme. The endogenous ferredoxin and ferredoxin reductase homologues Yah1 and Arh1, respectively, are localized to the mitochondria.
Figure 2A:
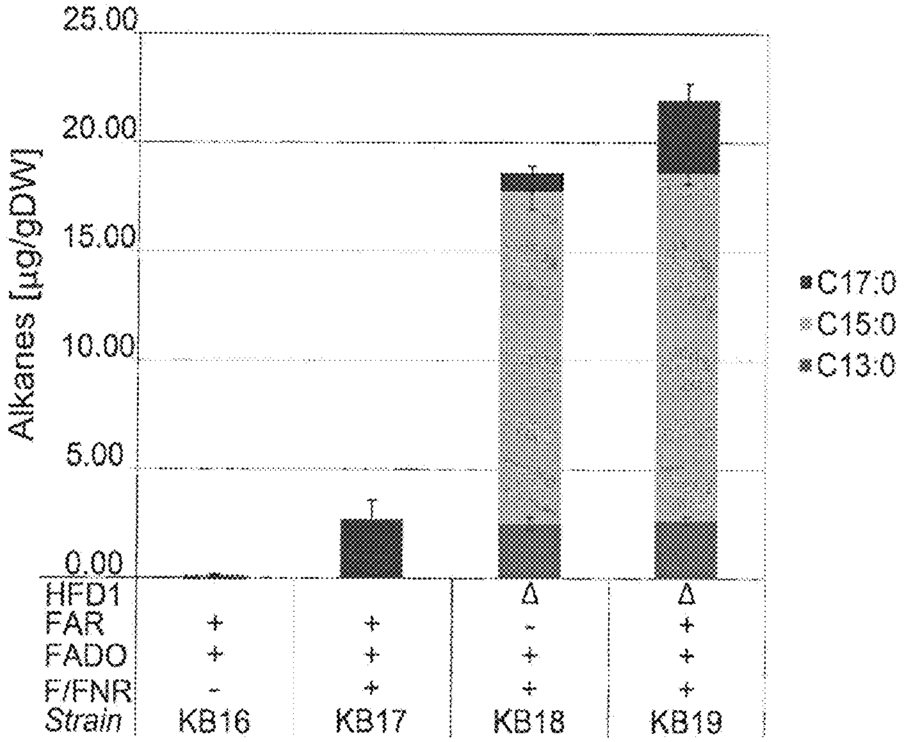
FIGS. 2A-2B shows analysis of alkane (A) and fatty alcohol production (B) in engineered *S. cerevisiae* strains. Strains carry either the WT allele or a deletion of the HFD1 gene encoding hexadecenal dehydrogenase and express *S. elongatus* fatty acyl-CoA/ACP reductase (FAR), *S. elonga-*

In the present invention, the inventors demonstrate fatty acid derived alkane biosynthesis in the yeast *S. cerevisiae* by expression of an alkane biosynthetic pathway consisting of a FAR, encoded by *Synechoccocus elongatus* orf1594, and a FADO, encoded by *S. elongatus* orf1593 (see FIG. 1). However, upon first instance of expression of the SeFAR and SeFADO in a *S. cerevisiae* CEN.PK background, no alkanes could be detected (FIG. 2A, KB16). The inventors suspected that an explanation for the absence of alkanes could be the lack of a compatible redox partner that is required by the FADO enzyme in the CEN.PK background strain. For the FADO enzyme it has been shown in vitro that it requires ferredoxin (F) and ferredoxin NADP+ reductase (FNR) to supply electrons. Yeast possesses the ferredoxin and the ferredoxin reductase homologs Yah1 and Arh1, respectively, which both play a role in iron-sulfur cluster protein biosynthesis. Nonetheless, these proteins reside in the mitochondria, which makes them inaccessible as redox partners for the cytosolic alkane pathway. Since *E. coli* was able to support in vivo alkane production, we chose to co-express the *E. coli* ferredoxin (F) Fdx and ferredoxin NADP+ reductase (FNR) Fpr. The co-expression of the EcF/FNR reducing system resulted in the biosynthesis of 2.7±0.9 mg/gDW heptadecane (FIG. 2A, KB17) and no detection of pentadecane. This result is in contrast with the alkane profile that was found in *E. coli* as well as the fatty acid profile of *S. cerevisiae*, in which C16 and C18 are the predominant fatty acid species. The inventors speculated that there might be a problem with supplying C16 fatty aldehydes for the decarbonylation reaction.

Figure 2B:
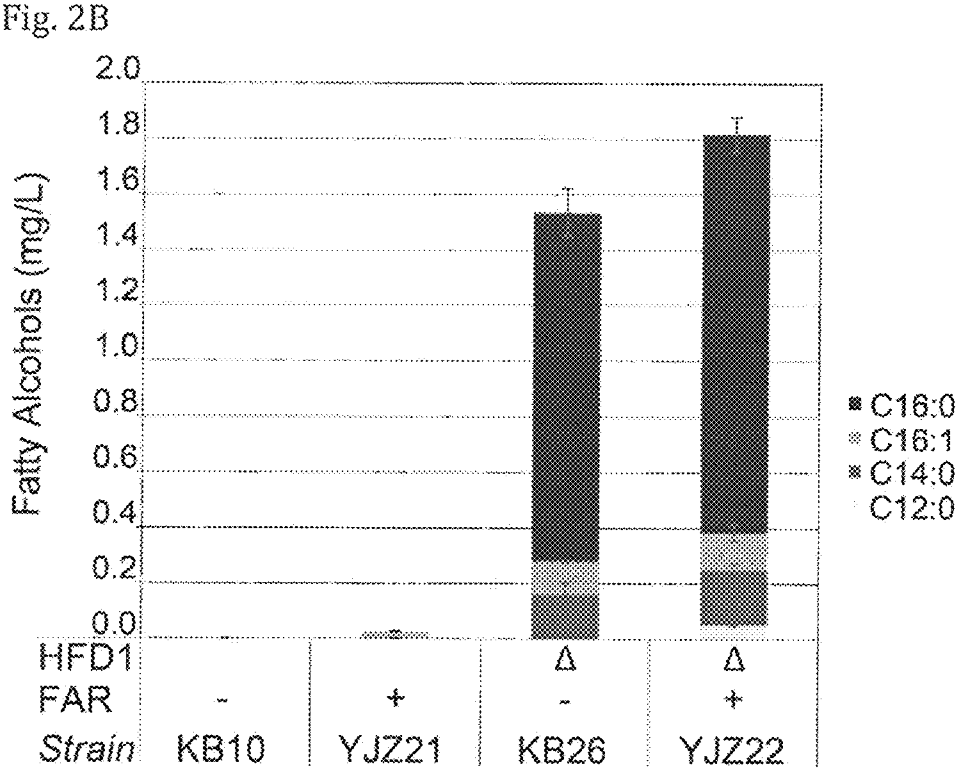

Hence, to ensure efficient functionality of the pathway the inventors chose to verify the fatty aldehyde supply by FAR. To confirm the supply of fatty aldehydes, fatty alcohol synthesis was used as an indicator. The detection of fatty alcohols as byproducts of alkane biosynthesis has been observed in *E. coli*, and is suspected to be a result of the activity of endogenous promiscuous aldehyde reductases and alcohol dehydrogenases. Yeast contains around 40 homologues of such reductases and dehydrogenases, and consequently fatty alcohol synthesis was expected to occur after the introduction of FAR. Nevertheless, when SeFAR was overexpressed in a wild-type yeast strain, it yielded only trace amounts of fatty alcohols (FIG. 2B). These results indicated that there could be an additional (irreversible) reaction, not present in *E. coli*, which competes for the fatty aldehyde substrate. In the case of *S. elongatus* it has recently been shown that such an enzyme is present and that overexpression of FAR results in fatty acid secretion due to the presence of the fatty aldehyde dehydrogenase AldE. This enzyme converts fatty aldehydes very efficiently into fatty acids. Alignment of AldE against the *S. cerevisiae* proteome yielded the hexadecenal dehydrogenase Hfd1 as the primary candidate. To test the hypothesis that Hfd1 prevents the biosynthesis of fatty alcohols by converting fatty aldehydes into fatty acids, HFD1 was knocked-out followed by SeFAR overexpression. Surprisingly, the deletion of HFD1 alone sufficed to enable fatty alcohol production (1.5±0.1 mg/L, FIG. 2B). The fatty aldehydes observed in this hfd1Δ strain most likely resulted from the sphingolipid breakdown pathway in which Hfd1 catalyzes the final step. The additional overexpression of SeFAR increased the fatty alcohol titer to 1.8±0.1 mg/L. The main fatty alcohol was hexadecanol (C16:0; 79%), followed by tetradecanol (C14:0; 11%), hexadecenol (C16:1; 7.3%), and dodecanol (C12:0; 2.8%). The drastic increase of C16 fatty alcohols illustrated that Hfd1 catalyzed the oxidation of C16 fatty aldehydes toward the corresponding fatty acids.

The detection of heptadecane in the wild-type background strain KB17 carrying SeFAR, SeFADO, and EcF/FNR and the absence of the fatty alcohol octadecanol in the hfd1Δ SeFAR strain suggests that Hfd1 and the endogenous aldehyde reductases/alcohol dehydrogenases cannot use octadecanal as a substrate. This is in agreement with the detection of very long chain alkanes. The modest increase in fatty alcohol titer after FAR expression in a hfd1 strain, is most likely due to the low affinity of FAR for fatty acyl-CoA (it prefers fatty acyl-ACP). These results illustrate the importance of HFD1 deletion to enable fatty aldehyde supply.

Subsequently, the SeFADO and the EcF/FNR reducing system were introduced in the hfd1Δ strain, as deletion of HFD1 alone is sufficient to provide fatty aldehydes for the upstream part of the alkane pathway (which had been shown by the increased production of fatty alcohols). Subsequently, the alkane production increased drastically to 18.6±1.4 mg/gDW in this hfd1Δ SeFADO EcF/FNR strain (FIG. 2A, KB18). Accumulation of tridecane and pentadecane was observed together with heptadecane, which was the sole product in the wild-type genetic background strain KB17. The chain length profile of these alkanes is in agreement with those of the observed fatty alcohols. Additional expression of SeFAR in the hfd1Δ strain resulted in a titer of 22.0±1.4 mg/gDW. The slight increase in titer suggests again that SeFAR has low catalytic efficiency on acyl-CoAs. No alkanes were detected extracellularly indicating that the alkanes are not excreted, which is in contrast with the detection of 80% of the produced alkanes in the extracellular medium in *E. coli.*

Similarly, we also realized medium-chain alkane production after HFD1 disruption in a S288C background. Interestingly, expression of only SeFAR and SeFADO in this strain resulted in pentadecane and heptadecane biosynthesis, possibly indicating the presence of a reducing system that is absent in the CEN.PK background strain.

In some embodiments of the invention, yeasts can be modified to overproduce acyl-CoA, fatty acids or acyl-ACPs in order to further increase the production of alkanes, alkenes and/or fatty alcohols. In one embodiment, increasing the fatty acid synthesis can be accomplished by overexpressing fatty acid biosynthetic genes, including but not limited to ACC1 (encoding acetyl-CoA carboxylase), FAS1 (encoding the beta-subunit of fatty acid synthetase) and FAS2 (encoding the alpha-subunit of fatty acid synthetase). The inventors have in addition to these pathways also expressed several alternative alkane/alkene biosynthetic pathways in order to enable the biosynthesis of short, medium, and long chain alkanes, alkenes, and the like.

In some aspects of the invention, alkenes and/or alkanes with 5-17 carbon atoms are preferred. To achieve these chain lengths, the chain length of the fatty-acids used for conversion to alkanes and/or alkenes can be regulated.

For example, shorter chain molecules can be obtained by introducing a fatty acid synthase from humans, by expression of the alkane/alkene pathways in the mitochondria, or by reversed beta-oxidation in the cytosol.

A still further aspect comprises eliminating non-essential pathways in the yeast that consume (activated) fatty acids and thus compete with the production of fatty acid derivatives. Such nonessential pathways can include but are not limited to elimination of storage lipid formation and peroxisomal beta-oxidation.

In an additional embodiment, the NADPH supply can be modified (e.g., increased) in the recombinant yeast. Since NADPH is an essential cofactor of fatty acid biosynthesis, by increasing the supply of NADPH, it may be possible to further increase the production of fatty acid derivatives according to this invention.

Hence, in one embodiment, the invention provides a genetically modified/non-native strain of yeast comprising a disrupted gene encoding hexadecenal dehydrogenase (HFD1).

In some aspects of the invention, the disruption of the HFD1 gene results in a gene that is inoperative or knocked out and/or a nonfunctional gene product (e.g., a polypeptide having no activity as compared to the activity of the Hfd1 wild type polypeptide). In other embodiments, the disruption of the HFD1 gene results in a gene product that has reduced activity (e.g., 0 to 20% of the activity of the HFD1 wild type polypeptide). In still other embodiments, the disruption of the HFD1 gene results in reduced expression of a gene product as compared to the Hfd1 wild type polypeptide.

As used herein the terms a ype polypepHFD1 geneed herein the terms a ype polypepHFD1" are used interchangeably.

A "disrupted gene" as defined herein involves any mutation or modification to a gene resulting in a partial or fully non-functional gene and gene product. Such a mutation or modification includes, but is not limited to, a missense mutation, a nonsense mutation, a deletion, a substitution, an insertion, and the like. Furthermore, a disruption of a gene can be achieved also, or alternatively, by mutation or modification of control elements controlling the transcription of the gene, such as mutation or modification in a promoter and/or enhancement elements. In such a case, such a mutation or modification results in partially or fully loss of transcription of the gene, i.e. a lower or reduced transcription as compared to native and non-modified control elements. As a result a reduced, if any, amount of the gene product will be available following transcription and translation.

The objective of gene disruption is to reduce the available amount of the gene product, including fully preventing any production of the gene product, or to express a gene product that lacks or having lower enzymatic activity as compared to the native or wild type gene product.

A yeast useful with this invention can be any yeast useful in industrial and fermentation practices. In one embodiment, the yeast can be from the genus *Saccharomyces*. In other embodiments, the yeast is *Saccharomyces cerevisiae.*

In some embodiments, the genetically modified yeast strain of this invention (e.g., comprising at least a disrupted HDF1 gene) can further comprise one or more additional genetic modifications to improve production of desired products. Such modifications can include, but are not limited to:

(1) introduction of new enzymes, and/or biosynthetic and/or metabolic pathways, including, but not limited to expression of an alkane biosynthetic pathway consisting of *Synechoccous elongatus* FAR and *Synechoccous elongatus* FADO and;

(2) optionally, ferrodoxin (F) and ferrodoxin NADP+ reductase (FNR) may be introduced to supply electrons.

In still some embodiments, the yeast strains of the invention can additionally comprise genetic modifications that eliminate or reduce non-essential pathways. Such modifications can eliminate or reduce the utilization or consumption of fatty acids by enzymes or pathways that compete with the production of fatty acid derivatives such as alkanes, alkenes and fatty alcohols in the recombinant yeast strains. Exemplary embodiments of such non-essential pathways can include but are not limited to storage lipid formation and beta-oxidation. In particular embodiments, storage lipid formation can be eliminated or reduced by disrupting the genes encoding, for example, acyl-CoA:sterol acyltransferase (ARE1, ARE2), diacylglycerol acyltransferase (DGA1, LRO1). In other embodiments, beta-oxidation and free fatty acid activation can be eliminated or reduced by disrupting the genes encoding, for example, PDX1, FAA1, FAA4.

In additional aspects of the invention, the genetically modified yeast of the invention can be further modified to express heterologous fatty acid biosynthetic polypeptides for increased production of fatty acids. Nonlimiting examples of genes encoding such heterologous polypeptides Acc1, Fas1 and Fas2 (from e.g., *Rhodosporidium toruloides*).

NADPH is a cofactor in the synthesis of fatty acids. To increase the availability of NADPH for fatty acid biosynthesis, the genetically modified yeast of the invention can be further modified for heterologous expression of non-phosphorylating NADP+-dependent glyceraldehydes-3-phosphate dehydrogenase (GAPN) (from e.g., *Streptococcus mutans*). In other aspects, the yeast can be modified to disrupt GDH1 encoding NADP-dependent glutamate dehydrogenase. In still other embodiments, the yeast of the invention can be further modified to overexpress GDH2 encoding NAD-dependent glutamate dehydrogenase.

In additional embodiments, the yeast of the invention (e.g., comprising at least a disrupted HDF1 gene) can be further modified to comprise genetic modifications to increase production of fatty acid derivatives having particular chain lengths (e.g., short, medium, long chain fatty acid derivatives). In one aspect, the yeast can be modified to express a chimeric cytosolic pathway for the production of medium chain fatty acids or an increased ratio of medium-chain to long-chain fatty acids. Thus, for example, the yeast can be modified to (over)express in the cytosol FOX2, FOX3, ERG10 and TES1 (derived from, for example, *S. cerevisiae*), and/or yqeF, fadA, fabB and tdTER (from bacteria).

Fatty acid chain length can also be regulated through modification of expression of thioesterases. Thus, in some embodiments, the yeast of this invention can be further modified to express a thiesterase having a desired chain length specificity (e.g., tesA, tesB, fadM, yciA from, e.g. *E. coli*).

In particular embodiments, the genetically modified yeast of the invention can be further modified to produce short chain fatty acid derivatives (e.g., alkanes, alkenes, fatty alcohols and the like). Non-limiting examples of genes useful for such modifications include fpr and fdx from, for example, *E. coli*; and/or ferredoxin (orf_1499, petF) and ferredoxin-NADPH reductase (orf_0978, petH) from *Synechococcus elongatus*. Accordingly, in some embodiments, a genetically modified yeast of this invention can further comprise nucleic acid constructs comprising nucleotide sequences encoding fpr and/or fdx and/or nucleotide sequences encoding petF and/or petH.

In additional embodiments, the yeast strains of this invention (e.g., comprising at least a disrupted HFD1 gene) can further comprise nucleic acid constructs comprising nucleotide sequences encoding enzymes and/or biosynthetic pathways for conversion of fatty acids to alkanes and/or alkenes. Thus in some embodiments, the genetically modified yeast of the invention can be further modified to express *Mycobacterium marinum* carboxylic acid reductase and *Musca domestica* CYP4G2 decarbonylase (decarbonylase is also referred to as deformylating oxygenase in the art). In a representative embodiment, the yeast can be further modified to express a thioesterase, or an additional thioesterase, to relieve fatty acid biosynthess repression by acyl-CoA and to increase substrate availability for alkane and alkene biosynthesis. In other embodiments, the yeast strains of the invention can be modified to comprise expression of *Synechococcus elongatus* orf1594 and ACS, *Musca domestica* CYP4GT decarbonylase and NADPH-cytochrome P450 reductase. In further embodiments, the yeast strains of the invention can be modified to express *Acinetobacter* baylyi Acrl, *Musca domestica* CYP4GT decarbonylase and NADPH-cytochrome P450 reductase.

In further aspects of the invention, the bacterial luminescence pathway and a cyanobacterial fatty aldehyde decarbonylase can be expressed in the yeast strains of the invention in order to utilize fatty acyl-CoA in the synthesis of alkanes and alkenes. Thus, in a representative embodiment, the yeast strains of the invention comprising at least a disrupted HFD1 gene further comprises LuxC, LuxD and LuxE from *Photorhabdus luminescens* and *Nostoc punctiforme* FAD.

In other embodiments, the yeast strains of the invention can be further modified to comprise a pathway for conversion of fatty acids to terminal alkenes. A nonlimiting example of such a pathway includes *Jeotgalicoccus* spp orf880, *Escherichia coli* GroEL and *Escherichia coli* GroES.

The genetically modified yeast strain can additionally comprise carboxylic acid reductase (from e.g., *Mycobacterium marinum*) and decarbonylase (from e.g., *Musca domestica*) for conversion of fatty acids to alkanes and alkenes.

In some embodiments, short chain alkanes and alkenes are the desired product. Accordingly, in some embodiments, the genetically modified yeast of the invention can comprise modifications to their mitochondrial fatty acid biosynthetic pathway. In a representative embodiment, the genetically modified yeast of the invention can be modified to express in their mitochondria the *Mycobacterium marinum* CAR fatty acid reductase, the *Nostoc puntiforme* fatty aldehyde decarbonylase and *Aspergillus nidulans* phosphopantetheinyl transferase NpgA, optionally, the yeast can be modified to additionally overexpress components of the yeast mitochondrial fatty acid biosynthetic pathway, including but not limited to Etr1 (2-enoyl thioester reductase) and Hfa1 (acetyl-CoA carboxylase). In some embodiments, the yeast mitochondrial fatty acid biosynthetic pathway components to be overexpressed can further comprise CEM1, HTD2, OAR1, and MCT1. In further embodiments, the yeast comprising modifications to their mitochondrial fatty acid biosynthetic pathway can additionally comprise fdx and fpr from *E. coli*, wherein the respective protein sequences comprise mitochondrial localization signal(s) to direct them to the mitochondria. In still further embodiments, the yeast comprising modifications to their mitochondrial fatty acid biosynthetic pathway can additionally comprise nucleic acids encoding thioesterase to be expressed in the mitochondria. Non-limiting examples of thiesterases with activity towards medium chain fatty acyl-ACP include *Acinetobacter* baylyi TesA, *Cocos nucifera* FatB1, or homologue thioesterases thereof.

In additional embodiments, the yeast of the invention can be further modified to express a formate dehydrogenase enzyme in the mitochondria. Non-limiting examples of formate dehydrogenase enzymes include Fdh1 and/or Fdh2, which can be introduced into the yeast with mitochondrial localization signals.

In some embodiments the genetically modified yeast of the invention can be modified to have improved fatty aldehyde decarbonylase activity (thereby improving alkane and/or alkene production) by fusing a catalase to a fatty aldehyde decarbonylase (e.g., *Synechoccocus elongatus* orf1593 or *Nostoc punctiforme* FAD).

In other embodiments, the genetically modified yeast strains of the invention can comprise *Yarrowia lipoytica* Yas3 repressor and a fluorescent protein expressed from an alkane response element, ARE1 containing promoter in order to be able to screen genetically modified yeast strains, including, but not limited to, the yeast strains described in this invention, for modified alkane production (e.g., increased and/or reduced as compared to a control yeast strain not comprising said modification(s)). Thus, in some embodiments, a method of screening for modified production of alkanes comprises, introducing into a yeast strain of interest a *Yarrowia lipoytica* Yas3 repressor, the activators Yas1 and Yas2 and a fluorescent protein expressed from an alkane response element, ARE1, containing promoter, and detecting modified production of alkanes.

The present invention provides a further method of screening for modified production of alkanes and/or alkenes (e.g., increased and/or reduced as compared to a control yeast strain not comprising said modification(s)) based on the toxicity of fatty acid accumulation in yeast strains that are modified to have reduced or no storage lipid formation and/or beta-oxidation. Thus, the consumption of fatty acids by the introduced alkane biosynthetic pathways can be evaluated by monitoring the toxicity of the genetically modified yeast strains.

The present invention further provides methods for the production of hydrocarbons in genetically modified yeast, comprising culturing a genetically modified yeast of this invention and collecting the hydrocarbons. In some embodiments, a hydrocarbon can be a fatty acid derivative, for example, an alkane, an alkene, or a fatty alcohol.

Definitions

As used in the description of the invention and the appended claims, the singular forms “a,” “an” and “the” are intended to include the plural forms as well, unless the context clearly indicates otherwise.

Also as used herein, “and/or” refers to and encompasses any and all possible combinations of one or more of the associated listed items, as well as the lack of combinations when interpreted in the alternative (“or”).

The term “about,” as used herein when referring to a measurable value such as a dosage or time period and the like, is meant to encompass variations of ±20%, ±10%, ±5%, ±1%, ±0.5%, or even ±0.1% of the specified amount.

As used herein, phrases such as “between X and Y” and “between about X and Y” should be interpreted to include X and Y. As used herein, phrases such as “between about X and Y” mean “between about X and about Y” and phrases such as “from about X to Y” mean “from about X to about Y.”

The term “comprise,” “comprises” and “comprising” as used herein, specify the presence of the stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.”

As used herein, the terms “increase,” “increases,” “increased,” “increasing,” and similar terms indicate an elevation of at least about 25%, 50%, 75%, 100%, 150%, 200%, 300%, 400%, 500% or more.

As used herein, the terms “reduce,” “reduces,” “reduced,” “reduction,” and similar terms mean a decrease of at least about 5%, 10%, 15%, 20%, 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

As used herein, the terms “express,” “expresses,” “expressed” or “expression,” and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or a functional untranslated RNA. A “functional” RNA includes any untranslated RNA that has a biological function in a cell, e.g., regulation of gene expression. Such functional RNAs include but are not limited to RNAi (e.g., siRNA, shRNA), miRNA, antisense RNA, anti-microRNA antisense oligodeoxyribonucleotide (AMO; see e.g., Lu et al. Nucleic Acids Res. 37(3):e24: 10.1093/nar/gkn1053), ribozymes, RNA aptamers and the like.

As used herein, “overexpress,” “overexpressed,” “overexpression” and the like, in reference to a polynucleotide means that the expression level of said polynucleotide is greater than that for the same polynucleotide in its native or wild type genetic context (e.g., in the same position in the genome and/or associated with the native/endogenous regulatory sequences). A nucleotide sequence can be overexpressed by inserting it into an overexpression vector. Such vectors are known in the art.

A “heterologous” or a “recombinant” nucleotide sequence is a nucleotide sequence not naturally associated with a host cell into which it is introduced, including non-naturally occurring multiple copies of a naturally occurring nucleotide sequence. A heterologous gene may optionally be codon optimized for expression in yeast according to techniques well known in the art and as further described herein. A heterologous gene also encompasses, in some embodiments, an endogenous gene controlled by a heterologous promoter and/or control elements to achieve an expression of the gene that is different from, typically higher, i.e. so-called overexpression, than normal or baseline expression of the gene in a yeast comprising the endogenous gene under control of wild type (endogenous) promoter and control elements.

A “native” or “wild type” nucleic acid, nucleotide sequence, polypeptide or amino acid sequence refers to a naturally occurring or endogenous nucleic acid, nucleotide sequence, polypeptide or amino acid sequence. Thus, for example, a “wild type mRNA” is an mRNA that is naturally occurring in or endogenous to the organism. A “homologous” nucleic acid sequence is a nucleotide sequence naturally associated with a host cell into which it is introduced.

Also as used herein, the terms “nucleic acid,” “nucleic acid molecule,” “nucleotide sequence” and “polynucleotide” refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

"Introducing" in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term "transformation" as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear genome. Stable transformation as used herein can also refer to a nucleic acid molecule that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a yeast). Stable transformation of a cell can be detected by, for example, a Northern blot hybridization assay of RNA of the cell with nucleic acid sequences which specifically hybridize with a nucleotide sequence of a nucleic acid molecule introduced into a yeast or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

A "portion" or "fragment" of a nucleotide sequence of the invention will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of the invention, the substantial identity exists over a region of the sequences that is at least about 16, at least about 18, at least about 22, at least about 25, at least about 30, at least about 40, at least about 50, about 60, about 70, about 80, about 90, about 100, about 110, about 120, about 130, about 140, about 150, or more residues in length, and any range therein. In representative embodiments, the sequences can be substantially identical over at least about 22 nucleotides. In still other embodiments, the substantial identity exists over the full length or nearly the full length of the sequence.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tij ssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In particular embodiments, a further indication that two nucleotide sequences or two polypeptide sequences are substantially identical can be that the protein encoded by the first nucleic acid is immunologically cross reactive with, or specifically binds to, the protein encoded by the second nucleic acid. Thus, in some embodiments, a polypeptide can be substantially identical to a second polypeptide, for example, where the two polypeptides differ only by conservative substitutions.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In some embodiments, the nucleotide sequences and/or recombinant nucleic acid molecules of the invention can be operatively associated with a variety of promoters for expression in yeast cells. Thus, in representative embodiments, a recombinant nucleic acid of this invention can further comprise one or more promoters operably linked to one or more nucleotide sequences.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." In particular aspects, a "promoter" useful with the invention is a promoter capable of initiating transcription of a nucleotide sequence in a yeast cell.

The choice of promoter will vary depending on the temporal and spatial requirements for expression, and also depending on the host cell to be transformed. Promoters useful with the invention include, but are not limited to, those that drive expression of a nucleotide sequence constitutively, those that drive expression when induced, and those that drive expression in a tissue- or developmentally-specific manner. These various types of promoters are known in the art.

As used herein the terms "fatty acid derivative" or "fatty acid derivatives" includes but are not limited to hydrocarbons, such as for example alkanes and/or alkenes as well as fatty alcohols, of any length (e.g., short, medium and long chain).

Hexadecenal dehydrogenase gene HFD1 is found in *Saccharomyces cerevisiae* and encodes hexadecenal dehydrogenase Hfd1. HFD1 homologues can be found in other yeasts and are also envisioned to be part of this invention even though the gene name may not be the same.

Acyl-CoA or fatty acyl-CoA is a group of molecules involved in the metabolism of fatty acids. It is a transient intermediate compound formed when coenzyme A (CoA) attaches to the end of a fatty acid inside living cells.

ACP (acyl carrier protein) is a protein that covalently binds fatty acyl intermediates via a phosphopantetheine linker during the synthesis process.

Fatty acid derivatives (e.g., alkanes, alkenes and/or fatty alcohols, and the like) may be produced in yeasts by conversion of acyl coenzyme A (acyl-CoA), fatty acids, or fatty acyl-ACP. Several pathways may be used to get the yeasts to produce acyl-CoA, fatty acids, fatty acyl-ACP. However the production of the fatty acid derivatives from acyl-CoA, fatty acids and/or fatty acyl-ACP via fatty aldehydes will only be possible to a substantial extend if HDF1 is deleted.

An aspect of the embodiments relates to a yeast lacking a gene encoding hexadecanal dehydrogenase (HFD1) or comprising a disrupted gene encoding HFD1. The yeast also comprises at least one heterologous gene encoding an enzyme involved in a pathway of producing hydrocarbons.

In an embodiment, the yeast comprises at least one heterologous gene encoding an enzyme involved in a pathway of producing hydrocarbons from fatty acyl-CoA through fatty aldehydes.

In an embodiment, the yeast comprises a heterologous gene encoding a fatty acyl-CoA reductase or a fatty acyl-Acyl Carrier Protein (ACP) reductase, preferably *Synechococcus elongates* orf1594 or *Acinetobacter baylyi* Acr1.

In an embodiment, the yeast comprises a heterologous gene encoding a fatty aldehyde-deformylating oxygenase, preferably *Synechococcus elongates* orf1593 or *Nostoc puntiforme* fatty aldehyde-deformylating oxygenase.

In a particular embodiment, the heterologous gene is a fusion gene encoding a fusion of said fatty aldehyde-deformylating oxygenase and a catalase.

In a particular embodiment the yeast further comprises a heterologous gene encoding cytosolic ferredoxin, preferably *Escherichia coli* fdx or *Synechococcus elongates* petF, and a heterologous gene encoding a cytosolic ferredoxin nicotinamide adenine dinucleotide phosphate (NADP+) reductase and/or a cytosolic ferredoxin NAD+ reductase, preferably *E. coli* fdr or *S. elongates* petH and/or an *E. coli* or *S. elongates* ferredoxin NAD+ reductase.

In an embodiment, the yeast comprises a heterologous gene encoding *Acinetobacter baylyi* Acr1, a heterologous gene encoding *Musca domestica* CYP4G2 deformylating oxygenase, and a heterologous gene encoding *M. domestica* NADPH-cytochrome P450 reductase.

In an embodiment, the yeast comprises a heterologous gene encoding *Jeotgalicoccus* spp Orf80.

In a particular embodiment, the yeast further comprises a heterologous gene encoding a chaperon selected from a group consisting of *Escherichia coli* GroEL and *E. coli* GroES.

In an embodiment, the yeast comprises *Photorhabdus luminescens* genes LuxC, LuxD and LuxE, and a cyanobacterial fatty aldehyde-deformylating oxygenase, preferably *Synechococcus elongates* orf1593 or *Nostoc puntiforme* fatty aldehyde-deformylating oxygenase.

In an embodiment, the yeast comprises a heterologous gene encoding *Mycobacterium marinum* carboxylic acid reductase, a heterologous gene encoding *Musca domestica* CYP4G2 deformylating oxygenase, and a heterologous gene encoding a phosphopantetheinyl transferase, preferably *Aspergillus nidulans* phosphopantetheinyl transferase.

In an embodiment, the yeast comprises a heterologous gene encoding a fatty acyl-Acyl Carrier Protein (ACP) synthase, preferably *Synechococcus elongates* fatty acyl-ACP synthase, a heterologous gene encoding a fatty acyl-ACP reductase, preferably *Synechococcus elongates* orf1594, a heterologous gene encoding *Musca domestica* CYP4G2 decarbonylase, and a heterologous gene encoding *M. domestica* NADPH-cytochrome P450 reductase.

In an embodiment, the yeast comprises a heterologous gene encoding a fatty acid reductase and a mitochondrial localization signal (MLS), preferably *Mycobacterium marinum* CAR fatty acid reductase and the MLS, a heterologous gene encoding a fatty aldehyde decarbonylase and the MLS, preferably *Nostoc punctiforme* fatty aldehyde-deformylating oxygenase and the MLS, and a heterologous gene encoding a phosphopantetheinyl transferase and the MLS, preferably *Aspergillus nidulans* phosphopantetheinyl transferase and the MLS.

In a particular embodiment, the yeast further comprises at least one gene encoding a respective enzyme involved in the yeast mitochondrial fatty acid biosynthetic pathway selected from the group consisting of a yeast mitochondrial 2-enoyl thioester reductase and a yeast mitochondrial acetyl-Coenzyme A (CoA) carboxylase, a yeast mitochondrial beta-ketoacyl synthase, a yeast mitochondrial 3-hydroxyacyl-Acyl Carrier Protein (ACP) dehydratase, a yeast mitochondrial 3-oxoacyl-ACP reductase, and a yeast mitochondrial malonyl-CoA:ACP transferase, preferably selected from the group consisting of *Saccharomyces cerevisiae* HFA1, ETR1, CEM1, HTD2, OAR1 and MCT1.

In a particular embodiment, the yeast further comprises a heterologous gene encoding a mitochondrial thoesterase, preferably selected from the group consisting of *Acinetobacter baylyi* TesA and *Cocos nucifera* FatB1.

In an embodiment, the yeast comprises a gene encoding a mitochondrial formate dehydrogenase, preferably an endogenous format dehydrogenase and a mitochondrial localization signal (MLS), more preferably *Saccharomyces cerevisiae* FDH1 and/or FDH2 and the MLS.

In an embodiment, the yeast comprises at least one heterologous gene encoding cytosolic enzyme selected from the group consisting of acetyl-Coenzyme A (CoA)C-acetyltransferase, a 3-ketoacyl-CoA thiolase, a 3-hydroxyacyl-CoA dehydrogenase, an enoyl-CoA hydratase, a trans-enoyl-CoA reductase and a thioesterase, preferably selected from the group consisting of *Saccharomyces cerevisiae* FOX2, FOX3, ERG10 and TES1 and bacterial yqeF, fadA, fabB and tdTER.

In an embodiment, the yeast comprises a heterologous gene encoding a thioesterase, preferably selected from the group consisting of *Escherichia coli* tesA, tesB, fadM and yciA.

In an embodiment the yeast lacks or has reduced non-essential storage lipid formation, preferably by lacking one or more genes selected from the group consisting of any acyl-Coenzyme A (CoA):sterol acyltransferase and any diacylglycerol acyltransferase, more preferably by lacking one or more of *Saccharomyces cerevisiae* LRO1, DGA1, ARE1 and ARE2, or comprising one or more disrupted genes selected from the group.

In an embodiment, the yeast lacks or has reduced non-essential beta oxidation, preferably by lacking one or more genes selected from the group consisting of any peroxisomal fatty acyl-Coenzyme A (CoA) oxidase and any long chain fatty acyl-CoA synthetase, more preferably by lacking one or more of *Saccharomyces cerevisiae* FAA1, FAA4 and PDX1, or comprising one or more disrupted genes selected from the group.

In an embodiment, the yeast comprises genes adapted for overexpression enzymes involved in the fatty acid biosynthetic pathway selected from the group consisting of acetyl-Coenzyme A (CoA) carboxylase and fatty acid synthase, preferably *Saccharomyces cerevisiae* ACC1, FAS1, FAS2 and ACB1.

In an embodiment, the yeast comprises heterologous genes adapted for overexpression enzymes involved in the fatty acid biosynthetic pathway selected from the group consisting of acetyl-Coenzyme A (CoA) carboxylase and fatty acid synthase, preferably *Rhodosporidium toruloides* RtACC1, RtFAS1 and RtFAS2.

In an embodiment, the yeast is characterized by supply of nicotinamide adenine dinucleotide phosphate (NADPH) by:

comprising a heterologous gene encoding a non-phosphorylating NADP+-dependent glyceraldehyde-3-phosphate dehydrogenase, preferably *Streptococcus mutans* GAPN;

lacking an endogenous GDH1 gene encoding NAD-dependent glutamate dehydrogenase, or comprising a disrupted GDH1 gene; and/or comprising a GDH2 gene adapted for overexpression of NAD-dependent glutamate dehydrogenase.

In an embodiment, the yeast is selected from the group consisting of a *Saccharomyces* yeast, *Hansenula polymorpha*, a *Kluyveromyces* yeast, a *Pichia* yeast, a *Candida* yeast, a *Trichoderma* yeast and *Yarrowia lipolytica*, preferably *Saccharomyces cerevisiae.*

Another aspect of the embodiments relates to a method for producing hydrocarbons. The method comprises culturing a yeast lacking a gene encoding hexadecenal dehydrogenase (HFD1) or comprising a disrupted gene encoding HFD1 in culture conditions suitable for production of the hydrocarbons from the yeast. The method also comprises collecting the hydrocarbons from the culture medium in which the yeast is cultured and/or from the yeast.

In an embodiment, culturing the yeast comprises culturing a yeast according to any of the embodiments in the culture conditions suitable for production of the hydrocarbons from the yeast.

In an embodiment, the hydrocarbons are a fatty acid derivative selected from a group consisting of an alkane, an alkene and a fatty alcohol, preferably selected from the group consisting of an alkane and an alkene.

A further aspect of the embodiments relates to use of a yeast lacking a gene encoding hexadecenal dehydrogenase (HFD1) or comprising a disrupted gene encoding HFD1 for the production of hydrocarbons.

In an embodiment, the yeast is according to any of the embodiments.

In an embodiment, the hydrocarbons are a fatty acid derivative selected from a group consisting of an alkane, an alkene and a fatty alcohol, preferably selected from the group consisting of an alkane and an alkene.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Expression of an Alkane Biosynthetic Pathway in *Saccharomyces cerevisiae* hfd1Δ

The purpose of this example is to illustrate the importance of HFD1 deletion in yeast to enable, for example, alkane, alkene and fatty alcohol biosynthesis via a two-step pathway involving a fatty aldehyde as intermediate. As a proof of principal, a commercially available knock-out strain *Saccharomyces cerevisiae* BY4741 6550 (MATa his3Δ1 leu2Δ0 met15Δ0 ura3Δ0 hf1Δ) was transformed with the plasmids pAlkane0 and pKB02 carrying the *Synechococcus elongatus* fatty acyl-CoA/ACP reductase gene orf1594 and fatty aldehyde decarbonylase gene orf1593, and *Escherichia coli* DH5 ferredoxin gene fdx and ferredoxin reductase gene fpr. A control strain harboring two empty plasmids and a wild-type BY4741 (MATa his3Δ1 leu2Δ0 met15Δ0 ura3Δ0) strain (harboring the same plasmids as the producer strain) were constructed simultaneously.

The genes orf1594 (NT ID 1, codon-optimized for yeast) and orf1593 (NT ID 2, idem) coding for the two-step cyanobacterial alkane biosynthetic pathway described by Schirmer et al (2010) were ordered codon-optimized for yeast from GenScript (Piscataway, N.J., USA). Orf1594 was flanked by the restriction sites BamHI/HindIII, and orf1593 by NotI/SacI. The genes were cloned into pSPGM1 (Chen et al, 2012) by restriction, ligation, and amplification in *Escherichia coli* DH5α resulting in plasmid pAlkane0. The *Escherichia coli* DH5α fdx (NT ID 8) was cloned from a single colony by PCR using the primers PR ID 158 and PR ID 159. These primers contained the restriction site NotI/SacI. The gene fpr (NT ID 9), flanked by the restriction sites BamHI/XhoI, was cut from the plasmid pISP08 (Partow et al, 2012). Both genes were cloned into pIYC04 (Chen et al, 2013) by restriction, ligation, and amplification in *Escherichia coli* DH5α resulting in plasmid KB02. Both plasmids were verified by restriction analysis and sequencing of each gene (PR ID 187-190). After verification, both plasmids were co-transformed into chemical competent yeast cells (Gietz et al, 2002).

Four independent clones were isolated for both the producer and control strain by streak purification onto fresh SD-His-Ura 2% glucose plates. Successful transformation of the producer was verified by colony PCR (using primers PR ID 150-151, 154-155, and 158-161). Each clone was grown overnight in a 5 ml YPD (yeast peptone dextrose) pre-culture and inoculated the next day at 0.2 OD in 25 ml 2% glucose synthetic medium (dropout uracil and histidine) in 250 ml shake flasks. The cultures were incubated at 30° C. and 200 rpm. After 48 h, cell pellets were collected by centrifugation 5 minutes at 1000 rcf, washed twice with 5 ml phosphate buffer (10 mM $KH_2PO_4$, pH 7.5). Extraction of lipids and alkanes was carried out as described by Khoomrung et al (2013), with the exception that the final sample was dissolved in hexane (instead of chloroform/methanol). Subsequently, 2 μl injections were analyzed using a gas chromatograph (Focus GC, ThermoScientific) mass spectrometer (DSQII ThermoScientific) equipped with a ZB-5MS Guardian (L=30 m, ID 0.25 mm, df=0.25 Phenomenex) column. The inlet temperature was set to 250° C., the helium (carrier) gas flow to 1 ml/min splitless. The initial oven temperature was set to 50° C. and held for 5 minutes, then the temperature was ramped to 310° C. by 10° C./min and held for 6 minutes. The mass transfer line temperature was set to 300° C., the ion source temperature was set to 230° C. and a full scan for m/z of 50 to 650 was performed.

A gas chromatogram spectrum of one independent clone of the producing strain, one control, and a standard run is shown in FIG. 5. In FIG. 4 another spectrum is shown for another independent clone of the producing strain, one wild-type strain harboring the pathway, and a standard run. These figures illustrate that HFD1 is required to enable alkane production in *Saccharomyces cerevisiae.*

Example 2

Deletion of Hexadecenal Dehydrogenase HFD1 in *Saccharomyces cerevisiae* CEN.PK113-11C The purpose of this example is to show how HFD1 was deleted in *Saccharomyces cerevisiae* CEN.PK113-11C which is a commercially available strain. The yeast *Saccharomyces cerevisiae* possesses hexadecenal dehydrogenase Hfd1, an enzyme which will compete for substrate with the heterologous fatty aldehyde decarbonylases and leads to an ATP consuming futile cycle. In cyanobacteria, it has been shown that deletion of a similar gene led to fatty aldehyde accumulation. *Saccharomyces cerevisiae* HFD1 was deleted using the strategy depicted in FIG. 6. Using two primer pairs (PR ID 122-125) up and downstream fragments of HFD1 were cloned, and using primer pair PR ID 127-128 *Kluyveromyces lactis* URA3 was cloned from plasmid pWJ1042 (Reid et al., 2002). Subsequently all three fragments were fused using primer pair (PR ID 122 and 125) as described Zhou et al., 2012. The deletion cassette was transformed into *Saccharomyces cerevisiae* CEN.PK113-11C (MATaMAL2-8c SUC2 his3Δ1 ura 3-52) by electroporation at 1.5 kV, 10 μF, and 200Ω in a 0.2 cm gap electroporation cuvette using Bio-Rad MicroPulser electroporation apparatus (Bio-Rad Laboratories AB, Sweden) and selected on URA drop out plates for integration. Transformants were verified by colony PCR and the KlURA3 marker was subsequently looped out using flanking direct repeats as illustrated in FIG. 6. Successful clones were selected by growth on 5-FOA and URA dropout plates.

Example 3

Expression of *Escherichia coli* Ferredoxin and *Escherichia coli* Ferredoxin:NADPH Reductase in *Saccharomyces cerevisiae*

It has been shown that cyanobacterial fatty aldehyde decarbonylases require an electron transfer system and that *Escherichia coli* ferredoxin and ferredoxin:NADPH reductase can be used as such. The yeast *Saccharomyces cerevisiae* contains ferredoxin and ferredoxin:NADPH reductase homologues (Yah1 and Arh1, respectively), but they are localized to the mitochondria and can therefore most likely not be used by the cytosolic expressed fatty aldehyde decarbonylase. The *Escherichia coli* DH5α fdx (NT ID 8) was cloned from a single colony by PCR using the primers PR ID 212 and PR ID 213. The gene fpr (NT ID 9), was cloned from the plasmid pISP08 (Partow et al, 2012) by PCR using the primers PR ID 214 and PR ID 215.To enable alka/ene biosynthesis, this plasmid carries a fatty acid reductase and fatty aldehyde decarbonylase homologous (as described in Example 1; cloned using primers PR ID 208-211). Combinations of these genes were introduced into pYX212 by using a modular pathway engineering strategy as described before (Zhou et al., 2012), resulting in the plasmids pAlkane1, pAlkane 7, pAlkane 8, and pFAR see FIG. 13. Plasmids were extracted from single yeast colonies using the Zymoprep Yeast Plasmid Miniprep II kit (Nordic Biolabs, Täby, Sweden) and transformed into *E. coli* DH5α competent cells. After purification of the plasmid, verification by restriction analysis, and sequencing, the plasmids were transformed into *Saccharomyces cerevisiae* CEN.PK113-11C and *Saccharomyces cerevisiae* hfd1Δ. Yeast competent cells were prepared and transformed with 1 μg of plasmid according to the lithium acetate/single-stranded carrier DNA/polyethylene glycol method (Gietz and Woods, 2002) and successful transformants were selected on URA dropout plates.

Shake flask batch fermentations were carried out in minimal medium containing 30 g/l glucose (Verduyn et al., 1992). Cultures were inoculated, from overnight precultures, at 0.1 OD in 25 ml minimal medium supplemented with histidine (40 mg/1; Sigma Aldrich) in 250 ml shake flasks. The shake flasks were incubated at 30° C. and 200 rpm orbital shaking. After 48 hours the cells were harvested by centrifugation (5 minutes; 1000 g) and washed once with 5 ml phosphate buffer (10 mM KH2PO4, pH 7.5). The supernatant was removed, the pellet frozen in liquid nitrogen and freeze dried (Christ Alpha 2-4 LSC, Martin Christ Gefriertrocknungsanlagen GmbH, Osterode am Harz, Germany) for 48 hours. Alkanes were extracted from the freeze dried cell pellets as described before (Khoomrung et al., 2013), with the exceptions that the extracted fraction was dissolved in hexane (alkanes) and that hexadecane (alkanes) was used as an internal standard. Samples were analyzed by gas chromatography (FocusGC, ThermoFisher Scientific) coupled to mass spectrometry (DSQII, ThermoFisher Scientific) using a Zebron ZB-5MS Guardian capillary GC column (30 m×0.25 mm×0.25 Phenomenex, Væløse, Denmark). The GC-MS conditions are described in Example 1. Analytical standards for alkanes (Sigma Aldrich) were analyzed during the same run for peak identification and quantification. The alkane production levels as observed for the wild-type and hfd1Δ strains carrying the plasmid pAlkane1 (KB17 and KB19), pAlkane 7 (KB18), or pAlkane 8 (KB16) is shown in FIG. 2A. This figure illustrates that expression of a ferredoxin/ferredoxin reductase reducing system is required to enable alkane production in *Saccharomyces cerevisiae* CEN.PK. The gas chromatogram spectra of *Saccharomyces cerevisiae* CEN.PK113-11C and *Saccharomyces cerevisiae* hfd1Δ expressing the plasmid pAlkane1, pAlkane7, or pAlkane8 are further shown in FIG. 3.

Example 4

Expression of *Synechococcus Elongatus* PCC7942 Ferredoxin and *Synechococcus elongatus* Ferredoxin: NADPH Reductase in *Saccharomyces cerevisiae*

Recently the endogenous *Synechococcus elongatus* electron transfer system was identified and shown to be more efficient in vitro than the heterologous system. The *Synechococcus elongatus* PCC7942 ferredoxin (orf_1499, petF, P ID 6) and ferredoxin-NADPH reductase (orf_0978, petH, P ID 7) genes are codon optimized for expression in yeast. Subsequently they are cloned similar to the *E. coli* homologues, as described in example 3, and cotransformed with fatty aldehyde decarbonylase homologue carrying plasmid as described in example 1.

Example 5

Conversion of Fatty Acyl-CoA to alka/enes by Expression of *Acinetobacter baylyi* Acr1 and *Musca domestica* CYP4G2 Decarbonylase in *Saccharomyces cerevisiae* hfd1Δ

The purpose of this example is to illustrate the possibility of expression of a fatty acyl-CoA preferring fatty acid reductase in combination with a P450 type decarbonylase. Thus this pathway will convert fatty acyl-CoA to alkanes and alkenes via the intermediates fatty acyl-CoA and fatty aldehydes.

The plasmid pAlkane3 was constructed similar to the method described in example 8. For expression in yeast codon optimized genes encoding *Acinetobacter baylyi* Acr1 (NT ID 22), *Musca domestica* CYP4G2 (NT ID 14), and *Musca domestica* NADPH-cytochrome P450 reductase (NT ID 15) were cloned using primers with to the gene homologous regions (PR ID 201-202, 196-197, 192-193). The pathway was subsequently assembled as described in Shao et al, 2009 and Zhou et al, 2012.

Cells were cultivated and analyzed as described in example 1.

Example 6

Conversion of Fatty Acids to Terminal Alkenes by Expression of *Jeotgalicoccus* Spp orf880, *Escherichia coli* GroEL and *Escherichia coli* GroES in *Saccharomyces cerevisiae*

The purpose of this example is to illustrate the improvement of conversion efficiency of the decarboxylation pathway by expression of chaperones. This will improve the folding of *Jeotgalicoccus* spp Orf880p. Overexpression of GroEL and GroES is done e.g. according to Guadelupe-Medina et al, 2013 on a HIS marker plasmid (e.g. pIYC04).

The gene *Jeotgalicoccus* spp Orf880 (NT ID 4, codon-optimized for yeast) coding for the one-step cyanobacterial alkane biosynthetic pathway was ordered codon-optimized for yeast from GenScript (Piscataway, N.J., USA). The gene was flanked by the restriction sites NotI/SacI and it was cloned into pSP-GM1 (Chen et al, 2012) by restriction, ligation, and amplification in *Escherichia coli* DH5α. The resulting plasmid OleT was verified by restriction analysis and sequencing (PR ID 188-189). After verification, the plasmids were cotransformed into chemical competent yeast cells (Gietz et al, 2002).

Cells are cultivated and analyzed as described in example 1.

Example 7

Conversion of Acyl-CoA to Alka/Enes by Expression of *Escherichia coli* TesA, *Photorhabdus luminescens* LuxC, LuxD, and LuxE, and *Nostoc punctiforme* FAD in *Saccharomyces cerevisiae* hfd1Δ

This invention demonstrates the utilization of fatty acyl-CoA for the synthesis of alkanes and alkenes (see FIG. 14) using (part of) the bacterial luminescence pathway and a cyanobacterial fatty aldehyde decarbonylase. The expression of a thioesterase might relieve the inhibitory effect of fatty acyl-CoA on fatty acid synthesis and will provide the substrate of the enzymes LuxC, LuxD, and LuxE.

The *Photorhabdus luminescens* genes encoding LuxC (P ID 3), LuxD (P ID 4), and LuxE (P ID 5) were codon-optimized for expression in yeast, and cloned using primers PR ID 212-217. A pathway consisting of these three genes, a *Synechoccous elongatus* (NT ID 2, cloned using primers PR ID 220-221) or a *Nostoc punctiforme* FAD gene (NT ID 3, cloned using primers PR ID 218-219), and *Escherichia coli* truncated thioesterase TesA (NT ID 56, cloned using primers PR ID) is assembled on a plasmid pAlkane8 and pAlkane5 similar to the method described in examples 3. The transformation of the plasmids into CEN.PK113-11C hfd1Δ was carried out according to Gietz et al, 2002. Cells were cultivated and analyzed as described in example 1.

The gas chromatogram spectra as observed for the hfd1Δ strain carrying the plasmid pAlkane5 (carrying the *Nostoc punctiforme* FAD) or pAlkane9 (carrying the *Synechoccous elongatus* FAD) are shown in FIG. 15. This figure illustrates that expression of a bacterial luminescence pathway and a cyanobacterial fatty aldehyde decarbonylase enables alkane production in *Saccharomyces cerevisiae* CEN.PK.

Example 8

Conversion of Fatty Acids to alka/enes by Expression of *Mycobacterium marinum* Carboxylic Acid Reductase and *Musca domestica* CYP4G2 Decarbonylase in *Saccharomyces cerevisiae* hfd1Δ

In this invention the *Mycobacterium marinum* carboxylic acid reductase (NT ID 7) was expressed in *Saccharomyces*

*cerevisiae* CEN.PK113-11C hfd1Δ to convert fatty acids to fatty aldehydes. The *Musca domestica* CYP4G2 P450 decarbonylase (NT ID 14) enzyme was also expressed to subsequently convert these fatty aldehydes into alka/enes. The plasmid pAlkane4 was constructed by cloning the for yeast codon optimized genes encoding *Mycobacterium marinum* CAR (NT ID 14), *Musca domestica* CYP4G2 (NT ID 14), *Musca domestica* NADPH-cytochrome P450 reductase (NT ID 15), and the *Aspergillus nidulans* phosphopantetheinyl transferase NpgA (NT ID 5) with overlap primers (PR ID114-115, 112-113, 192-193 and 108-109, respectively). The pathway was subsequently assembled as described in Shao et al, 2009 and Zhou et al, 2012. Cells were cultivated and analyzed as described in example 1. In addition to these four enzymes, an additional thioesterase is expressed to relieve fatty acid biosynthesis repression by acyl-CoA and to increase substrate availability for this pathway.

Example 9

Conversion of Fatty Acids to alka/enes by Expression of *Synechococcus elongatus* PCC7942 ACS, *Synechococcus elongatus* PCC7942 Orf1594 and *Musca domestica* CYP4G2 Decarbonylase in *Saccharomyces cerevisiae* hfd1Δ

The purpose of this example is to illustrate the possibility of expression of a fatty acyl-ACP synthase to provide more of the preferred substrate acyl-ACP for the fatty acyl-ACP reductase, and the combination of a P450 type decarbonylase and cyanobacterial reductase. Thus this pathway will convert fatty acids to alkanes and alkenes via the intermediates fatty acyl-ACP and fatty aldehydes.

The plasmid pAlkane2 was constructed similar to the method described in example 8. For expression in yeast codon optimized genes encoding *Synechococcus elongatus* PCC7942 orf1594 (NT ID 1), *Musca domestica* CYP4G2 (NT ID 14), *Musca domestica* NADPH-cytochrome P450 reductase (NT ID 15), and *Synechococcus elongatus* ACS (NT ID 6?) were cloned using primers with to the gene homologous regions (PR ID 194-195, 196-197, 192-193, 110-111, respectively). The pathway was subsequently assembled as described in Shao et al, 2009 and Zhou et al, 2012.

Cells were cultivated and analyzed as described in example 1. In addition to these four genes, an additional thioesterase with preference for acyl-CoA over acyl-ACP is expressed to increase the levels of free fatty acids.

Example 10

Fusing of *Nostoc punctiforme* Fatty Aldehyde Decarbonylase to Catalase and Expression in *Saccharomyces cerevisiae* hfd1Δ for Improved Fatty Aldehyde to alka/ene Conversion The purpose of this invention is to improve the catalytic activity of the fatty aldehyde decarbonylase, which can be the *Synechoccocus elongatus* PCC7942 orf1593 (NT ID 2) or the *Nostoc punctiforme* FAD (NT ID 3), or a homologue.

The fatty aldehyde decarbonylase can be fused to a catalase as has been shown by Andre et al (2013). This will improve the activity of this enzyme and thus the alka/ene formation. The proposed mechanism is that the toxic byproduct hydrogen peroxide is broken down by the catalase, thereby avoiding that it can inhibit the decarbonylase. The novelty would be to express such a fusion enzyme in yeast together with HFD1 deletion. A heterologously expressed fatty acid reductase, as described in, for example, example 8, and the endogenous fatty acid synthesis via the breakdown of spingholipids, can supply the fatty aldehydes for the decarbonylase-catalase fusion enzyme.

Example 11

Expression of Alkane or Alkene Biosynthetic Pathway in the Mitochondria of *Saccharomyces cerevisiae*

The purpose of this example is to illustrate the utilization of the mitochondrial fatty acid biosynthetic machinery for the synthesis of short chain fatty acids, and its subsequent conversion into short chain alkanes and alkenes.

In this experiment the *Mycobacterium marinum* CAR (NT ID 7) fatty acid reductase and the *Nostoc puntiforme* (NT ID 3) fatty aldehyde decarbonylase encoding genes were expressed in the mitochondria of *Saccharomyces cerevisiae* CEN.PK113-11C. All enzymes not localized by default into the mitochondria were directed there by attaching a mitochondrial localization signal (Hurt et al, 1985) to the front of each gene. In addition to the alkane biosynthetic pathway, the genes encoding key components of the mitochondrial fatty acid machinery Etr1 (2-enoyl thioester reductase) and Hfa1 (acetyl-CoA carboxylase) were overexpressed to ensure sufficient precursor supply for the alkane pathway.

The plasmid pAlkane6 was constructed similar to the method described in example 5, 8 and 9. For expression in yeast codon optimized genes encoding *Mycobacterium marinum* CAR (NT ID 14, attached MLS), *Nostoc punctiforme* FAD (NT ID 3, attached MLS), *Aspergillus nidulans* phosphopantetheinyl transferase NpgA (NT ID 5, attached MLS), *Saccharomyces cerevisiae* Hfa1 (NT ID 61), and *Saccharomyces cerevisiae* Etr1 (NT ID 60) were cloned using primers with to the gene homologous regions (PR ID 165-178, respectively, HFA1 was split up in three parts due to its length). The pathway was subsequently assembled as described in Shao et al, 2009 and Zhou et al, 2012.

*Escherichia coli* fdx (NT ID 8) and fpr (NT ID 9) were cloned from *Escherichia coli* DH5α genomic DNA, a mitochondrial localization signal (Hurt et al, 1985) was included in the forward primers in front of each gene, and the resulting gene fragments were ligated into the plasmid pIYC04 (Chen et al, 2012). The resulting plasmid, KB03, was verified by sequencing using primers PR ID 187-190. Subsequently the pAlkane6 and pKB03 plasmids were transformed into *Saccharomyces cerevisiae* CEN.PK113-11C by chemical transformation (Gietz et al, 2002) and successful transformants were selected on HIS dropout plates. To enable alka/ene biosynthesis, this plasmid can be co-transformed with a plasmid carrying fatty acid reductase and fatty aldehyde decarbonylase homologous and auxiliary enzymes.

Precursor supply can possibly be enhanced by removing post translational modification sites in Etr1 (K301) and Hfa1 (1157S), and by further overexpression of the remaining fatty acid biosynthetic enzymes (e.g. Cem1, Htd2, Oar1, and Mct1).

Expression of a thioesterase is required to provide sufficient precursors to the mitochondrial alkane pathway since there is no known yeast mitochondrial thioesterase with activity towards medium chain fatty acyl-ACP. *Acinetobacter baylyi* TesA (P ID 2), *Cocos nucifera* FatB1 (P ID 1), or homologue thioesterases have been shown to have preference for C8-C14 fatty acyl-ACPs. A thioesterase gene will be codon-optimized for expression in yeast, and subsequently expressed and directed to the mitochondria in a similar fashion as described above.

Example 12

Expression of Mitochondrial Formate Dehydrogenase in *Saccharomyces cerevisiae*

Yeast contains a formate dehydrogenase enzyme which is localized to the cytosol. Expression of formate dehydrogenase in the mitochondria might be required to breakdown the toxic byproduct formate of the decarbonylation reaction. Overexpression of endogenous formate dehydrogenase Fdh1 and/or Fdh2 and localization of these proteins to the mitochondria can be achieved by introducing a 5' mitochondrial localization signal into each gene (as has been described for others genes in example 11).

Example 13

Construction of a Cytosolic Pathway for Medium-Chain Saturated Fatty Acid Production in *Saccharomyces cerevisiae*

This chimeric cytosolic pathway, composed of an acetyl-CoA C-acetyltransferase (YqeF or Erg10p), a 3-ketoacyl-CoA thiolase (FadA or Fox3p), a 3-hydroxyacyl-CoA dehydrogenase and enoyl-CoA hydratase multifunctional enzyme (FadB or Fox2p), a trans-enoyl-CoA reductase (tdTER) and a thioesterase (Tes1p) (FIG. 7), allows the increased total production of medium-chain fatty acids from cytosolic acetyl-CoA as well as an increase in the medium-chain/long-chain fatty acid production ratio. This was shown by analysis of produced fatty alcohols after transforming the constructed strains with a "fatty-acid to fatty alcohol" pathway (FIG. 8). It can also be coupled with different thioesterase homologues (with different chain-length specificities) as terminator enzymes (see example 14) for regulation of the desired fatty acid chain-length. Yeast genes FOX2 (NT ID 48), FOX3 (NT ID 49), ERG10 (NT ID 50) and TES1 (NT ID 51) were amplified by PCR from genomic DNA extracted from *S. cerevisiae* strain CEN.PK 113-11C, using the primers PR ID 80 to 87. These primers were designed to amplify these genes excluding the correspondent peroxisome-targeting signal peptide present in FOX2, FOX3 and TES1. Truncated genes lacking the sequence coding for the signal peptide were then named FOX2c, FOX3c and TES1c respectively. The bacterial genes yqeF (NT ID 54), fadA (NT ID 52), fadB (NT ID 53) and tdTER (NT ID 55) were optimized for expression in *S. cerevisiae* and synthesized by GenScript (Piscataway, N.J., USA). These bacterial genes were amplified using primers PR ID 72-79. The primers from PR ID 69-87 allow the cloning of the genes with the pPGK1 promoter or the bidirectional promoter pPGK1-pTEF1 in the pX-2-loxP-KlURA3, pXI-3-loxP-URA3 and pXI-5-loxp-Sphis5 vectors (Mikkelsen et al, 2012) following the USER cloning method (Nour-Eldin et al, 2006). Primers PR ID 69 and 70 were used to amplify the bidirectional promoter pPGK1-pTEF1 from pSP-GM1, primers PR ID 71 and 70 were used to amplify the pPGK1 promoter also from pSP-GM1. pPGK1-TES1c was cloned into the pX-2-loxP-KlURA3 vector; either fadA-pPGK1-pTEF1-fadB or FOX3c-pPGK1-pTEF1-FOX2c were cloned into pXI-3-loxP-URA3 vector; and either tdTER-pPGK1-pTEF1-yqeF or tdTER-pPGK1-pTEF1-ERG10 were cloned into pXI-5-loxp-Sphis5 vector FIG. 9. All the integration constructs were linearized by restriction using NotI restriction enzyme and transformed into a pox1 faa1 faa4 strain (EXAMPLE 16). After integration of the pXI-3-loxP-URA3- and the pXI-5-loxp-Sphis5-derived constructs, the cells were transformed with a Cre recombinase expression plasmid to delete auxotrophy markers by recombination of loxP sites flanking the marker. Next, the originated strain was transformed with the pX-2-loxP-KlURA3 vector containing the pPGK1-TES1 insert. This resulted in the following strains:

Rbee (pox1Δ faa1Δ faa4Δ yqeF fadA fadB tdTER TES1c)

Rbye (pox1Δ faa1Δ faa4Δ ERG10 fadA fadB tdTER TES1c)

Rbey (pox1Δ faa1Δ faa4Δ yqeF FOX3c FOX2c tdTER TES1c)

Rbyy (pox1Δ faa1Δ faa4Δ ERG10 FOX3c FOX2c tdTER TES1c)

Example 14

Regulation of produced fatty-acid chain length by expression of different thioesterase genes Different thioesterase homologues have different chain-length specificities. Therefore, coupling of any of the homologues with a fatty-acyl-CoA producing pathway results in production of fatty acids with different chain lengths depending on the thioesterase gene being expressed. Integration of this regulation on an alkane/alkene producing pathway from acetyl-CoA allows production of hydrocarbons with a desired specific chain-length. Thioesterase genes tesA, tesB, fadM or yciA from *E. coli* were used for construction of Rbyy strain (EXAMPLE 13) instead of the TES1c thioesterase gene. The genes tesA (NT ID 56), tesB (NT ID 57), fadM (NT ID 58) and yciA (NT ID 59) were optimized for expression in yeast and synthesized by GenScript (Piscataway, N.J., USA). These genes were amplified using primers PR ID 88 to 95. All the primers used allow the cloning of any of the selected amplified genes with the pPGK1 promoter in the pX-2-loxP-KlURA3 (Mikkelsen et al, 2012) integration vector following the USER cloning method (Nour-Eldin et al, 2006). As explained in EXAMPLE 13, FOX3-pPGK1-pTEF1-FOX2 was cloned into pXI-3-loxP-URA3 vector and tdTER-pPGK1-pTEF1-ERG10 was cloned into pXI-5-loxp-Sphis5 vector. All the integration constructs were linearized by restriction using NotI restriction enzyme and transformed into strain pox1 faa1 faa4 strain (EXAMPLE 16). After integration of the pXI-3-loxP-URA3- and the pXI-5-loxp-Sphis5-derived constructs, the cells were transformed with a Cre recombinase expression plasmid to delete auxotrophy markers by recombination of loxP sites flanking the marker. The originated strain was then transformed with the pX-2-loxP-KlURA3 plasmid containing either pPGK1-tesA, pPGK1-tesB, pPGK1-fadM or pPGK1-yciA.

Example 15

Expression of Alternative Fatty Acid Synthases for Production of Short/Medium Chain Fatty Acids Expression of a heterologous fatty acid synthase and alternative thioesterase modules as described by Leber and DaSilva (2013) will enable the synthesis of medium chain fatty acids and products derived thereof Example 16

Elimination of Storage Lipid Formation (Deletion of LRO1, DGA1, ARE1, ARE2) and Beta-Oxidation (Deletion of PDX1), and Free Fatty Acid Activation (Deletion of FAA1, FAA4)

This example describes the elimination of non-essential pathways that consume (activated) fatty acids and thus compete with alkane/alkene production, i.e. storage lipid formation and beta-oxidation. "Activated fatty acid" as used herein means fatty acids coupled to CoA or ACP.

For the deletion of ARE1, the 5' and 3' ends of the ARE1 open reading frame were individually amplified from genomic DNA of CEN.PK 113-5D (MATa ura3-52) by PCR using primers PR ID 1/2 and PR ID 3/4, respectively. The kanMX expression cassette was amplified in two overlapping parts from plasmid pUG6 (Güldener et al, 1996) using primers PR ID 5/6 and 7/8, respectively. KanMX was looped out as described previously with help of the Cre recombinase expression plasmid pSH47 (Güldener et al, 1996).

The same approach was used for deletion of ARE2, DGA1, LRO1, and PDX1. Primers PR ID 9-12 were used for deletion of ARE2, primers PR ID 13-16 were used for deletion of DGA1, primers PR ID 17-20 were used for deletion of LRO1, and primers PR ID 21-24 were used for deletion of PDX1.

Deletion of FAA1 and FAA4 is e.g. described in Runguphan and Keasling (2013).

Example 17

Overexpression of Fatty Acid Biosynthetic Genes (ACC1, FAS1, FAS2, ACB1)

This example describes the overexpression of genes leading to increased production of (activated) fatty acids.

Overexpression of ACC1, FAS1 and FAS2 is e.g. described in Runguphan and Keasling (2013).

Mutations S659A and S1157A were introduced into the ACC1 gene by PCR to prevent enzyme regulation by phosphorylation, i.e. to increase enzyme activity.

ACB1 (NT ID 47) was amplified by PCR from genomic DNA of *S. cerevisiae* with the oligonucleotide primers PR ID 25/26 and restricted with BamHI/KpnI. The BamHI/KpnI digested DNA fragment was ligated into the BamHI/KpnI sites of vector pSP-GM2 (Partow et al, 2010; Chen et al, 2012) to construct pSP-A. Yeast strains were transformed with the resulting plasmid.

Example 18

Expression of *Rhodosporidium toruloides* fatty acid biosynthetic genes ACC1, FAS1, and FAS2 in *Saccharomyces cerevisiae*

As *Rhodosporidium toruloides* has higher efficiency in lipid production, fatty acid biosynthetic genes RtACC1 (NT ID 19), RtFAS1 (NT ID 20), and RtFAS2 (NT ID 21) from *R. toruloides* can be used for improving the production of fatty acids as well as fatty acid derivatives. The genes were cloned from a cDNA library as described previously (Zhu et al, 2012) with primers pairs RtACC-F (PR ID 120)/RtACC-R (PR ID 121), RtFAS1-F (PR ID 116)/RtFAS1-R (PR ID 117) and RtFAS2-F (PR ID 118)/RtFAS2-R (PR ID 119) and assembled as has been described in Shao et al (2009) and Zhou et al (2012). The expression of RtACC1 and RtFAS1/2, as well their combined expression, increased fatty acid biosynthesis in JV03 (*Saccharomyces cerevisiae* MATaMAL2-8c SUC2 ura3-52 HIS3 are1Δ dga1Δ are2Δ lro1Δ pox1Δ, Valle-Rodriguez et al 2014) (FIG. 10).

Example 19

Increase of NADPH Supply (GAPN, GDH)

This example describes different ways to increase the supply of NADPH, an essential cofactor in fatty acid biosynthesis.

Heterologous expression of a non-phosphorylating NADP+-dependent glyceraldehyde-3-phosphate dehydrogenase (GAPN) from *Streptococcus mutans* is e.g. described in Kocharin et al (2013).

Deletion of GDH1 encoding NADP-dependent glutamate dehydrogenase and overexpression of GDH2 encoding NAD-dependent glutamate dehydrogenase is e.g. described in Asadollahi et al (2009).

Example 20

Conversion of Fatty Acyl-CoA to Fatty Alcohols by Expression of *Marinobacter aquaeolei* VT8 Maqu_2507 Fatty Acyl-CoA Reductase in *Saccharomyces cerevisiae*

This invention relates to the direct conversion of fatty acyl-CoA into fatty alcohols by a fatty acyl-CoA reductase.

The plasmid pAlcohol1 was constructed similar to the method described in example 5, 7, 8, 9. For expression in yeast codon optimized genes *Marinobacter aquaeolei* VT8 Maqu_2507 (NT ID 16) was cloned using primers with to the gene homologous regions (PR ID 206-207). The pathway was subsequently assembled in PYX212 as described in Shao et al, 2009 and Zhou et al, 2012. pAlcohol1 enabled the production of 3.4 mg/L fatty alcohol in *S. cerevisiae* CEN.PK 113-11C in shake flask fermentation.

Cells are cultivated and analyzed as described in example 1.

Example 21

Construction of an Intracellular Alkane Sensor by the Expression of *Yarrowia lipolytica* Yas3 Repressor and Yas1, Yas2 Activator and a Fluorescent Protein Expressed from an ARE1 Containing Promoter in *Saccharomyces cerevisiae.*

The purpose of this example is to describe the design of an alkane biosensor that can be used to screen for better alkane producer. This can be a strain in which the fatty acid substrate is overproduced (e.g. as described in example 16), or classical mutagenesis experiments to optimize the enzymes of the pathway, or screening of homologue and/or libraries to improve the alkane production. It is based on the negative regulator (Yas3) and two activators (Yas1, Yas2) of alkane metabolism enzymes in the alkane consuming yeast *Yarrowia lipolytica*. The repressor Yas3 is released from the alkane response elements (ARE1) in a promoter in the presence of medium chain alkanes.

The *Yarrowia* alkane-responsive promoter of the ALK1 gene was cloned in front of a reporter gene such as GFP to screen for alkane production. Alternatively, the alkane response element was integrated as one or several copies into a *S. cerevisiae* promoter (here the TEF1 promoter) and cloned in front of the reporter gene. For this, a truncated version of the TEF1 promoter was used and combined with three ARE1 binding sites in front of it (NT ID 64). For another strategy three ARE1 binding sites were integrated at specific positions in the complete TEF promoter (NT ID 65).

In addition, the *Yarrowia lypolytica* transcriptional activators Yas1 and Yas2 as well as the repressor Yas3 necessary for alkane-mediated transcription regulation will be introduced into *S. cerevisiae* together with the reporter construct.

Expressing the repressor gene Yas3 in presence of the two activators Yas1 and Yas2 leads to a 100-fold repression of the green fluorescence reporter signal, indicating the functionality of the system and the sensor range. Exposing the system to alkanes gave a clear response and increased green fluorescence signal, as demonstrated in FIG. 11.

REFERENCES

Andre C, Kim S W, Yu X-H, Shanklin J: Fusing catalase to an alkane-producing enzyme maintains enzymatic activity by converting the inhibitory byproduct H2O2 to the cosubstrate O2. Proc Natl Acad Sci USA 2013, 110:3191-3196

Asadollahi M A, Maury J, Patil K R, Schalk M, Clark A, Nielsen J (2009) Enhancing sesquiterpene production in *Saccharomyces cerevisiae* through in silico driven metabolic engineering. Metab Eng 11:328-34

Chen, Y., Partow, S., Scalcinati, G., Siewers, V., Nielsen, J., 2012. Enhancing the copy number of episomal plasmids in *Saccharomyces cerevisiae* for improved protein production. FEMS Yeast Res. 12, 598-607

Chen Y, Daviet L, Schalk M, Siewers V, Nielsen J (2013) Establishing a platform cell factory through engineering of yeast acetyl-CoA metabolism. Metab Eng 15:48-54

Gietz, R. D., Woods, R. A., 2002. Transformation of yeast by lithium acetate/single-stranded carrier DNA/polyethylene-96

Güldener U, Heck S, Fiedler T, Beinhauer J, Hegemann J H (1996) A new efficient gene disruption cassette for repeated use in budding yeast. Nucleic Acids Res 24:2519-2524

Hurt, E. C., Pesold-Hurt, B., Suda, K., Oppliger, W., & Schatz, G. (1985). The first twelve amino acids (less than half of the pre-sequence) of an imported mitochondrial protein can direct mouse cytosolic dihydrofolate reductase into the yeast mitochondrial matrix. The EMBO journal, 4(8), 2061-8. Nature Publishing Group Khoomrung S, Chumnanpuen P, Jansa-Ard S, Ståhlman M, Nookaew I, Borén J, Nielsen J. (2013) Rapid quantification of yeast lipid using microwave-assisted total lipid extraction and HPLC-CAD. Anal Chem. 85(10):4912-9

Khoomrung S, Chumnanpuen P, Jansa-ard S, Nookaew I, Nielsen J. (2012) Fast and accurate preparation fatty acid methyl esters by microwave-assisted derivatization in the yeast *Saccharomyces cerevisiae*. Appl Microbiol Biotechnol. 94(6):1637-46

Kocharin K, Siewers V, Nielsen J (2013) Improved polyhydroxybutyrate production by *Saccharomyces cerevisiae* through the use of the phosphoketolase pathway. Biotechnol Bioeng 110:2216-24

Leber C, Da Silva N A. (2013) Engineering of *Saccharomyces cerevisiae* for the synthesis of short chain fatty acids. Biotechnol Bioeng. (in press)

Mikkelsen M D, Buron L D, Salomonsen B, Olsen C E, Hansen B G, Mortensen U H, Halkier B A. Microbial production of indolylglucosinolate through engineering of a multi-gene pathway in a versatile yeast expression platform. Metab Eng. 2012 March; 14(2):104-11

Nour-Eldin, H., Hansen, B., Nørholm, M., Jensen, J., Halkier, B., (2006). Advancing uracil-excision based cloning towards an ideal technique for cloning PCR fragments. Nucleic Acids Res. 34, E122

Partow S, Siewers V, Bjørn S, Nielsen J, Maury J (2010) Characterization of different promoters for designing a new expression vector in *Saccharomyces cerevisiae*. Yeast 27:955-964

Partow S, Siewers V, Daviet L, Schalk M, Nielsen J. PLoS One. Reconstruction and evaluation of the synthetic bacterial MEP pathway in *Saccharomyces cerevisiae*. 2012; 7(12):e52498. doi: 10.1371/journal.pone.0052498. Epub 2012 Dec. 28

Reid R, Lisby M, Rothstein R. (2002) Cloning-free genome alterations in *Saccharomyces cerevisiae* using adaptamer-mediated PCR Methods Enzymol 350:258-277

Runguphan W, Keasling JD (2013) Metabolic engineering of *Saccharomyces cerevisiae* for production of fatty-acid derived biofuels and chemicals. Metab Eng (in press)

Schirmer A, Rude M A, Li X, Popova E, del Cardayre S B: Microbial biosynthesis of alkanes. Science 2010, 329: 559-562

Shao Z, Zhao H, Zhao H (2009) DNA assembler, an in vivo genetic method for rapid construction of biochemical pathways. Nucleic Acids Res. 37:e16

Verduyn C, Postma E, Scheffers W A, Van Dijken J P. 1992. Effect of benzoic acid on metabolic fluxes in yeasts: a continuous-culture study on the regulation of respiration and alcoholic fermentation. Yeast 8:501-17

Zhou Y. J., Gao W., Rong Q., et al. (2012) Modular pathway engineering of diterpenoid synthases and the mevalonic acid pathway for miltiradiene production J. Am. Chem. 134:3234-3241

Zhu Z, Zhang S, Liu H, Shen H, Lin X, Yang F, Zhou Y J, Jin G, Ye M, Zou H, Zhao Z K. (2012) A multi-omic map of the lipid-producing yeast *Rhodosporidium toruloides*. Nat Commun. 3:1112

TABLE 1

Plasmids.

| Plasmid | Backbone | Genes/Characteristics | Source |
|---|---|---|---|
| pKB01 | PIYC04 | EcFLDA, EcFPR | |
| pKB02 | pIYC04 | EcFDX, EcFPR | |
| pKB03 | pIYC04 | MLS-fdx, MLS-fpr (added mitochondrial localization signal in front of genes) | |
| pAlkane0 | pSPGM1 | SeOrf1594, SeOrf1593 | |
| pOleT | pSPGM1 | JOleT/orf880 | |
| pAlkane1 | p423GPD | SeOrf1594, SeOrf1593, Ecfdx, Ecfpr | |
| pAlkane2 | p423GPD | SeOrf1594, MdP450G2, MdCPR, SynAAC | |
| pAlkane3 | p423GPD | AbAcr1, MdP450G2, MdCPR | |
| pAlkane4 | | MmCAR, MdP450G2, MdCPR, AnnpgA | |
| pAlkane5 | pYX212 | PlLuxD, PlLuxC, PlLuxE, NpFAD, EcTesA' | |
| pAlkane6 | pYX212 | AnnpgA, NpFAD, MmCAR, HFA1, ETR1 | |
| pISP08 | pSPGM1 | fldA, fpr | |
| pYX212 | | ampR, URA3, pYX212t, TPIp | |
| p423GPD | | ampR, HIS3, TDH3p, CYC1t | ATCC 87355 |
| pSP-A | pSPGM2 | ACB1 | |
| pScACC1 | p423GPD | ACC1 | |
| pRtACC1 | p423GPD | RtACC1 | |
| pAlcohol1 | pYX212 | FaCoAR | |
| pAlkane9 | pYX212 | PlLuxD, PlLuxC, PlLuxE, SeFAD, EcTesA' | |
| pFAR | pYX212 | SeFAR | |

TABLE 2

Oligonucleotide primers.

| PR ID | Name | Sequence (5'-3') | SEQ ID NO |
|---|---|---|---|
| 1 | ARE1-UP-f | TGTGTTTCCGTACCGCAC | 1 |
| 2 | ARE1-UP-r | CAGCGTACGAAGCTTCAGCTGCGGAATTGAGTCTGC | 2 |
| 3 | ARE1-DW-f | GTGATATCAGATCCACTAGGCAACACCAAGTTTCTACGG | 3 |
| 4 | ARE1-DW-r | ATTTTTGTCACCTGCAAACTC | 4 |
| 5 | kanMX-1-f | CTGAAGCTTCGTACGCTG | 5 |
| 6 | kanMX-1-r | TCACCATGAGTGACGACTGA | 6 |
| 7 | kanMX-2-f | TTCCAACATGGATGCTGAT | 7 |
| 8 | kanMX-2-r | CTAGTGGATCTGATATCAC | 8 |
| 9 | ARE2-UP-f | CTCGTCGGTTTATCTGCC | 9 |
| 10 | ARE2-UP-r | CAGCGTACGAAGCTTCAGCGTTGAGCTTTTGGATGC | 10 |
| 11 | ARE2-DW-f | GTGATATCAGATCCACTAGGCTCGGTATCTGCATGGG | 11 |
| 12 | ARE2-DW-r | GCACGATATGAATAGCAGTGG | 12 |
| 13 | DGA1-UP-f | CGTTATTGTAACTGGTAATCAGAG | 13 |
| 14 | DGA1-UP-r | CAGCGTACGAAGCTTCAGCCTTTCGGTAATACCGGC | 14 |
| 15 | DGA1-DW-f | GTGATATCAGATCCACTAGAATGTTGTTGTTGGAAGGC | 15 |
| 16 | DGA1-DW-r | GCTTTCCTAAACTTACATTCAAA | 16 |
| 17 | LRO1-UP-f | CTCCTTTGTACTTCTTTGTTCC | 17 |
| 18 | LRO1-UP-r | CAGCGTACGAAGCTTCAGCCTGTTGATGATGAATGTGG | 18 |
| 19 | LRO1-DW-f | GTGATATCAGATCCACTAGCAAGCGGTAATGGCGATC | 19 |
| 20 | LRO1-DW-r | CGGTTGTTTTTCCTCTATGC | 20 |
| 21 | POX1-UP-f | GCCCTATATTTACGGTATTAGTTG | 21 |
| 22 | POX1-UP-r | CAGCGTACGAAGCTTCAGGGGATTAATAGTAGTACGTCTCGT | 22 |
| 23 | POX1-DW-f | GTGATATCAGATCCACTAGCAGATGGGGCAGGGAAG | 23 |
| 24 | POX1-DW-r | GTAGTCATGTCATTGATTCGTCA | 24 |
| 25 | ACB1-f | AGTTTTAATTACAAGGATCCACTATGGTTTCCCAATTATTCG | 25 |

TABLE 2-continued

| PR ID | Name | Sequence (5'-3') | SEQ ID NO |
|---|---|---|---|
| | | Oligonucleotide primers. | |
| 26 | ACB1-r | GCGGATCTTAGCTAGCCGCGGTACCCTAAGAGGAGTACTTGGCA | 26 |
| 69 | PPGK1-PTEF1-fw | AACTTAGAUTAGATTGCTATGCTTTC | 27 |
| 70 | PPGK1-PTEF1-rev | ATTTGTTGUAAAAAGTAGATAATTACTTCC | 28 |
| 71 | PPGK1-fw | CGTGCGAUGGAAGTACCTTCAAAGAATGG | 29 |
| 72 | yqeF-fw | ACAACAAAUATAAAACAATGAAGGATGTCGTAATCGTTG | 30 |
| 73 | yqeF-rev | CACGCGAUTTATTCGTCTCTTTCGATAGTCAATG | 31 |
| 74 | fadA-fw | CGTGCGAUTTAGACTCTTTCAAATACAGTAGCG | 32 |
| 75 | fadA-rev | ATCTAAGTUTTAATAAAACAATGGAACAAGTAGTAATCGTAGAC | 33 |
| 76 | fadB-fw | ACAACAAAUATAAAACAATGTTGTATAAAGGTGACACATTGTAC | 34 |
| 77 | fadB-rev | CACGCGAUTTAGGCAGTTTTCAAGTCACC | 35 |
| 78 | tdTER-fw | CGTGCGAUTTAGATTCTATCGAATCTTTCGAC | 36 |
| 79 | tdTER-rev | ATCTAAGTUTTAATAAAACAATGATAGTAAAGCCAATGGTAAGG | 37 |
| 80 | FOX3c-fw | CGTGCGAUCTATTCTTTAATAAAGATGGCGG | 38 |
| 81 | FOX3c-rev | ATCTAAGTUTTAATAAAACAATGGGTAAGGGTGAATCGAAG | 39 |
| 82 | FOX2c-fw | ACAACAAAUATAAAACAATGCCTGGAAATTTATCCTTC | 40 |
| 83 | FOX2c-rev | CACGCGAUTTATTTTGCCTGCGATAGTTTTAC | 41 |
| 84 | ERG10-fw | ACAACAAAUATAAAACAATGTCTCAGAACGTTTACATTGTATC | 42 |
| 85 | ERG10-rev | CACGCGAUTCATATCTTTTCAATGACAATAGAGG | 43 |
| 86 | TES1c-fw | ACAACAAAUATAAAACAATGAGTGCTTCCAAAATGGCCATG | 44 |
| 87 | TES1c-rev | CACGCGAUTCATCGAATGTCTCGTTCTGACC | 45 |
| 88 | tesA-fw | ACAACAAAUATAAAACAATGGCCGATACTTTGTTAATTTTG | 46 |
| 89 | tesA-rev | CACGCGAUTCAAGAATCGTGATTGACTAATGG | 47 |
| 90 | tesB-fw | ACAACAAAUATAAAACAATGTCTCAAGCTTTGAAGAACTTG | 48 |
| 91 | tesB-rev | CACGCGAUTCAGTTGTGGTTTCTCATAACACC | 49 |
| 92 | fadM-fw | ACAACAAAUATAAAACAATGCAAACTCAAATCAAGGTTAGA | 50 |
| 93 | fadM-rev | CACGCGAUTCACTTAACCATTTGTTCCAACTT | 51 |
| 94 | yciA-fw | ACAACAAAUATAAAACAATGTCTACTACTCACAACGTTCCA | 52 |

TABLE 2-continued

Oligonucleotide primers.

| PR ID | Name | Sequence (5'-3') | SEQ ID NO |
|---|---|---|---|
| 95 | yciA-rev | CACGCGAUTCATTCAACTGGCAAAGCTCTTGG | 53 |
| 104 | Acr1-F1 | GCATAGCAATCTAATCTAAGTTTTAATTACAAAATGAA TAAGAAGTTGGAAGC | 54 |
| 105 | Acr1-R1 | GGATACCCGGGTCGACGCGTAAGCTTGTGGGCCCTATC ACCAATGTTCACCAGGG | 55 |
| 106 | FAcoAR 1-F | GCATAGCAATCTAATCTAAGTTTTAATTACAAAATGAA TTATTTCTTGACAGGTG | 56 |
| 107 | FAcoAR 1-R | GGATACCCGGGTCGACGCGTAAGCTTGTGGGCCCTATT ACCAATAGATACCTCTCA | 57 |
| 108 | npgA-F2 | GGAAGTAATTATCTACTTTTTACAACAAATATAACAAA ATGGTGCAAGACACATCAAG | 58 |
| 109 | npgA-R2 | GACATAACTAATTACATGACTCGAGGTCGACGGTATCT TAGGATAGGCAATTACACAC | 59 |
| 110 | SynaaC-F | GGAAGTAATTATCTACTTTTTACAACAAATATAACAAA ATGGACTCAGGTCACGGTGC | 60 |
| 111 | SynaaC-R | GACATAACTAATTACATGACTCGAGGTCGACGGTATCT CAGAACATTTCGTCTATCAAG | 61 |
| 112 | CYP4G2-R | CTCATTAAAAAACTATATCAATTAATTTGAATTAACTT ACATTGCCTTCATTGCTTC | 62 |
| 113 | CYP4G2-F | GAAAGCATAGCAATCTAATCTAAGTTTTAATTACAAAA TGGACTCCGCCAACAACTC | 63 |
| 114 | MmCAR-F1 | CAAGAACTTAGTTTCGAATAAACACACATAAACAAAC AAAATGTCACCTATCACCAGAGAAG | 64 |
| 115 | MmCAR-R1 | CTTATTTAATAATAAAAATCATAAATCATAAGAAATTC GCTTACAACAAACCCAACAATCTC | 65 |
| 116 | RtFAS1-F | CTATAACTACAAAAAACACATACATAAACTAAAAATG AACGGCCGAGCGACGCGGAG | 66 |
| 117 | RtFAS1-R | CTCATTAAAAAACTATATCAATTAATTTGAATTAACTC AGAGCCCGCCGAAGACGTCGAG | 67 |
| 118 | RtFAS2-R | GACATAACTAATTACATGACTCGAGGTCGACGGTATCC TACTTCTGGGCGATGACGACGG | 68 |
| 119 | RtFAS2-F | GAAAGCATAGCAATCTAATCTAAGTTTTAATTACAAAA TGGTCGCGGCGCAGGACTTGC | 69 |
| 120 | RtACC1-F | CAAGAACTTAGTTTCGAATAAACACACATAAACAAAC AAAATGCCATTCTCTGGCGAGGCGAAG | 70 |
| 121 | RtACC1-R | GGATACCCGGGTCGACGCGTAAGCTTGTGGGCCCTACT AGGCGAGGATGCGGGCGAGG | 71 |
| 122 | hfd1(up)-F | GATTATCAATGTCCCAGTTATACG | 72 |
| 123 | hfd1(up)-R | TAAGTTTGGTCGTTTCATTCAG | 73 |
| 124 | hfd(dn)-F | GAGTACGAGGATCTTGATGAGAC | 74 |
| 125 | hfd(dn)R | CACTTGTTATTGCCATTTCTGTC | 75 |
| 126 | hfd1(up)-URA3-R | CGAAAGGTTACTTATACATCAAATAATTAATTAACCTT AAACATTACGTTCACATGTTGGTGATAAATTACTATG | 76 |
| 127 | URA3(hf d1)-F | GGTTAATTAATTATTTGATGTATAAGTAACCTTTCGTTT AAAAATTTCATATGGGCGATAATATATCGTGATTCTGG GTAGAAGATCG | 77 |

TABLE 2-continued

Oligonucleotide primers.

| PR ID | Name | Sequence (5'-3') | SEQ ID NO |
|---|---|---|---|
| 128 | URA3(hf d1)-R | CTATTATCTTGTTAATGGTCTCATCAAGATCCTCGTACT CCATCGATAAGCTTGATATCG | 78 |
| 129 | Pox1(up)-F | GATTCCTTCAGTTCCACTTTTTGC | 79 |
| 130 | Pox1(up)-R | GTAGCATCGTAATAGTCCGTGTC | 80 |
| 131 | Pox1(dn)-F | GATCTCTAAAGTTGTGCAGCCAC | 81 |
| 132 | Pox1(dn)-R | CGCATTAGCTGCACCACCTAAC | 82 |
| 133 | Pox1(up)-UAR3-R | GAATTGAAACAAAAGTCGCAAAACAGAGGGTTCGAAG GAAAACAGGAAACCTCTACTCACATATCGCAATACTAA TTTATTAT | 83 |
| 134 | URA3(p ox1)-F | CTTCGAACCCTCTGTTTTGCGACTTTTGTTTCAATTCAA CTAGTGTCGCCAAGTTTTAACGTGATTCTGGGTAGAAG ATCG | 84 |
| 135 | URA3(p ox1)-R | GAGCCAATAGTTGTGGCTGCACAACTTTAGAGATCCAT CGATAAGCTTGATATCG | 85 |
| 136 | FAA1(u p)-F | CACCCACCCATCGCATATCAGG | 86 |
| 137 | FAA1(u p)-R | CTTAACATCCCTCCAACCCATAGC | 87 |
| 138 | FAA1(d n)-F | GAAATTAGAGTCCGTTTACAGATC | 88 |
| 139 | FAA1(d n)-R | GTCAAAGAACACTATGCCTGCTAG | 89 |
| 140 | FAA1(u p)-URA3-R | CTGAAAAAGTGCTTTAGTATGATGAGGCTTTCCTATCA TGGAAATGTTGATCCATTACATATTGTTGTCTTTTTTTG TC | 90 |
| 141 | URA3(F AA1)-F GATCG | GATAGGAAAGCCTCATCATACTAAAGCACTTTTTCAGT TTTTTGCTTTAGAACTGCTACCGTGATTCTGGGTAGAA | 91 |
| 142 | URA3(F AA1)-R | CAACATATTCGTTAGATCTGTAAACGGACTCTAATTTC CATCGATAAGCTTGATATCG | 92 |
| 143 | FAA4(u p)-F | GTCCCCATCAATTAAGAACCCTC | 93 |
| 144 | FAA4(u p)-R | GATGCTGAGGAGTTTATGGGTC | 94 |
| 145 | FAA4(d n)-F | CCTTTACCGATGATGGCTGGTTC | 95 |
| 146 | FAA4(d n)-R | GATGTAACAAGACCGTTTTCTGGAG | 96 |
| 147 | FAA4(u p)-URA3-R | GAAAATGAAACGTAGTGTTTATGAAGGGCAGGGGGGA AAGTAAAAAACTATGTCTTCCTTTACATTTTGATGCGT ACTTCTTAG | 97 |
| 148 | URA3(F AA4)-F | CTTTCCCCCCTGCCCTTCATAAACACTACGTTTCATTTT CTAAGAGCATCAATTTGCGTGATTCTGGGTAGAAGATC G | 98 |
| 149 | URA3(F AA4)-R | GATATCACCGGTACGGAACCAGCCATCATCGGTAAAG GCATCGATAAGCTTGATATCG | 99 |
| 150 | Orf1594-CP FW | GGATCCAAAACAATGTTCGG | 100 |

TABLE 2-continued

Oligonucleotide primers.

| PR ID | Name | Sequence (5'-3') | SEQ ID NO |
|---|---|---|---|
| 151 | Orf1594-CP RV | GATTGCTAAGGCTAAAGGTTGG | 101 |
| 152 | Acr1-CP FW | GCTTTAATCACTGGTGCCTC | 102 |
| 153 | Acr1-CP RV | TTCACCAATGTTCACCAGG | 103 |
| 154 | Orf1593-CP FW | GCCACAATTAGAAGCCTCCTTAG | 104 |
| 155 | Orf1593-CP RV | CTGCTGCCAAACCGTATGC | 105 |
| 156 | NpFAD-CP FW | GCCTACTCCAGAATCAACGC | 106 |
| 157 | NpFAD-CP RV | GCCTTACTCTCTGCGAAGTG | 107 |
| 158 | Fdx FW TTGC | ATCGAAGCGGCCGCAAAACAATGCCAAAGATTGTTATT | 108 |
| 159 | Fdx RV | ATCGTCGAGCTCTTAATGCTCACGCGCATG | 109 |
| 160 | Fpr FW | ATGGCTGATTGGGTAACAGG | 110 |
| 161 | Fpr RV | ACAGCGGAGCATTACTGGTAA | 111 |
| 162 | Fdx M FW | ATCGAAGCGGCCGCAAAACAATGCTTTCTCTTCGTCAA TCTATTCGTTTTTTTAAACGTTCTGGTATTATGCCAAAG ATTGTTATTTTGC | 112 |
| 163 | Fpr M FW | CATTATCCCGGGAAAACAATGCTTTCTCTTCGTCAATCT ATTCGTTTTTTTAAACGTTCTGGTATTATGGCTGATTGG GTAACAGG | 113 |
| 164 | Fpr M RV | CATTATCTCGAGTTACCAGTAATGCTCCGCTGT | 114 |
| 165 | npgA FW | AACTACAAAAAACACATACATAAACTAAAAATGCTTTC TCTTCGTCAATCTATTCGTTTTTTTAAACGTTCTGGTAT TATGGTGCAAGACACATCAAGCG | 115 |
| 166 | npgA RV | AAAAAACTATATCAATTAATTTGAATTAACTTAGGATA GGCAATTACACACCCCA | 116 |
| 167 | NPFAD FW | GTTTCGAATAAACACACATAAACAAACAAAATGCTTTC TCTTCGTCAATCTATTCGTTTTTTTAAACGTTCTGGTAT TATGCAACAATTAACAGACCAATCAAAGG | 117 |
| 168 | NPFAD RV | CTAATTACATGACTCGAGGTCGACGGTATCTCAAGCAC CTATCAAACCGTAAGCAC | 118 |
| 169 | MmCAR FW | ACAAAAAGTTTTTTTAATTTTAATCAAAAAATGCTTTCT CTTCGTCAATCTATTCGTTTTTTTAAACGTTCTGGTATT ATGTCACCTATCACCAGAGAAGAAAG | 119 |
| 170 | MmCAR RV | AAATCATTAAAGTAACTTAAGGAGTTAAATTTACAACA AACCCAACAATCTCAAA | 120 |
| 171 | ETR1 FW | TAGCAATCTAATCTAAGTTTTAATTACAAAATGCTTCC CACATTCAAACGTTACATG | 121 |
| 172 | ETR1 RV | GGGTCGACGCGTAAGCTTGTGGGCCCTATTACCATTCT AAAACAACCATTTTTTTCTTCC | 122 |
| 173 | HFA1 FW | TTATCTACTTTTTACAACAAATATAACAAAATGAGATC TATAAGAAAATGGGCGTACG | 123 |
| 174 | HFA1b FW | TTGGTCCGAAGTGGTGATCACG | 124 |

TABLE 2-continued

Oligonucleotide primers.

| PR ID | Name | Sequence (5'-3') | SEQ ID NO |
|---|---|---|---|
| 175 | HFA1b RV | GATCATGTTACGCCCTTCAGGATATTC | 125 |
| 176 | HFA1a RV | GCAGGAAAAGAAACAGATTTCTTGACTAG | 126 |
| 177 | HFA1c FW | CAGTACATCGTCTCGAGGAAATTGTG | 127 |
| 178 | HFA1 RV | AATAAAAATCATAAATCATAAGAAATTCGCCTATCTCT TTCGCTTACTGTCCACCAAC | 128 |
| 187 | PGK1 SEQ | GGGGTGGTTTAGTTTAGTAGAA | 129 |
| 188 | ADH1 SEQ | GCAACCTGACCTACAGGAAAGA | 130 |
| 189 | TEF1 SEQ | TTTTACTTCTTGCTCATTAGAAAG | 131 |
| 190 | CYC1 SEQ | GGACCTAGACTTCAGGTTGTC | 132 |
| 192 | MdCPR-R | GTGACATAACTAATTACATGACTCGAGGTCGACGGTAT CTTAACTCCAAACATCAGCGGAG | 133 |
| 193 | MdCPR-F | CAAGAACTTAGTTTCGAATAAACACACATAAACAAAC AAAATGAGTGCCGAACACGTTGAAG | 134 |
| 194 | Orf1594-F | CAAGAACTTAGTTTCGAATAAACACACATAAACAAAC AAAATGTTCGGTTTAATAGGTC | 135 |
| 195 | Orf1594-R | CTTATTTAATAATAAAAATCATAAATCATAAGAAATTC GCTCAGATTGCTAAGGCTAAAG | 136 |
| 196 | P450G2-R | CTCATTAAAAAACTATATCAATTAATTTGAATTAACTT ACATTGCCTTCATTGCTTC | 137 |
| 197 | P450G2-F | GAAAGCATAGCAATCTAATCTAAGTTTTAATTACAAAA TGGACTCCGCCAACAACTC | 138 |
| 198 | TPIp-F2 | GAGTAAAAAAGGAGTAGAAACATTTTGAAGCTATGTTT AAAGATTACGGATATTTAAC | 139 |
| 199 | TPIp-R2 | GCTTCTTCGACGAGGGTTCCATTTTTAGTTTATGTATGT GTTTTTTG | 140 |
| 200 | TDH2t-R2 | CAAATGCCTATTGTGCAGATGTTATAATATCTGTGCGT GCGAAAAGCCAATTAGTGTG | 141 |
| 201 | Acr1-F2 | CAAGAACTTAGTTTCGAATAAACACACATAAACAAAC AAAATGAATAAGAAGTTGGAAG | 142 |
| 202 | Acr1-R2 | CTTATTTAATAATAAAAATCATAAATCATAAGAAATTC GCTCACCAATGTTCACCAGGG | 143 |
| 203 | SmCPR-R2 | GACATAACTAATTACATGACTCGAGGTCGACGGTATCT TACCATACATCGCGCAAGTAC | 144 |
| 206 | FaCoAR 1(pYX)-F | GCTTAAATCTATAACTACAAAAAACACATACATAAACT AAAAATGAATTATTTCTTGACAGGTGG | 145 |
| 207 | FaCoAR 2(pYX)-R | CGGATACCCGGGTCGACGCGTAAGCTTGTGGGCCCTAT TACCAATAGATACCTCTCATAATGG | 146 |
| 208 | SeFAR-F2 | CTATAACTACAAAAAACACATACATAAACTAAAAATG TTCGGTTTAATAGGTCAC | 147 |
| 209 | SeFAR-R2 | CTCATTAAAAAACTATATCAATTAATTTGAATTAACTC AGATTGCTAAGGCTAAAG | 148 |

TABLE 2-continued

Oligonucleotide primers.

| PR ID | Name | Sequence (5'-3') | SEQ ID NO |
|---|---|---|---|
| 210 | SeADO-F1 | CAAGAACTTAGTTTCGAATAAACACACATAAACAAAC AAAATGCCACAATTAGAAGCCTC | 149 |
| 211 | SeADO-R1 | CTTATTTAATAATAAAAATCATAAATCATAAGAAATTC GCTTAGACTGCTGCCAAACCGTATG | 150 |
| 212 | EcFd-F1 | GAAAGCATAGCAATCTAATCTAAGTTTTAATTACAAAA TGCCAAAGATTGTTATTTTG | 151 |
| 213 | EcFd-R1 | CTAAATCATTAAAGTAACTTAAGGAGTTAAATTTAATG CTCACGCGCATGGTTG | 152 |
| 214 | EcFNR-F1 | GACATAACTAATTACATGACTCGAGGTCGACGGTATCT TACCAGTAATGCTCCGCTG | 153 |
| 215 | EcFNR-R1 | GGAAGTAATTATCTACTTTTTACAACAAATATAACAAA ATGGCTGATTGGGTAACAGG | 154 |
| 216 | SeFAD FW | TTATCTACTTTTTACAACAAATATAACAAAATGCCACA ATTAGAAGCCTCCTTAGAAT | |
| 217 | SeFAD RV | AATAAAAATCATAAATCATAAGAAATTCGCTTAGACTG CTGCCAAACCGTATGC | |
| 218 | NpFAD RV | AATAAAAATCATAAATCATAAGAAATTCGCTCAAGCA CCTATCAAACCGTAAGCAC | |
| 219 | TesA FW | TAGCAATCTAATCTAAGTTTTAATTACAAAATGGCCGA TACTTTGTTAATTTTGG | |
| 220 | TesA RV | CCGGGTCGACGCGTAAGCTTGTGGGCCCTATCAAGAAT CGTGATTGACTAATGGTTG | |

TABLE 3

Polypeptide sequences.

| PID | Gene name | Sequence | SEQ ID NO |
|---|---|---|---|
| 1 | CnFatB 1 | MVASVAASAFFPTPSFSSTASAKASKTIGEGSESLDVRGIVAK PTSSSAAMQGKVKAQAVPKINGTKVGLKTESQKAEEDAAPSS APRTFYNQLPDWSVLLAAVTTIFLAAEKQWTLLDWKPRRPD MLTDAFSLGKIVQDGLIFRQNFSIRSYEIGADRTASIETLMNHL QETALNHVRNAGLLGDGFGATPEMSKRNLIWVVTKMQVLV EHYPSWGDVVEVDTWVGASGKNGMRRDWHVRDYRTGQTI LRATSVWVMMNKHTRKLSKMPEEVRAEIGPYFVEHAAIVDE DSRKLPKLDDDTADYIKWGLTPRWSDLDVNQHVNNVKYIG WILESAPISILENHELASMTLEYRRECGRDSVLQSLTAISNDCT GGLPEASIECQHLLQLECGAEIVRGRTQWRPRRASGPTSAGSA | 155 |
| 2 | AbTesA | MAKTILILGDSLSAGYGINPEQGWVALLQKRLDQQFPKQHKV INASVSGETTSGALARLPKLLTTYRPNVVVIELGGNDALRGQP PQMIQSNLEKLIQHSQKAKSKVVVFGMKIPPNYGTAYSQAFE NNYKVVSQTYQVKLLPFFLDGVAGHKSLMQNDQIHPNAKAQ SILLNNAYPYIKGAL | 156 |
| 3 | PlLuxC | MTKKISFIINGQVEIFPESDDLVQSINFGDNSVYLPILNNSHVK NIIDYNENNKLRLHNIVNFLYTVGQRWKNEEYSRRRTYIRDL KKYMGYSEAMAKLEANWISMILCSKGGLYDVVENELGSRHI MDEWLPQDESYIKAFPKGKSIHLLAGNVPLSGIMSILRAILTK NQCIIKTSSTDPFTANALALSFIDVDPNHPITRSLSVVYWPHQG DTSLAKEIMQHMDVIVAWGGEDAINWAVEHAPPYADVIKFG SKKSFCIIDNPVDLTSAATGAAHDICFYDQRACFSAQNIYYMG NQYEEFKLALIEKLNLYAHILPNAKKDFDEKAAYSLVQKESL FAGLKVEVDVHQRWMIIESNAGVEFNQPLGRCVYLHHVDNI EQVLPYVQKNKTQTISIFPWESAFKYRDALALRGAERIVEAG MNNIFRVGGSHDGMRPLQRLVTYISHERPSHYTAKDVAVEIE QTRFLEEDKFLVFVP | 157 |

TABLE 3-continued

Polypeptide sequences.

| PID | Gene name | Sequence | SEQ ID NO |
|---|---|---|---|
| 4 | PlLuxD | MENKSKYKTIDHVLCVEGNKKIHVWETLPEENSPKRKNTIIIA SGFARRMDHFAGLAEYLSRNGFHVIRYDSLHHVGLSSGTIDE FTMSIGKQSLLAVVDWLNTRKINNRGILASSLSARIVYASLSEI NVSFLITAVGVVNLRYTLERALGFDYLSLPINELPNNLDFEGH KLGAEVFARDCLDFGWEDLTSTINSMMYLDIPFIAFTANNDN WVKQDEVITLLSNIRSNRCKIYSLLGSSHDLGENLVVLRNFYQ SVTKAAIAMDNDRLDIDVDIIEPSFEHLTIATVNERRMKIEIEN QAISLS | 158 |
| 5 | PlLuxE | MTSYVDKQEIIASSEIDDLIFSSDPLAWSYDEQEKIRNKFVLDA FRNHYKHCQEYRHYCQVHKVDDNITEIDDIPVFPTSVFKFTRL LTSQENEIESWFTSSGTSGLKSQVARNRLSIERLLGSVSYGMK YVGSWFDHQIELVNLGPDRFNAHNIWFKYVMSLVELLYPTTF TVMEERIDFVKTLNSLERIKNQGKDICLIGSPYFIYLLCQYMK DKNISFYGDKNLYIITGGGWKSYEKESLKRDDFNHLLFDTFN LNNISQIRDIFNQVELNTCFFEDEMQRKRVPPWVYARALDPET LKPVPDGMPGLMSYMDASSTSYPAFIVTDDVGIMSREYGQYP GVLVEILRRVNTRAQKGCALSLNQAFNS | 159 |
| 6 | SePetF | MATYKVTLVNAAEGLNTTIDVADDTYILDAAEEQGIDLPYSC RAGACSTCAGKVVSGTVDQSDQSFLDDDQIAAGFVLTCVAY PTSDVTIETHKEEDLY | 160 |
| 7 | SePetH | MLNASVAGGAATTTYGNRLFIYEVIGLRQAEGEPSDSSIRRSG STFFKVPYSRMNQEMQRILRLGGKIVSIRPAEEAAANNGAAP LQAAAEEPAAAPTPAPAAKKHSAEDVPVNIYRPNKPFVGKVL SNEPLVQEGGIGVVQHLTFDISEGDLRYIEGQSIGIIPDGTDDK GKPHKLRLYSIASTRHGDHVDDKTVSLCVRQLQYQNEAGETI NGVCSTFLCGLKPGDDVKITGPVGKEMLLPADTDANVIMMG TGTGIAPFRAYLWRMFKDNERAINSEYQFNGKAWLIFGIPTT ANILYKEELEALQAQYPDNFRLTYAISREQKNEAGGRMYIQD RVAEHADEIWNLLKDEKTHVYICGLRGMEDGIDQAMTVAAA KEDVVWSDYQRTLKKAGRWHVETY | 161 |

TABLE 4

Codon optimized gene sequences.

| NT ID | Gene name | Sequence | SEQ ID NO |
|---|---|---|---|
| 1 | Orf1594 | GGATCCAAAACAATGTTCGGTTTAATAGGTCACTTAACAAGTTT AGAACAAGCCAGAGATGTCAGTAGAAGAATGGGTTACGATGA ATACGCAGACCAAGGTTTAGAATTTTGGTCTTCAGCCCCACCTC AAATCGTAGATGAAATTACAGTTACCTCTGCTACTGGTAAAGT CATTCATGGTAGATACATCGAATCATGTTTCTTGCCAGAAATGT TGGCTGCAAGAAGATTCAAAACTGCAACAAGAAAGGTTTTGAA TGCAATGTCCCATGCCCAAAAGCACGGTATCGATATTTCCGCAT TGGGTGGTTTTACAAGTATAATCTTCGAAAACTTCGATTTGGCT AGTTTGAGACAAGTTAGAGACACTACATTGGAATTCGAAAGAT TCACCACTGGTAACACCCACACTGCTTACGTCATTTGTAGACAA GTAGAAGCCGCTGCAAAAACCTTGGGTATAGATATCACACAAG CCACCGTTGCTGTTGTCGGTGCTACTGGTGACATCGGTTCCGCA GTATGCAGATGGTTGGATTTGAAATTGGGTGTTGGTGACTTAAT CTTGACAGCTAGAAACCAAGAAAGATTGGATAACTTGCAAGCA GAATTAGGTAGAGGTAAAATCTTGCCATTGGAAGCCGCTTTGC CTGAAGCCGATTTTATCGTTTGGGTCGCTTCTATGCCACAAGGT GTAGTTATTGATCCAGCTACCTTAAAACAACCTTGCGTTTTGAT AGACGGTGGTTATCCTAAAAATTTGGGTTCTAAGGTTCAAGGT GAAGGTATCTATGTCTTGAACGGTGGTGTCGTAGAACATTGTTT CGATATAGACTGGCAAATCATGTCAGCAGCCGAAATGGCAAGA CCTGAAAGACAAATGTTTGCCTGCTTCGCTGAAGCAATGTTGTT AGAATTTGAAGGTTGGCACACTAATTTCTCTTGGGGTAGAAAC CAAATTACAATAGAAAAGATGGAAGCCATCGGTGAAGCCTCTG TTAGACACGGTTTCCAACCTTTAGCCTTAGCAATCTGAAAGCTT | 162 |
| 2 | Orf1593 | ATCTAGTTTTATTACAGCGGCCGCAAAACAATGCCACAATTAG AAGCCTCCTTAGAATTAGACTTTCAATCAGAATCATATAAAGA TGCTTACAGTAGAATCAACGCAATCGTCATTGAAGGTGAACAA | 163 |

TABLE 4-continued

Codon optimized gene sequences.

| NT ID | Gene name | Sequence | SEQ ID NO |
|---|---|---|---|
| | | GAAGCATTTGATAACTACAACAGATTGGCAGAAATGTTACCAG<br>ATCAAAGAGACGAATTGCATAAATTGGCCAAGATGGAACAAA<br>GACACATGAAAGGTTTCATGGCTTGTGGTAAAAATTTGTCCGTT<br>ACTCCTGATATGGGTTTCGCACAAAAGTTTTTCGAAAGATTGCA<br>TGAAAACTTCAAAGCTGCAGCCGCTGAGGGTAAAGTTGTCACA<br>TGTTTGTTGATCCAATCTTTGATAATCGAATGCTTTGCTATCGC<br>AGCCTATAATATCTACATTCCAGTCGCTGATGCATTCGCCAGAA<br>AGATTACCGAAGGTGTAGTTAGAGACGAATATTTGCACAGAAA<br>CTTCGGTGAAGAATGGTTGAAGGCAAACTTCGATGCTTCTAAG<br>GCAGAATTGGAAGAAGCTAATAGACAAAACTTGCCTTTAGTCT<br>GGTTGATGTTAAATGAAGTAGCCGATGACGCTAGAGAATTGGG<br>TATGGAAAGAGAATCATTAGTTGAAGACTTCATGATCGCATAC<br>GGTGAAGCCTTAGAAAACATCGGTTTTACTACCAGAGAAATAA<br>TGAGAATGTCCGCATACGGTTTGGCAGCAGTCTAAGAGCTC | |
| 3 | NpFA<br>D | TCTAGTTTTATTACAGCGGCCGCAAAACAATGCAACAATTAAC<br>AGACCAATCAAAGGAATTAGACTTCAAATCAGAAACTTACAAA<br>GATGCCTACTCCAGAATCAACGCAATCGTCATTGAAGGTGAAC<br>AAGAAGCACATGAAAACTACATCACCTTGGCCCAATTATTACC<br>AGAATCCCATGATGAATTGATCAGATTGTCTAAGATGGAATCA<br>AGACACAAAAAGGGTTTTGAAGCCTGTGGTAGAAATTTGGCTG<br>TTACTCCTGACTTACAATTTGCCAAAGAATTTTTCTCTGGTTTGC<br>ACCAAAACTTCCAAACTGCTGCAGCCGAGGGTAAAGTTGTCAC<br>ATGTTTGTTGATCCAATCATTAATAATCGAATGCTTTGCTATCG<br>CTGCATATAATATCTACATTCCAGTTGCCGATGACTTCGCTAGA<br>AAAATTACAGAAGGTGTAGTTAAGGAAGAATATTCCCATTTGA<br>ACTTTGGTGAAGTCTGGTTAAAAGAACACTTCGCAGAGAGTAA<br>GGCCGAATTGGAATTAGCAAATAGACAAAACTTGCCTATCGTC<br>TGGAAAATGTTAAATCAAGTAGAAGGTGACGCTCATACCATGG<br>CAATGGAAAAGGATGCTTTGGTTGAAGACTTCATGATTCAATA<br>CGGTGAAGCATTATCAAACATAGGTTTTTCTACCAGAGACATT<br>ATGAGATTGAGTGCTTACGGTTTGATAGGTGCTTGAGAGCTC | 164 |
| 4 | Orf88<br>0/OleT | CTAAGTTTTATTACAGCGGCCGCAAAACAATGGCTACATTGAA<br>GAGAGACAAGGGTTTAGACAACACATTGAAAGTATTGAAGCA<br>AGGTTACTTATACACCACCAACCAAAGAAATAGATTGAACACT<br>TCTGTTTTCCAAACAAAGGCATTAGGTGGTAAACCTTTCGTTGT<br>CGTAACTGGTAAAGAAGGTGCCGAAATGTTCTACAACAACGAT<br>GTTGTCCAAAGAGAAGGCATGTTGCCAAAGAGAATCGTTAACA<br>CTTTGTTCGGTAAAGGTGCCATCCATACAGTCGATGGTAAAAA<br>GCACGTAGACAGAAAAGCTTTGTTCATGTCATTGATGACTGAG<br>GGTAATTTGAACTACGTCAGAGAATTGACCAGAACTTTATGGC<br>ATGCCAATACACAAAGAATGGAATCTATGGATGAAGTCAACAT<br>ATACAGAGAATCAATCGTATTGTTGACAAAGGTTGGTACCAGA<br>TGGGCTGGTGTACAAGCACCACCTGAAGACATCGAAAGAATTG<br>CAACAGATATGGACATAATGATCGATTCCTTTAGAGCCTTGGG<br>TGGTGCTTTCAAAGGTTACAAAGCAAGTAAAGAAGCTAGAAGA<br>AGAGTTGAAGATTGGTTGGAAGAACAAATCATCGAAACCAGA<br>AAGGGTAACATTCATCCACCTGAAGGTACTGCCTTGTATGAATT<br>TGCTCACTGGGAAGATTACTTAGGTAACCCTATGGACTCCAGA<br>ACATGTGCTATTGATTTGATGAATACCTTCAGACCATTGATCGC<br>TATAAACAGATTCGTTTCTTTCGGTTTGCATGCAATGAATGAAA<br>ACCCTATAACCAGAGAAAAGATTAAATCAGAACCAGATTACGC<br>TTACAAGTTCGCACAAGAAGTTAGAAGATATTACCCATTTGTCC<br>CTTTCTTACCTGGTAAAGCTAAGGTTGATATCGACTTCCAAGGT<br>GTTACAATTCCAGCAGGTGTCGGTTTGGCCTTAGACGTATATGG<br>TACTACACATGATGAATCCTTGTGGGATGACCCTAATGAATTCA<br>GACCAGAAAGATTCGAAACATGGGATGGTAGTCCTTTTGACTT<br>AATTCCACAAGGTGGTGGTGACTACTGGACCAACCACAGATGC<br>GCTGGTGAATGGATTACCGTTATCATCATGGAAGAAACTATGA<br>AGTACTTCGCAGAAAAGATTACTTACGATGTACCTGAACAAGA<br>TTTGGAAGTTGACTTAAACTCTATTCCAGGTTATGTAAAGAGTG<br>GTTTCGTTATTAAAAATGTCAGAGAAGTAGTAGATAGAACTTG<br>AGAGCTC | 165 |
| 5 | npgA | ATGGTGCAAGACACATCAAGCGCAAGCACTTCGCCAATTTTAA<br>CAAGATGGTACATCGACACCCGCCCTCTAACCGCCTCAACAGC<br>AGCCCTTCCTCTCCTTGAAACCCTCCAGCCCGCTGATCAAATCT<br>CCGTCCAAAAATACTACCATCTGAAGGATAAACACATGTCTCT<br>CGCCTCTAATCTGCTCAAATACCTCTTCGTCCACCGAAACTGTC<br>GCATCCCCTGGTCTTCAATCGTGATCTCTCGAACCCCAGATCCG<br>CACAGACGACCATGCTATATTCCACCCTCAGGCTCACAGGAAG<br>ACAGCTTCAAAGACGGATATACCGGCATCAACGTTGAGTTCAA<br>CGTCAGCCACCAAGCCTCAATGGTCGCGATCGCGGGAACAGCT | 166 |

TABLE 4-continued

Codon optimized gene sequences.

| NT ID | Gene name | Sequence | SEQ ID NO |
|---|---|---|---|
| | | TTTACTCCCAATAGTGGTGGGGACAGCAAACTCAAACCCGAAG<br>TCGGAATTGATATTACGTGCGTAAACGAGCGGCAGGGACGGAA<br>CGGGGAAGAGCGGAGCCTGGAATCGCTACGTCAATATATTGAT<br>ATATTCTCGGAAGTGTTTTCCACTGCAGAGATGGCCAATATAA<br>GGAGGTTAGATGGAGTCTCATCATCCTCACTGTCTGCTGATCGT<br>CTTGTGGACTACGGGTACAGACTCTTCTACACTTACTGGGCGCT<br>CAAAGAGGCGTATATAAAAATGACTGGGGAGGCCCTCTTAGCA<br>CCGTGGTTACGGGAACTGGAATTCAGTAATGTCGTCGCCCCGG<br>CCGCTGTTGCGGAGAGTGGGGATTCGGCTGGGGATTTCGGGGA<br>GCCGTATACGGGTGTCAGGACGACTTTATATAAAAATCTCGTT<br>GAGGATGTGAGGATTGAAGTTGCTGCTCTGGGCGGTGATTACC<br>TATTTGCAACGGCTGCGAGGGGTGGTGGGATTGGAGCTAGTTC<br>TAGACCAGGAGGTGGTCCAGACGGAAGTGGCATCCGAAGCCA<br>GGATCCCTGGAGGCCTTTCAAGAAGTTAGATATAGAGCGAGAT<br>ATCCAGCCCTGTGCGACTGGGGTGTGTAATTGCCTATCCTAA | |
| 6 | SynA<br>AC | ATGGACTCAGGTCACGGTGCTCAATCAAGAATCAAGTTAGGTC<br>AAACAGGTTACAAGTTATCAACATATTTCTGCAAAAGTGGTCC<br>TAATTGGGAAAACCAACCACAAATCCATTGGAACTCTTTATTTT<br>CAACTGTCAAGATCCAATTGTCCTTATTCCCTTCTTCATTTCACT<br>TAATCATGGTAACTCCAATTAATTACCATAGTATCCACTGTTTG<br>GCAGATATTTGGGCCATAACAGGTGAAAATTTCGCTGATATTG<br>TAGCATTGAACGACAGACATTCTCACCCACCTGTTACCTTGACT<br>TACGCACAATTAAGAGAAGAAATTACAGCCTTTGCTGCTGGTT<br>TGCAATCATTAGGTGTTACCCCTCATCAACACTTAGCTATTTTC<br>GCAGATAATTCCCCAAGATGGTTTATAGCAGACCAAGGTAGTA<br>TGTTGGCAGGTGCCGTTAACGCTGTTAGATCAGCTCAAGCAGA<br>AAGACAAGAATTGTTGTACATCTTGGAAGATTCCAATAGTAGA<br>ACATTGATCGCAGAAAACAGACAAACCTTGTCTAAATTGGCTT<br>TAGATGGTGAAACCATTGACTTGAAGTTAATAATCTTGTTGACT<br>GATGAAGAAGTTGCCGAAGACTCAGCTATACCACAATATAATT<br>TCGCACAAGTCATGGCCTTAGGTGCTGGTAAAATTCCAACTCCT<br>GTACCAAGACAAGAAGAAGATTTGGCTACCTTAATATACACTT<br>CTGGTACTACAGGTCAACCAAAGGGTGTTATGTTGTCACATGG<br>TAATTTGTTGCACCAAGTTAGAGAATTGGATTCCGTCATCATTC<br>CTAGACCAGGTGACCAAGTTTTGAGTATTTTACCATGTTGGCAT<br>TCCTTGGAAAGAAGTGCTGAATATTTCTTGTTATCCAGAGGTTG<br>CACAATGAACTACACCAGTATCAGACATTTCAAGGGTGACGTT<br>AAGGACATAAAGCCTCATCACATAGTAGGTGTTCCAAGATTGT<br>GGGAATCTTTATATGAAGGTGTCCAAAAGACTTTTAGAGAAAA<br>GTCACCTGGTCAACAAAAATTGATTAATTTCTTTTTCGGTATCT<br>CACAAAAGTACATATTGGCAAAGAGAATCGCCAACAACTTGTC<br>TTTAAACCATTTGCACGCCTCAGCTATTGCAAGATTGGTAGCTA<br>GATGTCAAGCATTGGTTTTATCTCCATTGCATTATTTGGGTGAC<br>AAAATCGTATACCACAAGGTTAGACAAGCCGCTGGTGGTAGAT<br>TGGAAACTTTAATTTCTGGTGGTGGTGCCTTGGCTAGACATTTG<br>GATGACTTCTATGAAATCACCTCAATTCCTGTCTTAGTAGGTTA<br>CGGTTTAACAGAAACCGCCCCAGTCACAAATGCTAGAGTACAT<br>AAGCACAACTTAAGATATTCCAGTGGTAGACCTATCCCTTTTAC<br>TGAAATCAGAATCGTTGATATGGAAACTAAGGAAGACTTGCCA<br>CCTGAAACACAAGGTTTGGTCTTAATTAGAGGTCCTCAAGTAA<br>TGCAAGGTTATTACAATAAGCCAGAAGCAACTGCCAAGGTATT<br>AGATCAAGAAGGTTGGTTCGATTCCGGTGACTTGGGTTGGGTT<br>ACACCACAAAACGATTTGATATTAACTGGTAGAGCTAAAGACA<br>CAATCGTTTTATCTAATGGTGAAAACGTCGAACCTCAACCAATT<br>GAAGATGCATGCTTAAGATCCGCCTACATAGATCAAATCATGT<br>TGGTTGGTCAAGACCAAAAGAGTTTGGGTGCTTTAATCGTCCC<br>AAACTTCGATGCTTTACAAAAATGGGCAGAAACCAAGAACTTG<br>CAAATCACTGTTCCTGAACCATCTGCCTCTTCAGAGGGTATGCA<br>AGCATCTGGTTTGTATGATCCTCAAGTTGTCGGTTTGATGAGAT<br>CAGAATTACATAGAGAAGTTAGAGATAGACCAGGTTACAGAGC<br>AGATGACCAAATCAAAGATTTCAGATTCATTCCTGCTCCATTTT<br>CTTTAGAAAACGGTATGATGACTCAAACATTGAAATTGAAGAG<br>ACCTGTAGTCACCCAAACTTACCAACACTTGATAGACGAAATG<br>TTCTGA | 167 |
| 7 | MmC<br>AR | ATGTCACCTATCACCAGAGAAGAAAGATTAGAAAGAAGAATA<br>CAAGACTTATACGCCAACGATCCTCAATTCGCCGCTGCCAAGC<br>CAGCAACAGCCATCACCGCTGCAATTGAAAGACCAGGTTTGCC<br>ATTGCCTCAAATCATCGAAACTGTTATGACAGGTTATGCTGATA<br>GACCTGCTTTGGCACAAAGATCAGTAGAATTTGTTACAGATGC<br>AGGTACTGGTCATACTACATTGAGATTGTTACCACACTTCGAAA<br>CTATCTCTTACGGTGAATTATGGGACAGAATTTCTGCCTTGGCT<br>GATGTTTTATCAACCGAACAAACTGTTAAACCTGGTGACAGAG | 168 |

TABLE 4-continued

Codon optimized gene sequences.

| NT ID | Gene name | Sequence | SEQ ID NO |
|---|---|---|---|
| | | TCTGTTTGTTGGGTTTTAATTCTGTTGACTACGCAACTATAGAT<br>ATGACATTGGCCAGATTAGGTGCAGTAGCCGTTCCATTGCAAA<br>CCTCTGCCGCTATTACTCAATTACAACCAATAGTCGCTGAAACA<br>CAACCTACCATGATAGCAGCCTCTGTAGATGCTTTGGCAGACG<br>CCACTGAATTGGCTTTATCAGGTCAAACTGCAACAAGAGTCTT<br>AGTATTCGACCATCACAGACAAGTTGATGCCCATAGAGCTGCT<br>GTTGAATCCGCTAGAGAAAGATTGGCAGGTAGTGCCGTTGTCG<br>AAACTTTAGCTGAAGCAATAGCTAGAGGTGACGTTCCAAGAGG<br>TGCTTCTGCTGGTTCTGCTCCTGGTACAGACGTCTCCGATGACA<br>GTTTGGCATTGTTAATCTATACCTCTGGTTCAACTGGTGCCCCA<br>AAAGGTGCTATGTACCCTAGAAGAAATGTTGCTACATTTTGGA<br>GAAAGAGAACCTGGTTCGAAGGTGGTTACGAACCATCTATCAC<br>TTTGAACTTCATGCCTATGTCACATGTTATGGGTAGACAAATCT<br>TGTATGGTACTTTATGCAACGGTGGTACAGCATACTTTGTTGCC<br>AAGTCTGACTTGTCAACATTATTCGAAGATTTGGCTTTAGTCAG<br>ACCAACTGAATTAACATTCGTCCCTAGAGTATGGGATATGGTTT<br>TTGACGAATTTCAATCAGAAGTCGATAGAAGATTGGTAGATGG<br>TGCTGACAGAGTAGCTTTAGAAGCACAAGTTAAGGCAGAAATA<br>AGAAACGATGTTTTGGGTGGTAGATATACATCTGCCTTAACCG<br>GTTCTGCTCCAATATCAGACGAAATGAAGGCTTGGGTAGAAGA<br>ATTGTTAGATATGCATTTGGTTGAAGGTTACGGTTCAACTGAAG<br>CTGGTATGATATTAATCGACGGTGCAATTAGAAGACCAGCCGT<br>TTTGGATTATAAATTGGTTGATGTCCCTGACTTGGGTTACTTTTT<br>AACTGATAGACCACACCCTAGAGGTGAATTGTTGGTTAAGACA<br>GATTCTTTGTTCCCAGGTTATTACCAAAGAGCTGAAGTTACAGC<br>AGATGTCTTTGATGCTGACGGTTTCTATAGAACCGGTGACATTA<br>TGGCAGAAGTCGGTCCTGAACAATTCGTATACTTAGATAGAAG<br>AAACAACGTTTTGAAATTGTCTCAGGGTGAATTTGTAACTGTTT<br>CAAAGTTGGAAGCTGTATTCGGTGACTCTCCATTAGTTAGACA<br>AATATATATATACGGTAATTCAGCCAGAGCTTATTTGTTAGCAG<br>TCATAGTACCAACACAAGAAGCCTTGGATGCTGTTCCTGTCGA<br>AGAATTGAAAGCCAGATTGGGTGACTCCTTGCAAGAAGTTGCA<br>AAGGCCGCTGGTTTGCAAAGTTACGAAATCCCAAGAGATTTCA<br>TCATCGAAACCACTCCTTGGACCTTAGAAAACGGTTTGTTAACT<br>GGTATCAGAAAATTGGCTAGACCACAATTGAAAAAGCATTACG<br>GTGAATTGTTAGAACAAATATATACTGACTTGGCCCACGGTCA<br>AGCTGATGAATTGAGATCCTTAAGACAAAGTGGTGCAGATGCC<br>CCAGTATTAGTTACAGTCTGTAGAGCAGCCGCTGCATTGTTAGG<br>TGGTTCCGCTAGTGATGTTCAACCTGACGCACATTTTACCGATT<br>TGGGTGGTGACTCTTTGTCAGCTTTATCTTTTACAAATTTGTTGC<br>ACGAAATCTTCGATATAGAAGTACCAGTTGGTGTCATTGTATCA<br>CCTGCTAACGATTTGCAAGCATTGGCAGATTATGTTGAAGCCG<br>CTAGAAAACCAGGTTCTTCAAGACCTACTTTTGCTTCTGTTCAT<br>GGTGCATCAAATGGTCAAGTTACAGAAGTCCACGCTGGTGACT<br>TGTCTTTGGATAAGTTCATTGATGCAGCCACTTTGGCCGAAGCT<br>CCAAGATTACCTGCTGCAAACACTCAAGTAAGAACAGTTTTGT<br>TAACCGGTGCTACTGGTTTCTTGGGTAGATATTTGGCATTAGAA<br>TGGTTAGAAAGAATGGATTTGGTTGACGGTAAATTGATTTGCTT<br>AGTCAGAGCAAAGTCCGACACTGAAGCAAGAGCCAGATTGGA<br>TAAAACATTCGATAGTGGTGACCCAGAATTGTTAGCACATTAC<br>AGAGCTTTAGCAGGTGACCACTTGGAAGTTTTAGCCGGTGACA<br>AGGGTGAAGCTGACTTGGGTTTAGATAGACAAACATGGCAAAG<br>ATTGGCTGATACCGTAGACTTAATCGTTGATCCAGCCGCTTTAG<br>TCAACCATGTATTGCCATACTCCCAATTGTTCGGTCCTAACGCA<br>TTGGGTACTGCTGAATTGTTGAGATTGGCTTTGACTTCTAAAAT<br>TAAGCCTTACTCCTACACCAGTACTATCGGTGTTGCAGATCAAA<br>TTCCACCTTCAGCCTTCACTGAAGATGCTGACATAAGAGTCATC<br>TCCGCAACAAGAGCCGTAGATGACAGTTATGCTAATGGTTACT<br>CCAACAGTAAATGGGCAGGTGAAGTTTTGTTAAGAGAAGCCCA<br>TGATTTGTGTGGTTTACCAGTTGCTGTCTTTAGATGCGACATGA<br>TTTTGGCAGATACAACCTGGGCCGGTCAATTGAACGTTCCAGA<br>TATGTTCACAAGAATGATCTTGTCCTTAGCAGCCACCGGTATAG<br>CTCCTGGTAGTTTCTATGAATTGGCTGCTGATGGTGCTAGACAA<br>AGAGCACATTACGATGGTTTGCCAGTTGAGTTTATTGCCGAAG<br>CTATCTCCACCTTAGGTGCTCAAAGTCAAGATGGTTTCCATACT<br>TATCACGTAATGAATCCATACGATGACGGTATTGGTTTGGACG<br>AATTTGTTGATTGGTTAAACGAATCTGGTTGTCCTATTCAAAGA<br>ATAGCTGATTATGGTGACTGGTTACAAAGATTCGAAACTGCTTT<br>GAGAGCATTACCAGATAGACAAAGACATTCCAGTTTGTTACCT<br>TTGTTACACAATTACAGACAACCAGAAAGACCTGTCAGAGGTT<br>CTATTGCTCCTACAGATAGATTCAGAGCCGCTGTACAAGAAGC<br>AAAAATAGGTCCAGATAAGGACATCCCTCATGTTGGTGCTCCT<br>ATTATCGTAAAGTATGTATCAGATTTGAGATTGTTGGGTTTGTT<br>GTAA | |

TABLE 4-continued

Codon optimized gene sequences.

| NT ID | Gene name | Sequence | SEQ ID NO |
|---|---|---|---|
| 8 | Fdx | ATGCCAAAGATTGTTATTTTGCCTCATCAGGATCTCTGTCCTGA<br>TGGCGCTGTTCTGGAAGCTAATAGCGGTGAAACCATTCTCGAC<br>GCAGCGCTGCGTAACGGTATCGAGATTGAACACGCCTGTGAAA<br>AATCCTGTGCTTGCACCACCTGCCACTGCATCGTTCGTGAAGGT<br>TTTGACTCACTGCCGGAAAGCTCAGAGCAGGAAGACGACATGC<br>TGGACAAAGCCTGGGGACTGGAGCCGGAAAGCCGTTTAAGCTG<br>CCAGGCGCGCGTCACCGACGAAGATTTAGTGGTTGAAATCCCG<br>CGTTACACTATCAACCATGCGCGTGAGCATTAA | 169 |
| 9 | Fpr | ATGGCTGATTGGGTAACAGGCAAAGTCACTAAAGTGCAGAACT<br>GGACCGACGCCCTGTTTAGTCTCACCGTTCACGCCCCCGTGCTT<br>CCGTTTACCGCCGGGCAATTTACCAAGCTTGGCCTTGAAATCGA<br>CGGCGAACGCGTCCAGCGCGCCTACTCCTATGTAAACTCGCCC<br>GATAATCCCGATCTGGAGTTTTACCTGGTCACCGTCCCCGATGG<br>CAAATTAAGCCCACGACTGGCGGCACTGAAACCAGGCGATGAA<br>GTGCAGGTGGTTAGCGAAGCGGCAGGATTCTTTGTGCTCGATG<br>AAGTGCCGCACTGCGAAACGCTATGGATGCTGGCAACCGGTAC<br>AGCGATTGGCCCTTATTTATCGATTCTGCAACTAGGTAAAGATT<br>TAGATCGCTTCAAAAATCTGGTCCTGGTGCACGCCGCACGTTAT<br>GCCGCCGACTTAAGCTATTTGCCACTGATGCAGGAACTGGAAA<br>AACGCTACGAAGGAAAACTGCGCATTCAGACGGTGGTCAGTCG<br>GGAAACGGCAGCGGGGTCGCTCACCGGACGGATACCGGCATTA<br>ATTGAAAGTGGGGAACTGGAAAGCACGATTGGCCTGCCGATGA<br>ATAAAGAAACCAGCCATGTGATGCTGTGCGGCAATCCACAGAT<br>GGTGCGCGATACACAACAGTTGCTGAAAGAGACCCGGCAGATG<br>ACGAAACATTTACGTCGCCGACCGGGCCATATGACAGCGGAGC<br>ATTACTGGTAA | 170 |
| 14 | CYP4 G2 | ATGGACTCCGCCAACAACTCTACAGCCGGTCCTGCCACAGTAT<br>TGAATCCTATCTGGACAGCATTATTAGGTATTGCCGTCGTCGTC<br>TCATTGTACGAAATTTGGTTGAGAAACACTAGAAAGTACAAAT<br>TGACAGCAAATATGCCAAACCCACCTATGTTGCCTTTAATTGGT<br>AATGGTCATTTGGTTGCCCACTTAACAAACGCCGAAATTTTGGC<br>TAGAGGTATAGGTTATATGCAAACCTACGGTGGTGCCATGAGA<br>GGTTTCTTGGGTCCAATGTTAGTTGTCTTCTTGTGGAATGCTCCT<br>GATATCGAATTGATCTTAAGTACTCATACACACTTAGAAAAGT<br>CTATCGAATACAGATTTTTCAAACCTTGGTTTGGTGACGGTTTG<br>TTAATCAGTAACGGTCATCACTGGCAACATCACAGAAAGATGA<br>TAGCTCCAACTTTCCATCAATCCATCTTGAAAAGTTTTGTTCCT<br>GCTTTCGTCCAACACTCTAAAAAGGTAGTTGAAAGAATGGCAA<br>AGGAATTGGGTAAAGAATTTGATGTCCATGACTACATGTCACA<br>AACTACAGTAGAAATTTTGTTATCCACAGCTATGGGTGTTAAG<br>AAAGTTCCAGAAGATAATAAGTCATTAGAATACGCTAAAGCAG<br>TCGTAGATATGTGTGACATCATCCATAAGAGACAATTGAAGTT<br>TTTCTATAGAATGGATGCATTGTACAACTTATCTTCAATGTCCG<br>AAAAGGGTAAAAAGATGATGGATATCATCTTGGGTATGACAAG<br>AAAGGTTGTCACCGAAAGACAACAAAACTTCAACGCAGAAAG<br>TAGAGCCATCGTTGAAGAAGATGACGAAATTTCTAAGCAAAAG<br>CAACAAGCTAAAAAGAAAGAAGGTTTGAGAGATGACTTGGAT<br>GACATTGATGAAAATGACGTTGGTGCCAAGAAAAGATTGGCTT<br>TGTTAGACGCCATGATGGCTATGTCAAAGAATCCAGATGTTGA<br>ATGGACCGATAAAGACGTAATGGACGAAGTTAACACTATAATG<br>TTCGAAGGTCATGATACCACTTCCGCTGGTTCCAGTTTCGTTTT<br>GTGTATGTTGGGTATCTATAAGGATATCCAAGAAAAGGTCTTG<br>GCTGAACAAAAGGCAATCTTCGGTGACAATTTCTTGAGAGACT<br>GCACCTTCGCTGATACTATGGAAATGAAGTATTTGGAAAGAGT<br>TATCATGGAAACTTTGAGATTGTACCCACCTGTCCCATTAATTG<br>CAAGAAGAGCCGAATTTGATGTAAAGTTGGCATCTGGTCCATA<br>TACAATTCCTAAAGGTACAACCGTAGTTATAGCTCAATTTGCAG<br>TTCATAGAAATCCTCAATACTTCCCAAACCCTGAAAAATTTGAT<br>CCAGACAATTTCTTGCCTGAAAGAATGGCTAACAGACACTACT<br>ACTCTTTTATTCCATTCTCAGCAGGTCCTAGATCCTGCGTTGGT<br>AGAAAGTACGCCATGTTGAAGTTAAAGGTCTTGTTATCTACTAT<br>CATCAGAAATTACTCTGTACAATCAAACCAACAAGAAAAGGAC<br>TTCAAATTACAAGCAGATATTATATTGAAAATAGAAAATGGTT<br>TTAATATAATGTTGAATAGAAGACCTGAAGCAATGAAGGCAAT<br>GTAA | 171 |
| 15 | MdCP R | ATGAGTGCCGAACACGTTGAAGAAGTAGTCAGTGAAGAACCAT<br>TTTTAGGTACATTGGATATTGCCTTATTAGTAGTATTATTAGTC<br>GGTGCCACTTGGTACTTCATGAGATCAAGAAAGAAAGAAGAAG<br>CTCCTATAAGATCATACTCAATCCAACCAACTACAGTCTCCACA<br>GTAAGTACCACTGAAAATTCCTTCATTAAAAAGTTGAAAGCAT | 172 |

TABLE 4-continued

Codon optimized gene sequences.

| NT ID | Gene name | Sequence | SEQ ID NO |
|---|---|---|---|
| | | CTGGTAGATCATTAGTTGTCTTTTATGGTTCACAAACTGGTACA | |
| | | GCTGAAGAATTTGCAGGTAGATTGGCCAAGGAAGGTTTAAGAT | |
| | | ACAGAATGAAGGGTATGGTTGCTGACCCTGAAGAATGTGATAT | |
| | | GGAAGAATTGTTACAAATGAAGGATATCCCAAATTCTTTGGCC | |
| | | GTCTTTTGCTTAGCTACCTATGGTGAAGGTGACCCAACTGATAA | |
| | | CGCTATGGAATTTTACGAATGGATTACAAACGGTGAAGTCGAT | |
| | | TTGACCGGTTTAAATTATGCCGTATTTGGTTTGGGTAACAAAAC | |
| | | TTATGAACATTACAATAAGGTTGCTATCTATGTCGATAAGAGAT | |
| | | TGGAAGAATTAGGTGCAACAAGAGTTTTCGAATTGGGTTTAGG | |
| | | TGACGACGATGCAAACATCGAAGACGATTTCATCACCTGGAAA | |
| | | GACAGATTCTGGCCATCCGTTTGTGATTTCTTTGGTATTGAAGG | |
| | | TAGTGGTGAAGAAGTCTTGATGAGACAATTCAGATTGTTAGAA | |
| | | CAACCTGACGTACAACCAGATAGAATCTATACAGGTGAAATAG | |
| | | CTAGATTGCATTCTATGCAAAACCAAAGACCACCTTTTGATGCT | |
| | | AAGAATCCTTTCTTGGCATCAGTCATTGTAAACAGAGAATTAC | |
| | | ACAAAGGTGGTGGTAGATCATGCATGCACATCGAATTGGACAT | |
| | | TGATGGTTCAAAGATGAGATATGACGCAGGTGACCATATCGCC | |
| | | ATGTACCCAATTAATGATAAAATCTTAGTTGAAAAATTGGGTA | |
| | | AATTGTGTGACGCTAATTTGGATACTGTCTTTTCTTTAATCAAC | |
| | | ACCGACACTGATTCTTCTAAGAAACACCCATTCCCTTGCCCAAC | |
| | | AACCTATAGAACCGCATTGACTCATTACTTAGAAATCACAGCC | |
| | | ATTCCTAGAACCCACATATTGAAGGAATTAGCAGAATATTGTT | |
| | | CCGACGAAAAGGATAAGGAATTTTTGAGAAACATGGCCAGTAT | |
| | | TACACCAGAGGGTAAAGAAAAGTACCAAAACTGGATACAAAA | |
| | | CTCCAGTAGAAACATCGTTCATATCTTGGAAGATATAAAATCTT | |
| | | GTAGACCACCTATAGATCATATTTGTGAATTGTTGCCTAGATTA | |
| | | CAACCAAGATACTACTCTATCTCTTCATCCAGTAAGTTGTATCC | |
| | | TACTAACGTTCATATTACAGCTGTTTTAGTCCAATACGAAACAC | |
| | | CAACCGGTAGAGTAAATAAGGGTGTTGCAACTTCTTACATGAA | |
| | | GGAAAAGAACCCTTCAGTTGGTGAAGTAAAGGTTCCAGTCTTT | |
| | | ATAAGAAAGTCCCAATTCAGATTGCCTACTAAGAGTGAAATCC | |
| | | CAATTATAATGGTTGGTCCTGGTACAGGTTTAGCACCTTTTAGA | |
| | | GGTTTCATTCAAGAAAGACAATTCTTGAGAGACGGTGGTAAAG | |
| | | TAGTTGGTGACACAATCTTGTACTTCGGTTGTAGAAAGAAAGA | |
| | | CGAAGATTTCATCTATAGAGAAGAATTAGAACAATACGTTCAA | |
| | | AACGGTACTTTGACATTGAAGACCGCCTTTTCAAGAGATCAAC | |
| | | AAGAAAAGATATATGTAACTCATTTGATCGAACAAGACGCTGA | |
| | | TTTGATTTGGAAAGTTATAGGTGAACAAAAGGGTCACTTCTAC | |
| | | ATTTGCGGTGACGCTAAGAACATGGCAGTAGATGTTAGAAACA | |
| | | TCTTGGTCAAAATTTTATCTACTAAGGGTAACATGAACGAATCA | |
| | | GATGCTGTACAATACATTAAGAAAATGGAAGCCCAAAAGAGAT | |
| | | ACTCCGCTGATGTTTGGAGTTAA | |
| 16 | FacoA | ATGAATTATTTCTTGACAGGTGGTACAGGTTTTATCGGTAGATT | 173 |
| | R | CTTGGTTGAAAAGTTGTTAGCCAGAGGTGGTACAGTTTATGTTT | |
| | | TAGTTAGAGAACAATCTCAGGATAAGTTGGAAAGATTGAGAGA | |
| | | AAGATGGGGTGCCGATGACAAACAAGTCAAGGCTGTAATAGGT | |
| | | GACTTGACATCTAAAAATTTGGGTATCGATGCTAAGACCTTGA | |
| | | AGTCTTTAAAGGGTAACATCGATCATGTATTCCACTTAGCTGCT | |
| | | GTTTATGATATGGGTGCCGACGAAGAAGCTCAAGCCGCTACTA | |
| | | ATATTGAAGGTACAAGAGCAGCCGTCCAAGCTGCTGAAGCTAT | |
| | | GGGTGCTAAACATTTCCATCACGTTTCTTCAATCGCTGCTGCTG | |
| | | GTTTGTTCAAGGGTATTTTTAGAGAAGACATGTTTGAAGAAGCT | |
| | | GAAAAATTGGATCATCCATATTTGAGAACTAAGCACGAAAGTG | |
| | | AAAAAGTTGTCAGAGAAGAATGTAAAGTTCCTTTTAGAATCTA | |
| | | CAGACCTGGTATGGTTATTGGTCATTCTGAAACCGGTGAAATG | |
| | | GATAAAGTTGACGGTCCATACTACTTTTTCAAGATGATCCAAA | |
| | | AGATTAGACACGCTTTGCCACAATGGGTTCCTACTATCGGTATT | |
| | | GAAGGTGGTAGATTAAACATCGTACCTGTTGATTTTGTAGTTGA | |
| | | TGCATTGGACCATATTGCCCACTTAGAAGGTGAAGATGGTAAT | |
| | | TGTTTCCATTTGGTCGATTCTGACCCATACAAAGTAGGTGAAAT | |
| | | TTTAAACATATTTTGCGAAGCAGGTCACGCCCCTAGAATGGGT | |
| | | ATGAGAATCGATTCAAGAATGTTCGGTTTCATTCCACCTTTTAT | |
| | | AAGACAATCTATTAAAAATTTGCCACCTGTTAAGAGAATTACT | |
| | | GGTGCTTTGTTAGATGACATGGGTATTCCACCTTCTGTTATGTC | |
| | | ATTCATAAACTACCCAACCAGATTTGACACTAGAGAATTGGAA | |
| | | AGAGTTTTGAAGGGTACAGATATAGAAGTCCCAAGATTACCTT | |
| | | CTTATGCTCCAGTTATATGGGATTACTGGGAAAGAAACTTAGA | |
| | | TCCAGATTTGTTTAAAGATAGAACATTGAAGGGTACTGTAGAG | |
| | | GGTAAAGTTTGTGTCGTAACAGGTGCTACCTCCGGTATTGGTTT | |
| | | GGCTACAGCAGAAAAATTGGCCGAAGCTGGTGCAATCTTGGTT | |
| | | ATTGGTGCAAGAACTAAGGAAACATTGGATGAAGTTGCCGCTA | |
| | | GTTTAGAAGCAAAAGGTGGTAATGTCCATGCCTATCAATGTGA | |
| | | TTTCTCTGACATGGATGACTGCGATAGATTCGTTAAGACTGTCT | |

TABLE 4-continued

Codon optimized gene sequences.

| NT ID | Gene name | Sequence | SEQ ID NO |
|---|---|---|---|
| | | TGGATAATCATGGTCACGTTGATGTATTAGTTAATAACGCTGGT AGATCCATAAGAAGAAGTTTGGCATTATCTTTTGATAGATTCCA TGACTTCGAAAGAACAATGCAATTGAACTACTTCGGTTCAGTT AGATTGATTATGGGTTTTGCCCCAGCTATGTTGGAAAGAAGAA GAGGTCATGTTGTCAATATATCCAGTATCGGTGTATTAACAAAC GCTCCTAGATTCTCAGCATACGTTTCTTCAAAATCAGCTTTGGA CGCATTTTCCAGATGCGCAGCCGCTGAATGGTCCGATAGAAAC GTCACCTTTACTACAATTAACATGCCATTGGTAAAGACCCCAAT GATTGCTCCTACTAAAATCTATGATTCTGTTCCAACCTTGACTC CTGACGAAGCAGCCCAAATGGTTGCAGATGCCATAGTCTACAG ACCAAAGAGAATCGCTACTAGATTGGGTGTCTTCGCACAAGTA TTGCATGCTTTGGCACCTAAGATGGGTGAAATCATCATGAACA CAGGTTACAGAATGTTTCCAGATTCACCAGCTGCTGCTGGTTCT AAGAGTGGTGAAAAACCTAAGGTTTCCACAGAACAAGTAGCAT TTGCCGCCATTATGAGAGGTATCTATTGGTAA | |
| 17 | RtACC1 | ATGCCATTCTCTGGCGAGGCGAAGGCGGTCAACGGATCGCACT CGGTCGACGAGGCGCCGAAGAACCCCAAGTACGACCATGGGC GGGTCGTAAAGTACCTCGGCGGCAACTCGCTCGAATCTGCGCC CCCTTCCAAGGTCGCCGACTGGGTCAGGGAGCGTGGTGGACAC ACCGTCATCACAAAGATCCTCATCGCCAACAATGGTATCGCCG CAGTCAAGGAGATCCGCTCGGTGCGCAAGTGGGCGTACGAGAC GTTCGGAAGCGAGCGCGCGATCGAGTTTACCGTCATGGCGACC CCGGAGGACCTCAAGGTCAACGCAGACTACATCCGCATGGCCG ATCAGTACGTCGAGGTTCCCGGTGGAACCAACAACAACAACTA CGCCAACGTCGATGTCATCGTCGATGTTGCCGAGCGCGCAGGC GTCCACGCCGTCTGGGCAGGATGGGGCCACGCCTCCGAGAACC CCCGCCTTCCCGAGTCGCTCGCCGCCTCGAAGCACAAGATCGT CTTCATCGGTCCTCCCGGCTCCGCCATGCGCTCGCTCGGAGACA AGATCTCGTCGACCATCGTCGCGCAGCACGCCCAGGTTCCGTG CATGGACTGGTCCGGCCAGGGCGTCGACCAAGTCACCCAGTCG CCCGAGGGCTACGTTACTGTCGCCGACGACGTCTACCAGCAGG CCTGTGTGCACGACGCCGACGAGGGTCTCGCCCGCGCGTCGAG GATCGGATACCCCGTCATGATCAAGGCGTCCGAGGGAGGAGGA GGAAAGGGTATTCGCAAGGTCGAGAAGGAGCAGGACTTTAAG CAGGCCTTCCAGGCTGTCCTCACCGAGGTTCCCGGCTCGCCCGT CTTTATCATGAAGCTCGCCGGCGCAGCTCGCCACCTCGAGGTCC AGGTTCTCGCCGACCAGTACGGCAACGCCATCTCGCTCTTCGGC CGTGACTGCTCGGTTCAGCGTCGCCACCAGAAGATCATCGAAG AGGCGCCCGTCACCATCGCCAAGCCCGACACGTTCGAGCAGAT GGAAAAGTCGGCCGTCCGCCTTGCCAAGCTCGTCGGCTACGTC TCGGCGGGTACCGTCGAGTTCCTCTACTCGGCTGCCGACGACA AGTTTGCCTTCCTCGAGCTCAACCCGCGTCTCCAGGTCGAGCAC CCGACCACCGAGATGGTTTCGGGCGTCAACCTTCCCGCCGCCC AGCTCCAGGTCGCTATGGGTGTTCCCCTCCATCGCATCCGCGAC ATCCGCACGCTCTACGGCAAGGCACCCAACGGCAGCAGCGAGA TCGATTTCGACTTCGAGAACCCCGAGTCGGCCAAGACGCAGCG CAAGCCCTCGCCGAAGGGTCACGTCGTTGCCGTACGTATCACG GCTGAGAACCCTGACGCCGGCTTCAAGCCGTCCATGGGTACTC TCCAAGAGCTCAACTTCCGCTCGAGCACGAACGTCTGGGGTTA CTTCTCCGTCGGCAGCGCCGGTGGACTGCACGAGTTTGCCGACT CGCAGTTCGGCCACATCTTTGCGTACGGCTCGGACCGTTCCGAG TCGCGCAAGAACATGGTCGTCGCGCTCAAGGAGCTCTCGATTC GCGGTGACTTCCGCACGACCGTCGAGTACCTCATCAAGCTTCTC GAGACGGACGCGTTCGAGCAGAACACGATCACGACCGCGTGG CTCGACAGCCTCATCTCGGCTCGCCTGACCGCCGAGAGGCCCG ACACGACTCTCGCCATCATCTGCGGCGCCGTTACCAAGGCCCA CCTCGCTTCCGAGGCCAACATCGCCGAGTACAAGCGCATCCTC GAGAAGGGTCAGAGCCCGCCAAGGAGCTCCTCGCCACCGTCG TCCCGCTCGAGTTCGTCCTCGAGGACGTCAAGTACCGCGCGAC CGCCTCGCGCTCGTCGCCTTCGAGCTGGTCCATCTACGTCAACG GCTCGAACGTCTCCGTCGGCATCCGCCCTCTCGCCGACGGCGGT CTCCTCATCCTCCTTGACGGCCGCTCGTACACCTGCTACGCCAA GGAGGAGGTCGGCGCGCTCCGCCTCTCGATCGACTCGAGGACC GTCCTCATTGCTCAGGAGAACGACCCCACCCAGCTTCGCTCGCC TTCACCCGGCAAGCTCGTCCGCTACTTCATCGAGTCCGGCGAGC ACATCTCGAAGGGCGAGGCGTACGCTGAGATCGAGGTCATGAA GATGATCATGCCCCTCATCGCTGCCGAGGACGGTATCGCGCAA TTCATCAAGCAGCCGGGAGCGACGCTCGAGGCCGGCGACATCC TCGGTATCTTGTCGCTCGACGACCCGAGCCGCGTCCACCACGCC AAGCCGTTCGATGGCCAGCTTCCCGCCCTTGGCTTGCCCTCCAT CGTCGGCAACAAGCCGCACCAGCGCTTCGCCTACCTCAAAGAC GTGCTCTCAAACATCCTCATGGGCTACGACAACCAGGCCGTCA TGCAGTCGAGCATCAAGGAGCTCATCTCGGTTCTTCGCAACCCC | 174 |

TABLE 4-continued

Codon optimized gene sequences.

| NT ID | Gene name | Sequence | SEQ ID NO |
|---|---|---|---|
| | | GAGCTCCCCTACGGCGAGGCCAACGCTGTCCTCTCGACGCTTTC | |
| | | GGGTCGCATCCCCGCCAAGCTCGAGCAGACCCTCCGCCAGTAC | |
| | | ATCGACCAGGCTCACGAGTCTGGCGCCGAGTTCCCGTCCGCCA | |
| | | AGTGCCGCAAGGCGATCGACACGACCCTTGAGCAGCTCCGCCC | |
| | | CGCCGAGGCGCAGACTGTCCGCAACTTCCTCGTCGCGTTCGAC | |
| | | GACATCGTCTACCGCTACCGCTCGGGCCTCAAGCACCACGAGT | |
| | | GGTCAACGCTCGCCGGCATCTTTGCCGCGTACGCCGAGACGGA | |
| | | GAAGCCGTTCAGCGGCAAGGACGGCGACGTCGTCCTCGAGCTC | |
| | | CGCGACGCCCACCGCGACTCGCTCGACTCGGTCGTCAAGATCG | |
| | | TTCTCTCGCACTACAAGGCTGCCTCGAAGAACTCGCTTGTCCTT | |
| | | GCGCTCCTCGACATCGTCAAGGACTCGGACGCGGTTCCGCTCA | |
| | | TCGAGCAGGTCGTCAGCCCTGCGCTCAAGGACCTCGCCGACCT | |
| | | CGACTCGAAGGCCACGACTAAGGTCGCCCTGAAGGCCCGCGAG | |
| | | GTGCTCATCCACATCCAGCTCCCCTCGCTCGACGAGCGCCTCGG | |
| | | ACAGCTCGAGCAGATTCTCAAGGCCTCGGTGACGCCCACCGTT | |
| | | TACGGCGAGCCCGGCCACGACCGCACTCCTCGCGGTGAAGTCC | |
| | | TTAAGGACGTCATCGACTCGCGCTTCACCGTCTTTGACGTTCTC | |
| | | CCGAGCTTCTTCCAGCACCAGGACCACTGGGTCTCGCTCGCCGC | |
| | | GCTCGACACCTACGTCCGCCGCGCCTACCGCTCGTACAACCTCC | |
| | | TCAACATCGAGCACATCGAGGCCGATGCCGCCGAGGACGAGCC | |
| | | CGCGACGGTTGCCTGGTCGTTCCGCATGCGCAAGGCTGCGTCC | |
| | | GAGTCTGAGCCGCCCACGCCCACGACCGGCCTCACGTCGCAGC | |
| | | GCACCGCCTCGTACTCGGACTTGACGTTCCTCCTCAACAACGCC | |
| | | CAGTCCGAGCCGATCCGCTACGGCGCGATGTTCTCGGTCCGCTC | |
| | | GCTCGACCGCTTCCGCCAGGAGCTCGGTACCGTCCTCCGACACT | |
| | | TCCCCGACTCGAACAAGGGCAAGCTCCAGCAGCAGCCTGCCGC | |
| | | GTCGTCGAGCCAGGAGCAGTGGAACGTCATCAACGTCGCGCTC | |
| | | ACGGTCCCCGCCAGCGCGCAGGTCGACGAGGACGCTCTCCGCG | |
| | | CCGACTTTGCCGCTCACGTGAACGCGATGAGCGCCGAGATCGA | |
| | | CGCTCGCGGCATGCGCCGCCTCACCCTCCTCATCTGCCGCGAGG | |
| | | GCCAGTACCCGTCCTACTACACCGTCCGCAAGCAGGACGGCAC | |
| | | CTGGAAGGAGCTCGAGACGATCCGCGACATCGAGCCCGCCCTC | |
| | | GCCTTCCAGCTCGAGTTGGGCCGCCTCTCCAACTTCCACCTCGA | |
| | | GCCGTGCCCCGTTGAGAACCGCCAGGTCCACGTCTACTACGCG | |
| | | ACCGCCAAGGGCAACTCGTCCGACTGCCGCTTCTTCGTCCGCGC | |
| | | ACTCGTCCGCCCTGGCCGTCTCCGCGGTAACATGAAGACGGCC | |
| | | GACTACCTCGTCTCCGAGGCTGACCGCCTCGTCACCGATGTCCT | |
| | | CGACTCGCTCGAGGTCGCCAGCTCGCAGCGCCGCGCTGCCGAC | |
| | | GGCAACCACATCTCGCTCAACTTCCTGTACTCTCTCCGTCTCGA | |
| | | CTTTGACGAGGTCCAGGCTGCCCTCGCCGGCTTCATCGACCGCC | |
| | | ACGGCAAGCGCTTCTGGCGTCTCCGCGTCACCGGCGCCGAGAT | |
| | | CCGCATCGTCCTCGAGGACGCGCAGGGCAACATTCAGCCCATC | |
| | | CGCGCCATCATCGAGAACGTCTCGGGTTTCGTCGTCAAGTACG | |
| | | AGGCGTACCGCGAGGTCACGACCGACAAGGGCCAGGTCATCCT | |
| | | CAAGTCGATCGGTCCGCAGGGCGCGTTGCACCTTCAGCCGGTC | |
| | | AACTTCCCCTACCCGACCAAGGAGTGGCTTCAGCCGAAGCGCT | |
| | | ACAAGGCCCACGTCGTCGGCACGACGTACGTCTACGACTTCCC | |
| | | CGACCTTTTCCGCCAGGCAATCCGCAAGCAGTGGAAGGCGGCC | |
| | | GGCAAGACTGCGCCCGCCGAGCTCCTCGTCGCCAAGGAGCTCG | |
| | | TCCTCGACGAGTTCGGCAAGCCTCAGGAGGTCGCCCGCCCGCC | |
| | | TGGCACCAACAATATCGGCATGGTCGGCTGGATCTACACGATC | |
| | | TTCACGCCCGAATACCCCTCTGGCCGCCGCGTCGTCGTCATCGC | |
| | | GAACGACATCACGTTCAAGATTGGTTCGTTCGGCCCGGAGGAG | |
| | | GACCGCTACTTCTTCGCCGTCACGCAGCTCGCGCGCCAACTTGG | |
| | | CTTGCCGCGCGTCTACCTCTCGGCCAACTCGGGTGCTCGTCTCG | |
| | | GCATTGCCGAGGAGCTCGTCGACTTGTTCAGCGTCGCGTGGGT | |
| | | CGACAGCTCGCGGCCGGAGAAGGGCTTCAAGTACCTCTACCTA | |
| | | ACCGCCGAGAAGCTCGGCGAGCTCAAGAACAAGGGCGAGAAG | |
| | | AGCGTCATCACGAAGCGCATCGAGGACGAGGGCGAGACGCGC | |
| | | TACCAGATCACCGACATCATCGGCTTGCAGGAGGGTCTCGGTG | |
| | | TCGAGTCGCTCAAGGGCTCTGGCCTCATCGCCGGTGAGACGTC | |
| | | GCGCGCGTACGACGACATCTTCACGATCACGCTCGTCACCGCC | |
| | | CGCTCGGTCGGTATCGGTGCGTACCTCGTCCGCCTCGGCCAGCG | |
| | | TGCCGTCCAGGTCGAGGGCCAGCCGATCATCCTCACCGGTGCC | |
| | | GGCGCGCTCAACAAGGTCCTCGGTCGCGAGGTGTACTCGTCCA | |
| | | ACTTGCAGCTCGGCGGCACGCAGATCATGTACAAGAACGGTGT | |
| | | CTCGCACTTGACGGCCGCCAACGACCTCGAGGGTGTCCTCAGC | |
| | | ATCGTCCAGTGGCTCGCCTTCGTCCCCGAGCACCGCGGCGCGC | |
| | | CTCTCCCGATCATGCCTTCGCCCGTCGACCCGTGGGACCGCTCG | |
| | | ATCGACTACACGCCCATCAAGGGCGCGTACGACCCGCGCTGGT | |
| | | TCCTCGCCGGCAAGACGGACGAGGCCGACGGTCGCTGGCTCTC | |
| | | TGGCTTCTTCGACAAGGGCTCGTTCCAGGAGACGCTCTCGGGCT | |
| | | GGGCGCAGACCGTCGTCGTCGGTCGCGCTCGCCTCGGCGGCAT | |
| | | CCCCATGGGCGCCATCGCGGTCGAGACCCGCACCATCGAGCGC | |

TABLE 4-continued

Codon optimized gene sequences.

| NT ID | Gene name | Sequence | SEQ ID NO |
|---|---|---|---|
| | | GTCGTGCCCGCCGACCCTGCCAACCCTCTCTCGAACGAGCAGA<br>AGATCATGGAGGCCGGTCAGGTCTGGTATCCCAACAGCTCGTT<br>CAAGACGGGACAGGCGATCTTCGACTTCAACCGCGAGGGTCTC<br>CCGCTCATCATCTTCGCCAACTGGCGCGGCTTCTCGGGCGGCCA<br>GCAGGACATGTTCGACGAGGTCCTCAAGCGCGGTTCGCTCATT<br>GTCGACGGTCTCTCGGCGTACAAGCAGCCCGTCTTCGTCTACAT<br>CGTCCCGAACGGCGAACTTCGCGGCGGTGCTTGGGTCGTCCTC<br>GACCCGTCGATCAACGCCGAGGGCATGATGGAGATGTACGTCG<br>ACGAGACTGCTCGCGCCGGTGTCCTCGAGCCCGAGGGCATCGT<br>CGAGATCAAGCTCCGCAAGGACAAGCTCCTCGCCCTCATGGAC<br>CGCCTCGACCCGACCTACCACGCCCTCCGCGTCAAGTCGACCG<br>ACGCTTCGCTCTCGCCCGCCGACGCCGCGCAGGCCAAGACCGA<br>GCTCGCCGCGCGCGAGAAGCAGCTCATGCCGATCTACCAGCAG<br>GTCGCGCTCCAGTTCGCCGACTCGCACGACAAGGCCGGCCGCA<br>TCCTCAGCAAGGGCTGCGCGCGCGAGGCCCTCGAGTGGTCGAA<br>CGCTCGTCGCTACTTCTACGCCCGCCTCCGCCGCCGTCTCGCCG<br>AGGAGGCCGCCGTCAAGCGTCTCGGCGACGCCGACCCGACCCT<br>CTCGCGCGACGAGCGCCTCGCCATCGTCCACGACGCCGTCGGC<br>CAGGGTGTCGACCTCAACAACGACCTCGCTGCTGCCGCCGCGT<br>TCGAGCAGGGCGCCGCCGCCATCACCGAGCGCGTCAAGCTCGC<br>GCGCGCGACGACCGTCGCCTCGACTCTCGCGCAGCTCGCGCAG<br>GACGACAAGGAGGCTTTCGCCGCCTCGCTCCAGCAGGTCCTCG<br>GCGACAAGCTCACCGCCGCCGACCTCGCCCGCATCCTCGCCTA<br>G | |
| 20 | RtFAS 1 | ATGAACGGCCGAGCGACGCGGAGCGTGACTGGGACGTCGACG<br>CCGGTCCACACGGCGACGACCCGACCCCTCGTCCTCTTGCACCC<br>CTCGACCCAAACCCGCATCTCGCTGCACGTCCCCTCCACGTCGC<br>AGGAATGGATCGCCGCCGAAGTCGCGCGCGACACCTTCCAGGA<br>CTGGCTTCACGCTGCCGAGAAGAGCGGAAACCTCGTCGGATTC<br>GAGGCGGCCGAGCTTGACGACGAGCAGGCTGGCGAGGGCGAC<br>GACGAGAAGGAGCTCGTCCTCACCGCCTACTTCTTGAAGCACG<br>TTGCCGGCCTTCTCCCCTTCCCGTCGACAGCTACCTCCCCCGCC<br>ACCGCCGCCGTCCTCCTCGCCGCCTTCAACCACTTTGCGTCCGT<br>CTACCTCAGCGGAACCGATGTTCACACCCTCACTGCCTCGCTCG<br>CTGCTCCCGTCCGCGCTCTCGTCATCTCGTCCTTCTTCCTCGCCA<br>AGACCAAGCTCGAGGTCGAGGGACTCGGCAAGGTCTTGCCCAA<br>GCAGTCCGAGTCGGCGCTCCTGCAGAAGGCTGCGACCGGCCAG<br>GCAGAGGTCTTCGCTCTCTTCGGTGGTCAGGGAATGAACGAGG<br>TCTACTTTGACGAGCTCCAGACCCTCCACGACCTTTACACCCCG<br>CTGCTTACGCCCTTCCTCGCCCGCGCCTCCGAACACCTCGTCTC<br>TCTCGCTGCCGCCGAGCAGCACACCCTCCTTTACGACCACTCGC<br>TCGACGCCCTTGCCTGGCTGCAAGATCCCTCTACCCGCCCCGAA<br>GTCCCCTACCTCGCGACTTGCGCCGTCTCGCTCCCTCTCATCGG<br>TCTCACTCAGCTCTGCCAGTACGTCGTGTACGGCAAGGGCTCGT<br>CGCTCGGTCCCGCCGAGCTCGGCGCCAAGTTCAAGGGCGCGAC<br>CGGCCACTCGCAGGGTGTCGTCTCGGCTCTTGTCATCGCGCACG<br>AGTACCCTCCCGCGTCCAAGGACGGCAGCGACGCGTGGGAGCC<br>TTTCTACGAGCAGGCCCTTCGCGGTTTGACCGTCCTCTTCCAGA<br>TCGGTCTCCAGGGCACGCTCGCCTTCCCCTCCATCGCCATTTCG<br>CCCGCTCTCGAGTCGAGCTCGGTCGAGAATGGCGAGGGTGTCC<br>CGACTGCCATGCTTGCCGTCACCGGCCTCGACCTCAAGTCGCTC<br>GAGAAGAAGATCGCCGAGGTCAATGGGCACGTCAAGTCTGAG<br>GGCCGCGACGAGACCGTCTCGATCAGTCTCTACAACGGTGCGA<br>GGGCGTTCGTCGTCACTGGTGCGCCGAAGGACCTCGTCGGTCT<br>CGCCGACGGCCTTCGCAAGAACCGCGCGCCGGCCGGCAAGGAC<br>CAGTCGAAGATCCCGCACTCGAAGCGTCTCCCCGTCTTCTCGAT<br>GCGCTTCCTCCCCATCAACGTTCCCTACCACTCGCATCTCCTCC<br>AAGGCGCGACCGAGAAGGCGCTCGCGACGTTCTCGGCTGAGGA<br>GGCCGCCCACTGGGCGCCTTCATCGTTCACCTGCGCCGTCTACA<br>ACACCGAGGACGGCTCCGACATGCGCCAGCTCTCGGCTTCGTC<br>GGTTCTCGAGTCGGTCTTCCAGCAGATCTTCACCTCGCCCATTC<br>ACTGGGTCTCGCACGCCACCAACTTCCCCTCGTCCGCGACGCAC<br>GCCATCGATTTCGGCACGGGCGGCGCGAGCGGCATCGGTTCGC<br>TCTGCGCGCGCAACTGGGAGGGCCGCGGTATCCGCACGATTAT<br>GCTCGGCAACCGCGGCGAGGGCGTTGGTGCCGGCAAGGAGGCT<br>TGGGGCAAGAAGGTCCCGACCGAGGAGAAGTGGAACGAGCGC<br>TTCCACCCTCGCCTCGTCCGCACCAGCGACGGCAAGATCCACCT<br>CGACACGCCCTTCTCGCGCCTCCTCTCGAAGCCGCCCCTCATGG<br>TCGGTGGTATGACCCCGACGACCGTCAAGGCCGGCTTCGTCTC<br>GGCCGTTCTCCGCGCGGGCTACCACATCGAGCTCGCTGGCGGC<br>GGTCACTACAACGAGAAGGCTGTCCGTGCCAAGGTCGCCGAGA<br>TCCAGAAGCTCGTGAACAAGCCCGGCATGGGCATCACCCTCAA<br>CTCGCTCTACATCAACCAGCGCCAGTGGACGTTCCAGTTCCCGC | 175 |

TABLE 4-continued

Codon optimized gene sequences.

| NT ID | Gene name | Sequence | SEQ ID NO |
|---|---|---|---|
| | | TCTGGGCCAAGATGAAGCAGGAGGGCGAGCCCGTCGAGGGTCT<br>CTGTGTTGCTGCCGGTATTCCCTCAACCGAGAAGGCCAAGGAG<br>ATCATCGACACGCTCCGCGAGGCCGGCATCAAGCACGTCTCGT<br>TCAAGCCCGGTTCGGTCGACGGCATCCGCCAGGTCGTCAACAT<br>CGCCTCCGCCAACCCCGACTTCCCCATCATCCTCCAGTGGACTG<br>GTGGTCGCGCCGGCGGTCACCACTCGTGCGAGGACTTCCACGC<br>CCCGATCCTCGCGACGTACGCTTCGATCCGTCAGCACCCCAAC<br>ATCAAGCTCGTCGCCGGCTCTGGCTTCGGCTCGGCTGAGGGAT<br>GCTACCCTTACCTTTCGGGCGAGTGGTCGGAGAAGCAGTACGG<br>CGTCGCGCGCATGCCGTTCGACGGCTTCATGTTTGCTTCGTGGG<br>TCATGGTCGCCAAGGAGGCGCACACGAGCGAGTCGGTCAAGCA<br>GCTCATCGTCGACGCGCCTGGTGTCGAGGATGGCCAGTGGGAG<br>CAGACGTACGACAAGCCGACCGGCGGCATCCTCACCGTCAACT<br>CGGAGCTTGGCGAGCCGATCCACAAGGTCGCGACTCGTGGTGT<br>CAAGCTGTGGGCCGAGTTCGACAAGAAGGTCTTCTCGCTGTCG<br>AAGGAGAAGCAGCTCGCATGGCTCGCCGACAACAAGAAGTAC<br>GTTATCGACCGCCTCAACGCCGATTTCCAGAAGCCCTGGTTCCC<br>CGCCAAGGCCGACGGCTCTCCTTGCGACCTTGCCGACATGACC<br>TACGCCGAGGTCAACGCCCGCCTCGTCCGCCTCATGTACGTCGC<br>GCACGAGAAGCGCTGGATCGACCCGTCGCTCCGCAACCTCGTC<br>GGCGACTGGATCCGCCGTGTTGAGGAGCGTCTCTCGAACGTCA<br>ACGACTCGGGCATCAAGATCTCGGCACTCCAGTCGTACTCGGA<br>GCTGAACGAGCCTGAGGCGTTCCTCAAGCAGTTCCTCGCCCAG<br>TACCCGCAGGCCGAGGACCAGATCCTCGCCTCCGCCGACGTTT<br>CCTACTTCCTCGCCATCTCTCAACGCCCCGGACAGAAGCCCGTC<br>CCCTTCATCCCCGTCCTCGACGCCAACTTCAGCATCTGGTTCAA<br>GAAGGACTCGCTGTGGCAGGCCGAGGACATCGAGGCCGTCTTT<br>GACCAGGACCCGCAGCGTGTCTGCATCCTCCAGGGACCGGTCG<br>CCGCCAAGCACTGCACCTCGACGCAGACGCCCATCGCCGAGAT<br>GCTCGGCAACATCGAGCACCAGCTCGTCAAGAACGTCCTGGAC<br>GACTACTACGGCGGCGACGAGTCCCAGATCCCGACTATCGACT<br>ACCTCGCGCCCCCTCCCAAGCCGGTCGACGCCGGCGCTATCCTC<br>GCCGAGAACAACATCGCGCACTCGGTCGAGGAGCTCGCCGACG<br>GCGGCAAGAAGCATGTCTACTCGATCAACGGTGTCCTCCCGCC<br>GACGGGCGACTGGCATGCCGCACTCGCCGGCCCCAAGCTCGAC<br>TGGCTCCAGGCGTTCCTCTCCAACGTCTCGATTCAGGCGGGCGA<br>GCAGTCGATTCCTAACCCCGTCAAGAAGGTGCTGGCGCCGAGG<br>CACGGGCAGCGGGTCGAGCTCACCCTGAACAAGGACGGCCAG<br>CCCCTCAAGCTCGACGTCTTCGGCGGGCTCTGA | |
| 21 | RtFAS 2 | ATGGTCGCGGCGCAGGACTTGCCGCTCGCGCTGAGCATCAGCT<br>TCGCGCCCGAGTCGTCGACCATCTCGATGACGCTGTTCAACCA<br>GCCCGAGGCGTCGAAACCCGCCCTCCCCCTCGAGCTCAAGTAC<br>AAGTACGACCCCTCGACGCCGTACGCCCCGATCCACGAGATCA<br>CCGAGGACCGTAATCAGAGGATCAAGCAGCACTACTGGGACCT<br>CTGGGGCCTCGGCAACAAGGCAGACCAGGGCATCTCGCAGCTC<br>AAGATCACCGACGAGTTCCAGGGCGACCTCGTCACCATCTCGG<br>CCGACGAGATCGAGGCGTTCTGCCGTGTTGTCGGCATCGAGGG<br>CGAGGCGTACAAGCGCAACCACAAGGCCGGCATGCAGGTCCC<br>GCTCGACTTCGCCATCAAGCTCGGCTGGAAGGCCATCATGAAG<br>CCGATCTTCCCCTCGACGATTGACGGCGACCTGCTCAAGCTCGT<br>CCACCTCTCGAACGGCTTCCGCGTCCTCCCCGACACGCCCACAC<br>TCCAGGTTGGCGACGTCGTGACGACCACGTCGCGCATCGAATC<br>AATCACGAACTCGGACACGGGCAAAACCGTCTCGGTTCGCGGC<br>GTCATCTCGCTCGTCTCGTCCGCCGACTCGAAGGGCAAGGACG<br>CCTCGACCGAGGACCGCATCCCGCTCATCGAGGTCACCTCGTC<br>CTTCTTCTACCGCGGCAAGTTCAGCGACTACGCCCAGACATTCT<br>CCCGCGTCGCCCACCCGACCTACTCTGTCCCGATCACCACGCCC<br>GAGGCCGTCGCCGTCCTCCAGTCCAAGGAGTGGTTCCAGTGGG<br>ACGACGACTCGAAGCCCCTCGAGGTCGGCACCAAGCTCCAGTT<br>CAAGGTCGAGTCGAACTATGTCTACGCCGACAAGTCGTCCTAC<br>GCGATGGCTACCGTCACCGGCGGCGCGTACGTCATCACCCCCG<br>AGCTCAAGCTCGCTGTCAAGGTTGCCACGGTCGACTACACGTC<br>CGAGGGCGAGGGCGTCATCCAGGGCGACCCGGTCATCGAGTAC<br>CTCAAGCGCCACGGCTCGGCCCTCGACCAGCCCATCATGCTCG<br>AGAACGGCGGCTATTCGCTCACCAAGGCCGGCCAGTGCACCTT<br>CACGACGCCCGCGTCCAACCTCGACTACTCGCTCACCTCGGGC<br>GACACGAACCCGATTCACACGAACCCGTACTTTGCCTCGCTCG<br>CCTACCTCCCCGGCACCATCACGCACGGCATGCACTCGTCGGC<br>CCGCACGCGCAAGTTTGTCGAGCAGGTCGCCGCAGACAACGTC<br>GGCGCGCGCGTCCGCAAGTACGAGGTCGGCTTCACGGCCATGT<br>GCCTCCCCTCGCGCAAGATGGAGGTCCGCCTTAAGCACGTCGG<br>CATGACCGCGGACGGAAACCGCCTCATCAAGGTCGAGACCGTC<br>GACGTCGAGGGCGGCAACGTCGTTCTCAGCGGAACCGCCGAGG | 176 |

TABLE 4-continued

| Codon optimized gene sequences. | | | |
|---|---|---|---|
| NT ID | Gene name | Sequence | SEQ ID NO |
| | | TCGCCCAGGCTCCCACCGCGTACGTCTTCACCGGTCAAGGTTCG<br>CAAGAGCCCGGCATGGGCATGGAGCTCTACGCCAACTCGCCCG<br>TCGCCCGCGCCGTCTGGGACGAGGCTGACCGCCACCTCGGCGA<br>GGTCTACGGCTTCTCCATCCTCGAGATTGTCCGTACGAACCCCA<br>AGGAAAAGACTGTGCACTTCGGCGGGTTGAAAGGCCAAGCAA<br>CCCGTCAGAAGTACATGGACATGTCGTACACAACGACTGACCA<br>TGAGGGCAACGTTAAGACTCTCCCGCTCTTCGGCGACATCGAC<br>CTCCGTACCTCACGCTACACGTTCTCGTCGCCGACCGGTCTCCT<br>CTACGCCACCCAGTTCGCCCAGATCGCCCTCGTCGTAACGGAG<br>AAGGCCGCCTTCGAGGACATGCGCGCCAAGGGTCTCGTTCAGA<br>AGGACTGCGTCTTTGCCGGTCACTCGCTCGGAGAGTACTCGGCT<br>CTCGCCTCGATCGCCGACATCCTCCCCATCTCGGCCCTCGTCGA<br>CGTCGTCTTCTACCGCGGTATCACCATGCAGCGCGCCGTCGAAC<br>GCGACCACCTCAACCGCTCGTCGTACGGAATGGTCGCCGTCAA<br>CCCGAGCCGCATCGGCAAGAGCTTTGGCGACGCCGCCCTCCGC<br>GAGGTCGTCGACACCATCGCCCGCCGCGGAAACATCCTCATCG<br>AGGTCGTCAACTACAACGTCGAGGGACAGCAATACGTCGTCGC<br>CGGTCACCTCGTCGCCCTCCAATCCCTCACAAACGTCCTCAACT<br>TCCTCAAGATCCAGAAGATCGACCTCGCCAAGCTCACCGAGAC<br>GATGTCGATCGAGCAGGTCAAGGAGCACCTGTGCGAGATCGTC<br>GACGAGTGCGTCCAGAAGGCGCGCGACCTCCAGGCCAAGACG<br>GGCTTCATCACCCTCGAGCGCGGCTTTGCGACGATCCCGCTCCC<br>CGGTATCGACGTGCCGTTCCACTCGCGCTACCTCTGGGCGGGA<br>GTCATGCCGTTCCGCACTTACCTCTCGAAGAAGGTCAACCCGG<br>CGCACTTCAACGCCGACCTCCTCGTCGGCCGCTACATCCCCAAC<br>TTGACCGCCGTCCACTACGAGGTCTCGAAGGAGTACGCCGAAC<br>GCATCCACACCCAGACGTCGTCGCCGCGCCTCAACAAGATTCT<br>CAAGGCCTGGGACGAGGAGCGCTGGGGCGCACCCGAGAACCG<br>CAACAAGCTCGGCTACGCCATCCTCATCGAGCTCCTCGCGTACC<br>AGTTCGCCTCGCCCGTCCGCTGGATCGAGACGCAGGACATCCT<br>CTTCCGCGACTTCAAGTTTGAGCGCCTCGTCGAGCTTGGCCCGT<br>CGCCCACTCTCACCGGCATGGCTACGCGCACGCAGAAGCTCAA<br>GTACGACGCGCACGACTCGTCGGTCGGCATCAAGCGCTCGATC<br>TACTGCATCGCCAAGCACCAGAAGGAGATCTACTACCAGTTCG<br>ATGACGTTGCCGGCGAAGAGGCGCCCGCTCCTGCCGCAGTTGC<br>GCCTTCCGCTCCCGCTCCCAAGGCCGCCCCAGTCGCCGCCGCCC<br>CTCCCCCTCCCGCTCCTGTCGCTGCCGCGCCTGCCGCCGCCGTC<br>GCCGACGAGCCGCTCAAGGCTGTCGACACGCTCCGCATCATCA<br>TCGCGCAGAAGCTCAAGAAGCCCGTTGGCGAAGTCCCCCTCAC<br>CAAGTCGATCAAGGAGCTCGTCGGCGGCAAGTCGACCCTCCAG<br>AACGAGATTCTCGGCGACCTTCAAGGCGAGTTCAGCAGCGCGC<br>CTGAAAAGGGCGAGGAGATGCCTCTCCAGGAGCTCGGCGCGGC<br>CCTCCAGCAGGGCTACTCTGGCAAGCTCGGCAAGTACACCACC<br>GGCGTCATCTCGCGCATGATTGGCGCCAAGATGCCCGGCGGTT<br>TTGGTCTCTCCGCCGTCCAGGGTCACCTCGGCAAGACCTACGGC<br>CTCGGCGCCGGTCGCATCGATGGCGTCCTCCTCTTCGCCGTCAC<br>GCAGGAGCCGGCTAAGCGTCTCGCCAACGAGGGTGAGGCGAA<br>GGCTTGGGTCGACTCGGTCGCGCAAGGCTACGCCTCGATGGCT<br>GGCATCTCGCTCGCCGCCGGCGGTGGAGCTGCTGCTGCTGCCC<br>CCGCGATGGCGTTCGCCGCTCCGGCCGCAGCTGGCGGTGGAGC<br>GCCCGCTGCCGTCCCCGACGAGCCGCTCAAGGCGACCGACACG<br>CTTCGCGCCATCATCGCTCAGAAGCTCAAGAAGCAGATCCCCG<br>ACGTCCCCCTCACCAAGTCCATCAAGGACCTTGTCGGCGGCAA<br>GTCGACCCTGCAGAACGAGATCCTCGGCGACCTCCAGGGCGAG<br>TTCAGCAGTGCGCCCGAGAAGGGCGAGGAGATGCCGCTCCAGG<br>AGCTTGGCGCCGCACTCAACCAAGGCTACTCGGGCACGCTCGG<br>CAAGCACACGAGCGGTCTCGTCGCCCGCATGATGGGCGCCAAG<br>ATGCCCGGTGGCTTCGGTCTCTCGGCGGCGAAGGCGCACCTCT<br>CGAAGGCTCACGGTCTCGGGCCCGGCCGCACCGACGGCGCTCT<br>CCTCGTCGCGCTCACCAAGGAGCCCGAGAAACGTCTCGGTAGC<br>GAGGCCGACGCCAAGGCCTGGCTCGACGGCGTCGCTCAGGCGT<br>ACGCCTCGCAGGCTGGCATCACCCTCGGCGCTGGTGGAGGCGG<br>AGGCGGCGCGGCTGTCGGCGGCGCCGGCTTTATGATCAACACC<br>GAGCAGCTCGACAAGATGCAGGAGAAGCAGGACAACTTCGTCT<br>CGCAGCAGGTCGAGCTCTTCCTCCGCTACCTCGGCAAGGACTC<br>GCGCGAGGGCCACCGCCTCGCCGACATGCAGAAGGCAGAGGT<br>CGCCAACCTCCAGGAGAAGCTCGACTCGATCGCTCGCGAGCAC<br>GGCGACGCCTATGTCCAGGGCATCCAGCCCGTCTTCGACCCGC<br>TCAAGGCCCGCCACTTCAACTCGTCGTGGAACTGGGTCCGTCA<br>GGACGCGCTCATGATGTGGATGGACATCCTCTTCGGCCGCCTC<br>ACCACCGTCGACCGCGACATCACCGCTCGCTGCCTTGTCATCAT<br>GAACCGCGCCGACCCTTCTCTCATCGACTACATGCAGTACACC<br>ATCGACAACACCCCCGTCGAGCGCGGCGAGCATTACGTCCTCG<br>CCAAGCAATTCGGCCAGCAGCTCCTCGACAACTGCCGCGAGAT | |

TABLE 4-continued

| Codon optimized gene sequences. | | | |
|---|---|---|---|
| NT ID | Gene name | Sequence | SEQ ID NO |
| | | GATCGGCCAGGCTCCGCTCTACAAGGACGTCACCTTCCCGACC<br>GCGCCCAAGACGACCGTCAACGCCAAGGGCGACATCATCACCG<br>AGGAGGTCAACCGCCCCGGCGTCTCTCGCCTCGAGAAGTATGT<br>CGCCGAGATGGCTGCCGGCTCAAAGGTCACCGTCGCCAGCGTC<br>AACCTCGACAAGGTCCAGGAGCAGGTCGAGAAGCTGTACAAG<br>CTCGTCAAGTCGCAGCCGCAGATTTCGAAGCAGCACATGACGT<br>CGATCAAGTCGCTGTACGCTGAGGTCGTTCGCGGTCTCGGCAA<br>GGACGCCGGCCCTCCTCCGGTCCACAAGGCCGGCACTCGCGCC<br>CGCCGCCCCTCGAGCCAGTTCCTCCGTCCCGCAGCCGTCTCCGA<br>GGCGACTTTCCTCCCCGAGGACAAGGTGCCTCTCCTGCACCTCA<br>AGCGCAAGATCGGCAACGACTGGCAATACTCGAGCAAGCTCAC<br>GTCGCTCTACCTCGACATCCTCAAGGAGATTGCCACGTCGGGT<br>GTCACCTTCGAGCACAAGAACGCGCTCATGACCGGTGTCGGCA<br>AGGGCTCCATCGGTATCGAGATCGTCAAGGGTCTCCTCGCTGG<br>TGGCGCTCGCGTCGTCATCACGACCTCGCGCTACTCGCGCTCGA<br>CTGTCGAGTACTACCAGGCGATCTACCAGGAGGTCGGCTCGAA<br>GGGCTCGTCGCTCACCGTCGTCCCCTTCAACCAGGGCTCGAAG<br>CAGGATGTCGAGGCGCTCGTCGACTTCATTTATTCGAAGGATA<br>AGGGTCTCGGCATGGACCTCGACTACATCCTCCCCTTCGCCGCC<br>CTTCCCGAGAACGGCCGCGAGATCGACGGCATCGACGACCGCT<br>CCGAGCTCGCCCACCGCATCATGCTCACCAACCTCCTCCGCCTC<br>CTCGGTGCCGTCAAGTCGAAGAAGGCCGCCCTCAAGCTCACGA<br>CCCGCCCAACCGAGGTCGTCCTCCCGCTTTCGCCGAACCACGG<br>CCTCTTCGGCAACGACGGTCTCTACTCGGAGTCGAAGATCTCGC<br>TCGAGACGCTCTTCAACCGCTGGAGCTCGGAGAGCTGGGGCGA<br>GTACCTCTGCCTCGCTGGCGCTGTCATCGGATGGACGCGCGGT<br>ACCGGTCTCATGTCGGCGACGAACTCGGTCGCCGAAGGTATCG<br>AGGCGCAGGGTTGCAGGACGTTCTCCGCCAAGGAGATGGCCTT<br>CAACATTCTCGGCCTCATGCACCCGCTCGTCTTCGACGTCGCGC<br>AGATCGAGCCTGTCTGGGCCGACCTCAACGGTGGCATGGACAA<br>GCTCCCCGACCTTGCCAACCTCACGACCGAGATCCGCAAGAAG<br>CTCAACCTCACCGCGTCGACCCGCCGCGCCATCGCCAAGGACA<br>ACTCGTTCGACTACAAGGTCGCGCACGGCCCGGCGATGGAGCA<br>GATACACCAGCGGATCAACGTCGCCCCGCGCGCCAACTTCTCC<br>CTTCCCTTCCCCGAGCTCAAGCCGATCGATGCCAAGTCGGAGCT<br>CGCGAAGCTCCGTGGCCTCATCGACCTCGAGAAGGTCGTAGTC<br>ATGACCGGTTACGCCGAGGTCGGACCGTTCGGCTCGTCGCGCA<br>CGCGCTGGGAGATGGAGGCGAACGGCACCTTCTCCATCCAGGG<br>CACACTCGAGCTTGCGTACGTCATGGGCCTCATCAAGCACTTTG<br>AGGGTCGCCTCAAGGACGGCACGCTCTACGTCGGATGGGTCGA<br>CGCCAAGACGAACGAACCGCTGGACGACAAGGACGTCAAGGC<br>TGCGTACGAGAAGCACATTCTCGCGCACACCGGCATCCGCCTC<br>ATCGAGCCGGAGATCTTCAACGGCTACGACCCGAAGCGCAAGG<br>GCTTCACGCAGGAGATCGAGATCCAGCACGACCTCGAGCCCAT<br>CGAGGCGTCCGAGGAGGACGCGGCTCGCTTCAAGCGCGAGCAC<br>GGCGCGCTCGTCGACGTCTACACCGAGGACGGCAGCAAGTTCT<br>TCGTCAAGTTCAAGAAGGGCGCCAAGCTGCACATTCCCAAGGC<br>TGTTGCCTTCGACCGCCTTGTCGCCGGACAGATCCCGACTGGCT<br>GGTCGCACAAGGCCTTCGGTATCCCCGACGACATTGCCTCGCA<br>GGTTGACCGCACCTCGCTGTGGGCGCTCGTCTCGGTCGCCGAG<br>GCGCTCATGATGGCCGGCATCACCGACCCGTATGAGCTCTACA<br>AGTGGATTCACCCGAGCGAGGTCGGTTCGTCGCTCGGATCCGG<br>CATGGGAGGCATCACGAGTATCTCGAAGATGTTCCGCGACCGC<br>CGCGAGGAGAAGGACGTCCAGAAGGACATCCTCCAGGAGACC<br>TTCATCAATACGGTCGCCGGATGGGTCAACCTCCTCCTTCTCTC<br>GTCATCCGGACCGATCAAGATCCCCGTCGGCGCCTGCGCGACT<br>GCCCTCCAGTCGGTCGAGATCGCCTGCGACACCATCCTCAGCG<br>GCAAGGCCAAGATCATGGTCTCGGGAGGCTACGACGACTTCTC<br>CGAGGAGGGCTCGTACGAGTTCGCAAACATGAAGGCGACCTCG<br>AACAGCGAGACCGAGTTCGCTGCCGGCCGCGAGCCGAACGAG<br>ATGTCGCGTCCGACGACCAGCACCCGTGCCGGCTTCATGGAGT<br>CGATGGGTTGCGGTGCTCAGGTCCTGATGTCGGCGAAGACGGC<br>CATCGAGATGGGCGCCACCATCTACGGCATCGTCGCCTACACC<br>GCGACCGCCACCGACAAGGCTGGTCGCTCGATTCCCGCCCCCG<br>GACGCGGTGTCATGGGTACCGCGCGCGAGATCACCTCCAAGTA<br>CCCCTCGCCCATCCTCGATGTCACCTACCGCCGCCGCCAGCTCG<br>AGTTCCGTCGCAAGCAGATCTCGCAGTGGCTCGAGAACGAGAC<br>CGAGCTCCTCAAGTTCGAGGTCTCCTCGCACGGACAGGCCACA<br>AAGCTCCCCGACGACTACGTCTCCGAGCGCCTCGCATCCATCG<br>AACGCGAAGCCAAGCGCCAGGAGGCCGAGGCTCTCGCGACGT<br>ACGGCATGCTCGCCGGCCAGGACCCGACCATCGCCCCGCTCCG<br>TCGCGCTCTCGCCGTTTGGGGTCTCACCATCGACGACGTTGGAG<br>TCGCCTCGTTCCACGGCACCTCGACCGTTGCCAACGACAAGAA<br>CGAGTCGAACGCGTACAACGAGCAGTTCCGTCACCTTGGCCGC | |

TABLE 4-continued

Codon optimized gene sequences.

| NT ID | Gene name | Sequence | SEQ ID NO |
|---|---|---|---|
| | | GCCAAGGGTAACGCCTGCCCCGTCATCGCTCAGAAGTGGCTCA<br>CCGGACACCCGAAGGGAGGTGCCGCCGCCTGGATGCTCAACGG<br>CTTGGCCCAGGTCATTCAGAGCGGTCTCGTTCCCGGCAACCGC<br>AACGCCGACAACATCGGCGAAGAGCTTCGCGCGTTCGAGTACC<br>TGCTCTACCCGTCCAAGTCGATCCAGACCGACGGCATCAAGGC<br>TGGTCTCCTCACCTCGTTCGGCTTCGGTCAAGTCGGTGGCCAGG<br>CTCTCATCGTTCACCCGAGTCTGCTCATCGGCGCGCTCGAGCCC<br>GCCCAGTTCGAGGCGTACAAGAAGCTCAACGACCAGCGCAAG<br>AAGTGGTCATACCGTCGCTTCAACGATTTCTTCACGAACGGCA<br>AGCTCGTCATTATCAAGGACGGCACGCCCCTTCACGCCCGAGCA<br>GGAGAACACGACCCTCCTCAACCCGCTCGTCCGCGCCGTGCCC<br>GACAAGACTGGCTCGTACTCGATGCCGAAGGAGTTCCCTGCCA<br>CCGTCCCTCGCAGCAACAACGCCGAAGTCGCCAACAAGCTCGT<br>CAGCGCGGCTGTCGGCGGTGCTTTCGGCGTCGGCACGGACGTC<br>GAGCTGATCAGCGCCGTCCCGACCTCGGAGTCGTTCCTCGAGA<br>GGAACTTCACCCAGGACGAGATCGCCTACTGCAAGGCCGCACC<br>CGACTTCCGCGCTAGCCTCGCCGCGCGCTGGTCCGCCAAGGAG<br>GCCACTTTCAAGGCTCTCAAGACCGAGTCGAAGGGCGCCGCCG<br>CCAGCATGCAGGACATCGAGGTCGTCTCCACGTCGCAGGGCCC<br>GACTATCAAGCTCCACGGCGAGGTCGAGAAGATCGCCCAGGCC<br>GCCGGCATCACGGCCTTCGAGGTCTCGCTCTCGCACTCGGAGG<br>ACGTCGCTTGCGCCGTCGTCATCGCCCAGAAGTAG | |
| 22 | Acr1 | GGATCCAAAACAATGAATAAGAAGTTAGAAGCATTGTTTAGAGA<br>AAATGTCAAGGGTAAAGTCGCTTTAATCACTGGTGCCTCCTCAGG<br>TATCGGTTTAACTATCGCAAAAAGAATTGCTGCAGCCGGTGCCC<br>ATGTTTTGTTAGTCGCTAGAACTCAAGAAACATTGGAAGAAGTT<br>AAGGCTGCAATCGAACAACAAGGTGGTCAAGCATCTATATTCCC<br>ATGTGATTTGACAGACATGAATGCAATAGATCAATTATCCCAAC<br>AAATCATGGCCAGTGTAGATCATGTTGACTTTTTGATTAATAACG<br>CAGGTAGATCTATAAGAAGAGCCGTTCATGAATCATTTGATAGA<br>TTCCACGACTTCGAAAGAACAATGCAATTAAACTACTTCGGTGCT<br>GTCAGATTGGTATTGAACTTGTTGCCTCACATGATCAAGAGAAA<br>GAATGGTCAAATTATAAACATCTCTTCAATCGGTGTATTGGCCAA<br>CGCTACCAGATTCTCTGCTTATGTTGCATCAAAAGCCGCTTTAGA<br>TGCTTTTTCCAGATGCTTGAGTGCAGAAGTTTTGAAGCATAAGAT<br>CTCTATAACTTCAATCTATATGCCATTGGTCAGAACACCAATGAT<br>CGCACCTACCAAAATCTATAAGTACGTTCCAACATTGTCTCCTGA<br>AGAAGCAGCCGATTTGATAGTTTATGCTATCGTCAAGAGACCTA<br>CCAGAATTGCCACTCACTTGGGTAGATTAGCTTCCATTACCTACG<br>CAATAGCCCCAGACATAAACAACATCTTGATGTCTATTGGTTTTA<br>ATTTGTTTCCTTCCAGTACTGCTGCATTAGGTGAACAAGAAAAAT<br>TGAACTTATTACAAAGAGCCTACGCAAGATTATTCCCTGGTGAAC<br>ATTGGTGAAAGCTT | 177 |
| 47 | ACB1 | ATGGTTTCCCAATTATTCGAAGAAAAAGCTAAAGCCGTCAACGA<br>GCTACCAACGAAGCCCTCCACTGATGAATTATTAGAATTGTATGC<br>TCTGTACAAGCAAGCCACTGTAGGTGACAACGACAAGGAAAAGC<br>CTGGTATTTTCAACATGAAGGACCGCTACAAGTGGGAAGCCTGG<br>GAAAACTTAAAAGGTAAATCCCAGGAAGATGCCGAAAAGGAAT<br>ACATTGCCCTTGTTGATCAACTGATTGCCAAGTACTCCTCTTAG | 178 |
| 48 | FOX2 | ATGCCTGGAAATTTATCCTTCAAAGATAGAGTTGTTGTAATCACG<br>GGCGCTGGAGGGGGCTTAGGTAAGGTGTATGCACTAGCTTACGC<br>AAGCAGAGGTGCAAAAGTGGTCGTCAATGATCTAGGTGGCACTT<br>TGGGTGGTTCAGGACATAACTCCAAAGCTGCAGACTTAGTGGTG<br>GATGAGATAAAAAAAGCCGGAGGTATAGCTGTGGCAAATTACGA<br>CTCTGTTAATGAAAATGGAGAGAAAATAATTGAAACGGCTATAA<br>AAGAATTCGGCAGGGTTGATGTACTAATTAACAACGCTGGAATA<br>TTAAGGGATGTTTCATTTGCAAAGATGACAGAACGTGAGTTTGC<br>ATCTGTGGTAGATGTTCATTTGACAGGTGGCTATAAGCTATCGCG<br>TGCTGCTTGGCCTTATATGCGCTCTCAGAAATTTGGTAGAATCAT<br>TAACACCGCTTCCCCTGCCGGTCTATTTGGAAATTTTGGTCAAGC<br>TAATTATTCAGCAGCTAAAATGGGCTTAGTTGGTTTGGCGGAAAC<br>CCTCGCGAAGGAGGGTGCCAAATACAACATTAATGTTAATTCAA<br>TTGCGCCATTGGCTAGATCACGTATGACAGAAAACGTGTTACCA<br>CCACATATCTTGAAACAGTTAGGACCGGAAAAAATTGTTCCCTTA<br>GTACTCTATTTGACACACGAAAGTACGAAAGTGTCAAACTCCATT<br>TTTGAACTCGCTGCTGGATTCTTTGGACAGCTCAGATGGGAGAGG<br>TCTTCTGGACAAATTTTCAATCCAGACCCCAAGACATATACTCCT<br>GAAGCAATTTTAAATAAGTGGAAGGAAATCACAGACTATAGGGA<br>CAAGCCATTTAACAAAACTCAGCATCCATATCAACTCTCGGATTA<br>TAATGATTTAATCACCAAAGCAAAAAAATTACCTCCCAATGAAC<br>AAGGCTCAGTGAAAATCAAGTCGCTTTGCAACAAAGTCGTAGTA | 179 |

TABLE 4-continued

Codon optimized gene sequences.

| NT ID | Gene name | Sequence | SEQ ID NO |
|---|---|---|---|
| | | GTTACGGGTGCAGGAGGTGGTCTTGGGAAGTCTCATGCAATCTG<br>GTTTGCACGGTACGGTGCGAAGGTAGTTGTAAATGACATCAAGG<br>ATCCTTTTTCAGTTGTTGAAGAAATAAATAAACTATATGGTGAAG<br>GCACAGCCATTCCAGATTCCCATGATGTGGTCACCGAAGCTCCTC<br>TCATTATCCAAACTGCAATAAGTAAGTTTCAGAGAGTAGACATCT<br>TGGTCAATAACGCTGGTATTTTGCGTGACAAATCTTTTTTAAAAA<br>TGAAAGATGAGGAATGGTTTGCTGTCCTGAAAGTCCACCTTTTTT<br>CCACATTTTCATTGTCAAAAGCAGTATGGCCAATATTTACCAAAC<br>AAAAGTCTGGATTTATTATCAATACTACTTCTACCTCAGGAATTT<br>ATGGTAATTTTGGACAGGCCAATTATGCCGCTGCAAAAGCCGCC<br>ATTTTAGGATTCAGTAAAACTATTGCACTGGAAGGTGCCAAGAG<br>AGGAATTATTGTTAATGTTATCGCTCCTCATGCAGAAACGGCTAT<br>GACAAAGACTATATTCTCGGAGAAGGAATTATCAAACCACTTTG<br>ATGCATCTCAAGTCTCCCCACTTGTTGTTTTGTTGGCATCTGAAG<br>AACTACAAAAGTATTCTGGAAGAAGGGTTATTGGCCAATTATTC<br>GAAGTTGGCGGTGGTTGGTGTGGGCAAACCAGATGGCAAAGAAG<br>TTCCGGTTATGTTTCTATTAAAGAGACTATTGAACCGGAAGAAAT<br>TAAAGAAAATTGGAACCACATCACTGATTTCAGTCGCAACACTA<br>TCAACCCGAGCTCCACAGAGGAGTCTTCTATGGCAACCTTGCAA<br>GCCGTGCAAAAAGCGCACTCTTCAAAGGAGTTGGATGATGGATT<br>ATTCAAGTACACTACCAAGGATTGTATCTTGTACAATTTAGGACT<br>TGGATGCACAAGCAAAGAGCTTAAGTACACCTACGAGAATGATC<br>CAGACTTCCAAGTTTTGCCCACGTTCGCCGTCATTCCATTTATGC<br>AAGCTACTGCCACACTAGCTATGGACAATTTAGTCGATAACTTCA<br>ATTATGCAATGTTACTGCATGGAGAACAATATTTTAAGCTCTGCA<br>CGCCGACAATGCCAAGTAATGGAACTCTAAAGACACTTGCTAAA<br>CCTTTACAAGTACTTGACAAGAATGGTAAAGCCGCTTTAGTTGTT<br>GGTGGCTTCGAAACTTATGACATTAAAACTAAGAAACTCATAGC<br>TTATAACGAAGGATCGTTCTTCATCAGGGGCGCACATGTACCTCC<br>AGAAAAGGAAGTGAGGGATGGGAAAAGAGCCAAGTTTGCTGTC<br>CAAAATTTTGAAGTGCCACATGGAAAGGTACCAGATTTTGAGGC<br>GGAGATTTCTACGAATAAAGATCAAGCCGCATTGTACAGGTTAT<br>CTGGCGATTTCAATCCTTTACATATCGATCCCACGCTAGCCAAAG<br>CAGTTAAATTTCCTACGCCAATTCTGCATGGGCTTTGTACATTAG<br>GTATTAGTGCGAAAGCATTGTTTGAACATTATGGTCCATATGAGG<br>AGTTGAAAGTGAGATTTACCAATGTTGTTTTCCCAGGTGATACTC<br>TAAAGGTTAAAGCTTGGAAGCAAGGCTCGGTTGTCGTTTTTCAAA<br>CAATTGATACGACCAGAAACGTCATTGTATTGGATAACGCCGCT<br>GTAAAACTATCGCAGGCAAAATAA | |
| 49 | FOX3 | ATGGGTAAGGGTGAATCGAAGAGGAAGAACTCGTTGCTGGAGA<br>AAAGACCCGAAGATGTAGTTATTGTGGCTGCTAACAGGTCTGCC<br>ATCGGTAAAGGTTTTAAAGGTGCCTTCAAAGATGTAAACACAGA<br>CTACTTATTATACAACTTTCTCAATGAGTTCATCGGGAGGTTTCC<br>GGAACCTTTGAGGGCTGATTTGAACTTAATCGAAGAAGTTGCCT<br>GTGGAAATGTTCTCAATGTTGGAGCCGGTGCTACAGAACACAGG<br>GCTGCATGCTTGGCAAGTGGGATTCCCTACTCGACGCCATTTGTC<br>GCTTTAAACAGACAATGTTCTTCAGGTTTAACGGCGGTGAACGAT<br>ATTGCCAACAAGATTAAGGTTGGGCAAATTGATATTGGTTTGGC<br>GCTGGGAGTGGAATCAATGACCAATAACTACAAAAACGTCAATC<br>CCTTGGGCATGATCTCCTCTGAAGAGCTGCAAAAAAACCGAGAA<br>GCGAAGAAATGTCTAATACCAATGGGCATTACTAATGAGAATGT<br>TGCCGCTAATTTCAAGATCAGTAGAAAGGATCAAGACGAGTTCG<br>CTGCGAATTCATATCAAAAAGCTTACAAGGCGAAAAATGAGGGG<br>CTTTTCGAAGATGAAATTTTACCTATAAAATTACCAGATGGCTCA<br>ATTTGCCAGTCGGACGAAGGGCCACGCCCTAACGTCACTGCGGA<br>GTCGCTTTCAAGCATCAGGCCTGCCTTTATCAAAGACAGAGGAA<br>CCACAACTGCGGGCAATGCATCCCAGGTCTCCGATGGTGTGGCA<br>GGTGTCTTGTTAGCCCGCAGGTCCGTAGCCAACCAGTTAAATCTG<br>CCTGTGCTAGGTCGCTACATCGATTTTCAAACAGTGGGGGTTCCC<br>CCTGAAATCATGGGTGTGGGCCCTGCATACGCCATACCAAAAGT<br>CCTGGAAGCTACTGGCTTGCAAGTCCAAGATATCGATATTTTTGA<br>AATAAATGAAGCATTCGCGGCCCAAGCATTATACTGCATCCATA<br>AACTGGGCATCGATTTGAATAAAGTAAATCCAAGAGGTGGTGCA<br>ATCGCGTTAGGCCATCCCTTGGGTTGTACTGGCGCAAGGCAAGT<br>AGCTACCATACTAAGAGAACTGAAAAAGGATCAAATCGGGGTTG<br>TTAGTATGTGTATCGGTACTGGTATGGGTGCCGCCGCCATCTTTA<br>TTAAAGAATAG | 180 |
| 50 | ERG10 | ATGTCTCAGAACGTTTACATTGTATCGACTGCCAGAACCCCAATT<br>GGTTCATTCCAGGGTTCTCTATCCTCCAAGACAGCAGTGGAATTG<br>GGTGCTGTTGCTTTAAAAGGCGCCTTGGCTAAGGTTCCAGAATTG<br>GATGCATCCAAGGATTTTGACGAAATTATTTTTGGTAACGTTCTT<br>TCTGCCAATTTGGGCCAAGCTCCGGCCAGACAAGTTGCTTTGGCT | 181 |

TABLE 4-continued

| Codon optimized gene sequences. | | | |
|---|---|---|---|
| NT ID | Gene name | Sequence | SEQ ID NO |
| | | GCCGGTTTGAGTAATCATATCGTTGCAAGCACAGTTAACAAGGT<br>CTGTGCATCCGCTATGAAGGCAATCATTTTGGGTGCTCAATCCAT<br>CAAATGTGGTAATGCTGATGTTGTCGTAGCTGGTGGTTGTGAATC<br>TATGACTAACGCACCATACTACATGCCAGCAGCCCGTGCGGGTG<br>CCAAATTTGGCCAAACTGTTCTTGTTGATGGTGTCGAAAGAGATG<br>GGTTGAACGATGCGTACGATGGTCTAGCCATGGGTGTACACGCA<br>GAAAAGTGTGCCCGTGATTGGGATATTACTAGAGAACAACAAGA<br>CAATTTTGCCATCGAATCCTACCAAAAATCTCAAAAATCTCAAAA<br>GGAAGGTAAATTCGACAATGAAATTGTACCTGTTACCATTAAGG<br>GATTTAGAGGTAAGCCTGATACTCAAGTCACGAAGGACGAGGAA<br>CCTGCTAGATTACACGTTGAAAAATTGAGATCTGCAAGGACTGTT<br>TTCCAAAAAGAAAACGGTACTGTTACTGCCGCTAACGCTTCTCCA<br>ATCAACGATGGTGCTGCAGCCGTCATCTTGGTTTCCGAAAAAGTT<br>TTGAAGGAAAAGAATTTGAAGCCTTTGGCTATTATCAAAGGTTG<br>GGGTGAGGCCGCTCATCAACCAGCTGATTTTACATGGGCTCCATC<br>TCTTGCAGTTCCAAAGGCTTTGAAACATGCTGGCATCGAAGACAT<br>CAATTCTGTTGATTACTTTGAATTCAATGAAGCCTTTTCGGTTGTC<br>GGTTTGGTGAACACTAAGATTTTGAAGCTAGACCCATCTAAGGTT<br>AATGTATATGGTGGTGCTGTTGCTCTAGGTCACCCATTGGGTTGT<br>TCTGGTGCTAGAGTGGTTGTTACACTGCTATCCATCTTACAGCAA<br>GAAGGAGGTAAGATCGGTGTTGCCGCCATTTGTAATGGTTGA | |
| 51 | TES1 | ATGAGTGCTTCCAAAATGGCCATGTCCAACCTAGAGAAAATATT<br>GGAACTGGTTCCTCTTTCGCCTACCAGTTTTGTCACAAAGTATCT<br>GCCTGCCGCGCCCGTAGGGTCTAAGGGCACTTTTGGTGGAACGC<br>TGGTATCACAATCGCTGCTGGCGTCATTGCATACTGTGCCATTGA<br>ACTTCTTCCCCACATCGCTACATTCGTATTTCATCAAGGGTGGTG<br>ATCCGCGGACCAAGATCACGTACCATGTGCAGAATCTGAGAAAC<br>GGTAGAAATTTCATCCATAAGCAGGTTAGTGCTTATCAGCACGA<br>CAAGTTGATATTTACGTCGATGATCTTATTTGCCGTGCAACGGTC<br>CAAGGAGCACGACTCCTTGCAGCACTGGGAGACGATTCCAGGCC<br>TGCAAGGTAAGCAGCCAGACCCTCATCGTTATGAAGAGGCCACT<br>TCGCTTTTCCAGAAAGAAGTTCTGGACCCACAGAAATTGAGCAG<br>GTATGCCTCATTGTCCGACAGGTTCCAAGACGCAACCTCGATGA<br>GCAAGTATGTGGATGCGTTTCAATACGGAGTCATGGAGTACCAA<br>TTCCCCAAGGACATGTTCTACTCGGCAAGACACACCGACGAGCT<br>GGATTATTTCGTCAAAGTGAGACCTCCCATCACTACCGTGGAGCA<br>CGCGGGCGACGAGTCTTCTTTACACAAGCATCATCCGTACAGGA<br>TCCCGAAGAGCATTACTCCTGAGAACGACGCTCGCTACAACTAC<br>GTGGCCTTTGCGTATCTGTCCGATTCCTACCTCCTACTCACGATCC<br>CGTACTTCCACAACCTGCCTTTGTACTGCCACAGTTTCAGTGTCT<br>CGCTCGACCACACGATTTACTTTCACCAGTTGCCTCATGTGAACA<br>ATTGGATCTATCTTAAGATTTCGAATCCCAGGTCCCACTGGGACA<br>AGCACCTCGTACAGGGCAAGTATTTCGACACACAGTCGGGACGC<br>ATCATGGCAAGCGTCTCTCAGGAGGGCTACGTTGTCTACGGGTC<br>AGAACGAGACATTCGATGA | 182 |
| 52 | FadA | ATGGAACAAGTAGTAATCGTAGACGCAATCAGAACTCCTATGGG<br>TAGAAGTAAAGGTGGTGCATTCAGAAATGTCAGAGCAGAAGACT<br>TGTCCGCTCATTTGATGAGAAGTTTGTTAGCAAGAAATCCAGCCT<br>TGGAAGCTGCAGCCTTAGATGACATCTATTGGGGTTGTGTTCAAC<br>AAACTTTGGAACAAGGTTTTAATATCGCAAGAAACGCTGCATTG<br>TTAGCCGAAGTTCCACATTCTGTCCCTGCTGTAACCGTTAACAGA<br>TTGTGTGGTTCTTCAATGCAAGCATTACACGATGCCGCTAGAATG<br>ATTATGACTGGTGACGCCCAAGCTTGCTTGGTCGGTGGTGTAGAA<br>CATATGGGTCACGTCCCAATGTCCCATGGTGTAGATTTCCACCCT<br>GGTTTAAGTAGAAATGTTGCTAAAGCAGCCGGTATGATGGGTTT<br>GACAGCTGAAATGTTAGCAAGAATGCATGGTATTTCTAGAGAAA<br>TGCAAGATGCATTTGCTGCAAGATCTCACGCAAGAGCCTGGGCC<br>GCTACTCAATCAGCAGCCTTCAAAAATGAAATTATACCAACAGG<br>TGGTCATGATGCTGACGGTGTTTTGAAGCAATTCAATTACGATGA<br>AGTTATAAGACCTGAAACTACAGTCGAAGCTTTGGCAACCTTAA<br>GACCAGCATTCGATCCTGTAAATGGTATGGTTACAGCTGGTACCT<br>CCAGTGCATTGTCCGACGGTGCTGCAGCCATGTTAGTAATGTCTG<br>AATCAAGAGCTCACGAATTGGGTTTAAAACCAAGAGCCAGAGTT<br>AGATCTATGGCTGTTGTCGGTTGCGATCCTTCAATAATGGGTTAC<br>GGTCCAGTCCCTGCCTCAAAGTTGGCTTTGAAGAAAGCAGGTTTG<br>TCCGCCAGTGACATCGGTGTTTTTGAAATGAATGAAGCTTTCGCT<br>GCACAAATATTGCCATGTATCAAGGATTTGGGTTTGATCGAACA<br>AATAGACGAAAAGATTAATTTGAACGGTGGTGCCATAGCTTTGG<br>GTCATCCTTTAGGTTGCTCTGGTGCTAGAATCTCAACCACTTTGTT<br>GAACTTAATGGAAAGAAAGGATGTTCAATTTGGTTTGGCAACTA<br>TGTGTATCGGTTTAGGTCAAGGTATCGCTACTGTATTTGAAAGAG<br>TCTAA | 183 |

TABLE 4-continued

Codon optimized gene sequences.

| NT ID | Gene name | Sequence | SEQ ID NO |
|---|---|---|---|
| 53 | FadB | ATGTTGTATAAAGGTGACACATTGTACTTAGACTGGTTAGAAGAT<br>GGTATCGCTGAATTGGTATTTGATGCTCCTGGTTCCGTAAACAAA<br>TTGGATACTGCCACAGTAGCTTCCTTAGGTGAAGCAATTGGTGTT<br>TTGGAACAACAATCCGACTTAAAGGGTTTGTTGTTGAGAAGTAA<br>TAAGGCTGCTTTTATTGTAGGTGCTGATATCACAGAATTCTTGAG<br>TTTGTTTTTAGTTCCAGAAGAACAATTGTCTCAATGGTTGCATTTC<br>GCAAACTCAGTTTTTAACAGATTGGAAGATTTGCCAGTCCCTACC<br>ATTGCCGCTGTAAACGGTTACGCTTTAGGTGGTGGTTGTGAATGC<br>GTTTTGGCTACCGACTATAGATTAGCAACTCCAGATTTGAGAATC<br>GGTTTACCTGAAACTAAATTGGGTATTATGCCAGGTTTTGGTGGT<br>TCTGTTAGAATGCCTAGAATGTTGGGTGCAGATTCAGCCTTAGAA<br>ATTATAGCAGCCGGTAAAGACGTTGGTGCTGATCAAGCATTGAA<br>GATCGGTTTAGTCGATGGTGTTGTCAAAGCTGAAAAGTTGGTTGA<br>AGGTGCCAAAGCTGTCTTAAGACAAGCCATTAATGGTGACTTGG<br>ACTGGAAAGCTAAGAGACAACCAAAGTTAGAACCTTTGAAGTTG<br>TCTAAGATCGAAGCAACAATGTCTTTTACTATAGCCAAGGGTATG<br>GTCGCCCAAACTGCTGGTAAACATTACCCAGCCCCTATAACTGCT<br>GTTAAAACAATCGAAGCTGCAGCCAGATTCGGTAGAGAAGAAGC<br>ATTGAATTTGGAAAACAAGTCTTTTGTTCCATTGGCTCACACAAA<br>TGAAGCAAGAGCCTTGGTCGGTATTTTCTTGAACGACCAATACGT<br>AAAGGGTAAAGCTAAGAAATTGACTAAAGATGTTGAAACACCAA<br>AGCAAGCTGCAGTCTTGGGTGCTGGTATCATGGGTGGTGGTATTG<br>CATATCAATCCGCCTGGAAAGGTGTTCCTGTAGTTATGAAGGATA<br>TCAACGACAAGAGTTTGACCTTGGGTATGACTGAAGCCGCTAAG<br>TTGTTGAACAAGCAATTAGAAAGAGGTAAAATTGACGGTTTGAA<br>GTTAGCTGGTGTTATATCTACAATCCATCCAACCTTGGATTATGC<br>TGGTTTCGATAGAGTTGACATTGTCGTAGAAGCAGTTGTCGAAA<br>ATCCTAAAGTTAAAAAGGCAGTCTTAGCCGAAACAGAACAAAAA<br>GTTAGACAAGATACCGTTTTGGCTTCCAACACCAGTACTATCCCA<br>ATTTCAGAATTGGCTAATGCATTAGAAAGACCTGAAAACTTCTGT<br>GGTATGCATTTCTTTAATCCAGTACACAGAATGCCTTTGGTTGAA<br>ATCATAAGAGGTGAAAAATCTTCAGATGAAACTATCGCTAAGGT<br>AGTTGCCTGGGCTTCTAAAATGGGTAAAACACCAATCGTCGTAA<br>ATGATTGCCCTGGTTTCTTTGTCAACAGAGTATTGTTTCCATACTT<br>CGCAGGTTTTTCACAATTATTGAGAGATGGTGCCGACTTCAGAAA<br>GATAGATAAGGTTATGGAAAAGCAATTTGGTTGGCCAATGGGTC<br>CTGCCTATTTGTTGGACGTTGTCGGTATAGATACAGCTCATCACG<br>CACAAGCCGTTATGGCAGCCGGTTTCCCACAAAGAATGCAAAAA<br>GATTACAGAGACGCTATTGATGCATTATTCGACGCTAATAGATTT<br>GGTCAAAAGAATGGTTTGGGTTTTTGGAGATATAAGGAAGATTC<br>CAAAGGTAAACCTAAAAAGGAAGAAGACGCTGCAGTCGAAGAT<br>TTGTTGGCAGAAGTATCCCAACCAAAGAGAGATTTCAGTGAAGA<br>AGAAATCATCGCTAGAATGATGATTCCTATGGTCAACGAAGTAG<br>TTAGATGTTTAGAAGAAGGTATCATCGCTACCCCAGCTGAAGCA<br>GATATGGCATTGGTTTACGGTTTAGGTTTCCCACCTTTTCACGGT<br>GGTGCTTTTAGATGGTTGGACACTTTAGGTTCTGCCAAATATTTG<br>GATATGGCTCAACAATACCAACATTTGGGTCCATTATATGAAGTT<br>CCTGAAGGTTTGAGAAACAAGGCTAGACACAATGAACCTTATTA<br>CCCTCCTGTTGAACCTGCCAGACCTGTTGGTGACTTGAAAACTGC<br>CTAA | 184 |
| 54 | yqeF | ATGAAGGATGTCGTAATCGTTGGTGCTTTAAGAACCCCTATCGGT<br>TGCTTTAGAGGTGCATTGGCTGGTCACTCCGCTGTAGAATTGGGT<br>TCTTTGGTTGTCAAAGCTTTAATAGAAAGAACTGGTGTACCAGCA<br>TATGCCGTCGATGAAGTAATCTTGGGTCAAGTTTTAACAGCTGGT<br>GCAGGTCAAAATCCAGCAAGACAATCAGCCATCAAAGGTGGTTT<br>GCCTAACTCTGTTTCAGCTATAACTATTAATGACGTCTGTGGTTC<br>TGGTTTAAAGGCATTGCATTTGGCAACCCAAGCCATTCAATGCGG<br>TGAAGCAGATATCGTCATTGCCGGTGGTCAAGAAAACATGTCAA<br>GAGCCCCTCACGTATTGACTGACTCCAGAACAGGTGCACAATTG<br>GGTAACTCACAATTGGTAGATTCCTTAGTTCATGATGGTTTGTGG<br>GACGCTTTTAATGATTACCACATCGGTGTTACTGCTGAAAACTTA<br>GCAAGAGAATACGGTATTTCAAGACAATTGCAAGATGCCTACGC<br>TTTATCTTCACAACAAAAAGCTAGAGCTGCAATTGACGCAGGTA<br>GATTCAAAGATGAAATAGTCCCAGTAATGACCCAAAGTAATGGT<br>CAAACCTTGGTAGTTGATACTGACGAACAACCAAGAACTGACGC<br>ATCTGCCGAAGGTTTGGCTAGATTAAACCCTTCCTTCGATAGTTT<br>AGGTTCTGTTACAGCTGGTAATGCATCCAGTATTAACGATGGTGC<br>CGCTGCAGTCATGATGATGTCAGAAGCTAAAGCAAGAGCCTTGA<br>ATTTGCCTGTTTTGGCTAGAATTAGAGCTTTTGCATCCGTTGGTGT<br>CGATCCAGCATTGATGGGTATAGCCCCTGTTTATGCTACCAGAAG<br>ATGTTTAGAAAGAGTCGGTTGGCAATTGGCTGAAGTAGACTTAA<br>TAGAAGCCAACGAAGCTTTCGCCGCTCAAGCATTGTCTGTTGGTA | 185 |

TABLE 4-continued

| Codon optimized gene sequences. | | | |
|---|---|---|---|
| NT ID | Gene name | Sequence | SEQ ID NO |
| | | AAATGTTAGAATGGGATGAAAGAAGAGTAAATGTTAACGGTGGT GCCATAGCTTTAGGTCATCCAATCGGTGCTAGTGGTTGCAGAATT TTGGTTTCTTTAGTCCACGAAATGGTTAAAAGAAATGCTAGAAA GGGTTTAGCAACATTGTGTATTGGTGGTGGTCAAGGTGTAGCATT GACTATCGAAAGAGACGAATAA | |
| 55 | tdTER | ATGATAGTAAAGCCAATGGTAAGGAACAATATCTGTCTTAACGC CCATCCACAGGGTTGCAAAAAGGGAGTTGAAGATCAAATTGAAT ACACCAAAAAGAGAATTACAGCAGAGGTCAAGGCAGGGGCAAA GGCTCCTAAGAACGTCTTAGTTTTGGGTTGTTCTAATGGATACGG CTTGGCAAGTAGAATAACTGCAGCCTTCGGTTATGGAGCCGCCA CTATAGGTGTATCATTCGAAAAAGCCGGCTCCGAAACCAAGTAC GGTACACCTGGCTGGTATAACAATCTAGCTTTTGATGAAGCTGCT AAGAGAGAAGGGTTATACTCTGTCACAATAGACGGTGACGCATT TTCTGATGAAATCAAAGCTCAGGTTATTGAAGAGGCCAAGAAAA AGGGTATCAAATTCGATCTGATAGTATACTCATTAGCATCCCCAG TGCGTACAGATCCAGATACTGGCATTATGCACAAATCTGTTTTGA AACCATTTGGAAAAACTTTCACTGGTAAAACAGTTGATCCTTTTA CAGGAGAACTGAAGGAAATCTCAGCTGAACCAGCTAATGATGAG GAGGCAGCTGCTACTGTGAAAGTTATGGGTGGAGAGGACTGGGA AAGATGGATCAAACAACTAAGTAAGGAAGGTTTACTTGAAGAGG GATGCATCACCTTAGCCTACTCTTACATTGGTCCTGAAGCAACAC AAGCCCTATACCGTAAAGGAACTATAGGTAAGGCAAAGGAACAC CTTGAAGCTACTGCTCATCGTCTGAATAAGGAAAATCCATCCATT AGGGCTTTCGTTAGTGTCAACAAAGGGTTAGTTACCAGAGCATC AGCTGTGATCCCTGTCATTCCACTTTACCTTGCTTCATTGTTTAAG GTTATGAAAGAGAAAGGCAATCATGAAGGATGTATCGAACAAAT CACAAGATTGTACGCTGAGAGATTGTATAGAAAGGATGGTACAA TTCCTGTGGACGAAGAGAATAGAATTAGAATCGATGATTGGGAG TTAGAAGAGGACGTTCAAAAAGCTGTTTCTGCATTGATGGAAAA AGTTACAGGCGAAAATGCTGAGTCACTAACAGACCTGGCAGGTT ATAGACATGACTTTTTGGCCTCAAACGGGTTTGATGTAGAAGGTA TCAACTACGAAGCTGAAGTCGAAAGATTCGATAGAATCTAA | 186 |
| 56 | tesA | ATGGCCGATACTTTGTTAATTTTGGGTGACTCTTTATCAGCCGGT TATAGAATGTCCGCTAGTGCTGCATGGCCAGCATTGTTAAACGAT AAATGGCAATCTAAGACTTCAGTTGTCAATGCATCTATATCAGGT GACACATCACAACAAGGTTTGGCCAGATTACCAGCTTTGTTAAA ACAACATCAACCTAGATGGGTCTTGGTAGAATTAGGTGGTAACG ATGGTTTGAGAGGTTTTCAACCTCAACAAACCGAACAAACTTTG AGACAAATCTTACAAGATGTTAAGGCCGCTAATGCAGAACCATT GTTAATGCAAATTAGATTACCTGCCAACTATGGTAGAAGATACA ATGAAGCATTTTCTGCAATCTATCCAAAATTGGCAAAGGAATTTG ATGTACCATTGTTGCCATTTTTCATGGAAGAAGTTTACTTAAAAC CTCAATGGATGCAAGATGACGGTATTCATCCAAACAGAGATGCT CAACCTTTTATAGCAGACTGGATGGCCAAACAATTGCAACCATT AGTCAATCACGATTCTTGA | 187 |
| 57 | tesB | ATGTCTCAAGCTTTGAAGAACTTGTTGACTTTGTTGAACTTGGAA AAGATCGAAGAAGGTTTGTTCAGAGGTCAATCTGAAGACTTGGG TTTGAGACAAGTTTTCGGTGGTCAAGTTGTTGGTCAAGCTTTGTA CGCTGCTAAGGAAACTGTTCCAGAAGAAAGATTGGTTCACTCTTT CCACTCTTACTTCTTGAGACCAGGTGACTCTAAGAAGCCAATCAT CTACGACGTTGAAACTTTGAGAGACGGTAACTCTTTCTCTGCTAG AAGAGTTGCTGCTATCCAAAACGGTAAGCCAATCTTCTACATGA CTGCTTCTTTCCAAGCTCCAGAAGCTGGTTTCGAACACCAAAAGA CTATGCCATCTGCTCCAGCTCCAGACGGTTTGCCATCTGAAACTC AAATCGCTCAATCTTTGGCTCACTTGTTGCCACCAGTTTTGAAGG ACAAGTTCATCTGTGACAGACCATTGGAAGTTAGACCAGTTGAA TTCCACAACCCATTGAAGGGTCACGTTGCTGAACCACACAGACA AGTTTGGATCAGAGCTAACGGTTCTGTTCCAGACGACTTGAGAGT TCACCAATACTTGTTGGGTTACGCTTCTGACTTGAACTTCTTGCC AGTTGCTTTGCAACCACACGGTATCGGTTTCTTGGAACCAGGTAT CCAAATCGCTACTATCGACCACTCTATGTGGTTCCACAGACCATT CAACTTGAACGAATGGTTGTTGTACTCTGTTGAATCTACTTCTGC TTCTTCTGCTAGAGGTTTCGTTAGAGGTGAATTCTACACTCAAGA CGGTGTTTTGGTTGCTTCTACTGTTCAAGAAGGTGTTATGAGAAA CCACAACTAA | 188 |
| 58 | fadM | ATGCAAACTCAAATCAAGGTTAGAGGTTACCACTTGGACGTTTA CCAACACGTTAACAACGCTAGATACTTGGAATTCTTGGAAGAAG CTAGATGGGACGGTTTGGAAAACTCTGACTCTTTCCAATGGATGA CTGCTCACAACATCGCTTTCGTTGTTGTTAACATCAACATCAACT ACAGAAGACCAGCTGTTTTGTCTGACTTGTTGACTATCACTTCTC | 189 |

TABLE 4-continued

Codon optimized gene sequences.

| NT ID | Gene name | Sequence | SEQ ID NO |
|---|---|---|---|
| | | AATTGCAACAATTGAACGGTAAGTCTGGTATCTTGTCTCAAGTTA<br>TCACTTTGGAACCAGAAGGTCAAGTTGTTGCTGACGCTTTGATCA<br>CTTTCGTTTGTATCGACTTGAAGACTCAAAAGGCTTTGGCTTTGG<br>AAGGTGAATTGAGAGAAAAGTTGGAACAAATGGTTAAGTAA | |
| 59 | yciA | ATGTCTACTACTCACAACGTTCCACAAGGTGACTTGGTTTTGAGA<br>ACTTTGGCTATGCCAGCTGACACTAACGCTAACGGTGACATCTTC<br>GGTGGTTGGTTGATGTCTCAAATGGACATCGGTGGTGCTATCTTG<br>GCTAAGGAAATCGCTCACGGTAGAGTTGTTACTGTTAGAGTTGA<br>AGGTATGACTTTCTTGAGACCAGTTGCTGTTGGTGACGTTGTTTG<br>TTGTTACGCTAGATGTGTTCAAAAGGGTACTACTTCTGTTTCTAT<br>CAACATCGAAGTTTGGGTTAAGAAGGTTGCTTCTGAACCAATCG<br>GTCAAAGATACAAGGCTACTGAAGCTTTGTTCAAGTACGTTGCTG<br>TTGACCCAGAAGGTAAGCCAAGAGCTTTGCCAGTTGAATAA | 190 |
| 60 | ETR1 | ATGCTCACTTATGGAGGAATGTCAAAACAACCTGTAACTTTACCA<br>ACATCTCTACACATTTTCAAAGGCTTGACATCCAAAGGATACTGG<br>GTGACTGAAAAGAACAAAAAAAACCCCCAAAGCAAAATTGACA<br>CCATCAGTGATTTTATCAAAATGTATAATGATGGTCACATTATTT<br>CACCAAGAGATGAAATTGAAACTCTTACCTGGAATACTAACACT<br>ACTACTGACGAACAGTTACTAGAACTAGTCAAAAAAGGCATAAC<br>TGGGAAGGGGAAGAAAAAAATGGTTGTTTTAGAATGGTAA | 191 |
| 61 | HFA1 | ATGAGATCTATAAGAAAATGGGCGTACGAGACGTTCAATG<br>ATGAAAAAATCATTCAATTCGTGGTAATGGCGACACCTGAT<br>GATTTACACGCAAATTCGGAGTATATTAGAATGGCAGACCA<br>ATATGTGCAGGTACCAGGGGGTACCAACAACAACAATTAC<br>GCCAACATAGACTTAATACTGGACGTGGCAGAGCAAACGG<br>ATGTGGATGCGGTCTGGGCTGGATGGGGCCATGCTTCTGAA<br>AATCCGTGTCTTCCTGAGCTGTTAGCTAGTTCACAAAGGAA<br>AATACTATTCATTGGTCCTCCTGGACGCGCTATGAGATCAT<br>TGGGTGACAAGATTTCTTCCACTATTGTAGCACAAAGCGCT<br>AAAATCCCGTGTATCCCTTGGTCTGGTTCACATATAGACAC<br>TATCCATATCGATAACAAGACGAACTTTGTATCTGTGCCGG<br>ATGATGTATATGTAAGGGGATGTTGTTCCTCACCTGAAGAT<br>GCTTTAGAAAAGGCTAAATTAATAGGATTTCCTGTAATGAT<br>TAAGGCATCCGAAGGTGGTGGAGGTAAGGGCATTAGGCGA<br>GTAGATAATGAGGATGATTTTATTGCATTATATCGCCAAGC<br>AGTGAATGAGACACCTGGGTCGCCTATGTTTGTTATGAAAG<br>TTGTCACTGATGCTCGTCACTTAGAGGTACAGTTATTAGCT<br>GACCAATATGGCACTAACATTACATTGTTTGGGAGAGACTG<br>TTCCATACAAAGGCGGCACCAAAAGATTATAGAAGAGGCA<br>CCAGTGACAATAACCAAGCCTGAAACGTTTCAAAGGATGG<br>AACGCGCAGCAATTCGTCTAGGTGAATTGGTAGGTTATGTT<br>TCTGCGGGCACTGTCGAATACTTATATTCACCAAAAGATGA<br>TAAATTTTACTTTTTAGAACTGAATCCAAGACTACAAGTAG<br>AGCATCCAACGACAGAAATGATATCTGGCGTAAACCTTCCT<br>GCCACTCAACTGCAAATCGCCATGGGTATTCCTATGCACAT<br>GATAAGTGATATCAGAAAACTTTATGGTTTAGATCCAACGG<br>GAACTTCGTATATTGATTTTAAAAATTTAAAGAGACCCTCG<br>CCAAAAGGCCATTGTATTTCATGCAGGATCACTTCAGAAGA<br>TCCTAATGAAGGTTTCAAGCCCTCCACTGGGAAAATACATG<br>AGCTCAATTTTCGTTCTTCTTCCAATGTTTGGGGTTACTTCT<br>CAGTAGGAAATAATGGTGCTATTCACTCATTTTCAGATTCC<br>CAATTTGGGCACATTTTTGCTGTAGGAAACGATAGGCAAGA<br>TGCAAAGCAAAACATGGTTTTAGCTCTAAAAGATTTTTCCA<br>TCCGAGGAGAATTCAAAACCCCTATAGAGTACCTGATAGA<br>GCTATTAGAAACTCGGGACTTTGAGAGTAATAACATATCGA<br>CTGGTTGGTTAGATGATTTGATTTTGAAAAATTTATCTTCCG<br>ATAGCAAACTAGATCCAACGCTCGCTATTATCTGTGGTGCC<br>GCAATGAAAGCATACGTTTTCACAGAAAAGGTGAGGAATA<br>AGTATTTGGAATTATTGCGGAGGGGCCAAGTTCCACCTAAA<br>GATTTTCTTAAAACGAAGTTTCCTGTTGACTTCATTTTCGAT<br>AATAATAGATACTTGTTCAATGTTGCTCAATCATCTGAAGA<br>ACAATTTATTCTTTCTATCAATAAGTCTCAATGTGAAGTTAA<br>TGTTCAAAAATTGTCCGGTGACTGCTTGTTGATCTCCGTTGA<br>CGGTAAATGCCATACAGTTTATTGGAAGGACGATATCAGA<br>GGTACAAGACTTTCGATAGACTCCAATACCATATTTTTAGA<br>AGCTGAACTCAATCCCACTCAAGTGATCTCTCCAACTCCGG<br>GGAAATTGGTGAAATATTTGGTCCGAAGTGGTGATCACGTT<br>TTTGCTGGACAGCAATATGCAGAAATAGAAATAATGAAAA<br>TGCAGATGCCACTAGTAGCGAAAAGTGATGGTGTAATTGA<br>GTTACTAAGACAGCCCGGTTCCATAATTGAGGCTGGTGATG<br>TCATCGCAAAATTGACTTTGGATTCACCGTCCAAAGCTAAC | 192 |

TABLE 4-continued

Codon optimized gene sequences.

| NT ID | Gene name | Sequence | SEQ ID NO |
|---|---|---|---|
| | | GAATCGTCTTTATACCGCGGAGAATTACCTGTTTTAGGTCC | |
| | | ACCGCTAATAGAGGGTAGCCGACCAAACCATAAGCTCAGA | |
| | | GTCTTAATAAATAGGTTAGAAAATATTCTCAATGGATATCA | |
| | | TGAAAACTCTGGAATAGAAACTACTCTAAAAGAGTTGATA | |
| | | AAAATATTGAGAGATGGTAGGCTTCCTTATTCAGAATGGGA | |
| | | TTCCCAAATTTCTACGGTACGCAATAGACTACCAAGGCAAT | |
| | | TGAATGAGGGGCTGGGAAATCTAGTCAAGAAATCTGTTTCT | |
| | | TTTCCTGCAAAGGAACTGCACAAATTAATGAAGCGCTACTT | |
| | | GGAAGAAAATACAAATGATCATGTAGTTTATGTTGCCTTAC | |
| | | AGCCACTTCTTAAAATTAGTGAAAGGTATAGCGAAGGTTTA | |
| | | GCTAATCACGAATGTGAAATTTTTTTAAAGTTGATTAAAAA | |
| | | GTATTATGCTGTTGAGAAAATTTTTGAAAATCATGATATAC | |
| | | ATGAAGAAAGAAACTTACTAAATCTGCGGAGGAAAGACCT | |
| | | TACAAACTTAAAAGAAATTTTGTGCATAAGTTTATCGCATG | |
| | | CTAACGTAGTCGCAAAGAACAAGTTAGTAACTGCAATATTG | |
| | | CATGAATACGAGCCATTGTGCCAGGATTCCTCTAAGATGTC | |
| | | TTTAAAATTCAGGGCTGTTATACATGATTTGGCAAGTTTGG | |
| | | AATCTAAGTGGGCTAAGGAGGTTGCTGTAAAGGCAAGATC | |
| | | AGTGCTACTCAGAGGGATTTTCCCTCCCATAAAGAAAAGAA | |
| | | AAGAGCATATTAAAACTCTCCTGCAATTGCACATAAAGGAT | |
| | | ACTGGTGCCAAAAACATTCACAGCAGGAACATATATTCCTG | |
| | | TATGAGGGATTTTGGTAATTTAATACATTCAAATCTGATAC | |
| | | AACTTCAGGATTTGTTCTTTTTTTTTGGCCATCAAGATACGG | |
| | | CTCTTTCCAGTATAGCATCTGAAATTTATGCAAGGTATGCC | |
| | | TACGGCAATTATCAATTAAAAAGTATTAAGATTCACAAAGG | |
| | | AGCGCCTGATTTACTAATGTCATGGCAATTCAGCTCATTAA | |
| | | GAAATTATTTAGTCAATCCTGATGGTGAGAGTGATGAGTTT | |
| | | ACAAAACTTTCTAAACCTCCCTCAACATCAGGTAAGAGCTC | |
| | | AGCAAATAGTTTTGGTCTTCTTGTCAACATGCGTGCGCTTG | |
| | | AATCTCTGGAAAAGACATTAGACGAGGTATACGAACAAAT | |
| | | TCATATTCCTGAGGAAAGACTTTCCAGCGGAGAGAACTCTC | |
| | | TTATTGTTAATATTTTATCTCCTATTCGTTACAGAAGTGAAA | |
| | | ATGATCTAATTAAAACTTTAAAAATTAAACTTCATGAAAAT | |
| | | GAGAGAGGTCTATCCAAGCTCAAGGTTAATCGTATTACATT | |
| | | TGCATTTATCGCCGCGAATGCGCCCACTGTTAAATTTTACTC | |
| | | CTTTGATGGAACTACGTACGATGAAATCTCTCAAATAAGAA | |
| | | ATATGGATCCATCCTATGAAGCACCGTTAGAGTTAGGAAAA | |
| | | ATGTCGAACTATAAAATCAGATCACTACCTACATACGATAG | |
| | | TAGTATACGCATTTTTGAAGGTATTAGCAAATTTACGCCGC | |
| | | TAGATAAAAGGTTCTTTGTCAGGAAAATCATAAATTCCTTC | |
| | | ATGTATAATGATCAAAAAACAACCGAAGAAAACTTGAAAG | |
| | | CGGAAATCAATGCTCAAGTGGTTTATATGTTAGAACATCTA | |
| | | GGAGCAGTTGACACCTCAAATTCAGACTTGAATCATATTTT | |
| | | TTTAAGTTTCAATACAGTTCTTAACATACCAGTACATCGTCT | |
| | | CGAGGAAATTGTGAGTACAATTCTAAAGACTCACGAAACC | |
| | | AGATTGTTTCAAGAAAGAATCACAGATGTAGAAATTTGCAT | |
| | | CTCTGTTGAGTGCCTAGAAACAAAGAAGCCAGCCCCGCTTA | |
| | | GATTACTTATTTCTAATAAATCTGGGTATGTGGTAAAAATT | |
| | | GAGACATATTACGAAAAGATAGGGAAAAATGGGAATCTGA | |
| | | TTTTGGAACCGTGTAGTGAGCAGAGCCATTATAGCCAGAAA | |
| | | TCTCTCTCTCTTCCTTACTCGGTCAAGGATTGGCTACAACCT | |
| | | AAAAGATACAAAGCTCAATTCATGGGTACAACATATGTGT | |
| | | ACGATTTCCCAGGTCTGTTTCATCAAGCTGCAATCCAACAG | |
| | | TGGAAAAGGTATTTTCCAAAACATAAGCTGAATGACAGTTT | |
| | | TTTTAGTTGGGTTGAATTGATAGAACAAAACGGTAATTTGA | |
| | | TAAAAGTAAACAGGGAGCCAGGCCTTAATAATATAGGGAT | |
| | | GGTT | |
| | | GCTTTTGAGATTATGGTTCAGACACCTGAATATCCTGAAGG | |
| | | GCGTAACATGATCGTGATTTCTAATGATATTACCTACAATA | |
| | | TTGGATCTTTTGGACCGAGAGAAGATTTGTTTTTTGATAGG | |
| | | GTCACAAATTATGCAAGAGAGAGAGGGATCCCGAGGATAT | |
| | | ACTTGGCGGCGAATTCAGGAGCTAAATTGGGTATAGCCGA | |
| | | AGAGCTGATCCCTCTATTTCGTGTAGCATGGAATGACCCCT | |
| | | CTGATCCAACAAAGGGTTTCCAGTACTTATACTTAGCTCCA | |
| | | AAAGACATGCAGCTACTGAAAGATTCTGGGAAAGGAAATT | |
| | | CGGTTGTTGTTGAACACAAGATGGTATACGGTGAAGAGAG | |
| | | ATATATTATTAAAGCAATAGTCGGATTCGAAGAGGGTTTAG | |
| | | GTGTTGAATGTTTACAGGGCTCAGGTTTAATTGCTGGTGCC | |
| | | ACTTCGAAAGCGTATAGAGACATTTTCACTATTACTGCTGT | |
| | | TACTTGTCGGTCCGTTGGTATAGGTTCCTATCTGGTCAGACT | |
| | | AGGACAACGTACTATTCAGGTGGAGGATAAGCCTATCATA | |
| | | CTGACGGGTGCATCGGCGATTAATAAAGTTTTGGGTACCGA | |
| | | TATCTATACATCTAACCTACAAATTGGCGGAACCCAAATCA | |
| | | TGTATAAAAACGGAATAGCGCATTTAACAGCCAGTAATGA | |

TABLE 4-continued

Codon optimized gene sequences.

| NT ID | Gene name | Sequence | SEQ ID NO |
|---|---|---|---|
| | | TATGAAAGCCATCGAAAAAATAATGACATGGTTATCATATG TCCCGGCGAAAAGAGATATGAGTCCTCCACTTCTTGAAACT ATGGATAGATGGGATAGGGATGTAGACTTCAAACCTGCCA AGCAAGTGCCATATGAGGCAAGGTGGTTGATAGAGGGTAA ATGGGACTCAAATAACAACTTCCAGTCAGGCCTATTTGATA AGGATTCGTTTTTTGAGACATTATCTGGATGGGCCAAAGGT GTAATAGTTGGAAGAGCACGTCTTGGAGGTATTCCCGTAGG TGTTATTGCGGTAGAAACTAAGACTATCGAAGAAACAATCC CCGCTGACCCAGCTAATCTGGATTCTTCAGAGTTTTCCGTTA AAGAAGCAGGACAGGTGTGGTATCCAAATTCCGCGTTCAA AACAGCTCAAACTATAAATGATTTTAACTATGGTGAGCAAT TACCATTGATTATCTTAGCCAATTGGAGGGGATTTTCTGGC GGTCAAAGGGATATGTACAATGAAGTACTAAAGTACGGGT CTTTTATTGTTGACGCTCTGGTTGACTACAAACAACCCATA CTGATATACATTCCGCCCTTTGGTGAATTAAGGGGCGGATC ATGGGTTGTTATAGATCCAACTATTAATCCTGAACAAATGG AAATGTATGCCGATGTTGAATCTAGGGGAGGTGTGTTAGAA CCTGACGGAGTAGTTAGCATAAAATACCGTAAGGAGAAAA TGATAGAGACGATGATTCGATTAGACTCCACATATGGACAT TTGAGAAGAACGTTGACAGAAAAAAAGTTATCTTTGGAAA AACAAAATGATCTTACGAAGAGATTGAAAATAAGAGAGAG ACAGTTGATACCAATTTATAATCAAATCAGCATACAGTTTG CAGATTTACATGATAGATCGACTAGGATGCTAGTTAAAGGA GTAATCCGAAAGGAGTTGGAATGGAAAAAGTCACGCAGAT TTTTATATTGGAGACTGAGAAGGAGGTTGAACGAGGGACA AGTGATCAAAAGACTGCAAAAAAAAACATGTGATAACAAA ACGAAAATGAAATACGACGACCTGTTGAAAATAGTTCAGT CATGGTATAACGATCTGGATGTTAATGATGACAGAGCAGTA GTGGAGTTCATAGAAAGAAATTCGAAAAAAATTGACAAGA ACATTGAAGAGTTTGAGATCTCGCTGTTGATCGATGAGCTT AAGAAAAAATTTGAAGACAGAAGGGGAAACATTGTCCTTG AAGAGCTAACTAGGTTGGTGGACAGTAAGCGAAAGAGATA G | |
| 62 | 3xARE 1 + pTE F1core | AATAAGGATCTCGAACCTTGTGCGATGACAACAGCATGTG AATAAGGATCTCGAACCTTGTGCGATGACAACAGCATGTG AATAAGGATCTCGAACCTTGTGCGATGACAACAGCATGTG AATAAGGATCTCGAACCATTGATATTTAAGTTAATAAACGG TCTTCAATTTCTCAAGTTTCAGTTTCATTTTTCTTGTTCTATT ACAACTTTTTTTACTTCTTGCTCATTAGAAAGAAAGCATAG CAATCTAATCTAAGTTTTAATTACAAA | 193 |
| 63 | pTEF1 (3xARE 1) | CACACACCATAGCTTCAAAATGTTTCTACTCCTTTTTTACTC TTCCAGATTTTCTCGGACTCCGCGCATCGCCGTACCACTTCA AAACACCCAAGCACAGCATACTAAATTTCCCCTCTTTCTTC CTCTAGGGTGTCGTTAATTACCCGTACTAAAGGTTTGGAAA AGAAAAAAGAGACCGCCTCGTTTCTTTTTCTTCGTCGAAAA AGGCAATAAAAATTTTTATCACGTTTCTTTTTCTTGAAAATT TTTTTTTTTGATTTTTTTCTCTTTCGATGACCTCCCATTGATA TTTAAGTTAATAAACGGTCTTCAATTTCTCAAGTTTCAGTTT CATTTTTCTTGTTCCTTGTGCGATGACAACAGCATGTGTATT ACAACTTTTTTTACTTCTTCTTGTGCGATGACAACAGCATGT GGCTCATTAGAAACTTGTGCGATGACAACAGCATGTGGAA AGCATAGCAATCTAATCTAAGTTTTAATTACAAA | 194 |

The invention claimed is:

1. A yeast, wherein said yeast lacks a gene encoding hexadecanal dehydrogenase (HFD1) or comprises a disrupted gene encoding HFD1; and said yeast comprises at least one heterologous gene encoding an enzyme involved in a pathway of producing fatty acids, fatty alcohols and/or fatty aldehydes.

2. The yeast according to claim 1, wherein said yeast comprises at least one additional heterologous gene encoding an enzyme involved in a pathway of producing fatty acids, fatty alcohols and/or fatty aldehydes from fatty acyl-Coenzyme A (CoA) through fatty aldehydes.

3. The yeast according to claim 1, wherein the at least one heterologous gene encoding an enzyme involved in a pathway of producing fatty acids, fatty alcohols and/or fatty aldehydes is a gene encoding carboxylic acid reductase.

4. The yeast according to claim 3, wherein the gene encoding carboxylic acid reductase is from *Mycobacterium marinum*.

5. The yeast according to claim 3, further comprising a gene encoding a phosphopantetheinyl transferase.

6. The yeast accordingly to claim 5, wherein the gene encoding a phosphopantetheinyl transferase is from *Aspergillus nidulans*.

7. The yeast according to claim 1, wherein the at least one heterologous gene encoding an enzyme involved in a pathway of producing fatty acids, fatty alcohols and/or fatty aldehydes is a heterologous gene encoding a thioesterase.

8. The yeast according to claim 7, wherein the gene encoding a thioesterase is selected from the group consisting of *Escherichia coli* testA, tesB, fadM and yciA.

9. The yeast according to claim 1, further comprising a gene encoding fatty acid synthase that is overexpressed.

10. The yeast according to claim 1, further comprising an acetyl-CoA carboxylase having increased activity via overexpression mutation.

11. The yeast according to claim 1, wherein the at least one heterologous gene encoding an enzyme involved in a pathway of producing fatty acids, fatty alcohols and/or fatty aldehydes is a gene encoding a fatty acyl-Coenzyme A (CoA) reductase or a fatty acyl-Acyl Carrier Protein (ACP) reductase.

12. The yeast according to claim 1, wherein said yeast is selected from the group consisting of a *Saccharomyces* yeast, *Hansenula polymorpha*, a *Kluyveromyces* yeast, a *Pichia* yeast, a *Candida* yeast, a *Trichoderma* yeast and *Yarrowia lipolytica*.

13. The yeast according to claim 1, wherein said yeast is *Saccharomyces cerevisiae*.

14. A method for producing a fatty acid, fatty alcohol and/or fatty aldehyde, said method comprising:

culturing the yeast of claim 1; and collecting said fatty acid, fatty alcohol and/or fatty aldehyde from said yeast and/or from the culture medium in which said yeast is cultured.

* * * * *

UNITED STATES PATENT AND TRADEMARK OFFICE

CERTIFICATE OF CORRECTION

PATENT NO. : 9,957,513 B2
APPLICATION NO. : 15/682002
DATED : May 1, 2018
INVENTOR(S) : Nielsen et al.

It is certified that error appears in the above-identified patent and that said Letters Patent is hereby corrected as shown below:

In the Specification

Column 2, Line 40:
Please insert a paragraph break between "fuels. These"

Column 9, Line 11:
Please correct "PDX1" to read -- POX1 --

Column 21, Line 54:
Please correct "PDX1" to read -- POX1 --

Column 30, Line 66:
Please correct "PDX1" to read -- POX1 --

Column 31, Line 17:
Please correct "PDX1" to read -- POX1 --

Column 31, Line 21:
Please correct "PDX1" to read -- POX1 --

In the Claims

Column 199, Claim 10, Lines 19-20:
Please correct "overexpression mutation." to read -- overexpression or mutation. --

Signed and Sealed this
Eleventh Day of September, 2018

Andrei Iancu
*Director of the United States Patent and Trademark Office*

SEQUENCE LISTING

<160> NUMBER OF SEQ ID NOS: 194

<210> SEQ ID NO 1
<211> LENGTH: 18
<212> TYPE: DNA
<213> ORGANISM: Saccharomyces cerevisiae

<400> SEQUENCE: 1
tgtgtttccg taccgcac 18

-continued

<210> SEQ ID NO 2
<211> LENGTH: 36
<212> TYPE: DNA
<213> ORGANISM: Saccharomyces cerevisiae

<400> SEQUENCE: 2
cagcgtacga agcttcagct gcggaattga gtctgc 36

<210> SEQ ID NO 3
<211> LENGTH: 39
<212> TYPE: DNA
<213> ORGANISM: Saccharomyces cerevisiae

<400> SEQUENCE: 3
gtgatatcag atccactagg caacaccaag tttctacgg 39

<210> SEQ ID NO 4
<211> LENGTH: 21
<212> TYPE: DNA
<213> ORGANISM: Saccharomyces cerevisiae

<400> SEQUENCE: 4
atttttgtca cctgcaaact c 21

<210> SEQ ID NO 5
<211> LENGTH: 18
<212> TYPE: DNA
<213> ORGANISM: Saccharomyces cerevisiae

<400> SEQUENCE: 5
ctgaagcttc gtacgctg 18

<210> SEQ ID NO 6
<211> LENGTH: 20
<212> TYPE: DNA
<213> ORGANISM: Saccharomyces cerevisiae

<400> SEQUENCE: 6
tcaccatgag tgacgactga 20

<210> SEQ ID NO 7
<211> LENGTH: 19
<212> TYPE: DNA
<213> ORGANISM: Saccharomyces cerevisiae

<400> SEQUENCE: 7
ttccaacatg gatgctgat 19

<210> SEQ ID NO 8
<211> LENGTH: 19
<212> TYPE: DNA
<213> ORGANISM: Saccharomyces cerevisiae

<400> SEQUENCE: 8
ctagtggatc tgatatcac 19

<210> SEQ ID NO 9
<211> LENGTH: 18
<212> TYPE: DNA
<213> ORGANISM: Saccharomyces cerevisiae

<400> SEQUENCE: 9
ctcgtcggtt tatctgcc 18

<210> SEQ ID NO 10
<211> LENGTH: 36
<212> TYPE: DNA
<213> ORGANISM: Saccharomyces cerevisiae

<400> SEQUENCE: 10
cagcgtacga agcttcagcg ttgagctttt ggatgc 36

<210> SEQ ID NO 11
<211> LENGTH: 37
<212> TYPE: DNA
<213> ORGANISM: Saccharomyces cerevisiae

<400> SEQUENCE: 11
gtgatatcag atccactagg ctcggtatct gcatggg 37

<210> SEQ ID NO 12
<211> LENGTH: 21
<212> TYPE: DNA
<213> ORGANISM: Saccharomyces cerevisiae

<400> SEQUENCE: 12
gcacgatatg aatagcagtg g 21

<210> SEQ ID NO 13
<211> LENGTH: 24
<212> TYPE: DNA
<213> ORGANISM: Saccharomyces cerevisiae

<400> SEQUENCE: 13
cgttattgta actggtaatc agag 24

<210> SEQ ID NO 14
<211> LENGTH: 36
<212> TYPE: DNA
<213> ORGANISM: Saccharomyces cerevisiae

<400> SEQUENCE: 14
cagcgtacga agcttcagcc tttcggtaat accggc 36

<210> SEQ ID NO 15
<211> LENGTH: 38
<212> TYPE: DNA
<213> ORGANISM: Saccharomyces cerevisiae

<400> SEQUENCE: 15
gtgatatcag atccactaga atgttgttgt tggaaggc 38

<210> SEQ ID NO 16
<211> LENGTH: 23
<212> TYPE: DNA
<213> ORGANISM: Saccharomyces cerevisiae

<400> SEQUENCE: 16
gctttcctaa acttacattc aaa 23

<210> SEQ ID NO 17
<211> LENGTH: 22
<212> TYPE: DNA
<213> ORGANISM: Saccharomyces cerevisiae

<400> SEQUENCE: 17
ctcctttgta cttctttgtt cc 22

<210> SEQ ID NO 18
<211> LENGTH: 38
<212> TYPE: DNA
<213> ORGANISM: Saccharomyces cerevisiae

<400> SEQUENCE: 18
cagcgtacga agcttcagcc tgttgatgat gaatgtgg 38

<210> SEQ ID NO 19
<211> LENGTH: 37
<212> TYPE: DNA
<213> ORGANISM: Saccharomyces cerevisiae

<400> SEQUENCE: 19
gtgatatcag atccactagc aagcggtaat ggcgatc 37

<210> SEQ ID NO 20
<211> LENGTH: 20
<212> TYPE: DNA
<213> ORGANISM: Saccharomyces cerevisiae

<400> SEQUENCE: 20
cggttgtttt tcctctatgc 20

<210> SEQ ID NO 21
<211> LENGTH: 24
<212> TYPE: DNA
<213> ORGANISM: Saccharomyces cerevisiae

<400> SEQUENCE: 21
gccctatatt tacggtatta gttg 24

<210> SEQ ID NO 22
<211> LENGTH: 42
<212> TYPE: DNA
<213> ORGANISM: Saccharomyces cerevisiae

<400> SEQUENCE: 22
cagcgtacga agcttcaggg gattaatagt agtacgtctc gt 42

<210> SEQ ID NO 23
<211> LENGTH: 36
<212> TYPE: DNA
<213> ORGANISM: Saccharomyces cerevisiae

<400> SEQUENCE: 23
gtgatatcag atccactagc agatggggca gggaag 36

<210> SEQ ID NO 24
<211> LENGTH: 23
<212> TYPE: DNA
<213> ORGANISM: Saccharomyces cerevisiae

<400> SEQUENCE: 24
gtagtcatgt cattgattcg tca 23

<210> SEQ ID NO 25
<211> LENGTH: 42
<212> TYPE: DNA
<213> ORGANISM: Saccharomyces cerevisiae

<400> SEQUENCE: 25

-continued agttttaatt acaaggatcc actatggttt cccaattatt cg 42

<210> SEQ ID NO 26
<211> LENGTH: 44
<212> TYPE: DNA
<213> ORGANISM: Saccharomyces cerevisiae

<400> SEQUENCE: 26
gcggatctta gctagccgcg gtaccctaag aggagtactt ggca 44

<210> SEQ ID NO 27
<211> LENGTH: 26
<212> TYPE: DNA
<213> ORGANISM: Saccharomyces cerevisiae

<400> SEQUENCE: 27
aacttagaut agattgctat gctttc 26

<210> SEQ ID NO 28
<211> LENGTH: 30
<212> TYPE: DNA
<213> ORGANISM: Saccharomyces cerevisiae

<400> SEQUENCE: 28
atttgttgua aaaagtagat aattacttcc 30

<210> SEQ ID NO 29
<211> LENGTH: 29
<212> TYPE: DNA
<213> ORGANISM: Saccharomyces cerevisiae

<400> SEQUENCE: 29
cgtgcgaugg aagtaccttc aaagaatgg 29

<210> SEQ ID NO 30
<211> LENGTH: 39
<212> TYPE: DNA
<213> ORGANISM: Saccharomyces cerevisiae

<400> SEQUENCE: 30
acaacaaaua taaaacaatg aaggatgtcg taatcgttg 39

<210> SEQ ID NO 31
<211> LENGTH: 34
<212> TYPE: DNA
<213> ORGANISM: Saccharomyces cerevisiae

<400> SEQUENCE: 31
cacgcgautt attcgtctct ttcgatagtc aatg 34

<210> SEQ ID NO 32
<211> LENGTH: 33
<212> TYPE: DNA
<213> ORGANISM: Saccharomyces cerevisiae

<400> SEQUENCE: 32
cgtgcgautt agactctttc aaatacagta gcg 33

<210> SEQ ID NO 33
<211> LENGTH: 44
<212> TYPE: DNA
<213> ORGANISM: Saccharomyces cerevisiae

<400> SEQUENCE: 33

-continued atctaagtut taataaaaca atggaacaag tagtaatcgt agac 44

<210> SEQ ID NO 34
<211> LENGTH: 44
<212> TYPE: DNA
<213> ORGANISM: Saccharomyces cerevisiae

<400> SEQUENCE: 34
acaacaaaua taaaacaatg ttgtataaag gtgacacatt gtac 44

<210> SEQ ID NO 35
<211> LENGTH: 29
<212> TYPE: DNA
<213> ORGANISM: Saccharomyces cerevisiae

<400> SEQUENCE: 35
cacgcgautt aggcagtttt caagtcacc 29

<210> SEQ ID NO 36
<211> LENGTH: 32
<212> TYPE: DNA
<213> ORGANISM: Saccharomyces cerevisiae

<400> SEQUENCE: 36
cgtgcgautt agattctatc gaatctttcg ac 32

<210> SEQ ID NO 37
<211> LENGTH: 44
<212> TYPE: DNA
<213> ORGANISM: Saccharomyces cerevisiae

<400> SEQUENCE: 37
atctaagtut taataaaaca atgatagtaa agccaatggt aagg 44

<210> SEQ ID NO 38
<211> LENGTH: 31
<212> TYPE: DNA
<213> ORGANISM: Saccharomyces cerevisiae

<400> SEQUENCE: 38
cgtgcgauct attctttaat aaagatggcg g 31

<210> SEQ ID NO 39
<211> LENGTH: 41
<212> TYPE: DNA
<213> ORGANISM: Saccharomyces cerevisiae

<400> SEQUENCE: 39
atctaagtut taataaaaca atgggtaagg gtgaatcgaa g 41

<210> SEQ ID NO 40
<211> LENGTH: 38
<212> TYPE: DNA
<213> ORGANISM: Saccharomyces cerevisiae

<400> SEQUENCE: 40
acaacaaaua taaaacaatg cctggaaatt tatccttc 38

<210> SEQ ID NO 41
<211> LENGTH: 32
<212> TYPE: DNA
<213> ORGANISM: Saccharomyces cerevisiae -continued

<400> SEQUENCE: 41
cacgcgautt attttgcctg cgatagtttt ac 32

<210> SEQ ID NO 42
<211> LENGTH: 42
<212> TYPE: DNA
<213> ORGANISM: Saccharomyces cerevisiae

<400> SEQUENCE: 42
acaacaaaua taaaacaatg tctcagaacg tttacattgt at 42

<210> SEQ ID NO 43
<211> LENGTH: 33
<212> TYPE: DNA
<213> ORGANISM: Saccharomyces cerevisiae

<400> SEQUENCE: 43
cacgcgautc atatcttttc aatgacaata gag 33

<210> SEQ ID NO 44
<211> LENGTH: 41
<212> TYPE: DNA
<213> ORGANISM: Saccharomyces cerevisiae

<400> SEQUENCE: 44
acaacaaaua taaaacaatg agtgcttcca aaatggccat g 41

<210> SEQ ID NO 45
<211> LENGTH: 31
<212> TYPE: DNA
<213> ORGANISM: Saccharomyces cerevisiae

<400> SEQUENCE: 45
cacgcgautc atcgaatgtc tcgttctgac c 31

<210> SEQ ID NO 46
<211> LENGTH: 41
<212> TYPE: DNA
<213> ORGANISM: Saccharomyces cerevisiae

<400> SEQUENCE: 46
acaacaaaua taaaacaatg gccgatactt tgttaatttt g 41

<210> SEQ ID NO 47
<211> LENGTH: 32
<212> TYPE: DNA
<213> ORGANISM: Saccharomyces cerevisiae

<400> SEQUENCE: 47
cacgcgautc aagaatcgtg attgactaat gg 32

<210> SEQ ID NO 48
<211> LENGTH: 41
<212> TYPE: DNA
<213> ORGANISM: Saccharomyces cerevisiae

<400> SEQUENCE: 48
acaacaaaua taaaacaatg tctcaagctt tgaagaactt g 41

<210> SEQ ID NO 49
<211> LENGTH: 32
<212> TYPE: DNA
<213> ORGANISM: Saccharomyces cerevisiae

<400> SEQUENCE: 49
cacgcgautc agttgtggtt tctcataaca cc 32

<210> SEQ ID NO 50
<211> LENGTH: 41
<212> TYPE: DNA
<213> ORGANISM: Saccharomyces cerevisiae

<400> SEQUENCE: 50
acaacaaaua taaaacaatg caaactcaaa tcaaggttag a 41

<210> SEQ ID NO 51
<211> LENGTH: 32
<212> TYPE: DNA
<213> ORGANISM: Saccharomyces cerevisiae

<400> SEQUENCE: 51
cacgcgautc acttaaccat ttgttccaac tt 32

<210> SEQ ID NO 52
<211> LENGTH: 41
<212> TYPE: DNA
<213> ORGANISM: Saccharomyces cerevisiae

<400> SEQUENCE: 52
acaacaaaua taaaacaatg tctactactc acaacgttcc a 41

<210> SEQ ID NO 53
<211> LENGTH: 32
<212> TYPE: DNA
<213> ORGANISM: Saccharomyces cerevisiae

<400> SEQUENCE: 53
cacgcgautc attcaactgg caaagctctt gg 32

<210> SEQ ID NO 54
<211> LENGTH: 53
<212> TYPE: DNA
<213> ORGANISM: Saccharomyces cerevisiae

<400> SEQUENCE: 54
gcatagcaat ctaatctaag ttttaattac aaaatgaata agaagttgga agc 53

<210> SEQ ID NO 55
<211> LENGTH: 55
<212> TYPE: DNA
<213> ORGANISM: Saccharomyces cerevisiae

<400> SEQUENCE: 55
ggatacccgg gtcgacgcgt aagcttgtgg gccctatcac caatgttcac caggg 55

<210> SEQ ID NO 56
<211> LENGTH: 54
<212> TYPE: DNA
<213> ORGANISM: Saccharomyces cerevisiae

<400> SEQUENCE: 56
gcatagcaat ctaatctaag ttttaattac aaaatgaatt atttcttgac aggt 54

<210> SEQ ID NO 57
<211> LENGTH: 56
<212> TYPE: DNA

-continued

<213> ORGANISM: Saccharomyces cerevisiae

<400> SEQUENCE: 57
ggatacccgg gtcgacgcgt aagcttgtgg gccctattac caatagatac ctctca 56

<210> SEQ ID NO 58
<211> LENGTH: 58
<212> TYPE: DNA
<213> ORGANISM: Saccharomyces cerevisiae

<400> SEQUENCE: 58
ggaagtaatt atctactttt tacaacaaat ataacaaaat ggtgcaagac acatcaag 58

<210> SEQ ID NO 59
<211> LENGTH: 58
<212> TYPE: DNA
<213> ORGANISM: Saccharomyces cerevisiae

<400> SEQUENCE: 59
gacataacta attacatgac tcgaggtcga cggtatctta ggataggcaa ttacacac 58

<210> SEQ ID NO 60
<211> LENGTH: 58
<212> TYPE: DNA
<213> ORGANISM: Saccharomyces cerevisiae

<400> SEQUENCE: 60
ggaagtaatt atctactttt tacaacaaat ataacaaaat ggactcaggt cacggtgc 58

<210> SEQ ID NO 61
<211> LENGTH: 59
<212> TYPE: DNA
<213> ORGANISM: Saccharomyces cerevisiae

<400> SEQUENCE: 61
gacataacta attacatgac tcgaggtcga cggtatctca gaacatttcg tctatcaag 59

<210> SEQ ID NO 62
<211> LENGTH: 57
<212> TYPE: DNA
<213> ORGANISM: Saccharomyces cerevisiae

<400> SEQUENCE: 62
ctcattaaaa aactatatca attaatttga attaacttac attgccttca ttgcttc 57

<210> SEQ ID NO 63
<211> LENGTH: 57
<212> TYPE: DNA
<213> ORGANISM: Saccharomyces cerevisiae

<400> SEQUENCE: 63
gaaagcatag caatctaatc taagttttaa ttacaaaatg gactccgcca acaactc 57

<210> SEQ ID NO 64
<211> LENGTH: 62
<212> TYPE: DNA
<213> ORGANISM: Saccharomyces cerevisiae

<400> SEQUENCE: 64
caagaactta gtttcgaata aacacacata aacaaacaaa atgtcaccta tcaccagaga 60
ag 62

-continued

<210> SEQ ID NO 65
<211> LENGTH: 62
<212> TYPE: DNA
<213> ORGANISM: Saccharomyces cerevisiae

<400> SEQUENCE: 65
cttatttaat aataaaaatc ataaatcata agaaattcgc ttacaacaaa cccaacaatc 60
tc 62

<210> SEQ ID NO 66
<211> LENGTH: 57
<212> TYPE: DNA
<213> ORGANISM: Saccharomyces cerevisiae

<400> SEQUENCE: 66
ctataactac aaaaaacaca tacataaact aaaaatgaac ggccgagcga cgcggag 57

<210> SEQ ID NO 67
<211> LENGTH: 60
<212> TYPE: DNA
<213> ORGANISM: Saccharomyces cerevisiae

<400> SEQUENCE: 67
ctcattaaaa aactatatca attaatttga attaactcag agcccgccga agacgtcgag 60

<210> SEQ ID NO 68
<211> LENGTH: 60
<212> TYPE: DNA
<213> ORGANISM: Saccharomyces cerevisiae

<400> SEQUENCE: 68
gacataacta attacatgac tcgaggtcga cggtatccta cttctgggcg atgacgacgg 60

<210> SEQ ID NO 69
<211> LENGTH: 59
<212> TYPE: DNA
<213> ORGANISM: Saccharomyces cerevisiae

<400> SEQUENCE: 69
gaaagcatag caatctaatc taagttttaa ttacaaaatg gtcgcggcgc aggacttgc 59

<210> SEQ ID NO 70
<211> LENGTH: 64
<212> TYPE: DNA
<213> ORGANISM: Saccharomyces cerevisiae

<400> SEQUENCE: 70
caagaactta gtttcgaata aacacacata aacaaacaaa atgccattct ctggcgaggc 60
gaag 64

<210> SEQ ID NO 71
<211> LENGTH: 58
<212> TYPE: DNA
<213> ORGANISM: Saccharomyces cerevisiae

<400> SEQUENCE: 71
ggatacccgg gtcgacgcgt aagcttgtgg gccctactag gcgaggatgc gggcgagg 58

<210> SEQ ID NO 72
<211> LENGTH: 24
<212> TYPE: DNA
<213> ORGANISM: Saccharomyces cerevisiae

<400> SEQUENCE: 72
gattatcaat gtcccagtta tacg 24

<210> SEQ ID NO 73
<211> LENGTH: 22
<212> TYPE: DNA
<213> ORGANISM: Saccharomyces cerevisiae

<400> SEQUENCE: 73
taagtttggt cgtttcattc ag 22

<210> SEQ ID NO 74
<211> LENGTH: 23
<212> TYPE: DNA
<213> ORGANISM: Saccharomyces cerevisiae

<400> SEQUENCE: 74
gagtacgagg atcttgatga gac 23

<210> SEQ ID NO 75
<211> LENGTH: 23
<212> TYPE: DNA
<213> ORGANISM: Saccharomyces cerevisiae

<400> SEQUENCE: 75
cacttgttat tgccatttct gtc 23

<210> SEQ ID NO 76
<211> LENGTH: 75
<212> TYPE: DNA
<213> ORGANISM: Kluyveromyces lactis

<400> SEQUENCE: 76
cgaaaggtta cttatacatc aaataattaa ttaaccttaa acattacgtt cacatgttgg 60
tgataaatta ctatg 75

<210> SEQ ID NO 77
<211> LENGTH: 88
<212> TYPE: DNA
<213> ORGANISM: Saccharomyces cerevisiae

<400> SEQUENCE: 77
ggttaattaa ttatttgatg tataagtaac ctttcgttta aaaatttcat atgggcgata 60
atatatcgtg attctgggta gaagatcg 88

<210> SEQ ID NO 78
<211> LENGTH: 60
<212> TYPE: DNA
<213> ORGANISM: Saccharomyces cerevisiae

<400> SEQUENCE: 78
ctattatctt gttaatggtc tcatcaagat cctcgtactc catcgataag cttgatatcg 60

<210> SEQ ID NO 79
<211> LENGTH: 24
<212> TYPE: DNA
<213> ORGANISM: Saccharomyces cerevisiae

<400> SEQUENCE: 79
gattccttca gttccacttt ttgc 24

<210> SEQ ID NO 80
<211> LENGTH: 23
<212> TYPE: DNA
<213> ORGANISM: Saccharomyces cerevisiae

<400> SEQUENCE: 80
gtagcatcgt aatagtccgt gtc 23

<210> SEQ ID NO 81
<211> LENGTH: 23
<212> TYPE: DNA
<213> ORGANISM: Saccharomyces cerevisiae

<400> SEQUENCE: 81
gatctctaaa gttgtgcagc cac 23

<210> SEQ ID NO 82
<211> LENGTH: 22
<212> TYPE: DNA
<213> ORGANISM: Saccharomyces cerevisiae

<400> SEQUENCE: 82
cgcattagct gcaccaccta ac 22

<210> SEQ ID NO 83
<211> LENGTH: 83
<212> TYPE: DNA
<213> ORGANISM: Saccharomyces cerevisiae

<400> SEQUENCE: 83
gaattgaaac aaaagtcgca aaacagaggg ttcgaaggaa aacaggaaac ctctactcac 60
atatcgcaat actaatttat tat 83

<210> SEQ ID NO 84
<211> LENGTH: 81
<212> TYPE: DNA
<213> ORGANISM: Saccharomyces cerevisiae

<400> SEQUENCE: 84
cttcgaaccc tctgttttgc gacttttgtt tcaattcaac tagtgtcgcc aagttttaac 60
gtgattctgg gtagaagatc g 81

<210> SEQ ID NO 85
<211> LENGTH: 55
<212> TYPE: DNA
<213> ORGANISM: Saccharomyces cerevisiae

<400> SEQUENCE: 85
gagccaatag ttgtggctgc acaactttag agatccatcg ataagcttga tatcg 55

<210> SEQ ID NO 86
<211> LENGTH: 22
<212> TYPE: DNA
<213> ORGANISM: Saccharomyces cerevisiae

<400> SEQUENCE: 86
cacccaccca tcgcatatca gg 22

<210> SEQ ID NO 87
<211> LENGTH: 24
<212> TYPE: DNA
<213> ORGANISM: Saccharomyces cerevisiae

<400> SEQUENCE: 87
cttaacatcc ctccaaccca tagc 24

<210> SEQ ID NO 88
<211> LENGTH: 24
<212> TYPE: DNA
<213> ORGANISM: Saccharomyces cerevisiae

<400> SEQUENCE: 88
gaaattagag tccgtttaca gatc 24

<210> SEQ ID NO 89
<211> LENGTH: 24
<212> TYPE: DNA
<213> ORGANISM: Saccharomyces cerevisiae

<400> SEQUENCE: 89
gtcaaagaac actatgcctg ctag 24

<210> SEQ ID NO 90
<211> LENGTH: 79
<212> TYPE: DNA
<213> ORGANISM: Saccharomyces cerevisiae

<400> SEQUENCE: 90
ctgaaaaagt gctttagtat gatgaggctt tcctatcatg gaaatgttga tccattacat 60
attgttgtct ttttttgtc 79

<210> SEQ ID NO 91
<211> LENGTH: 81
<212> TYPE: DNA
<213> ORGANISM: Saccharomyces cerevisiae

<400> SEQUENCE: 91
gataggaaag cctcatcata ctaaagcact ttttcagttt tttgctttag aactgctacc 60
gtgattctgg gtagaagatc g 81

<210> SEQ ID NO 92
<211> LENGTH: 58
<212> TYPE: DNA
<213> ORGANISM: Saccharomyces cerevisiae

<400> SEQUENCE: 92
caacatattc gttagatctg taaacggact ctaatttcca tcgataagct tgatatcg 58

<210> SEQ ID NO 93
<211> LENGTH: 23
<212> TYPE: DNA
<213> ORGANISM: Saccharomyces cerevisiae

<400> SEQUENCE: 93
gtccccatca attaagaacc ctc 23

<210> SEQ ID NO 94
<211> LENGTH: 22
<212> TYPE: DNA
<213> ORGANISM: Saccharomyces cerevisiae

<400> SEQUENCE: 94
gatgctgagg agtttatggg tc 22

<210> SEQ ID NO 95
<211> LENGTH: 23
<212> TYPE: DNA
<213> ORGANISM: Saccharomyces cerevisiae

<400> SEQUENCE: 95
cctttaccga tgatggctgg ttc 23

<210> SEQ ID NO 96
<211> LENGTH: 25
<212> TYPE: DNA
<213> ORGANISM: Saccharomyces cerevisiae

<400> SEQUENCE: 96
gatgtaacaa gaccgttttc tggag 25

<210> SEQ ID NO 97
<211> LENGTH: 84
<212> TYPE: DNA
<213> ORGANISM: Saccharomyces cerevisiae

<400> SEQUENCE: 97
gaaaatgaaa cgtagtgttt atgaagggca ggggggaaag taaaaaacta tgtcttcctt 60
tacattttga tgcgtacttc ttag 84

<210> SEQ ID NO 98
<211> LENGTH: 78
<212> TYPE: DNA
<213> ORGANISM: Saccharomyces cerevisiae

<400> SEQUENCE: 98
ctttcccccc tgcccttcat aaacactacg tttcattttc taagagcatc aatttgcgtg 60
attctgggta gaagatcg 78

<210> SEQ ID NO 99
<211> LENGTH: 58
<212> TYPE: DNA
<213> ORGANISM: Saccharomyces cerevisiae

<400> SEQUENCE: 99
gatatcaccg gtacggaacc agccatcatc ggtaaaggca tcgataagct tgatatcg 58

<210> SEQ ID NO 100
<211> LENGTH: 20
<212> TYPE: DNA
<213> ORGANISM: E.coli

<400> SEQUENCE: 100
ggatccaaaa caatgttcgg 20

<210> SEQ ID NO 101
<211> LENGTH: 22
<212> TYPE: DNA
<213> ORGANISM: E.coli

<400> SEQUENCE: 101
gattgctaag gctaaaggtt gg 22

<210> SEQ ID NO 102
<211> LENGTH: 20
<212> TYPE: DNA
<213> ORGANISM: Saccharomyces cerevisiae

<400> SEQUENCE: 102
gctttaatca ctggtgcctc 20

<210> SEQ ID NO 103
<211> LENGTH: 19
<212> TYPE: DNA
<213> ORGANISM: Saccharomyces cerevisiae

<400> SEQUENCE: 103
ttcaccaatg ttcaccagg 19

<210> SEQ ID NO 104
<211> LENGTH: 23
<212> TYPE: DNA
<213> ORGANISM: Saccharomyces cerevisiae

<400> SEQUENCE: 104
gccacaatta gaagcctcct tag 23

<210> SEQ ID NO 105
<211> LENGTH: 19
<212> TYPE: DNA
<213> ORGANISM: Saccharomyces cerevisiae

<400> SEQUENCE: 105
ctgctgccaa accgtatgc 19

<210> SEQ ID NO 106
<211> LENGTH: 20
<212> TYPE: DNA
<213> ORGANISM: Saccharomyces cerevisiae

<400> SEQUENCE: 106
gcctactcca gaatcaacgc 20

<210> SEQ ID NO 107
<211> LENGTH: 20
<212> TYPE: DNA
<213> ORGANISM: Saccharomyces cerevisiae

<400> SEQUENCE: 107
gccttactct ctgcgaagtg 20

<210> SEQ ID NO 108
<211> LENGTH: 42
<212> TYPE: DNA
<213> ORGANISM: Saccharomyces cerevisiae

<400> SEQUENCE: 108
atcgaagcgg ccgcaaaaca atgccaaaga ttgttatttt gc 42

<210> SEQ ID NO 109
<211> LENGTH: 30
<212> TYPE: DNA
<213> ORGANISM: Saccharomyces cerevisiae

<400> SEQUENCE: 109
atcgtcgagc tcttaatgct cacgcgcatg 30

<210> SEQ ID NO 110
<211> LENGTH: 20
<212> TYPE: DNA
<213> ORGANISM: Saccharomyces cerevisiae

<400> SEQUENCE: 110
atggctgatt gggtaacagg 20

<210> SEQ ID NO 111
<211> LENGTH: 21
<212> TYPE: DNA
<213> ORGANISM: Saccharomyces cerevisiae

<400> SEQUENCE: 111
acagcggagc attactggta a 21

<210> SEQ ID NO 112
<211> LENGTH: 90
<212> TYPE: DNA
<213> ORGANISM: Saccharomyces cerevisiae

<400> SEQUENCE: 112
atcgaagcgg ccgcaaaaca atgctttctc ttcgtcaatc tattcgtttt tttaaacgtt 60
ctggtattat gccaaagatt gttattttgc 90

<210> SEQ ID NO 113
<211> LENGTH: 86
<212> TYPE: DNA
<213> ORGANISM: Saccharomyces cerevisiae

<400> SEQUENCE: 113
cattatcccg ggaaaacaat gctttctctt cgtcaatcta ttcgtttttt taaacgttct 60
ggtattatgg ctgattgggt aacagg 86

<210> SEQ ID NO 114
<211> LENGTH: 33
<212> TYPE: DNA
<213> ORGANISM: Saccharomyces cerevisiae

<400> SEQUENCE: 114
cattatctcg agttaccagt aatgctccgc tgt 33

<210> SEQ ID NO 115
<211> LENGTH: 100
<212> TYPE: DNA
<213> ORGANISM: Saccharomyces cerevisiae

<400> SEQUENCE: 115
aactacaaaa aacacataca taaactaaaa atgctttctc ttcgtcaatc tattcgtttt 60
tttaaacgtt ctggtattat ggtgcaagac acatcaagcg 100

<210> SEQ ID NO 116
<211> LENGTH: 55
<212> TYPE: DNA
<213> ORGANISM: Saccharomyces cerevisiae

<400> SEQUENCE: 116
aaaaaactat atcaattaat ttgaattaac ttaggatagg caattacaca cccca 55

<210> SEQ ID NO 117
<211> LENGTH: 106
<212> TYPE: DNA
<213> ORGANISM: Saccharomyces cerevisiae

<400> SEQUENCE: 117
gtttcgaata aacacacata aacaaacaaa atgctttctc ttcgtcaatc tattcgtttt 60
tttaaacgtt ctggtattat gcaacaatta acagaccaat caaagg 106

<210> SEQ ID NO 118
<211> LENGTH: 56
<212> TYPE: DNA
<213> ORGANISM: Saccharomyces cerevisiae

<400> SEQUENCE: 118
ctaattacat gactcgaggt cgacggtatc tcaagcacct atcaaaccgt aagcac 56

<210> SEQ ID NO 119
<211> LENGTH: 104
<212> TYPE: DNA
<213> ORGANISM: Saccharomyces cerevisiae

<400> SEQUENCE: 119
acaaaaagtt tttttaattt taatcaaaaa atgctttctc ttcgtcaatc tattcgtttt 60
tttaaacgtt ctggtattat gtcacctatc accagagaag aaag 104

<210> SEQ ID NO 120
<211> LENGTH: 55
<212> TYPE: DNA
<213> ORGANISM: Saccharomyces cerevisiae

<400> SEQUENCE: 120
aaatcattaa agtaacttaa ggagttaaat ttacaacaaa cccaacaatc tcaaa 55

<210> SEQ ID NO 121
<211> LENGTH: 57
<212> TYPE: DNA
<213> ORGANISM: Saccharomyces cerevisiae

<400> SEQUENCE: 121
tagcaatcta atctaagttt taattacaaa atgcttccca cattcaaacg ttacatg 57

<210> SEQ ID NO 122
<211> LENGTH: 60
<212> TYPE: DNA
<213> ORGANISM: Saccharomyces cerevisiae

<400> SEQUENCE: 122
gggtcgacgc gtaagcttgt gggccctatt accattctaa aacaaccatt tttttcttcc 60

<210> SEQ ID NO 123
<211> LENGTH: 58
<212> TYPE: DNA
<213> ORGANISM: Saccharomyces cerevisiae

<400> SEQUENCE: 123
ttatctactt tttacaacaa atataacaaa atgagatcta taagaaaatg ggcgtacg 58

<210> SEQ ID NO 124
<211> LENGTH: 22
<212> TYPE: DNA
<213> ORGANISM: Saccharomyces cerevisiae

<400> SEQUENCE: 124
ttggtccgaa gtggtgatca cg 22

<210> SEQ ID NO 125
<211> LENGTH: 27

<212> TYPE: DNA
<213> ORGANISM: Saccharomyces cerevisiae

<400> SEQUENCE: 125
gatcatgtta cgcccttcag gatattc 27

<210> SEQ ID NO 126
<211> LENGTH: 29
<212> TYPE: DNA
<213> ORGANISM: Saccharomyces cerevisiae

<400> SEQUENCE: 126
gcaggaaaag aaacagattt cttgactag 29

<210> SEQ ID NO 127
<211> LENGTH: 26
<212> TYPE: DNA
<213> ORGANISM: Saccharomyces cerevisiae

<400> SEQUENCE: 127
cagtacatcg tctcgaggaa attgtg 26

<210> SEQ ID NO 128
<211> LENGTH: 58
<212> TYPE: DNA
<213> ORGANISM: Saccharomyces cerevisiae

<400> SEQUENCE: 128
aataaaaatc ataaatcata agaaattcgc ctatctcttt cgcttactgt ccaccaac 58

<210> SEQ ID NO 129
<211> LENGTH: 22
<212> TYPE: DNA
<213> ORGANISM: Saccharomyces cerevisiae

<400> SEQUENCE: 129
ggggtggttt agtttagtag aa 22

<210> SEQ ID NO 130
<211> LENGTH: 22
<212> TYPE: DNA
<213> ORGANISM: Saccharomyces cerevisiae

<400> SEQUENCE: 130
gcaacctgac ctacaggaaa ga 22

<210> SEQ ID NO 131
<211> LENGTH: 24
<212> TYPE: DNA
<213> ORGANISM: Saccharomyces cerevisiae

<400> SEQUENCE: 131
ttttacttct tgctcattag aaag 24

<210> SEQ ID NO 132
<211> LENGTH: 21
<212> TYPE: DNA
<213> ORGANISM: Saccharomyces cerevisiae

<400> SEQUENCE: 132
ggacctagac ttcaggttgt c 21

<210> SEQ ID NO 133

<211> LENGTH: 61
<212> TYPE: DNA
<213> ORGANISM: Saccharomyces cerevisiae

<400> SEQUENCE: 133
gtgacataac taattacatg actcgaggtc gacggtatct taactccaaa catcagcgga 60
g 61

<210> SEQ ID NO 134
<211> LENGTH: 62
<212> TYPE: DNA
<213> ORGANISM: Saccharomyces cerevisiae

<400> SEQUENCE: 134
caagaactta gtttcgaata aacacacata aacaaacaaa atgagtgccg aacacgttga 60
ag 62

<210> SEQ ID NO 135
<211> LENGTH: 59
<212> TYPE: DNA
<213> ORGANISM: Saccharomyces cerevisiae

<400> SEQUENCE: 135
caagaactta gtttcgaata aacacacata aacaaacaaa atgttcggtt taataggtc 59

<210> SEQ ID NO 136
<211> LENGTH: 60
<212> TYPE: DNA
<213> ORGANISM: Saccharomyces cerevisiae

<400> SEQUENCE: 136
cttatttaat aataaaaatc ataaatcata agaaattcgc tcagattgct aaggctaaag 60

<210> SEQ ID NO 137
<211> LENGTH: 57
<212> TYPE: DNA
<213> ORGANISM: Saccharomyces cerevisiae

<400> SEQUENCE: 137
ctcattaaaa aactatatca attaatttga attaacttac attgccttca ttgcttc 57

<210> SEQ ID NO 138
<211> LENGTH: 57
<212> TYPE: DNA
<213> ORGANISM: Saccharomyces cerevisiae

<400> SEQUENCE: 138
gaaagcatag caatctaatc taagttttaa ttacaaaatg gactccgcca acaactc 57

<210> SEQ ID NO 139
<211> LENGTH: 58
<212> TYPE: DNA
<213> ORGANISM: Saccharomyces cerevisiae

<400> SEQUENCE: 139
gagtaaaaaa ggagtagaaa cattttgaag ctatgtttaa agattacgga tatttaac 58

<210> SEQ ID NO 140
<211> LENGTH: 47
<212> TYPE: DNA
<213> ORGANISM: Saccharomyces cerevisiae

<400> SEQUENCE: 140
gcttcttcga cgagggttcc atttttagtt tatgtatgtg ttttttg 47

<210> SEQ ID NO 141
<211> LENGTH: 58
<212> TYPE: DNA
<213> ORGANISM: Saccharomyces cerevisiae

<400> SEQUENCE: 141
caaatgccta ttgtgcagat gttataatat ctgtgcgtgc gaaaagccaa ttagtgtg 58

<210> SEQ ID NO 142
<211> LENGTH: 59
<212> TYPE: DNA
<213> ORGANISM: Saccharomyces cerevisiae

<400> SEQUENCE: 142
caagaactta gtttcgaata aacacacata aacaaacaaa atgaataaga agttggaag 59

<210> SEQ ID NO 143
<211> LENGTH: 59
<212> TYPE: DNA
<213> ORGANISM: Saccharomyces cerevisiae

<400> SEQUENCE: 143
cttatttaat aataaaaatc ataaatcata agaaattcgc tcaccaatgt tcaccaggg 59

<210> SEQ ID NO 144
<211> LENGTH: 59
<212> TYPE: DNA
<213> ORGANISM: Saccharomyces cerevisiae

<400> SEQUENCE: 144
gacataacta attacatgac tcgaggtcga cggtatctta ccatacatcg cgcaagtac 59

<210> SEQ ID NO 145
<211> LENGTH: 65
<212> TYPE: DNA
<213> ORGANISM: Saccharomyces cerevisiae

<400> SEQUENCE: 145
gcttaaatct ataactacaa aaaacacata cataaactaa aaatgaatta tttcttgaca 60
ggtgg 65

<210> SEQ ID NO 146
<211> LENGTH: 63
<212> TYPE: DNA
<213> ORGANISM: Saccharomyces cerevisiae

<400> SEQUENCE: 146
cggatacccg ggtcgacgcg taagcttgtg ggccctatta ccaatagata cctctcataa 60
tgg 63

<210> SEQ ID NO 147
<211> LENGTH: 55
<212> TYPE: DNA
<213> ORGANISM: Saccharomyces cerevisiae

<400> SEQUENCE: 147
ctataactac aaaaaacaca tacataaact aaaaatgttc ggtttaatag gtcac 55

<210> SEQ ID NO 148

<211> LENGTH: 56
<212> TYPE: DNA
<213> ORGANISM: Saccharomyces cerevisiae

<400> SEQUENCE: 148
ctcattaaaa aactatatca attaatttga attaactcag attgctaagg ctaaag 56

<210> SEQ ID NO 149
<211> LENGTH: 60
<212> TYPE: DNA
<213> ORGANISM: Saccharomyces cerevisiae

<400> SEQUENCE: 149
caagaactta gtttcgaata aacacacata aacaaacaaa atgccacaat tagaagcctc 60

<210> SEQ ID NO 150
<211> LENGTH: 63
<212> TYPE: DNA
<213> ORGANISM: Saccharomyces cerevisiae

<400> SEQUENCE: 150
cttatttaat aataaaaatc ataaatcata agaaattcgc ttagactgct gccaaaccgt 60
atg 63

<210> SEQ ID NO 151
<211> LENGTH: 58
<212> TYPE: DNA
<213> ORGANISM: Saccharomyces cerevisiae

<400> SEQUENCE: 151
gaaagcatag caatctaatc taagttttaa ttacaaaatg ccaaagattg ttattttg 58

<210> SEQ ID NO 152
<211> LENGTH: 54
<212> TYPE: DNA
<213> ORGANISM: Saccharomyces cerevisiae

<400> SEQUENCE: 152
ctaaatcatt aaagtaactt aaggagttaa atttaatgct cacgcgcatg gttg 54

<210> SEQ ID NO 153
<211> LENGTH: 57
<212> TYPE: DNA
<213> ORGANISM: Saccharomyces cerevisiae

<400> SEQUENCE: 153
gacataacta attacatgac tcgaggtcga cggtatctta ccagtaatgc tccgctg 57

<210> SEQ ID NO 154
<211> LENGTH: 58
<212> TYPE: DNA
<213> ORGANISM: Saccharomyces cerevisiae

<400> SEQUENCE: 154
ggaagtaatt atctactttt tacaacaaat ataacaaaat ggctgattgg gtaacagg 58

<210> SEQ ID NO 155
<211> LENGTH: 417
<212> TYPE: PRT
<213> ORGANISM: Saccharomyces cerevisiae

<400> SEQUENCE: 155

Met Val Ala Ser Val Ala Ala Ser Ala Phe Phe Pro Thr Pro Ser Phe

-continued

```
1               5                   10                  15

Ser Ser Thr Ala Ser Ala Lys Ala Ser Lys Thr Ile Gly Glu Gly Ser
            20                  25                  30

Glu Ser Leu Asp Val Arg Gly Ile Val Ala Lys Pro Thr Ser Ser Ser
        35                  40                  45

Ala Ala Met Gln Gly Lys Val Lys Ala Gln Ala Val Pro Lys Ile Asn
    50                  55                  60

Gly Thr Lys Val Gly Leu Lys Thr Glu Ser Gln Lys Ala Glu Glu Asp
65                  70                  75                  80

Ala Ala Pro Ser Ser Ala Pro Arg Thr Phe Tyr Asn Gln Leu Pro Asp
                85                  90                  95

Trp Ser Val Leu Leu Ala Ala Val Thr Thr Ile Phe Leu Ala Ala Glu
            100                 105                 110

Lys Gln Trp Thr Leu Leu Asp Trp Lys Pro Arg Arg Pro Asp Met Leu
        115                 120                 125

Thr Asp Ala Phe Ser Leu Gly Lys Ile Val Gln Asp Gly Leu Ile Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Arg Asn Ala Gly Leu Leu Gly Asp Gly Phe Gly Ala Thr Pro
            180                 185                 190

Glu Met Ser Lys Arg Asn Leu Ile Trp Val Val Thr Lys Met Gln Val
        195                 200                 205

Leu Val Glu His Tyr Pro Ser Trp Gly Asp Val Val Glu Val Asp Thr
    210                 215                 220

Trp Val Gly Ala Ser Gly Lys Asn Gly Met Arg Arg Asp Trp His Val
225                 230                 235                 240

Arg Asp Tyr Arg Thr Gly Gln Thr Ile Leu Arg Ala Thr Ser Val Trp
                245                 250                 255

Val Met Met Asn Lys His Thr Arg Lys Leu Ser Lys Met Pro Glu Glu
            260                 265                 270

Val Arg Ala Glu Ile Gly Pro Tyr Phe Val Glu His Ala Ala Ile Val
        275                 280                 285

Asp Glu Asp Ser Arg Lys Leu Pro Lys Leu Asp Asp Asp Thr Ala Asp
    290                 295                 300

Tyr Ile Lys Trp Gly Leu Thr Pro Arg Trp Ser Asp Leu Asp Val Asn
305                 310                 315                 320

Gln His Val Asn Asn Val Lys Tyr Ile Gly Trp Ile Leu Glu Ser Ala
                325                 330                 335

Pro Ile Ser Ile Leu Glu Asn His Glu Leu Ala Ser Met Thr Leu Glu
            340                 345                 350

Tyr Arg Arg Glu Cys Gly Arg Asp Ser Val Leu Gln Ser Leu Thr Ala
        355                 360                 365

Ile Ser Asn Asp Cys Thr Gly Gly Leu Pro Glu Ala Ser Ile Glu Cys
    370                 375                 380

Gln His Leu Leu Gln Leu Glu Cys Gly Ala Glu Ile Val Arg Gly Arg
385                 390                 395                 400

Thr Gln Trp Arg Pro Arg Arg Ala Ser Gly Pro Thr Ser Ala Gly Ser
                405                 410                 415

Ala
```

<210> SEQ ID NO 156
<211> LENGTH: 183
<212> TYPE: PRT
<213> ORGANISM: Saccharomyces cerevisiae

<400> SEQUENCE: 156

```
Met Ala Lys Thr Ile Leu Ile Leu Gly Asp Ser Leu Ser Ala Gly Tyr
1               5                   10                  15

Gly Ile Asn Pro Glu Gln Gly Trp Val Ala Leu Leu Gln Lys Arg Leu
            20                  25                  30

Asp Gln Gln Phe Pro Lys Gln His Lys Val Ile Asn Ala Ser Val Ser
        35                  40                  45

Gly Glu Thr Thr Ser Gly Ala Leu Ala Arg Leu Pro Lys Leu Leu Thr
    50                  55                  60

Thr Tyr Arg Pro Asn Val Val Val Ile Glu Leu Gly Gly Asn Asp Ala
65                  70                  75                  80

Leu Arg Gly Gln Pro Pro Gln Met Ile Gln Ser Asn Leu Glu Lys Leu
                85                  90                  95

Ile Gln His Ser Gln Lys Ala Lys Ser Lys Val Val Val Phe Gly Met
            100                 105                 110

Lys Ile Pro Pro Asn Tyr Gly Thr Ala Tyr Ser Gln Ala Phe Glu Asn
        115                 120                 125

Asn Tyr Lys Val Val Ser Gln Thr Tyr Gln Val Lys Leu Leu Pro Phe
    130                 135                 140

Phe Leu Asp Gly Val Ala Gly His Lys Ser Leu Met Gln Asn Asp Gln
145                 150                 155                 160

Ile His Pro Asn Ala Lys Ala Gln Ser Ile Leu Leu Asn Asn Ala Tyr
                165                 170                 175

Pro Tyr Ile Lys Gly Ala Leu
            180
```

<210> SEQ ID NO 157
<211> LENGTH: 480
<212> TYPE: PRT
<213> ORGANISM: Saccharomyces cerevisiae

<400> SEQUENCE: 157

```
Met Thr Lys Lys Ile Ser Phe Ile Ile Asn Gly Gln Val Glu Ile Phe
1               5                   10                  15

Pro Glu Ser Asp Asp Leu Val Gln Ser Ile Asn Phe Gly Asp Asn Ser
            20                  25                  30

Val Tyr Leu Pro Ile Leu Asn Asn Ser His Val Lys Asn Ile Ile Asp
        35                  40                  45

Tyr Asn Glu Asn Asn Lys Leu Arg Leu His Asn Ile Val Asn Phe Leu
    50                  55                  60

Tyr Thr Val Gly Gln Arg Trp Lys Asn Glu Glu Tyr Ser Arg Arg Arg
65                  70                  75                  80

Thr Tyr Ile Arg Asp Leu Lys Lys Tyr Met Gly Tyr Ser Glu Ala Met
                85                  90                  95

Ala Lys Leu Glu Ala Asn Trp Ile Ser Met Ile Leu Cys Ser Lys Gly
            100                 105                 110

Gly Leu Tyr Asp Val Val Glu Asn Glu Leu Gly Ser Arg His Ile Met
        115                 120                 125

Asp Glu Trp Leu Pro Gln Asp Glu Ser Tyr Ile Lys Ala Phe Pro Lys
    130                 135                 140
```

-continued

```
Gly Lys Ser Ile His Leu Leu Ala Gly Asn Val Pro Leu Ser Gly Ile
145                 150                 155                 160

Met Ser Ile Leu Arg Ala Ile Leu Thr Lys Asn Gln Cys Ile Ile Lys
                165                 170                 175

Thr Ser Ser Thr Asp Pro Phe Thr Ala Asn Ala Leu Ala Leu Ser Phe
            180                 185                 190

Ile Asp Val Asp Pro Asn His Pro Ile Thr Arg Ser Leu Ser Val Val
        195                 200                 205

Tyr Trp Pro His Gln Gly Asp Thr Ser Leu Ala Lys Glu Ile Met Gln
    210                 215                 220

His Met Asp Val Ile Val Ala Trp Gly Gly Glu Asp Ala Ile Asn Trp
225                 230                 235                 240

Ala Val Glu His Ala Pro Pro Tyr Ala Asp Val Ile Lys Phe Gly Ser
                245                 250                 255

Lys Lys Ser Phe Cys Ile Ile Asp Asn Pro Val Asp Leu Thr Ser Ala
            260                 265                 270

Ala Thr Gly Ala Ala His Asp Ile Cys Phe Tyr Asp Gln Arg Ala Cys
        275                 280                 285

Phe Ser Ala Gln Asn Ile Tyr Tyr Met Gly Asn Gln Tyr Glu Glu Phe
    290                 295                 300

Lys Leu Ala Leu Ile Glu Lys Leu Asn Leu Tyr Ala His Ile Leu Pro
305                 310                 315                 320

Asn Ala Lys Lys Asp Phe Asp Glu Lys Ala Ala Tyr Ser Leu Val Gln
                325                 330                 335

Lys Glu Ser Leu Phe Ala Gly Leu Lys Val Glu Val Asp Val His Gln
            340                 345                 350

Arg Trp Met Ile Ile Glu Ser Asn Ala Gly Val Glu Phe Asn Gln Pro
        355                 360                 365

Leu Gly Arg Cys Val Tyr Leu His His Val Asp Asn Ile Glu Gln Val
    370                 375                 380

Leu Pro Tyr Val Gln Lys Asn Lys Thr Gln Thr Ile Ser Ile Phe Pro
385                 390                 395                 400

Trp Glu Ser Ala Phe Lys Tyr Arg Asp Ala Leu Ala Leu Arg Gly Ala
                405                 410                 415

Glu Arg Ile Val Glu Ala Gly Met Asn Asn Ile Phe Arg Val Gly Gly
            420                 425                 430

Ser His Asp Gly Met Arg Pro Leu Gln Arg Leu Val Thr Tyr Ile Ser
        435                 440                 445

His Glu Arg Pro Ser His Tyr Thr Ala Lys Asp Val Ala Val Glu Ile
    450                 455                 460

Glu Gln Thr Arg Phe Leu Glu Glu Asp Lys Phe Leu Val Phe Val Pro
465                 470                 475                 480
```

<210> SEQ ID NO 158
<211> LENGTH: 307
<212> TYPE: PRT
<213> ORGANISM: Saccharomyces cerevisiae

<400> SEQUENCE: 158

```
Met Glu Asn Lys Ser Lys Tyr Lys Thr Ile Asp His Val Leu Cys Val
1               5                   10                  15

Glu Gly Asn Lys Lys Ile His Val Trp Glu Thr Leu Pro Glu Glu Asn
            20                  25                  30

Ser Pro Lys Arg Lys Asn Thr Ile Ile Ile Ala Ser Gly Phe Ala Arg
        35                  40                  45
```

-continued

Arg Met Asp His Phe Ala Gly Leu Ala Glu Tyr Leu Ser Arg Asn Gly
50 55 60

Phe His Val Ile Arg Tyr Asp Ser Leu His His Val Gly Leu Ser Ser
65 70 75 80

Gly Thr Ile Asp Glu Phe Thr Met Ser Ile Gly Lys Gln Ser Leu Leu
85 90 95

Ala Val Val Asp Trp Leu Asn Thr Arg Lys Ile Asn Asn Arg Gly Ile
100 105 110

Leu Ala Ser Ser Leu Ser Ala Arg Ile Val Tyr Ala Ser Leu Ser Glu
115 120 125

Ile Asn Val Ser Phe Leu Ile Thr Ala Val Gly Val Val Asn Leu Arg
130 135 140

Tyr Thr Leu Glu Arg Ala Leu Gly Phe Asp Tyr Leu Ser Leu Pro Ile
145 150 155 160

Asn Glu Leu Pro Asn Asn Leu Asp Phe Glu Gly His Lys Leu Gly Ala
165 170 175

Glu Val Phe Ala Arg Asp Cys Leu Asp Phe Gly Trp Glu Asp Leu Thr
180 185 190

Ser Thr Ile Asn Ser Met Met Tyr Leu Asp Ile Pro Phe Ile Ala Phe
195 200 205

Thr Ala Asn Asn Asp Asn Trp Val Lys Gln Asp Glu Val Ile Thr Leu
210 215 220

Leu Ser Asn Ile Arg Ser Asn Arg Cys Lys Ile Tyr Ser Leu Leu Gly
225 230 235 240

Ser Ser His Asp Leu Gly Glu Asn Leu Val Val Leu Arg Asn Phe Tyr
245 250 255

Gln Ser Val Thr Lys Ala Ala Ile Ala Met Asp Asn Asp Arg Leu Asp
260 265 270

Ile Asp Val Asp Ile Ile Glu Pro Ser Phe Glu His Leu Thr Ile Ala
275 280 285

Thr Val Asn Glu Arg Arg Met Lys Ile Glu Ile Glu Asn Gln Ala Ile
290 295 300

Ser Leu Ser
305

<210> SEQ ID NO 159
<211> LENGTH: 370
<212> TYPE: PRT
<213> ORGANISM: Saccharomyces cerevisiae

<400> SEQUENCE: 159

Met Thr Ser Tyr Val Asp Lys Gln Glu Ile Ile Ala Ser Ser Glu Ile
1 5 10 15

Asp Asp Leu Ile Phe Ser Ser Asp Pro Leu Ala Trp Ser Tyr Asp Glu
20 25 30

Gln Glu Lys Ile Arg Asn Lys Phe Val Leu Asp Ala Phe Arg Asn His
35 40 45

Tyr Lys His Cys Gln Glu Tyr Arg His Tyr Cys Gln Val His Lys Val
50 55 60

Asp Asp Asn Ile Thr Glu Ile Asp Asp Ile Pro Val Phe Pro Thr Ser
65 70 75 80

Val Phe Lys Phe Thr Arg Leu Leu Thr Ser Gln Glu Asn Glu Ile Glu
85 90 95

Ser Trp Phe Thr Ser Ser Gly Thr Ser Gly Leu Lys Ser Gln Val Ala

-continued

```
            100                 105                 110

Arg Asn Arg Leu Ser Ile Glu Arg Leu Leu Gly Ser Val Ser Tyr Gly
        115                 120                 125

Met Lys Tyr Val Gly Ser Trp Phe Asp His Gln Ile Glu Leu Val Asn
    130                 135                 140

Leu Gly Pro Asp Arg Phe Asn Ala His Asn Ile Trp Phe Lys Tyr Val
145                 150                 155                 160

Met Ser Leu Val Glu Leu Leu Tyr Pro Thr Thr Phe Thr Val Met Glu
                165                 170                 175

Glu Arg Ile Asp Phe Val Lys Thr Leu Asn Ser Leu Glu Arg Ile Lys
            180                 185                 190

Asn Gln Gly Lys Asp Ile Cys Leu Ile Gly Ser Pro Tyr Phe Ile Tyr
        195                 200                 205

Leu Leu Cys Gln Tyr Met Lys Asp Lys Asn Ile Ser Phe Tyr Gly Asp
    210                 215                 220

Lys Asn Leu Tyr Ile Ile Thr Gly Gly Gly Trp Lys Ser Tyr Glu Lys
225                 230                 235                 240

Glu Ser Leu Lys Arg Asp Asp Phe Asn His Leu Leu Phe Asp Thr Phe
                245                 250                 255

Asn Leu Asn Asn Ile Ser Gln Ile Arg Asp Ile Phe Asn Gln Val Glu
            260                 265                 270

Leu Asn Thr Cys Phe Phe Glu Asp Glu Met Gln Arg Lys Arg Val Pro
        275                 280                 285

Pro Trp Val Tyr Ala Arg Ala Leu Asp Pro Glu Thr Leu Lys Pro Val
    290                 295                 300

Pro Asp Gly Met Pro Gly Leu Met Ser Tyr Met Asp Ala Ser Ser Thr
305                 310                 315                 320

Ser Tyr Pro Ala Phe Ile Val Thr Asp Asp Val Gly Ile Met Ser Arg
                325                 330                 335

Glu Tyr Gly Gln Tyr Pro Gly Val Leu Val Glu Ile Leu Arg Arg Val
            340                 345                 350

Asn Thr Arg Ala Gln Lys Gly Cys Ala Leu Ser Leu Asn Gln Ala Phe
        355                 360                 365

Asn Ser
    370


<210> SEQ ID NO 160
<211> LENGTH: 99
<212> TYPE: PRT
<213> ORGANISM: Saccharomyces cerevisiae

<400> SEQUENCE: 160

Met Ala Thr Tyr Lys Val Thr Leu Val Asn Ala Ala Glu Gly Leu Asn
1               5                   10                  15

Thr Thr Ile Asp Val Ala Asp Asp Thr Tyr Ile Leu Asp Ala Ala Glu
            20                  25                  30

Glu Gln Gly Ile Asp Leu Pro Tyr Ser Cys Arg Ala Gly Ala Cys Ser
        35                  40                  45

Thr Cys Ala Gly Lys Val Val Ser Gly Thr Val Asp Gln Ser Asp Gln
    50                  55                  60

Ser Phe Leu Asp Asp Asp Gln Ile Ala Ala Gly Phe Val Leu Thr Cys
65                  70                  75                  80

Val Ala Tyr Pro Thr Ser Asp Val Thr Ile Glu Thr His Lys Glu Glu
                85                  90                  95
```

-continued

Asp Leu Tyr

<210> SEQ ID NO 161
<211> LENGTH: 403
<212> TYPE: PRT
<213> ORGANISM: Saccharomyces cerevisiae

<400> SEQUENCE: 161

Met Leu Asn Ala Ser Val Ala Gly Gly Ala Ala Thr Thr Thr Tyr Gly
1 5 10 15

Asn Arg Leu Phe Ile Tyr Glu Val Ile Gly Leu Arg Gln Ala Glu Gly
20 25 30

Glu Pro Ser Asp Ser Ser Ile Arg Arg Ser Gly Ser Thr Phe Phe Lys
35 40 45

Val Pro Tyr Ser Arg Met Asn Gln Glu Met Gln Arg Ile Leu Arg Leu
50 55 60

Gly Gly Lys Ile Val Ser Ile Arg Pro Ala Glu Glu Ala Ala Ala Asn
65 70 75 80

Asn Gly Ala Ala Pro Leu Gln Ala Ala Ala Glu Glu Pro Ala Ala Ala
85 90 95

Pro Thr Pro Ala Pro Ala Ala Lys Lys His Ser Ala Glu Asp Val Pro
100 105 110

Val Asn Ile Tyr Arg Pro Asn Lys Pro Phe Val Gly Lys Val Leu Ser
115 120 125

Asn Glu Pro Leu Val Gln Glu Gly Gly Ile Gly Val Val Gln His Leu
130 135 140

Thr Phe Asp Ile Ser Glu Gly Asp Leu Arg Tyr Ile Glu Gly Gln Ser
145 150 155 160

Ile Gly Ile Ile Pro Asp Gly Thr Asp Asp Lys Gly Lys Pro His Lys
165 170 175

Leu Arg Leu Tyr Ser Ile Ala Ser Thr Arg His Gly Asp His Val Asp
180 185 190

Asp Lys Thr Val Ser Leu Cys Val Arg Gln Leu Gln Tyr Gln Asn Glu
195 200 205

Ala Gly Glu Thr Ile Asn Gly Val Cys Ser Thr Phe Leu Cys Gly Leu
210 215 220

Lys Pro Gly Asp Asp Val Lys Ile Thr Gly Pro Val Gly Lys Glu Met
225 230 235 240

Leu Leu Pro Ala Asp Thr Asp Ala Asn Val Ile Met Met Gly Thr Gly
245 250 255

Thr Gly Ile Ala Pro Phe Arg Ala Tyr Leu Trp Arg Met Phe Lys Asp
260 265 270

Asn Glu Arg Ala Ile Asn Ser Glu Tyr Gln Phe Asn Gly Lys Ala Trp
275 280 285

Leu Ile Phe Gly Ile Pro Thr Thr Ala Asn Ile Leu Tyr Lys Glu Glu
290 295 300

Leu Glu Ala Leu Gln Ala Gln Tyr Pro Asp Asn Phe Arg Leu Thr Tyr
305 310 315 320

Ala Ile Ser Arg Glu Gln Lys Asn Glu Ala Gly Gly Arg Met Tyr Ile
325 330 335

Gln Asp Arg Val Ala Glu His Ala Asp Glu Ile Trp Asn Leu Leu Lys
340 345 350

Asp Glu Lys Thr His Val Tyr Ile Cys Gly Leu Arg Gly Met Glu Asp
355 360 365

-continued

```
Gly Ile Asp Gln Ala Met Thr Val Ala Ala Ala Lys Glu Asp Val Val
    370                 375                 380

Trp Ser Asp Tyr Gln Arg Thr Leu Lys Lys Ala Gly Arg Trp His Val
385                 390                 395                 400

Glu Thr Tyr


<210> SEQ ID NO 162
<211> LENGTH: 1044
<212> TYPE: DNA
<213> ORGANISM: Synechococcus elongatus

<400> SEQUENCE: 162

ggatccaaaa caatgttcgg tttaataggt cacttaacaa gtttagaaca agccagagat      60

gtcagtagaa gaatgggtta cgatgaatac gcagaccaag gtttagaatt ttggtcttca     120

gccccacctc aaatcgtaga tgaaattaca gttacctctg ctactggtaa agtcattcat     180

ggtagataca tcgaatcatg tttcttgcca gaaatgttgg ctgcaagaag attcaaaact     240

gcaacaagaa aggttttgaa tgcaatgtcc catgcccaaa agcacggtat cgatatttcc     300

gcattgggtg gttttacaag tataatcttc gaaaacttcg atttggctag tttgagacaa     360

gttagagaca ctacattgga attcgaaaga ttcaccactg gtaacaccca cactgcttac     420

gtcatttgta gacaagtaga agccgctgca aaaaccttgg gtatagatat cacacaagcc     480

accgttgctg ttgtcggtgc tactggtgac atcggttccg cagtatgcag atggttggat     540

ttgaaattgg gtgttggtga cttaatcttg acagctagaa accaagaaag attggataac     600

ttgcaagcag aattaggtag aggtaaaatc ttgccattgg aagccgcttt gcctgaagcc     660

gattttatcg tttgggtcgc ttctatgcca caaggtgtag ttattgatcc agctacctta     720

aaacaacctt gcgttttgat agacggtggt tatcctaaaa atttgggttc taaggttcaa     780

ggtgaaggta tctatgtctt gaacggtggt gtcgtagaac attgtttcga tatagactgg     840

caaatcatgt cagcagccga aatggcaaga cctgaaagac aaatgtttgc ctgcttcgct     900

gaagcaatgt tgttagaatt tgaaggttgg cacactaatt tctcttgggg tagaaaccaa     960

attacaatag aaaagatgga agccatcggt gaagcctctg ttagacacgg tttccaacct    1020

ttagccttag caatctgaaa gctt                                           1044


<210> SEQ ID NO 163
<211> LENGTH: 732
<212> TYPE: DNA
<213> ORGANISM: Synechococcus elongatus

<400> SEQUENCE: 163

atctagtttt attacagcgg ccgcaaaaca atgccacaat tagaagcctc cttagaatta      60

gactttcaat cagaatcata taaagatgct tacagtagaa tcaacgcaat cgtcattgaa     120

ggtgaacaag aagcatttga taactacaac agattggcag aaatgttacc agatcaaaga     180

gacgaattgc ataaattggc caagatggaa caaagacaca tgaaaggttt catggcttgt     240

ggtaaaaatt tgtccgttac tcctgatatg ggtttcgcac aaaagttttt cgaaagattg     300

catgaaaact tcaaagctgc agccgctgag ggtaaagttg tcacatgttt gttgatccaa     360

tctttgataa tcgaatgctt tgctatcgca gcctataata tctacattcc agtcgctgat     420

gcattcgcca gaaagattac cgaaggtgta gttagagacg aatatttgca cagaaacttc     480

ggtgaagaat ggttgaaggc aaacttcgat gcttctaagg cagaattgga agaagctaat     540

agacaaaact tgcctttagt ctggttgatg ttaaatgaag tagccgatga cgctagagaa     600
```

ttgggtatgg aaagagaatc attagttgaa gacttcatga tcgcatacgg tgaagcctta 660
gaaaacatcg gttttactac cagagaaata atgagaatgt ccgcatacgg tttggcagca 720
gtctaagagc tc 732

<210> SEQ ID NO 164
<211> LENGTH: 734
<212> TYPE: DNA
<213> ORGANISM: Nostoc punctiforme

<400> SEQUENCE: 164
tctagtttta ttacagcggc cgcaaaacaa tgcaacaatt aacagaccaa tcaaaggaat 60
tagacttcaa atcagaaact tacaaagatg cctactccag aatcaacgca atcgtcattg 120
aaggtgaaca agaagcacat gaaaactaca tcaccttggc ccaattatta ccagaatccc 180
atgatgaatt gatcagattg tctaagatgg aatcaagaca caaaaagggt tttgaagcct 240
gtggtagaaa tttggctgtt actcctgact tacaatttgc caaagaattt ttctctggtt 300
tgcaccaaaa cttccaaact gctgcagccg agggtaaagt tgtcacatgt ttgttgatcc 360
aatcattaat aatcgaatgc tttgctatcg ctgcatataa tatctacatt ccagttgccg 420
atgacttcgc tagaaaaatt acagaaggtg tagttaagga agaatattcc catttgaact 480
ttggtgaagt ctggttaaaa gaacacttcg cagagagtaa ggccgaattg gaattagcaa 540
atagacaaaa cttgcctatc gtctggaaaa tgttaaatca agtagaaggt gacgctcata 600
ccatggcaat ggaaaaggat gctttggttg aagacttcat gattcaatac ggtgaagcat 660
tatcaaacat aggtttttct accagagaca ttatgagatt gagtgcttac ggtttgatag 720
gtgcttgaga gctc 734

<210> SEQ ID NO 165
<211> LENGTH: 1304
<212> TYPE: DNA
<213> ORGANISM: Jeotgalicoccus spp

<400> SEQUENCE: 165
ctaagtttta ttacagcggc cgcaaaacaa tggctacatt gaagagagac aagggtttag 60
acaacacatt gaaagtattg aagcaaggtt acttatacac caccaaccaa agaaatagat 120
tgaacacttc tgttttccaa acaaaggcat taggtggtaa acctttcgtt gtcgtaactg 180
gtaaagaagg tgccgaaatg ttctacaaca acgatgttgt ccaaagagaa ggcatgttgc 240
caaagagaat cgttaacact ttgttcggta aaggtgccat ccatacagtc gatggtaaaa 300
agcacgtaga cagaaaagct ttgttcatgt cattgatgac tgagggtaat ttgaactacg 360
tcagagaatt gaccagaact ttatggcatg ccaatacaca aagaatggaa tctatggatg 420
aagtcaacat atacagagaa tcaatcgtat tgttgacaaa ggttggtacc agatgggctg 480
gtgtacaagc accacctgaa gacatcgaaa gaattgcaac agatatggac ataatgatcg 540
attcctttag agccttgggt ggtgctttca aaggttacaa agcaagtaaa gaagctagaa 600
gaagagttga agattggttg gaagaacaaa tcatcgaaac cagaaagggt aacattcatc 660
cacctgaagg tactgccttg tatgaatttg ctcactggga agattactta ggtaacccta 720
tggactccag aacatgtgct attgatttga tgaatacctt cagaccattg atcgctataa 780
acagattcgt ttctttcggt ttgcatgcaa tgaatgaaaa ccctataacc agagaaaaga 840
ttaaatcaga accagattac gcttacaagt tcgcacaaga agttagaaga tattacccat 900

-continued ttgtcccttt cttacctggt aaagctaagg ttgatatcga cttccaaggt gttacaattc 960
cagcaggtgt cggtttggcc ttagacgtat atggtactac acatgatgaa tccttgtggg 1020
atgaccctaa tgaattcaga ccagaaagat tcgaaacatg ggatggtagt ccttttgact 1080
taattccaca aggtggtggt gactactgga ccaaccacag atgcgctggt gaatggatta 1140
ccgttatcat catggaagaa actatgaagt acttcgcaga aaagattact tacgatgtac 1200
ctgaacaaga tttggaagtt gacttaaact ctattccagg ttatgtaaag agtggtttcg 1260
ttattaaaaa tgtcagagaa gtagtagata gaacttgaga gctc 1304

<210> SEQ ID NO 166
<211> LENGTH: 1035
<212> TYPE: DNA
<213> ORGANISM: Aspergillus nidulans

<400> SEQUENCE: 166
atggtgcaag acacatcaag cgcaagcact tcgccaattt taacaagatg gtacatcgac 60
acccgccctc taaccgcctc aacagcagcc cttcctctcc ttgaaaccct ccagcccgct 120
gatcaaatct ccgtccaaaa atactaccat ctgaaggata aacacatgtc tctcgcctct 180
aatctgctca aatacctctt cgtccaccga aactgtcgca tcccctggtc ttcaatcgtg 240
atctctcgaa ccccagatcc gcacagacga ccatgctata ttccaccctc aggctcacag 300
gaagacagct tcaaagacgg atataccggc atcaacgttg agttcaacgt cagccaccaa 360
gcctcaatgg tcgcgatcgc gggaacagct tttactccca atagtggtgg ggacagcaaa 420
ctcaaacccg aagtcggaat tgatattacg tgcgtaaacg agcggcaggg acggaacggg 480
gaagagcgga gcctggaatc gctacgtcaa tatattgata tattctcgga agtgttttcc 540
actgcagaga tggccaatat aaggaggtta gatggagtct catcatcctc actgtctgct 600
gatcgtcttg tggactacgg gtacagactc ttctacactt actgggcgct caaagaggcg 660
tatataaaaa tgactgggga ggccctctta gcaccgtggt tacgggaact ggaattcagt 720
aatgtcgtcg ccccggccgc tgttgcggag agtggggatt cggctgggga tttcggggag 780
ccgtatacgg gtgtcaggac gactttatat aaaaatctcg ttgaggatgt gaggattgaa 840
gttgctgctc tgggcggtga ttacctattt gcaacggctg cgaggggtgg tgggattgga 900
gctagttcta gaccaggagg tggtccagac ggaagtggca tccgaagcca ggatccctgg 960
aggcctttca agaagttaga tatagagcga gatatccagc cctgtgcgac tggggtgtgt 1020
aattgcctat cctaa 1035

<210> SEQ ID NO 167
<211> LENGTH: 2091
<212> TYPE: DNA
<213> ORGANISM: Synechococcus elongates

<400> SEQUENCE: 167
atggactcag gtcacggtgc tcaatcaaga atcaagttag gtcaaacagg ttacaagtta 60
tcaacatatt tctgcaaaag tggtcctaat tgggaaaacc aaccacaaat ccattggaac 120
tctttatttt caactgtcaa gatccaattg tccttattcc cttcttcatt tcacttaatc 180
atggtaactc caattaatta ccatagtatc cactgtttgg cagatatttg ggccataaca 240
ggtgaaaatt tcgctgatat tgtagcattg aacgacagac attctcaccc acctgttacc 300
ttgacttacg cacaattaag agaagaaatt acagcctttg ctgctggttt gcaatcatta 360
ggtgttaccc ctcatcaaca cttagctatt ttcgcagata attccccaag atggtttata 420

```
gcagaccaag gtagtatgtt ggcaggtgcc gttaacgctg ttagatcagc tcaagcagaa    480
agacaagaat tgttgtacat cttggaagat tccaatagta gaacattgat cgcagaaaac    540
agacaaacct tgtctaaatt ggctttagat ggtgaaacca ttgacttgaa gttaataatc    600
ttgttgactg atgaagaagt tgccgaagac tcagctatac cacaatataa tttcgcacaa    660
gtcatggcct taggtgctgg taaaattcca actcctgtac caagacaaga agaagatttg    720
gctaccttaa tatacacttc tggtactaca ggtcaaccaa agggtgttat gttgtcacat    780
ggtaatttgt tgcaccaagt tagagaattg gattccgtca tcattcctag accaggtgac    840
caagttttga gtattttacc atgttggcat tccttggaaa gaagtgctga atatttcttg    900
ttatccagag gttgcacaat gaactacacc agtatcagac atttcaaggg tgacgttaag    960
gacataaagc ctcatcacat agtaggtgtt ccaagattgt gggaatcttt atatgaaggt   1020
gtccaaaaga cttttagaga aaagtcacct ggtcaacaaa aattgattaa tttctttttc   1080
ggtatctcac aaaagtacat attggcaaag agaatcgcca acaacttgtc tttaaaccat   1140
ttgcacgcct cagctattgc aagattggta gctagatgtc aagcattggt tttatctcca   1200
ttgcattatt tgggtgacaa aatcgtatac cacaaggtta gacaagccgc tggtggtaga   1260
ttggaaactt taatttctgg tggtggtgcc ttggctagac atttggatga cttctatgaa   1320
atcacctcaa ttcctgtctt agtaggttac ggtttaacag aaaccgcccc agtcacaaat   1380
gctagagtac ataagcacaa cttaagatat tccagtggta gacctatccc ttttactgaa   1440
atcagaatcg ttgatatgga aactaaggaa gacttgccac ctgaaacaca aggtttggtc   1500
ttaattagag gtcctcaagt aatgcaaggt tattacaata agccagaagc aactgccaag   1560
gtattagatc aagaaggttg gttcgattcc ggtgacttgg gttgggttac accacaaaac   1620
gatttgatat taactggtag agctaaagac acaatcgttt tatctaatgg tgaaaacgtc   1680
gaacctcaac caattgaaga tgcatgctta agatccgcct acatagatca aatcatgttg   1740
gttggtcaag accaaaagag tttgggtgct ttaatcgtcc caaacttcga tgctttacaa   1800
aaatgggcag aaaccaagaa cttgcaaatc actgttcctg aaccatctgc ctcttcagag   1860
ggtatgcaag catctggttt gtatgatcct caagttgtcg gtttgatgag atcagaatta   1920
catagagaag ttagagatag accaggttac agagcagatg accaaatcaa agatttcaga   1980
ttcattcctg ctccattttc tttagaaaac ggtatgatga ctcaaacatt gaaattgaag   2040
agacctgtag tcacccaaac ttaccaacac ttgatagacg aaatgttctg a            2091
```

<210> SEQ ID NO 168
<211> LENGTH: 3525
<212> TYPE: DNA
<213> ORGANISM: Mycobacterium marinum

<400> SEQUENCE: 168

```
atgtcaccta tcaccagaga agaaagatta gaaagaagaa tacaagactt atacgccaac     60
gatcctcaat tcgccgctgc caagccagca acagccatca ccgctgcaat tgaaagacca    120
ggtttgccat tgcctcaaat catcgaaact gttatgacag gttatgctga tagacctgct    180
ttggcacaaa gatcagtaga atttgttaca gatgcaggta ctggtcatac tacattgaga    240
ttgttaccac acttcgaaac tatctcttac ggtgaattat gggacagaat ttctgccttg    300
gctgatgttt tatcaaccga acaaactgtt aaacctggtg acagagtctg tttgttgggt    360
tttaattctg ttgactacgc aactatagat atgacattgg ccagattagg tgcagtagcc    420
```

-continued

```
gttccattgc aaacctctgc cgctattact caattacaac caatagtcgc tgaaacacaa    480
cctaccatga tagcagcctc tgtagatgct ttggcagacg ccactgaatt ggctttatca    540
ggtcaaactg caacaagagt cttagtattc gaccatcaca gacaagttga tgcccataga    600
gctgctgttg aatccgctag agaaagattg gcaggtagtg ccgttgtcga aactttagct    660
gaagcaatag ctagaggtga cgttccaaga ggtgcttctg ctggttctgc tcctggtaca    720
gacgtctccg atgacagttt ggcattgtta atctatacct ctggttcaac tggtgcccca    780
aaaggtgcta tgtaccctag aagaaatgtt gctacatttt ggagaaagag aacctggttc    840
gaaggtggtt acgaaccatc tatcactttg aacttcatgc ctatgtcaca tgttatgggt    900
agacaaatct tgtatggtac tttatgcaac ggtggtacag catactttgt tgccaagtct    960
gacttgtcaa cattattcga agatttggct ttagtcagac caactgaatt aacattcgtc   1020
cctagagtat gggatatggt ttttgacgaa tttcaatcag aagtcgatag aagattggta   1080
gatggtgctg acagagtagc tttagaagca caagttaagg cagaaataag aaacgatgtt   1140
ttgggtggta gatatacatc tgccttaacc ggttctgctc caatatcaga cgaaatgaag   1200
gcttgggtag aagaattgtt agatatgcat ttggttgaag gttacggttc aactgaagct   1260
ggtatgatat taatcgacgg tgcaattaga agaccagccg ttttggatta taaattggtt   1320
gatgtccctg acttgggtta ctttttaact gatagaccac accctagagg tgaattgttg   1380
gttaagacag attctttgtt cccaggttat taccaaagag ctgaagttac agcagatgtc   1440
tttgatgctg acggtttcta tagaaccggt gacattatgg cagaagtcgg tcctgaacaa   1500
ttcgtatact tagatagaag aaacaacgtt ttgaaattgt ctcagggtga atttgtaact   1560
gtttcaaagt tggaagctgt attcggtgac tctccattag ttagacaaat atatatatac   1620
ggtaattcag ccagagctta tttgttagca gtcatagtac caacacaaga agccttggat   1680
gctgttcctg tcgaagaatt gaaagccaga ttgggtgact ccttgcaaga agttgcaaag   1740
gccgctggtt tgcaaagtta cgaaatccca agagatttca tcatcgaaac cactccttgg   1800
accttagaaa acggtttgtt aactggtatc agaaaattgg ctagaccaca attgaaaaag   1860
cattacggtg aattgttaga acaaatatat actgacttgg cccacggtca agctgatgaa   1920
ttgagatcct taagacaaag tggtgcagat gccccagtat tagttacagt ctgtagagca   1980
gccgctgcat tgttaggtgg ttccgctagt gatgttcaac ctgacgcaca ttttaccgat   2040
ttgggtggtg actctttgtc agctttatct tttacaaatt tgttgcacga aatcttcgat   2100
atagaagtac cagttggtgt cattgtatca cctgctaacg atttgcaagc attggcagat   2160
tatgttgaag ccgctagaaa accaggttct tcaagaccta cttttgcttc tgttcatggt   2220
gcatcaaatg gtcaagttac agaagtccac gctggtgact tgtctttgga taagttcatt   2280
gatgcagcca ctttggccga agctccaaga ttacctgctg caaacactca agtaagaaca   2340
gttttgttaa ccggtgctac tggtttcttg ggtagatatt tggcattaga atggttagaa   2400
agaatggatt tggttgacgg taaattgatt tgcttagtca gagcaaagtc cgacactgaa   2460
gcaagagcca gattggataa aacattcgat agtggtgacc cagaattgtt agcacattac   2520
agagctttag caggtgacca cttggaagtt ttagccggtg acaagggtga agctgacttg   2580
ggtttagata gacaaacatg gcaaagattg gctgataccg tagacttaat cgttgatcca   2640
gccgctttag tcaaccatgt attgccatac tcccaattgt tcggtcctaa cgcattgggt   2700
actgctgaat tgttgagatt ggctttgact tctaaaatta agccttactc ctacaccagt   2760
actatcggtg ttgcagatca aattccacct tcagccttca ctgaagatgc tgacataaga   2820
```

gtcatctccg caacaagagc cgtagatgac agttatgcta atggttactc caacagtaaa 2880
tgggcaggtg aagttttgtt aagagaagcc catgatttgt gtggtttacc agttgctgtc 2940
tttagatgcg acatgatttt ggcagataca acctgggccg gtcaattgaa cgttccagat 3000
atgttcacaa gaatgatctt gtccttagca gccaccggta tagctcctgg tagtttctat 3060
gaattggctg ctgatggtgc tagacaaaga gcacattacg atggtttgcc agttgagttt 3120
attgccgaag ctatctccac cttaggtgct caaagtcaag atggtttcca tacttatcac 3180
gtaatgaatc catacgatga cggtattggt ttggacgaat ttgttgattg gttaaacgaa 3240
tctggttgtc ctattcaaag aatagctgat tatggtgact ggttacaaag attcgaaact 3300
gctttgagag cattaccaga tagacaaaga cattccagtt tgttaccttt gttacacaat 3360
tacagacaac cagaaagacc tgtcagaggt tctattgctc ctacagatag attcagagcc 3420
gctgtacaag aagcaaaaat aggtccagat aaggacatcc ctcatgttgg tgctcctatt 3480
atcgtaaagt atgtatcaga tttgagattg ttgggtttgt tgtaa 3525

<210> SEQ ID NO 169
<211> LENGTH: 336
<212> TYPE: DNA
<213> ORGANISM: Escherichia coli

<400> SEQUENCE: 169
atgccaaaga ttgttatttt gcctcatcag gatctctgtc ctgatggcgc tgttctggaa 60
gctaatagcg gtgaaaccat tctcgacgca gcgctgcgta acggtatcga gattgaacac 120
gcctgtgaaa aatcctgtgc ttgcaccacc tgccactgca tcgttcgtga aggttttgac 180
tcactgccgg aaagctcaga gcaggaagac gacatgctgg acaaagcctg gggactggag 240
ccggaaagcc gtttaagctg ccaggcgcgc gtcaccgacg aagatttagt ggttgaaatc 300
ccgcgttaca ctatcaacca tgcgcgtgag cattaa 336

<210> SEQ ID NO 170
<211> LENGTH: 747
<212> TYPE: DNA
<213> ORGANISM: Escherichia coli

<400> SEQUENCE: 170
atggctgatt gggtaacagg caaagtcact aaagtgcaga actggaccga cgccctgttt 60
agtctcaccg ttcacgcccc cgtgcttccg tttaccgccg ggcaatttac caagcttggc 120
cttgaaatcg acggcgaacg cgtccagcgc gcctactcct atgtaaactc gcccgataat 180
cccgatctgg agttttacct ggtcaccgtc cccgatggca aattaagccc acgactggcg 240
gcactgaaac caggcgatga agtgcaggtg gttagcgaag cggcaggatt ctttgtgctc 300
gatgaagtgc cgcactgcga aacgctatgg atgctggcaa ccggtacagc gattggccct 360
tatttatcga ttctgcaact aggtaaagat ttagatcgct tcaaaaatct ggtcctggtg 420
cacgccgcac gttatgccgc cgacttaagc tatttgccac tgatgcagga actggaaaaa 480
cgctacgaag gaaaactgcg cattcagacg gtggtcagtc gggaaacggc agcggggtcg 540
ctcaccggac ggataccggc attaattgaa agtggggaac tggaaagcac gattggcctg 600
ccgatgaata aagaaaccag ccatgtgatg ctgtgcggca atccacagat ggtgcgcgat 660
acacaacagt tgctgaaaga gacccggcag atgacgaaac atttacgtcg ccgaccgggc 720
catatgacag cggagcatta ctggtaa 747

<210> SEQ ID NO 171
<211> LENGTH: 1650
<212> TYPE: DNA
<213> ORGANISM: Musca domestica

<400> SEQUENCE: 171
atggactccg ccaacaactc tacagccggt cctgccacag tattgaatcc tatctggaca 60
gcattattag gtattgccgt cgtcgtctca ttgtacgaaa tttggttgag aaacactaga 120
aagtacaaat tgacagcaaa tatgccaaac ccacctatgt tgcctttaat tggtaatggt 180
catttggttg cccacttaac aaacgccgaa attttggcta gaggtatagg ttatatgcaa 240
acctacggtg gtgccatgag aggtttcttg ggtccaatgt tagttgtctt cttgtggaat 300
gctcctgata tcgaattgat cttaagtact catacacact tagaaaagtc tatcgaatac 360
agatttttca aaccttggtt tggtgacggt ttgttaatca gtaacggtca tcactggcaa 420
catcacagaa agatgatagc tccaactttc catcaatcca tcttgaaaag ttttgttcct 480
gctttcgtcc aacactctaa aaaggtagtt gaaagaatgg caaaggaatt gggtaaagaa 540
tttgatgtcc atgactacat gtcacaaact acagtagaaa ttttgttatc cacagctatg 600
ggtgttaaga aagttccaga agataataag tcattagaat acgctaaagc agtcgtagat 660
atgtgtgaca tcatccataa gagacaattg aagtttttct atagaatgga tgcattgtac 720
aacttatctt caatgtccga aaagggtaaa aagatgatgg atatcatctt gggtatgaca 780
agaaaggttg tcaccgaaag acaacaaaac ttcaacgcag aaagtagagc catcgttgaa 840
gaagatgacg aaatttctaa gcaaaagcaa caagctaaaa agaaagaagg tttgagagat 900
gacttggatg acattgatga aaatgacgtt ggtgccaaga aaagattggc tttgttagac 960
gccatgatgg ctatgtcaaa gaatccagat gttgaatgga ccgataaaga cgtaatggac 1020
gaagttaaca ctataatgtt cgaaggtcat gataccactt ccgctggttc cagtttcgtt 1080
ttgtgtatgt tgggtatcta taaggatatc caagaaaagg tcttggctga acaaaaggca 1140
atcttcggtg acaatttctt gagagactgc accttcgctg atactatgga aatgaagtat 1200
ttggaaagag ttatcatgga aactttgaga ttgtacccac ctgtcccatt aattgcaaga 1260
agagccgaat ttgatgtaaa gttggcatct ggtccatata caattcctaa aggtacaacc 1320
gtagttatag ctcaatttgc agttcataga aatcctcaat acttcccaaa ccctgaaaaa 1380
tttgatccag acaatttctt gcctgaaaga atggctaaca gacactacta ctcttttatt 1440
ccattctcag caggtcctag atcctgcgtt ggtagaaagt acgccatgtt gaagttaaag 1500
gtcttgttat ctactatcat cagaaattac tctgtacaat caaaccaaca agaaaaggac 1560
ttcaaattac aagcagatat tatattgaaa atagaaaatg gttttaatat aatgttgaat 1620
agaagacctg aagcaatgaa ggcaatgtaa 1650

<210> SEQ ID NO 172
<211> LENGTH: 2016
<212> TYPE: DNA
<213> ORGANISM: Mycobacterium marinum

<400> SEQUENCE: 172
atgagtgccg aacacgttga agaagtagtc agtgaagaac catttttagg tacattggat 60
attgccttat tagtagtatt attagtcggt gccacttggt acttcatgag atcaagaaag 120
aaagaagaag ctcctataag atcatactca atccaaccaa ctacagtctc cacagtaagt 180
accactgaaa attccttcat taaaaagttg aaagcatctg gtagatcatt agttgtcttt 240
tatggttcac aaactggtac agctgaagaa tttgcaggta gattggccaa ggaaggttta 300
agatacagaa tgaagggtat ggttgctgac cctgaagaat gtgatatgga agaattgtta 360
caaatgaagg atatcccaaa ttctttggcc gtcttttgct tagctaccta tggtgaaggt 420
gacccaactg ataacgctat ggaattttac gaatggatta caaacggtga agtcgatttg 480
accggtttaa attatgccgt atttggtttg ggtaacaaaa cttatgaaca ttacaataag 540
gttgctatct atgtcgataa gagattggaa gaattaggtg caacaagagt tttcgaattg 600
ggtttaggtg acgacgatgc aaacatcgaa gacgatttca tcacctggaa agacagattc 660
tggccatccg tttgtgattt ctttggtatt gaaggtagtg gtgaagaagt cttgatgaga 720
caattcagat tgttagaaca acctgacgta caaccagata gaatctatac aggtgaaata 780
gctagattgc attctatgca aaaccaaaga ccaccttttg atgctaagaa tcctttcttg 840
gcatcagtca ttgtaaacag agaattacac aaaggtggtg gtagatcatg catgcacatc 900
gaattggaca ttgatggttc aaagatgaga tatgacgcag gtgaccatat cgccatgtac 960
ccaattaatg ataaaatctt agttgaaaaa ttgggtaaat tgtgtgacgc taatttggat 1020
actgtctttt ctttaatcaa caccgacact gattcttcta agaaacaccc attcccttgc 1080
ccaacaacct atagaaccgc attgactcat tacttagaaa tcacagccat tcctagaacc 1140
cacatattga aggaattagc agaatattgt tccgacgaaa aggataagga atttttgaga 1200
aacatggcca gtattacacc agagggtaaa gaaaagtacc aaaactggat acaaaactcc 1260
agtagaaaca tcgttcatat cttggaagat ataaaatctt gtagaccacc tatagatcat 1320
atttgtgaat tgttgcctag attacaacca agatactact ctatctcttc atccagtaag 1380
ttgtatccta ctaacgttca tattacagct gttttagtcc aatacgaaac accaaccggt 1440
agagtaaata agggtgttgc aacttcttac atgaaggaaa agaacccttc agttggtgaa 1500
gtaaaggttc cagtctttat aagaaagtcc caattcagat tgcctactaa gagtgaaatc 1560
ccaattataa tggttggtcc tggtacaggt ttagcacctt ttagaggttt cattcaagaa 1620
agacaattct tgagagacgg tggtaaagta gttggtgaca caatcttgta cttcggttgt 1680
agaaagaaag acgaagattt catctataga gaagaattag aacaatacgt tcaaaacggt 1740
actttgacat tgaagaccgc cttttcaaga gatcaacaag aaaagatata tgtaactcat 1800
ttgatcgaac aagacgctga tttgatttgg aaagttatag gtgaacaaaa gggtcacttc 1860
tacatttgcg gtgacgctaa gaacatggca gtagatgtta gaaacatctt ggtcaaaatt 1920
ttatctacta agggtaacat gaacgaatca gatgctgtac aatacattaa gaaaatggaa 1980
gcccaaaaga gatactccgc tgatgtttgg agttaa 2016

<210> SEQ ID NO 173
<211> LENGTH: 1986
<212> TYPE: DNA
<213> ORGANISM: Marinobacter aquaeolei

<400> SEQUENCE: 173
atgaattatt tcttgacagg tggtacaggt tttatcggta gattcttggt tgaaaagttg 60
ttagccagag gtggtacagt ttatgtttta gttagagaac aatctcagga taagttggaa 120
agattgagag aaagatgggg tgccgatgac aaacaagtca aggctgtaat aggtgacttg 180
acatctaaaa atttgggtat cgatgctaag accttgaagt ctttaaaggg taacatcgat 240
catgtattcc acttagctgc tgtttatgat atgggtgccg acgaagaagc tcaagccgct 300

```
actaatattg aaggtacaag agcagccgtc caagctgctg aagctatggg tgctaaacat    360

ttccatcacg tttcttcaat cgctgctgct ggtttgttca agggtatttt tagagaagac    420

atgtttgaag aagctgaaaa attggatcat ccatatttga gaactaagca cgaaagtgaa    480

aaagttgtca gagaagaatg taaagttcct tttagaatct acagacctgg tatggttatt    540

ggtcattctg aaaccggtga aatggataaa gttgacggtc catactactt tttcaagatg    600

atccaaaaga ttagacacgc tttgccacaa tgggttccta ctatcggtat tgaaggtggt    660

agattaaaca tcgtacctgt tgattttgta gttgatgcat tggaccatat tgcccactta    720

gaaggtgaag atggtaattg tttccatttg gtcgattctg acccatacaa agtaggtgaa    780

attttaaaca tattttgcga agcaggtcac gcccctagaa tgggtatgag aatcgattca    840

agaatgttcg gtttcattcc acctttata agacaatcta ttaaaaattt gccacctgtt    900

aagagaatta ctggtgcttt gttagatgac atgggtattc caccttctgt tatgtcattc    960

ataaactacc caaccagatt tgacactaga gaattggaaa gagttttgaa gggtacagat   1020

atagaagtcc caagattacc ttcttatgct ccagttatat gggattactg ggaaagaaac   1080

ttagatccag atttgtttaa agatagaaca ttgaagggta ctgtagaggg taaagtttgt   1140

gtcgtaacag gtgctacctc cggtattggt ttggctacag cagaaaaatt ggccgaagct   1200

ggtgcaatct tggttattgg tgcaagaact aaggaaacat tggatgaagt tgccgctagt   1260

ttagaagcaa aggtggtaa tgtccatgcc tatcaatgtg atttctctga catggatgac   1320

tgcgatagat tcgttaagac tgtcttggat aatcatggtc acgttgatgt attagttaat   1380

aacgctggta gatccataag aagaagtttg gcattatctt ttgatagatt ccatgacttc   1440

gaaagaacaa tgcaattgaa ctacttcggt tcagttagat tgattatggg ttttgcccca   1500

gctatgttgg aaagaagaag aggtcatgtt gtcaatatat ccagtatcgg tgtattaaca   1560

aacgctccta gattctcagc atacgtttct tcaaaatcag ctttggacgc attttccaga   1620

tgcgcagccg ctgaatggtc cgatagaaac gtcaccttta ctacaattaa catgccattg   1680

gtaaagaccc caatgattgc tcctactaaa atctatgatt ctgttccaac cttgactcct   1740

gacgaagcag cccaaatggt tgcagatgcc atagtctaca gaccaaagag aatcgctact   1800

agattgggtg tcttcgcaca agtattgcat gctttggcac ctaagatggg tgaaatcatc   1860

atgaacacag gttacagaat gtttccagat tcaccagctg ctgctggttc taagagtggt   1920

gaaaaaccta aggtttccac agaacaagta gcatttgccg ccattatgag aggtatctat   1980

tggtaa                                                               1986
```

<210> SEQ ID NO 174
<211> LENGTH: 6702
<212> TYPE: DNA
<213> ORGANISM: Rhodosporidium toruloides

<400> SEQUENCE: 174

```
atgccattct ctggcgaggc gaaggcggtc aacggatcgc actcggtcga cgaggcgccg     60

aagaacccca agtacgacca tgggcgggtc gtaaagtacc tcggcggcaa ctcgctcgaa    120

tctgcgcccc cttccaaggt cgccgactgg gtcagggagc gtggtggaca caccgtcatc    180

acaaagatcc tcatcgccaa caatggtatc gccgcagtca aggagatccg ctcggtgcgc    240

aagtgggcgt acgagacgtt cggaagcgag cgcgcgatcg agtttaccgt catggcgacc    300

ccggaggacc tcaaggtcaa cgcagactac atccgcatgg ccgatcagta cgtcgaggtt    360

cccggtggaa ccaacaacaa caactacgcc aacgtcgatg tcatcgtcga tgttgccgag    420
```

-continued

```
cgcgcaggcg tccacgccgt ctgggcagga tggggccacg cctccgagaa cccccgcctt    480
cccgagtcgc tcgccgcctc gaagcacaag atcgtcttca tcggtcctcc cggctccgcc    540
atgcgctcgc tcggagacaa gatctcgtcg accatcgtcg cgcagcacgc ccaggttccg    600
tgcatggact ggtccggcca gggcgtcgac caagtcaccc agtcgcccga gggctacgtt    660
actgtcgccg acgacgtcta ccagcaggcc tgtgtgcacg acgccgacga gggtctcgcc    720
cgcgcgtcga ggatcggata ccccgtcatg atcaaggcgt ccgagggagg aggaggaaag    780
ggtattcgca aggtcgagaa ggagcaggac tttaagcagg ccttccaggc tgtcctcacc    840
gaggttcccg gctcgcccgt ctttatcatg aagctcgccg gcgcagctcg ccacctcgag    900
gtccaggttc tcgccgacca gtacggcaac gccatctcgc tcttcggccg tgactgctcg    960
gttcagcgtc gccaccagaa gatcatcgaa gaggcgcccg tcaccatcgc caagcccgac   1020
acgttcgagc agatggaaaa gtcggccgtc cgccttgcca agctcgtcgg ctacgtctcg   1080
gcgggtaccg tcgagttcct ctactcggct gccgacgaca agtttgcctt cctcgagctc   1140
aacccgcgtc tccaggtcga gcacccgacc accgagatgg tttcgggcgt caaccttccc   1200
gccgcccagc tccaggtcgc tatgggtgtt cccctccatc gcatccgcga catccgcacg   1260
ctctacggca aggcacccaa cggcagcagc gagatcgatt tcgacttcga gaaccccgag   1320
tcggccaaga cgcagcgcaa gccctcgccg aagggtcacg tcgttgccgt acgtatcacg   1380
gctgagaacc ctgacgccgg cttcaagccg tccatgggta ctctccaaga gctcaacttc   1440
cgctcgagca cgaacgtctg ggttacttc tccgtcggca gcgccggtgg actgcacgag    1500
tttgccgact cgcagttcgg ccacatcttt gcgtacggct cggaccgttc cgagtcgcgc   1560
aagaacatgg tcgtcgcgct caaggagctc tcgattcgcg gtgacttccg cacgaccgtc   1620
gagtacctca tcaagcttct cgagacggac gcgttcgagc agaacacgat cacgaccgcg   1680
tggctcgaca gcctcatctc ggctcgcctg accgccgaga ggcccgacac gactctcgcc   1740
atcatctgcg gcgccgttac caaggcccac ctcgcttccg aggccaacat cgccgagtac   1800
aagcgcatcc tcgagaaggg tcagagcccc gccaaggagc tcctcgccac cgtcgtcccg   1860
ctcgagttcg tcctcgagga cgtcaagtac cgcgcgaccg cctcgcgctc gtcgccttcg   1920
agctggtcca tctacgtcaa cggctcgaac gtctccgtcg gcatccgccc tctcgccgac   1980
ggcggtctcc tcatcctcct tgacggccgc tcgtacacct gctacgccaa ggaggaggtc   2040
ggcgcgctcc gcctctcgat cgactcgagg accgtcctca ttgctcagga gaacgacccc   2100
acccagcttc gctcgccttc acccggcaag ctcgtccgct acttcatcga gtccggcgag   2160
cacatctcga agggcgaggc gtacgctgag atcgaggtca tgaagatgat catgcccctc   2220
atcgctgccg aggacggtat cgcgcaattc atcaagcagc cgggagcgac gctcgaggcc   2280
ggcgacatcc tcggtatctt gtcgctcgac gacccgagcc gcgtccacca cgccaagccg   2340
ttcgatggcc agcttcccgc ccttggcttg ccctccatcg tcggcaacaa gccgcaccag   2400
cgcttcgcct acctcaaaga cgtgctctca aacatcctca tgggctacga caaccaggcc   2460
gtcatgcagt cgagcatcaa ggagctcatc tcggttcttc gcaaccccga gctcccctac   2520
ggcgaggcca acgctgtcct ctcgacgctt tcgggtcgca tccccgccaa gctcgagcag   2580
accctccgcc agtacatcga ccaggctcac gagtctggcg ccgagttccc gtccgccaag   2640
tgccgcaagg cgatcgacac gacccttgag cagctccgcc ccgccgaggc gcagactgtc   2700
cgcaacttcc tcgtcgcgtt cgacgacatc gtctaccgct accgctcggg cctcaagcac   2760
```

-continued

```
cacgagtggt caacgctcgc cggcatcttt gccgcgtacg ccgagacgga gaagccgttc   2820
agcggcaagg acggcgacgt cgtcctcgag ctccgcgacg cccaccgcga ctcgctcgac   2880
tcggtcgtca agatcgttct ctcgcactac aaggctgcct cgaagaactc gcttgtcctt   2940
gcgctcctcg acatcgtcaa ggactcggac gcggttccgc tcatcgagca ggtcgtcagc   3000
cctgcgctca aggacctcgc cgacctcgac tcgaaggcca cgactaaggt cgccctgaag   3060
gcccgcgagg tgctcatcca catccagctc ccctcgctcg acgagcgcct cggacagctc   3120
gagcagattc tcaaggcctc ggtgacgccc accgtttacg gcgagcccgg ccacgaccgc   3180
actcctcgcg gtgaagtcct taaggacgtc atcgactcgc gcttcaccgt ctttgacgtt   3240
ctcccgagct tcttccagca ccaggaccac tgggtctcgc tcgccgcgct cgacacctac   3300
gtccgccgcg cctaccgctc gtacaacctc ctcaacatcg agcacatcga ggccgatgcc   3360
gccgaggacg agcccgcgac ggttgcctgg tcgttccgca tgcgcaaggc tgcgtccgag   3420
tctgagccgc ccacgcccac gaccggcctc acgtcgcagc gcaccgcctc gtactcggac   3480
ttgacgttcc tcctcaacaa cgcccagtcc gagccgatcc gctacggcgc gatgttctcg   3540
gtccgctcgc tcgaccgctt ccgccaggag ctcggtaccg tcctccgaca cttccccgac   3600
tcgaacaagg gcaagctcca gcagcagcct gccgcgtcgt cgagccagga gcagtggaac   3660
gtcatcaacg tcgcgctcac ggtccccgcc agcgcgcagg tcgacgagga cgctctccgc   3720
gccgactttg ccgctcacgt gaacgcgatg agcgccgaga tcgacgctcg cggcatgcgc   3780
cgcctcaccc tcctcatctg ccgcgagggc cagtacccgt cctactacac cgtccgcaag   3840
caggacggca cctggaagga gctcgagacg atccgcgaca tcgagcccgc cctcgccttc   3900
cagctcgagt tgggccgcct ctccaacttc cacctcgagc cgtgccccgt tgagaaccgc   3960
caggtccacg tctactacgc gaccgccaag ggcaactcgt ccgactgccg cttcttcgtc   4020
cgcgcactcg tccgccctgg ccgtctccgc ggtaacatga agacggccga ctacctcgtc   4080
tccgaggctg accgcctcgt caccgatgtc ctcgactcgc tcgaggtcgc cagctcgcag   4140
cgccgcgctg ccgacggcaa ccacatctcg ctcaacttcc tgtactctct ccgtctcgac   4200
tttgacgagg tccaggctgc cctcgccggc ttcatcgacc gccacggcaa gcgcttctgg   4260
cgtctccgcg tcaccggcgc cgagatccgc atcgtcctcg aggacgcgca gggcaacatt   4320
cagcccatcc gcgccatcat cgagaacgtc tcgggtttcg tcgtcaagta cgaggcgtac   4380
cgcgaggtca cgaccgacaa gggccaggtc atcctcaagt cgatcggtcc gcagggcgcg   4440
ttgcaccttc agccggtcaa cttcccctac ccgaccaagg agtggcttca gccgaagcgc   4500
tacaaggccc acgtcgtcgg cacgacgtac gtctacgact tccccgacct tttccgccag   4560
gcaatccgca agcagtggaa ggcggccggc aagactgcgc ccgccgagct cctcgtcgcc   4620
aaggagctcg tcctcgacga gttcggcaag cctcaggagg tcgcccgccc gcctggcacc   4680
aacaatatcg gcatggtcgg ctggatctac acgatcttca cgcccgaata cccctctggc   4740
cgccgcgtcg tcgtcatcgc gaacgacatc acgttcaaga ttggttcgtt cggcccggag   4800
gaggaccgct acttcttcgc cgtcacgcag ctcgcgcgcc aacttggctt gccgcgcgtc   4860
tacctctcgg ccaactcggg tgctcgtctc ggcattgccg aggagctcgt cgacttgttc   4920
agcgtcgcgt gggtcgacag ctcgcggccg gagaagggct tcaagtacct ctacctaacc   4980
gccgagaagc tcggcgagct caagaacaag ggcgagaaga gcgtcatcac gaagcgcatc   5040
gaggacgagg gcgagacgcg ctaccagatc accgacatca tcggcttgca ggagggtctc   5100
ggtgtcgagt cgctcaaggg ctctggcctc atcgccggtg agacgtcgcg cgcgtacgac   5160
```

gacatcttca cgatcacgct cgtcaccgcc cgctcggtcg gtatcggtgc gtacctcgtc 5220
cgcctcggcc agcgtgccgt ccaggtcgag ggccagccga tcatcctcac cggtgccggc 5280
gcgctcaaca aggtcctcgg tcgcgaggtg tactcgtcca acttgcagct cggcggcacg 5340
cagatcatgt acaagaacgg tgtctcgcac ttgacggccg ccaacgacct cgagggtgtc 5400
ctcagcatcg tccagtggct cgccttcgtc cccgagcacc gcggcgcgcc tctcccgatc 5460
atgccttcgc ccgtcgaccc gtgggaccgc tcgatcgact acacgcccat caagggcgcg 5520
tacgacccgc gctggttcct cgccggcaag acggacgagg ccgacggtcg ctggctctct 5580
ggcttcttcg acaagggctc gttccaggag acgctctcgg gctgggcgca gaccgtcgtc 5640
gtcggtcgcg ctcgcctcgg cggcatcccc atgggcgcca tcgcggtcga gacccgcacc 5700
atcgagcgcg tcgtgcccgc cgaccctgcc aaccctctct cgaacgagca gaagatcatg 5760
gaggccggtc aggtctggta tcccaacagc tcgttcaaga cgggacaggc gatcttcgac 5820
ttcaaccgcg agggtctccc gctcatcatc ttcgccaact ggcgcggctt ctcgggcggc 5880
cagcaggaca tgttcgacga ggtcctcaag cgcggttcgc tcattgtcga cggtctctcg 5940
gcgtacaagc agcccgtctt cgtctacatc gtcccgaacg gcgaacttcg cggcggtgct 6000
tgggtcgtcc tcgacccgtc gatcaacgcc gagggcatga tggagatgta cgtcgacgag 6060
actgctcgcg ccggtgtcct cgagcccgag ggcatcgtcg agatcaagct ccgcaaggac 6120
aagctcctcg ccctcatgga ccgcctcgac ccgacctacc acgccctccg cgtcaagtcg 6180
accgacgctt cgctctcgcc cgccgacgcc gcgcaggcca agaccgagct cgccgcgcgc 6240
gagaagcagc tcatgccgat ctaccagcag gtcgcgctcc agttcgccga ctcgcacgac 6300
aaggccggcc gcatcctcag caagggctgc gcgcgcgagg ccctcgagtg gtcgaacgct 6360
cgtcgctact tctacgcccg cctccgccgc cgtctcgccg aggaggccgc cgtcaagcgt 6420
ctcggcgacg ccgacccgac cctctcgcgc gacgagcgcc tcgccatcgt ccacgacgcc 6480
gtcggccagg gtgtcgacct caacaacgac ctcgctgctg ccgccgcgtt cgagcagggc 6540
gccgccgcca tcaccgagcg cgtcaagctc gcgcgcgcga cgaccgtcgc ctcgactctc 6600
gcgcagctcg cgcaggacga caaggaggct ttcgccgcct cgctccagca ggtcctcggc 6660
gacaagctca ccgccgccga cctcgcccgc atcctcgcct ag 6702

<210> SEQ ID NO 175
<211> LENGTH: 3801
<212> TYPE: DNA
<213> ORGANISM: Rhodosporidium toruloides

<400> SEQUENCE: 175
atgaacggcc gagcgacgcg gagcgtgact gggacgtcga cgccggtcca cacggcgacg 60
acccgacccc tcgtcctctt gcacccctcg acccaaaccc gcatctcgct gcacgtcccc 120
tccacgtcgc aggaatggat cgccgccgaa gtcgcgcgcg acaccttcca ggactggctt 180
cacgctgccg agaagagcgg aaacctcgtc ggattcgagg cggccgagct tgacgacgag 240
caggctggcg agggcgacga cgagaaggag ctcgtcctca ccgcctactt cttgaagcac 300
gttgccggcc ttctcccctt cccgtcgaca gctacctccc ccgccaccgc cgccgtcctc 360
ctcgccgcct tcaaccactt tgcgtccgtc tacctcagcg gaaccgatgt tcacaccctc 420
actgcctcgc tcgctgctcc cgtccgcgct ctcgtcatct cgtccttctt cctcgccaag 480
accaagctcg aggtcgaggg actcggcaag gtcttgccca agcagtccga gtcggcgctc 540

-continued

```
ctgcagaagg ctgcgaccgg ccaggcagag gtcttcgctc tcttcggtgg tcagggaatg    600
aacgaggtct actttgacga gctccagacc ctccacgacc tttacacccc gctgcttacg    660
cccttcctcg cccgcgcctc cgaacacctc gtctctctcg ctgccgccga gcagcacacc    720
ctcctttacg accactcgct cgacgccctt gcctggctgc aagatccctc tacccgcccc    780
gaagtcccct acctcgcgac ttgcgccgtc tcgctccctc tcatcggtct cactcagctc    840
tgccagtacg tcgtgtacgg caagggctcg tcgctcggtc ccgccgagct cggcgccaag    900
ttcaagggcg cgaccggcca ctcgcagggt gtcgtctcgg ctcttgtcat cgcgcacgag    960
taccctcccg cgtccaagga cggcagcgac gcgtgggagc ctttctacga gcaggccctt   1020
cgcggtttga ccgtcctctt ccagatcggt ctccagggca cgctcgcctt cccctccatc   1080
gccatttcgc ccgctctcga gtcgagctcg gtcgagaatg gcgagggtgt cccgactgcc   1140
atgcttgccg tcaccggcct cgacctcaag tcgctcgaga agaagatcgc cgaggtcaat   1200
gggcacgtca agtctgaggg ccgcgacgag accgtctcga tcagtctcta caacggtgcg   1260
agggcgttcg tcgtcactgg tgcgccgaag gacctcgtcg gtctcgccga cggccttcgc   1320
aagaaccgcg cgccggccgg caaggaccag tcgaagatcc cgcactcgaa gcgtctcccc   1380
gtcttctcga tgcgcttcct ccccatcaac gttccctacc actcgcatct cctccaaggc   1440
gcgaccgaga aggcgctcgc gacgttctcg gctgaggagg ccgcccactg ggcgccttca   1500
tcgttcacct gcgccgtcta caacaccgag gacggctccg acatgcgcca gctctcggct   1560
tcgtcggttc tcgagtcggt cttccagcag atcttcacct cgcccattca ctgggtctcg   1620
cacgccacca acttcccctc gtccgcgacg cacgccatcg atttcggcac gggcggcgcg   1680
agcggcatcg gttcgctctg cgcgcgcaac tgggagggcc gcggtatccg cacgattatg   1740
ctcggcaacc gcggcgaggg cgttggtgcc ggcaaggagg cttggggcaa gaaggtcccg   1800
accgaggaga agtggaacga gcgcttccac cctcgcctcg tccgcaccag cgacggcaag   1860
atccacctcg acacgccctt ctcgcgcctc ctctcgaagc cgcccctcat ggtcggtggt   1920
atgaccccga cgaccgtcaa ggccggcttc gtctcggccg ttctccgcgc gggctaccac   1980
atcgagctcg ctggcggcgg tcactacaac gagaaggctg tccgtgccaa ggtcgccgag   2040
atccagaagc tcgtgaacaa gcccggcatg ggcatcaccc tcaactcgct ctacatcaac   2100
cagcgccagt ggacgttcca gttcccgctc tgggccaaga tgaagcagga gggcgagccc   2160
gtcgagggtc tctgtgttgc tgccggtatt ccctcaaccg agaaggccaa ggagatcatc   2220
gacacgctcc gcgaggccgg catcaagcac gtctcgttca agcccggttc ggtcgacggc   2280
atccgccagg tcgtcaacat cgcctccgcc aaccccgact tccccatcat cctccagtgg   2340
actggtggtc gcgccggcgg tcaccactcg tgcgaggact tccacgcccc gatcctcgcg   2400
acgtacgctt cgatccgtca gcaccccaac atcaagctcg tcgccggctc tggcttcggc   2460
tcggctgagg gatgctaccc ttacctttcg ggcgagtggt cggagaagca gtacggcgtc   2520
gcgcgcatgc cgttcgacgg cttcatgttt gcttcgtggg tcatggtcgc caaggaggcg   2580
cacacgagcg agtcggtcaa gcagctcatc gtcgacgcgc ctggtgtcga ggatggccag   2640
tgggagcaga cgtacgacaa gccgaccggc ggcatcctca ccgtcaactc ggagcttggc   2700
gagccgatcc acaaggtcgc gactcgtggt gtcaagctgt gggccgagtt cgacaagaag   2760
gtcttctcgc tgtcgaagga gaagcagctc gcatggctcg ccgacaacaa gaagtacgtt   2820
atcgaccgcc tcaacgccga tttccagaag ccctggttcc ccgccaaggc cgacggctct   2880
ccttgcgacc ttgccgacat gacctacgcc gaggtcaacg cccgcctcgt ccgcctcatg   2940
```

tacgtcgcgc acgagaagcg ctggatcgac ccgtcgctcc gcaacctcgt cggcgactgg 3000
atccgccgtg ttgaggagcg tctctcgaac gtcaacgact cgggcatcaa gatctcggca 3060
ctccagtcgt actcggagct gaacgagcct gaggcgttcc tcaagcagtt cctcgcccag 3120
tacccgcagg ccgaggacca gatcctcgcc tccgccgacg tttcctactt cctcgccatc 3180
tctcaacgcc ccggacagaa gcccgtcccc ttcatccccg tcctcgacgc caacttcagc 3240
atctggttca agaaggactc gctgtggcag gccgaggaca tcgaggccgt ctttgaccag 3300
gacccgcagc gtgtctgcat cctccaggga ccggtcgccg ccaagcactg cacctcgacg 3360
cagacgccca tcgccgagat gctcggcaac atcgagcacc agctcgtcaa gaacgtcctg 3420
gacgactact acggcggcga cgagtcccag atcccgacta tcgactacct cgcgccccct 3480
cccaagccgg tcgacgccgg cgctatcctc gccgagaaca acatcgcgca ctcggtcgag 3540
gagctcgccg acggcggcaa gaagcatgtc tactcgatca acggtgtcct cccgccgacg 3600
ggcgactggc atgccgcact cgccggcccc aagctcgact ggctccaggc gttcctctcc 3660
aacgtctcga ttcaggcggg cgagcagtcg attcctaacc ccgtcaagaa ggtgctggcg 3720
ccgaggcacg ggcagcgggt cgagctcacc ctgaacaagg acggccagcc cctcaagctc 3780
gacgtcttcg gcgggctctg a 3801

<210> SEQ ID NO 176
<211> LENGTH: 8787
<212> TYPE: DNA
<213> ORGANISM: Rhodosporidium toruloides

<400> SEQUENCE: 176
atggtcgcgg cgcaggactt gccgctcgcg ctgagcatca gcttcgcgcc cgagtcgtcg 60
accatctcga tgacgctgtt caaccagccc gaggcgtcga aacccgccct ccccctcgag 120
ctcaagtaca agtacgaccc ctcgacgccg tacgccccga tccacgagat caccgaggac 180
cgtaatcaga ggatcaagca gcactactgg gacctctggg gcctcggcaa caaggcagac 240
cagggcatct cgcagctcaa gatcaccgac gagttccagg gcgacctcgt caccatctcg 300
gccgacgaga tcgaggcgtt ctgccgtgtt gtcggcatcg agggcgaggc gtacaagcgc 360
aaccacaagg ccggcatgca ggtcccgctc gacttcgcca tcaagctcgg ctggaaggcc 420
atcatgaagc cgatcttccc ctcgacgatt gacggcgacc tgctcaagct cgtccacctc 480
tcgaacggct tccgcgtcct ccccgacacg cccacactcc aggttggcga cgtcgtgacg 540
accacgtcgc gcatcgaatc aatcacgaac tcggacacgg gcaaaaccgt ctcggttcgc 600
ggcgtcatct cgctcgtctc gtccgccgac tcgaagggca aggacgcctc gaccgaggac 660
cgcatcccgc tcatcgaggt cacctcgtcc ttcttctacc gcggcaagtt cagcgactac 720
gcccagacat tctcccgcgt cgcccacccg acctactctg tcccgatcac cacgcccgag 780
gccgtcgccg tcctccagtc caaggagtgg ttccagtggg acgacgactc gaagcccctc 840
gaggtcggca ccaagctcca gttcaaggtc gagtcgaact atgtctacgc cgacaagtcg 900
tcctacgcga tggctaccgt caccggcggc gcgtacgtca tcacccccga gctcaagctc 960
gctgtcaagg ttgccacggt cgactacacg tccgagggcg agggcgtcat ccagggcgac 1020
ccggtcatcg agtacctcaa gcgccacggc tcggccctcg accagcccat catgctcgag 1080
aacggcggct attcgctcac caaggccggc cagtgcacct tcacgacgcc cgcgtccaac 1140
ctcgactact cgctcacctc gggcgacacg aacccgattc acacgaaccc gtactttgcc 1200

-continued

```
tcgctcgcct acctccccgg caccatcacg cacggcatgc actcgtcggc ccgcacgcgc   1260
aagtttgtcg agcaggtcgc cgcagacaac gtcggcgcgc gcgtccgcaa gtacgaggtc   1320
ggcttcacgg ccatgtgcct cccctcgcgc aagatggagg tccgccttaa gcacgtcggc   1380
atgaccgcgg acggaaaccg cctcatcaag gtcgagaccg tcgacgtcga gggcggcaac   1440
gtcgttctca gcggaaccgc cgaggtcgcc caggctccca ccgcgtacgt cttcaccggt   1500
caaggttcgc aagagcccgg catgggcatg gagctctacg ccaactcgcc cgtcgcccgc   1560
gccgtctggg acgaggctga ccgccacctc ggcgaggtct acggcttctc catcctcgag   1620
attgtccgta cgaaccccaa ggaaaagact gtgcacttcg gcgggttgaa aggccaagca   1680
acccgtcaga agtacatgga catgtcgtac acaacgactg accatgaggg caacgttaag   1740
actctcccgc tcttcggcga catcgacctc cgtacctcac gctacacgtt ctcgtcgccg   1800
accggtctcc tctacgccac ccagttcgcc cagatcgccc tcgtcgtaac ggagaaggcc   1860
gccttcgagg acatgcgcgc caagggtctc gttcagaagg actgcgtctt tgccggtcac   1920
tcgctcggag agtactcggc tctcgcctcg atcgccgaca tcctccccat ctcggccctc   1980
gtcgacgtcg tcttctaccg cggtatcacc atgcagcgcg ccgtcgaacg cgaccacctc   2040
aaccgctcgt cgtacggaat ggtcgccgtc aacccgagcc gcatcggcaa gagctttggc   2100
gacgccgccc tccgcgaggt cgtcgacacc atcgcccgcc gcggaaacat cctcatcgag   2160
gtcgtcaact acaacgtcga gggacagcaa tacgtcgtcg ccggtcacct cgtcgccctc   2220
caatccctca caaacgtcct caacttcctc aagatccaga agatcgacct cgccaagctc   2280
accgagacga tgtcgatcga gcaggtcaag gagcacctgt gcgagatcgt cgacgagtgc   2340
gtccagaagg cgcgcgacct ccaggccaag acgggcttca tcaccctcga gcgcggcttt   2400
gcgacgatcc cgctccccgg tatcgacgtg ccgttccact cgcgctacct ctgggcggga   2460
gtcatgccgt tccgcactta cctctcgaag aaggtcaacc cggcgcactt caacgccgac   2520
ctcctcgtcg gccgctacat ccccaacttg accgccgtcc actacgaggt ctcgaaggag   2580
tacgccgaac gcatccacac ccagacgtcg tcgccgcgcc tcaacaagat tctcaaggcc   2640
tgggacgagg agcgctgggg cgcacccgag aaccgcaaca agctcggcta cgccatcctc   2700
atcgagctcc tcgcgtacca gttcgcctcg cccgtccgct ggatcgagac gcaggacatc   2760
ctcttccgcg acttcaagtt tgagcgcctc gtcgagcttg gcccgtcgcc cactctcacc   2820
ggcatggcta cgcgcacgca gaagctcaag tacgacgcgc acgactcgtc ggtcggcatc   2880
aagcgctcga tctactgcat cgccaagcac cagaaggaga tctactacca gttcgatgac   2940
gttgccggcg aagaggcgcc cgctcctgcc gcagttgcgc cttccgctcc cgctcccaag   3000
gccgccccag tcgccgccgc ccctccccct cccgctcctg tcgctgccgc gcctgccgcc   3060
gccgtcgccg acgagccgct caaggctgtc gacacgctcc gcatcatcat cgcgcagaag   3120
ctcaagaagc ccgttggcga agtcccccct accaagtcga tcaaggagct cgtcggcggc   3180
aagtcgaccc tccagaacga gattctcggc gaccttcaag gcgagttcag cagcgcgcct   3240
gaaaagggcg aggagatgcc tctccaggag ctcggcgcgg ccctccagca gggctactct   3300
ggcaagctcg gcaagtacac caccggcgtc atctcgcgca tgattggcgc caagatgccc   3360
ggcggttttg gtctctccgc cgtccagggt cacctcggca agacctacgg cctcggcgcc   3420
ggtcgcatcg atggcgtcct cctcttcgcc gtcacgcagg agccggctaa gcgtctcgcc   3480
aacgagggtg aggcgaaggc ttgggtcgac tcggtcgcgc aaggctacgc ctcgatggct   3540
ggcatctcgc tcgccgccgg cggtggagct gctgctgctg cccccgcgat ggcgttcgcc   3600
```

```
gctccggccg cagctggcgg tggagcgccc gctgccgtcc ccgacgagcc gctcaaggcg   3660
accgacacgc ttcgcgccat catcgctcag aagctcaaga agcagatccc cgacgtcccc   3720
ctcaccaagt ccatcaagga ccttgtcggc ggcaagtcga ccctgcagaa cgagatcctc   3780
ggcgacctcc agggcgagtt cagcagtgcg cccgagaagg gcgaggagat gccgctccag   3840
gagcttggcg ccgcactcaa ccaaggctac tcgggcacgc tcggcaagca cacgagcggt   3900
ctcgtcgccc gcatgatggg cgccaagatg cccggtggct tcggtctctc ggcggcgaag   3960
gcgcacctct cgaaggctca cggtctcggg cccggccgca ccgacggcgc tctcctcgtc   4020
gcgctcacca aggagcccga gaaacgtctc ggtagcgagg ccgacgccaa ggcctggctc   4080
gacggcgtcg ctcaggcgta cgcctcgcag gctggcatca ccctcggcgc tggtggaggc   4140
ggaggcggcg cggctgtcgg cggcgccggc tttatgatca acaccgagca gctcgacaag   4200
atgcaggaga agcaggacaa cttcgtctcg cagcaggtcg agctcttcct ccgctacctc   4260
ggcaaggact cgcgcgaggg ccaccgcctc gccgacatgc agaaggcaga ggtcgccaac   4320
ctccaggaga agctcgactc gatcgctcgc gagcacggcg acgcctatgt ccagggcatc   4380
cagcccgtct tcgacccgct caaggcccgc cacttcaact cgtcgtggaa ctgggtccgt   4440
caggacgcgc tcatgatgtg gatggacatc ctcttcggcc gcctcaccac cgtcgaccgc   4500
gacatcaccg ctcgctgcct tgtcatcatg aaccgcgccg acccttctct catcgactac   4560
atgcagtaca ccatcgacaa cacccccgtc gagcgcggcg agcattacgt cctcgccaag   4620
caattcggcc agcagctcct cgacaactgc cgcgagatga tcggccaggc tccgctctac   4680
aaggacgtca ccttcccgac cgcgcccaag acgaccgtca acgccaaggg cgacatcatc   4740
accgaggagg tcaaccgccc cggcgtctct cgcctcgaga agtatgtcgc cgagatggct   4800
gccggctcaa aggtcaccgt cgccagcgtc aacctcgaca aggtccagga gcaggtcgag   4860
aagctgtaca agctcgtcaa gtcgcagccg cagatttcga agcagcacat gacgtcgatc   4920
aagtcgctgt acgctgaggt cgttcgcggt ctcggcaagg acgccggccc tcctccggtc   4980
cacaaggccg gcactcgcgc ccgccgcccc tcgagccagt tcctccgtcc cgcagccgtc   5040
tccgaggcga ctttcctccc cgaggacaag gtgcctctcc tgcacctcaa gcgcaagatc   5100
ggcaacgact ggcaatactc gagcaagctc acgtcgctct acctcgacat cctcaaggag   5160
attgccacgt cgggtgtcac cttcgagcac aagaacgcgc tcatgaccgg tgtcggcaag   5220
ggctccatcg gtatcgagat cgtcaagggt ctcctcgctg gtggcgctcg cgtcgtcatc   5280
acgacctcgc gctactcgcg ctcgactgtc gagtactacc aggcgatcta ccaggaggtc   5340
ggctcgaagg gctcgtcgct caccgtcgtc cccttcaacc agggctcgaa gcaggatgtc   5400
gaggcgctcg tcgacttcat ttattcgaag gataagggtc tcggcatgga cctcgactac   5460
atcctcccct tcgccgccct tcccgagaac ggccgcgaga tcgacggcat cgacgaccgc   5520
tccgagctcg cccaccgcat catgctcacc aacctcctcc gcctcctcgg tgccgtcaag   5580
tcgaagaagg ccgccctcaa gctcacgacc cgcccaaccg aggtcgtcct cccgctttcg   5640
ccgaaccacg gcctcttcgg caacgacggt ctctactcgg agtcgaagat ctcgctcgag   5700
acgctcttca accgctggag ctcggagagc tggggcgagt acctctgcct cgctggcgct   5760
gtcatcggat ggacgcgcgg taccggtctc atgtcggcga cgaactcggt cgccgaaggt   5820
atcgaggcgc agggttgcag gacgttctcc gccaaggaga tggccttcaa cattctcggc   5880
ctcatgcacc cgctcgtctt cgacgtcgcg cagatcgagc ctgtctgggc cgacctcaac   5940
```

-continued ggtggcatgg acaagctccc cgaccttgcc aacctcacga ccgagatccg caagaagctc 6000
aacctcaccg cgtcgacccg ccgcgccatc gccaaggaca actcgttcga ctacaaggtc 6060
gcgcacggcc cggcgatgga gcagatacac cagcggatca acgtcgcccc gcgcgccaac 6120
ttctcccttc ccttccccga gctcaagccg atcgatgcca agtcggagct cgcgaagctc 6180
cgtggcctca tcgacctcga gaaggtcgta gtcatgaccg gttacgccga ggtcggaccg 6240
ttcggctcgt cgcgcacgcg ctgggagatg gaggcgaacg gcaccttctc catccagggc 6300
acactcgagc ttgcgtacgt catgggcctc atcaagcact ttgagggtcg cctcaaggac 6360
ggcacgctct acgtcggatg ggtcgacgcc aagacgaacg aaccgctgga cgacaaggac 6420
gtcaaggctg cgtacgagaa gcacattctc gcgcacaccg gcatccgcct catcgagccg 6480
gagatcttca acggctacga cccgaagcgc aagggcttca cgcaggagat cgagatccag 6540
cacgacctcg agcccatcga ggcgtccgag gaggacgcgg ctcgcttcaa gcgcgagcac 6600
ggcgcgctcg tcgacgtcta caccgaggac ggcagcaagt tcttcgtcaa gttcaagaag 6660
ggcgccaagc tgcacattcc caaggctgtt gccttcgacc gccttgtcgc cggacagatc 6720
ccgactggct ggtcgcacaa ggccttcggt atccccgacg acattgcctc gcaggttgac 6780
cgcacctcgc tgtgggcgct cgtctcggtc gccgaggcgc tcatgatggc cggcatcacc 6840
gacccgtatg agctctacaa gtggattcac ccgagcgagg tcggttcgtc gctcggatcc 6900
ggcatgggag gcatcacgag tatctcgaag atgttccgcg accgccgcga ggagaaggac 6960
gtccagaagg acatcctcca ggagaccttc atcaatacgg tcgccggatg ggtcaacctc 7020
ctccttctct cgtcatccgg accgatcaag atccccgtcg gcgcctgcgc gactgccctc 7080
cagtcggtcg agatcgcctg cgacaccatc ctcagcggca aggccaagat catggtctcg 7140
ggaggctacg acgacttctc cgaggagggc tcgtacgagt tcgcaaacat gaaggcgacc 7200
tcgaacagcg agaccgagtt cgctgccggc cgcgagccga acgagatgtc gcgtccgacg 7260
accagcaccc gtgccggctt catggagtcg atgggttgcg gtgctcaggt cctgatgtcg 7320
gcgaagacgg ccatcgagat gggcgccacc atctacggca tcgtcgccta caccgcgacc 7380
gccaccgaca aggctggtcg ctcgattccc gcccccggac gcggtgtcat gggtaccgcg 7440
cgcgagatca cctccaagta cccctcgccc atcctcgatg tcacctaccg ccgccgccag 7500
ctcgagttcc gtcgcaagca gatctcgcag tggctcgaga acgagaccga gctcctcaag 7560
ttcgaggtct cctcgcacgg acaggccaca aagctccccg acgactacgt ctccgagcgc 7620
ctcgcatcca tcgaacgcga agccaagcgc caggaggccg aggctctcgc gacgtacggc 7680
atgctcgccg gccaggaccc gaccatcgcc ccgctccgtc gcgctctcgc cgtttggggt 7740
ctcaccatcg acgacgttgg agtcgcctcg ttccacggca cctcgaccgt tgccaacgac 7800
aagaacgagt cgaacgcgta caacgagcag ttccgtcacc ttggccgcgc caagggtaac 7860
gcctgccccg tcatcgctca gaagtggctc accggacacc cgaagggagg tgccgccgcc 7920
tggatgctca acggcttggc ccaggtcatt cagagcggtc tcgttcccgg caaccgcaac 7980
gccgacaaca tcggcgaaga gcttcgcgcg ttcgagtacc tgctctaccc gtccaagtcg 8040
atccagaccg acggcatcaa ggctggtctc ctcacctcgt tcggcttcgg tcaagtcggt 8100
ggccaggctc tcatcgttca cccgagtctg ctcatcggcg cgctcgagcc cgcccagttc 8160
gaggcgtaca agaagctcaa cgaccagcgc aagaagtggt cataccgtcg cttcaacgat 8220
ttcttcacga acggcaagct cgtcattatc aaggacggca cgcccttcac gcccgagcag 8280
gagaacacga ccctcctcaa cccgctcgtc cgcgccgtgc ccgacaagac tggctcgtac 8340

```
tcgatgccga aggagttccc tgccaccgtc cctcgcagca acaacgccga agtcgccaac   8400

aagctcgtca gcgcggctgt cggcggtgct ttcggcgtcg gcacggacgt cgagctgatc   8460

agcgccgtcc cgacctcgga gtcgttcctc gagaggaact tcacccagga cgagatcgcc   8520

tactgcaagg ccgcacccga cttccgcgct agcctcgccg cgcgctggtc cgccaaggag   8580

gccactttca aggctctcaa gaccgagtcg aagggcgccg ccgccagcat gcaggacatc   8640

gaggtcgtct ccacgtcgca gggcccgact atcaagctcc acggcgaggt cgagaagatc   8700

gcccaggccg ccggcatcac ggccttcgag gtctcgctct cgcactcgga ggacgtcgct   8760

tgcgccgtcg tcatcgccca gaagtag                                       8787
```

<210> SEQ ID NO 177
<211> LENGTH: 906
<212> TYPE: DNA
<213> ORGANISM: Acinetobacter baylyi

<400> SEQUENCE: 177

```
ggatccaaaa caatgaataa gaagttagaa gcattgttta gagaaaatgt caagggtaaa     60

gtcgctttaa tcactggtgc ctcctcaggt atcggtttaa ctatcgcaaa aagaattgct    120

gcagccggtg cccatgtttt gttagtcgct agaactcaag aaacattgga agaagttaag    180

gctgcaatcg aacaacaagg tggtcaagca tctatattcc catgtgattt gacagacatg    240

aatgcaatag atcaattatc ccaacaaatc atggccagtg tagatcatgt tgactttttg    300

attaataacg caggtagatc tataagaaga gccgttcatg aatcatttga tagattccac    360

gacttcgaaa gaacaatgca attaaactac ttcggtgctg tcagattggt attgaacttg    420

ttgcctcaca tgatcaagag aaagaatggt caaattataa acatctcttc aatcggtgta    480

ttggccaacg ctaccagatt ctctgcttat gttgcatcaa aagccgcttt agatgctttt    540

tccagatgct tgagtgcaga agttttgaag cataagatct ctataacttc aatctatatg    600

ccattggtca gaacaccaat gatcgcacct accaaaatct ataagtacgt tccaacattg    660

tctcctgaag aagcagccga tttgatagtt tatgctatcg tcaagagacc taccagaatt    720

gccactcact tgggtagatt agcttccatt acctacgcaa tagccccaga cataaacaac    780

atcttgatgt ctattggttt taatttgttt ccttccagta ctgctgcatt aggtgaacaa    840

gaaaaattga acttattaca aagagcctac gcaagattat tccctggtga acattggtga    900

aagctt                                                               906
```

<210> SEQ ID NO 178
<211> LENGTH: 264
<212> TYPE: DNA
<213> ORGANISM: Saccharomyces cerevisiae

<400> SEQUENCE: 178

```
atggtttccc aattattcga agaaaaagct aaagccgtca acgagctacc aacgaagccc     60

tccactgatg aattattaga attgtatgct ctgtacaagc aagccactgt aggtgacaac    120

gacaaggaaa agcctggtat tttcaacatg aaggaccgct acaagtggga agcctgggaa    180

aacttaaaag gtaaatccca ggaagatgcc gaaaaggaat acattgccct tgttgatcaa    240

ctgattgcca agtactcctc ttag                                           264
```

<210> SEQ ID NO 179
<211> LENGTH: 2694
<212> TYPE: DNA

-continued

<213> ORGANISM: Saccharomyces cerevisiae

<400> SEQUENCE: 179

```
atgcctggaa atttatcctt caaagataga gttgttgtaa tcacgggcgc tggagggggc     60
ttaggtaagg tgtatgcact agcttacgca agcagaggtg caaaagtggt cgtcaatgat    120
ctaggtggca ctttgggtgg ttcaggacat aactccaaag ctgcagactt agtggtggat    180
gagataaaaa aagccggagg tatagctgtg gcaaattacg actctgttaa tgaaaatgga    240
gagaaaataa ttgaaacggc tataaaagaa ttcggcaggg ttgatgtact aattaacaac    300
gctggaatat taagggatgt ttcatttgca aagatgacag aacgtgagtt tgcatctgtg    360
gtagatgttc atttgacagg tggctataag ctatcgcgtg ctgcttggcc ttatatgcgc    420
tctcagaaat ttggtagaat cattaacacc gcttcccctg ccggtctatt tggaaatttt    480
ggtcaagcta attattcagc agctaaaatg ggcttagttg gtttggcgga aaccctcgcg    540
aaggagggtg ccaaatacaa cattaatgtt aattcaattg cgccattggc tagatcacgt    600
atgacagaaa acgtgttacc accacatatc ttgaaacagt taggaccgga aaaaattgtt    660
cccttagtac tctatttgac acacgaaagt acgaaagtgt caaactccat ttttgaactc    720
gctgctggat tctttggaca gctcagatgg gagaggtctt ctggacaaat tttcaatcca    780
gaccccaaga catatactcc tgaagcaatt ttaaataagt ggaaggaaat cacagactat    840
agggacaagc catttaacaa aactcagcat ccatatcaac tctcggatta taatgattta    900
atcaccaaag caaaaaaatt acctcccaat gaacaaggct cagtgaaaat caagtcgctt    960
tgcaacaaag tcgtagtagt tacgggtgca ggaggtggtc ttgggaagtc tcatgcaatc   1020
tggtttgcac ggtacggtgc gaaggtagtt gtaaatgaca tcaaggatcc tttttcagtt   1080
gttgaagaaa taaataaact atatggtgaa ggcacagcca ttccagattc ccatgatgtg   1140
gtcaccgaag ctcctctcat tatccaaact gcaataagta agtttcagag agtagacatc   1200
ttggtcaata acgctggtat tttgcgtgac aaatcttttt taaaaatgaa agatgaggaa   1260
tggtttgctg tcctgaaagt ccaccttttt tccacatttt cattgtcaaa agcagtatgg   1320
ccaatattta ccaaacaaaa gtctggattt attatcaata ctacttctac ctcaggaatt   1380
tatggtaatt ttggacaggc caattatgcc gctgcaaaag ccgccatttt aggattcagt   1440
aaaactattg cactggaagg tgccaagaga ggaattattg ttaatgttat cgctcctcat   1500
gcagaaacgg ctatgacaaa gactatattc tcggagaagg aattatcaaa ccactttgat   1560
gcatctcaag tctccccact tgttgttttg ttggcatctg aagaactaca aaagtattct   1620
ggaagaaggg ttattggcca attattcgaa gttggcggtg gttggtgtgg gcaaaccaga   1680
tggcaaagaa gttccggtta tgtttctatt aaagagacta ttgaaccgga agaaattaaa   1740
gaaaattgga accacatcac tgatttcagt cgcaacacta tcaacccgag ctccacagag   1800
gagtcttcta tggcaacctt gcaagccgtg caaaaagcgc actcttcaaa ggagttggat   1860
gatggattat tcaagtacac taccaaggat tgtatcttgt acaatttagg acttggatgc   1920
acaagcaaag agcttaagta cacctacgag aatgatccag acttccaagt tttgcccacg   1980
ttcgccgtca ttccatttat gcaagctact gccacactag ctatggacaa tttagtcgat   2040
aacttcaatt atgcaatgtt actgcatgga gaacaatatt ttaagctctg cacgccgaca   2100
atgccaagta atggaactct aaagacactt gctaaacctt tacaagtact tgacaagaat   2160
ggtaaagccg ctttagttgt tggtggcttc gaaacttatg acattaaaac taagaaactc   2220
atagcttata acgaaggatc gttcttcatc aggggcgcac atgtacctcc agaaaaggaa   2280
```

gtgagggatg ggaaaagagc caagtttgct gtccaaaatt ttgaagtgcc acatggaaag 2340
gtaccagatt ttgaggcgga gatttctacg aataaagatc aagccgcatt gtacaggtta 2400
tctggcgatt tcaatccttt acatatcgat cccacgctag ccaaagcagt taaatttcct 2460
acgccaattc tgcatgggct ttgtacatta ggtattagtg cgaaagcatt gtttgaacat 2520
tatggtccat atgaggagtt gaaagtgaga tttaccaatg ttgttttccc aggtgatact 2580
ctaaaggtta aagcttggaa gcaaggctcg gttgtcgttt ttcaaacaat tgatacgacc 2640
agaaacgtca ttgtattgga taacgccgct gtaaaactat cgcaggcaaa ataa 2694

<210> SEQ ID NO 180
<211> LENGTH: 1206
<212> TYPE: DNA
<213> ORGANISM: Saccharomyces cerevisiae

<400> SEQUENCE: 180
atgggtaagg gtgaatcgaa gaggaagaac tcgttgctgg agaaaagacc cgaagatgta 60
gttattgtgg ctgctaacag gtctgccatc ggtaaaggtt ttaaaggtgc cttcaaagat 120
gtaaacacag actacttatt atacaacttt ctcaatgagt tcatcgggag gtttccggaa 180
cctttgaggg ctgatttgaa cttaatcgaa gaagttgcct gtggaaatgt tctcaatgtt 240
ggagccggtg ctacagaaca cagggctgca tgcttggcaa gtgggattcc ctactcgacg 300
ccatttgtcg ctttaaacag acaatgttct tcaggtttaa cggcggtgaa cgatattgcc 360
aacaagatta aggttgggca aattgatatt ggtttggcgc tgggagtgga atcaatgacc 420
aataactaca aaaacgtcaa tcccttgggc atgatctcct ctgaagagct gcaaaaaaac 480
cgagaagcga agaaatgtct aataccaatg ggcattacta atgagaatgt tgccgctaat 540
ttcaagatca gtagaaagga tcaagacgag ttcgctgcga attcatatca aaaagcttac 600
aaggcgaaaa atgaggggct tttcgaagat gaaattttac ctataaaatt accagatggc 660
tcaatttgcc agtcggacga agggccacgc cctaacgtca ctgcggagtc gctttcaagc 720
atcaggcctg cctttatcaa agacagagga accacaactg cgggcaatgc atcccaggtc 780
tccgatggtg tggcaggtgt cttgttagcc cgcaggtccg tagccaacca gttaaatctg 840
cctgtgctag gtcgctacat cgattttcaa acagtggggg ttcccccctga aatcatgggt 900 gtgggccctg catacgccat accaaaagtc ctggaagcta ctggcttgca agtccaagat 960
atcgatattt ttgaaataaa tgaagcattc gcggcccaag cattatactg catccataaa 1020
ctgggcatcg atttgaataa agtaaatcca agaggtggtg caatcgcgtt aggccatccc 1080
ttgggttgta ctggcgcaag gcaagtagct accatactaa gagaactgaa aaaggatcaa 1140
atcggggttg ttagtatgtg tatcggtact ggtatgggtg ccgccgccat ctttattaaa 1200
gaatag 1206

<210> SEQ ID NO 181
<211> LENGTH: 1161
<212> TYPE: DNA
<213> ORGANISM: Saccharomyces cerevisiae

<400> SEQUENCE: 181
atgtctcaga acgtttacat tgtatcgact gccagaaccc caattggttc attccagggt 60
tctctatcct ccaagacagc agtggaattg ggtgctgttg ctttaaaagg cgccttggct 120
aaggttccag aattggatgc atccaaggat tttgacgaaa ttatttttgg taacgttctt 180

-continued

```
tctgccaatt tgggccaagc tccggccaga caagttgctt tggctgccgg tttgagtaat    240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg caccatacta catgccagca gcccgtgcgg gtgccaaatt tggccaaact    420
gttcttgttg atggtgtcga aagagatggg ttgaacgatg cgtacgatgg tctagccatg    480
ggtgtacacg cagaaaagtg tgcccgtgat tgggatatta ctagagaaca acaagacaat    540
tttgccatcg aatcctacca aaaatctcaa aaatctcaaa aggaaggtaa attcgacaat    600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca attctgttga ttactttgaa    960
ttcaatgaag ccttttcggt tgtcggtttg gtgaacacta agattttgaa gctagaccca   1020
tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggttg a                                             1161
```

<210> SEQ ID NO 182
<211> LENGTH: 1041
<212> TYPE: DNA
<213> ORGANISM: Saccharomyces cerevisiae

<400> SEQUENCE: 182

```
atgagtgctt ccaaaaatggc catgtccaac ctagagaaaa tattggaact ggttcctctt     60
tcgcctacca gttttgtcac aaagtatctg cctgccgcgc ccgtagggtc taagggcact    120
tttggtggaa cgctggtatc acaatcgctg ctggcgtcat tgcatactgt gccattgaac    180
ttcttcccca catcgctaca ttcgtatttc atcaagggtg gtgatccgcg gaccaagatc    240
acgtaccatg tgcagaatct gagaaacggt agaaatttca tccataagca ggttagtgct    300
tatcagcacg acaagttgat atttacgtcg atgatcttat ttgccgtgca acggtccaag    360
gagcacgact ccttgcagca ctgggagacg attccaggcc tgcaaggtaa gcagccagac    420
cctcatcgtt atgaagaggc cacttcgctt ttccagaaag aagttctgga cccacagaaa    480
ttgagcaggt atgcctcatt gtccgacagg ttccaagacg caacctcgat gagcaagtat    540
gtggatgcgt ttcaatacgg agtcatggag taccaattcc ccaaggacat gttctactcg    600
gcaagacaca ccgacgagct ggattatttc gtcaaagtga gacctcccat cactaccgtg    660
gagcacgcgg gcgacgagtc ttctttacac aagcatcatc cgtacaggat cccgaagagc    720
attactcctg agaacgacgc tcgctacaac tacgtggcct ttgcgtatct gtccgattcc    780
tacctcctac tcacgatccc gtacttccac aacctgcctt tgtactgcca cagtttcagt    840
gtctcgctcg accacacgat ttactttcac cagttgcctc atgtgaacaa ttggatctat    900
cttaagattt cgaatcccag gtcccactgg gacaagcacc tcgtacaggg caagtatttc    960
gacacacagt cgggacgcat catggcaagc gtctctcagg agggctacgt tgtctacggg   1020
tcagaacgag acattcgatg a                                             1041
```

<210> SEQ ID NO 183
<211> LENGTH: 1164
<212> TYPE: DNA
<213> ORGANISM: E.coli

<400> SEQUENCE: 183
atggaacaag tagtaatcgt agacgcaatc agaactccta tgggtagaag taaaggtggt 60
gcattcagaa atgtcagagc agaagacttg tccgctcatt tgatgagaag tttgttagca 120
agaaatccag ccttggaagc tgcagcctta gatgacatct attggggttg tgttcaacaa 180
actttggaac aaggttttaa tatcgcaaga aacgctgcat tgttagccga agttccacat 240
tctgtccctg ctgtaaccgt taacagattg tgtggttctt caatgcaagc attacacgat 300
gccgctagaa tgattatgac tggtgacgcc caagcttgct tggtcggtgg tgtagaacat 360
atgggtcacg tcccaatgtc ccatggtgta gatttccacc ctggtttaag tagaaatgtt 420
gctaaagcag ccggtatgat gggtttgaca gctgaaatgt tagcaagaat gcatggtatt 480
tctagagaaa tgcaagatgc atttgctgca agatctcacg caagagcctg ggccgctact 540
caatcagcag ccttcaaaaa tgaaattata ccaacaggtg gtcatgatgc tgacggtgtt 600
ttgaagcaat tcaattacga tgaagttata agacctgaaa ctacagtcga agctttggca 660
accttaagac cagcattcga tcctgtaaat ggtatggtta cagctggtac ctccagtgca 720
ttgtccgacg gtgctgcagc catgttagta atgtctgaat caagagctca cgaattgggt 780
ttaaaaccaa gagccagagt tagatctatg gctgttgtcg gttgcgatcc ttcaataatg 840
ggttacggtc cagtccctgc ctcaaagttg gctttgaaga aagcaggttt gtccgccagt 900
gacatcggtg tttttgaaat gaatgaagct ttcgctgcac aaatattgcc atgtatcaag 960
gatttgggtt tgatcgaaca aatagacgaa aagattaatt tgaacggtgg tgccatagct 1020
ttgggtcatc ctttaggttg ctctggtgct agaatctcaa ccactttgtt gaacttaatg 1080
gaaagaaagg atgttcaatt tggtttggca actatgtgta tcggtttagg tcaaggtatc 1140
gctactgtat ttgaaagagt ctaa 1164

<210> SEQ ID NO 184
<211> LENGTH: 2190
<212> TYPE: DNA
<213> ORGANISM: E.coli

<400> SEQUENCE: 184
atgttgtata aaggtgacac attgtactta gactggttag aagatggtat cgctgaattg 60
gtatttgatg ctcctggttc cgtaaacaaa ttggatactg ccacagtagc ttccttaggt 120
gaagcaattg gtgttttgga acaacaatcc gacttaaagg gtttgttgtt gagaagtaat 180
aaggctgctt ttattgtagg tgctgatatc acagaattct tgagtttgtt tttagttcca 240
gaagaacaat tgtctcaatg gttgcatttc gcaaactcag tttttaacag attggaagat 300
ttgccagtcc ctaccattgc cgctgtaaac ggttacgctt taggtggtgg ttgtgaatgc 360
gttttggcta ccgactatag attagcaact ccagatttga gaatcggttt acctgaaact 420
aaattgggta ttatgccagg ttttggtggt tctgttagaa tgcctagaat gttgggtgca 480
gattcagcct tagaaattat agcagccggt aaagacgttg gtgctgatca agcattgaag 540
atcggtttag tcgatggtgt tgtcaaagct gaaaagttgg ttgaaggtgc caaagctgtc 600
ttaagacaag ccattaatgg tgacttggac tggaaagcta agagacaacc aaagttagaa 660
cctttgaagt tgtctaagat cgaagcaaca atgtctttta ctatagccaa gggtatggtc 720

```
gcccaaactg ctggtaaaca ttacccagcc cctataactg ctgttaaaac aatcgaagct    780

gcagccagat tcggtagaga agaagcattg aatttggaaa acaagtcttt tgttccattg    840

gctcacacaa atgaagcaag agccttggtc ggtattttct tgaacgacca atacgtaaag    900

ggtaaagcta agaaattgac taaagatgtt gaaacaccaa agcaagctgc agtcttgggt    960

gctggtatca tgggtggtgg tattgcatat caatccgcct ggaaaggtgt tcctgtagtt   1020

atgaaggata tcaacgacaa gagtttgacc ttgggtatga ctgaagccgc taagttgttg   1080

aacaagcaat tagaaagagg taaaattgac ggtttgaagt tagctggtgt tatatctaca   1140

atccatccaa ccttggatta tgctggtttc gatagagttg acattgtcgt agaagcagtt   1200

gtcgaaaatc ctaaagttaa aaaggcagtc ttagccgaaa cagaacaaaa agttagacaa   1260

gataccgttt tggcttccaa caccagtact atcccaattt cagaattggc taatgcatta   1320

gaaagacctg aaaacttctg tggtatgcat ttctttaatc cagtacacag aatgcctttg   1380

gttgaaatca taagaggtga aaaatcttca gatgaaacta tcgctaaggt agttgcctgg   1440

gcttctaaaa tgggtaaaac accaatcgtc gtaaatgatt gccctggttt ctttgtcaac   1500

agagtattgt ttccatactt cgcaggtttt tcacaattat tgagagatgg tgccgacttc   1560

agaaagatag ataaggttat ggaaaagcaa tttggttggc caatgggtcc tgcctatttg   1620

ttggacgttg tcggtataga tacagctcat cacgcacaag ccgttatggc agccggtttc   1680

ccacaaagaa tgcaaaaaga ttacagagac gctattgatg cattattcga cgctaataga   1740

tttggtcaaa agaatggttt gggtttttgg agatataagg aagattccaa aggtaaacct   1800

aaaaaggaag aagacgctgc agtcgaagat ttgttggcag aagtatccca accaaagaga   1860

gatttcagtg aagaagaaat catcgctaga atgatgattc ctatggtcaa cgaagtagtt   1920

agatgtttag aagaaggtat catcgctacc ccagctgaag cagatatggc attggtttac   1980

ggtttaggtt tcccaccttt tcacggtggt gcttttagat ggttggacac tttaggttct   2040

gccaaatatt tggatatggc tcaacaatac caacatttgg gtccattata tgaagttcct   2100

gaaggtttga gaaacaaggc tagacacaat gaaccttatt accctcctgt tgaacctgcc   2160

agacctgttg gtgacttgaa aactgcctaa                                     2190
```

<210> SEQ ID NO 185
<211> LENGTH: 1182
<212> TYPE: DNA
<213> ORGANISM: E. coli

<400> SEQUENCE: 185

```
atgaaggatg tcgtaatcgt tggtgcttta agaaccccta tcggttgctt tagaggtgca     60

ttggctggtc actccgctgt agaattgggt tctttggttg tcaaagcttt aatagaaaga    120

actggtgtac cagcatatgc cgtcgatgaa gtaatcttgg gtcaagtttt aacagctggt    180

gcaggtcaaa atccagcaag acaatcagcc atcaaaggtg gtttgcctaa ctctgtttca    240

gctataacta ttaatgacgt ctgtggttct ggtttaaagg cattgcattt ggcaacccaa    300

gccattcaat gcggtgaagc agatatcgtc attgccggtg gtcaagaaaa catgtcaaga    360

gcccctcacg tattgactga ctccagaaca ggtgcacaat tgggtaactc acaattggta    420

gattccttag ttcatgatgg tttgtgggac gcttttaatg attaccacat cggtgttact    480

gctgaaaact tagcaagaga atacggtatt tcaagacaat tgcaagatgc ctacgcttta    540

tcttcacaac aaaaagctag agctgcaatt gacgcaggta gattcaaaga tgaaatagtc    600

ccagtaatga cccaaagtaa tggtcaaacc ttggtagttg atactgacga acaaccaaga    660
```

actgacgcat ctgccgaagg tttggctaga ttaaaccctt ccttcgatag tttaggttct 720
gttacagctg gtaatgcatc cagtattaac gatggtgccg ctgcagtcat gatgatgtca 780
gaagctaaag caagagcctt gaatttgcct gttttggcta gaattagagc ttttgcatcc 840
gttggtgtcg atccagcatt gatgggtata gcccctgttt atgctaccag aagatgttta 900
gaaagagtcg gttggcaatt ggctgaagta gacttaatag aagccaacga agctttcgcc 960
gctcaagcat tgtctgttgg taaaatgtta gaatgggatg aaagaagagt aaatgttaac 1020
ggtggtgcca tagctttagg tcatccaatc ggtgctagtg gttgcagaat tttggtttct 1080
ttagtccacg aaatggttaa aagaaatgct agaaagggtt tagcaacatt gtgtattggt 1140
ggtggtcaag gtgtagcatt gactatcgaa agagacgaat aa 1182

<210> SEQ ID NO 186
<211> LENGTH: 1194
<212> TYPE: DNA
<213> ORGANISM: E. coli

<400> SEQUENCE: 186
atgatagtaa agccaatggt aaggaacaat atctgtctta acgcccatcc acagggttgc 60
aaaaagggag ttgaagatca aattgaatac accaaaaaga gaattacagc agaggtcaag 120
gcaggggcaa aggctcctaa gaacgtctta gttttgggtt gttctaatgg atacggcttg 180
gcaagtagaa taactgcagc cttcggttat ggagccgcca ctataggtgt atcattcgaa 240
aaagccggct ccgaaaccaa gtacggtaca cctggctggt ataacaatct agcttttgat 300
gaagctgcta agagagaagg gttatactct gtcacaatag acggtgacgc attttctgat 360
gaaatcaaag ctcaggttat tgaagaggcc aagaaaaagg gtatcaaatt cgatctgata 420
gtatactcat tagcatcccc agtgcgtaca gatccagata ctggcattat gcacaaatct 480
gttttgaaac catttggaaa aactttcact ggtaaaacag ttgatccttt tacaggagaa 540
ctgaaggaaa tctcagctga accagctaat gatgaggagg cagctgctac tgtgaaagtt 600
atgggtggag aggactggga aagatggatc aaacaactaa gtaaggaagg tttacttgaa 660
gagggatgca tcaccttagc ctactcttac attggtcctg aagcaacaca agccctatac 720
cgtaaaggaa ctataggtaa ggcaaaggaa caccttgaag ctactgctca tcgtctgaat 780
aaggaaaatc catccattag ggctttcgtt agtgtcaaca aagggttagt taccagagca 840
tcagctgtga tccctgtcat tccactttac cttgcttcat tgtttaaggt tatgaaagag 900
aaaggcaatc atgaaggatg tatcgaacaa atcacaagat tgtacgctga gagattgtat 960
agaaaggatg gtacaattcc tgtggacgaa gagaatagaa ttagaatcga tgattgggag 1020
ttagaagagg acgttcaaaa agctgtttct gcattgatgg aaaaagttac aggcgaaaat 1080
gctgagtcac taacagacct ggcaggttat agacatgact tttggcctc aaacgggttt 1140 gatgtagaag gtatcaacta cgaagctgaa gtcgaaagat tcgatagaat ctaa 1194

<210> SEQ ID NO 187
<211> LENGTH: 552
<212> TYPE: DNA
<213> ORGANISM: E. coli

<400> SEQUENCE: 187
atggccgata ctttgttaat tttgggtgac tctttatcag ccggttatag aatgtccgct 60
agtgctgcat ggccagcatt gttaaacgat aaatggcaat ctaagacttc agttgtcaat 120

-continued

```
gcatctatat caggtgacac atcacaacaa ggtttggcca gattaccagc tttgttaaaa    180

caacatcaac ctagatgggt cttggtagaa ttaggtggta acgatggttt gagaggtttt    240

caacctcaac aaaccgaaca aactttgaga caaatcttac aagatgttaa ggccgctaat    300

gcagaaccat tgttaatgca aattagatta cctgccaact atggtagaag atacaatgaa    360

gcattttctg caatctatcc aaaattggca aaggaatttg atgtaccatt gttgccattt    420

ttcatggaag aagtttactt aaaacctcaa tggatgcaag atgacggtat tcatccaaac    480

agagatgctc aacctttat agcagactgg atggccaaac aattgcaacc attagtcaat    540

cacgattctt ga                                                        552
```

<210> SEQ ID NO 188
<211> LENGTH: 861
<212> TYPE: DNA
<213> ORGANISM: E. coli

<400> SEQUENCE: 188

```
atgtctcaag ctttgaagaa cttgttgact ttgttgaact tggaaaagat cgaagaaggt     60

ttgttcagag gtcaatctga agacttgggt ttgagacaag ttttcggtgg tcaagttgtt    120

ggtcaagctt tgtacgctgc taaggaaact gttccagaag aaagattggt tcactctttc    180

cactcttact tcttgagacc aggtgactct aagaagccaa tcatctacga cgttgaaact    240

ttgagagacg gtaactcttt ctctgctaga agagttgctg ctatccaaaa cggtaagcca    300

atcttctaca tgactgcttc tttccaagct ccagaagctg gtttcgaaca ccaaaagact    360

atgccatctg ctccagctcc agacggtttg ccatctgaaa ctcaaatcgc tcaatctttg    420

gctcacttgt tgccaccagt tttgaaggac aagttcatct gtgacagacc attggaagtt    480

agaccagttg aattccacaa cccattgaag ggtcacgttg ctgaaccaca cagacaagtt    540

tggatcagag ctaacggttc tgttccagac gacttgagag ttcaccaata cttgttgggt    600

tacgcttctg acttgaactt cttgccagtt gctttgcaac cacacggtat cggtttcttg    660

gaaccaggta tccaaatcgc tactatcgac cactctatgt ggttccacag accattcaac    720

ttgaacgaat ggttgttgta ctctgttgaa tctacttctg cttcttctgc tagaggtttc    780

gttagaggtg aattctacac tcaagacggt gttttggttg cttctactgt tcaagaaggt    840

gttatgagaa accacaacta a                                              861
```

<210> SEQ ID NO 189
<211> LENGTH: 399
<212> TYPE: DNA
<213> ORGANISM: E. coli

<400> SEQUENCE: 189

```
atgcaaactc aaatcaaggt tagaggttac cacttggacg tttaccaaca cgttaacaac     60

gctagatact tggaattctt ggaagaagct agatgggacg gtttggaaaa ctctgactct    120

ttccaatgga tgactgctca caacatcgct ttcgttgttg ttaacatcaa catcaactac    180

agaagaccag ctgttttgtc tgacttgttg actatcactt ctcaattgca acaattgaac    240

ggtaagtctg gtatcttgtc tcaagttatc actttggaac cagaaggtca agttgttgct    300

gacgctttga tcactttcgt ttgtatcgac ttgaagactc aaaaggcttt ggctttggaa    360

ggtgaattga gagaaaagtt ggaacaaatg gttaagtaa                           399
```

<210> SEQ ID NO 190
<211> LENGTH: 399

<212> TYPE: DNA
<213> ORGANISM: E. coli

<400> SEQUENCE: 190
atgtctacta ctcacaacgt tccacaaggt gacttggttt tgagaacttt ggctatgcca 60
gctgacacta acgctaacgg tgacatcttc ggtggttggt tgatgtctca aatggacatc 120
ggtggtgcta tcttggctaa ggaaatcgct cacggtagag ttgttactgt tagagttgaa 180
ggtatgactt tcttgagacc agttgctgtt ggtgacgttg tttgttgtta cgctagatgt 240
gttcaaaagg gtactacttc tgtttctatc aacatcgaag tttgggttaa gaaggttgct 300
tctgaaccaa tcggtcaaag atacaaggct actgaagctt tgttcaagta cgttgctgtt 360
gacccagaag gtaagccaag agctttgcca gttgaataa 399

<210> SEQ ID NO 191
<211> LENGTH: 306
<212> TYPE: DNA
<213> ORGANISM: Saccharomyces cerevisiae

<400> SEQUENCE: 191
atgctcactt atggaggaat gtcaaaacaa cctgtaactt taccaacatc tctacacatt 60
ttcaaaggct tgacatccaa aggatactgg gtgactgaaa agaacaaaaa aaaccccaa 120 agcaaaattg acaccatcag tgattttatc aaaatgtata atgatggtca cattatttca 180
ccaagagatg aaattgaaac tcttacctgg aatactaaca ctactactga cgaacagtta 240
ctagaactag tcaaaaaagg cataactggg aaggggaaga aaaaaatggt tgttttagaa 300
tggtaa 306

<210> SEQ ID NO 192
<211> LENGTH: 6372
<212> TYPE: DNA
<213> ORGANISM: Saccharomyces cerevisiae

<400> SEQUENCE: 192
atgagatcta taagaaaatg ggcgtacgag acgttcaatg atgaaaaaat cattcaattc 60
gtggtaatgg cgacacctga tgatttacac gcaaattcgg agtatattag aatggcagac 120
caatatgtgc aggtaccagg ggtaccaac aacaacaatt acgccaacat agacttaata 180
ctggacgtgg cagagcaaac ggatgtggat gcggtctggg ctggatgggg ccatgcttct 240
gaaaatccgt gtcttcctga gctgttagct agttcacaaa ggaaaatact attcattggt 300
cctcctggac gcgctatgag atcattgggt gacaagattt cttccactat tgtagcacaa 360
agcgctaaaa tcccgtgtat cccttggtct ggttcacata tagacactat ccatatcgat 420
aacaagacga actttgtatc tgtgccggat gatgtatatg taaggggatg ttgttcctca 480
cctgaagatg ctttagaaaa ggctaaatta ataggatttc ctgtaatgat taaggcatcc 540
gaaggtggtg gaggtaaggg cattaggcga gtagataatg aggatgattt tattgcatta 600
tatcgccaag cagtgaatga gacacctggg tcgcctatgt ttgttatgaa agttgtcact 660
gatgctcgtc acttagaggt acagttatta gctgaccaat atggcactaa cattacattg 720
tttgggagag actgttccat acaaaggcgg caccaaaaga ttatagaaga ggcaccagtg 780
acaataacca agcctgaaac gtttcaaagg atggaacgcg cagcaattcg tctaggtgaa 840
ttggtaggtt atgtttctgc gggcactgtc gaatacttat attcaccaaa agatgataaa 900
ttttactttt tagaactgaa tccaagacta caagtagagc atccaacgac agaaatgata 960

-continued

```
tctggcgtaa accttcctgc cactcaactg caaatcgcca tgggtattcc tatgcacatg   1020
ataagtgata tcagaaaact ttatggttta gatccaacgg gaacttcgta tattgatttt   1080
aaaaatttaa agagaccctc gccaaaaggc cattgtattt catgcaggat cacttcagaa   1140
gatcctaatg aaggtttcaa gccctccact gggaaaatac atgagctcaa ttttcgttct   1200
tcttccaatg tttggggtta cttctcagta ggaaataatg gtgctattca ctcattttca   1260
gattcccaat ttgggcacat tttgctgta ggaaacgata ggcaagatgc aaagcaaaac   1320
atggttttag ctctaaaaga tttttccatc cgaggagaat tcaaaacccc tatagagtac   1380
ctgatagagc tattagaaac tcgggacttt gagagtaata acatatcgac tggttggtta   1440
gatgatttga ttttgaaaaa tttatcttcc gatagcaaac tagatccaac gctcgctatt   1500
atctgtggtg ccgcaatgaa agcatacgtt ttcacagaaa aggtgaggaa taagtatttg   1560
gaattattgc ggaggggcca agttccacct aaagattttc ttaaaacgaa gtttcctgtt   1620
gacttcattt tcgataataa tagatacttg ttcaatgttg ctcaatcatc tgaagaacaa   1680
tttattcttt ctatcaataa gtctcaatgt gaagttaatg ttcaaaaatt gtccggtgac   1740
tgcttgttga tctccgttga cggtaaatgc catacagttt attggaagga cgatatcaga   1800
ggtacaagac tttcgataga ctccaatacc atatttttag aagctgaact caatcccact   1860
caagtgatct ctccaactcc ggggaaattg gtgaaatatt tggtccgaag tggtgatcac   1920
gtttttgctg gacagcaata tgcagaaata gaaataatga aaatgcagat gccactagta   1980
gcgaaaagtg atggtgtaat tgagttacta agacagcccg gttccataat tgaggctggt   2040
gatgtcatcg caaaattgac tttggattca ccgtccaaag ctaacgaatc gtctttatac   2100
cgcggagaat tacctgtttt aggtccaccg ctaatagagg gtagccgacc aaaccataag   2160
ctcagagtct taataaatag gttagaaaat attctcaatg gatatcatga aaactctgga   2220
atagaaacta ctctaaaaga gttgataaaa atattgagag atggtaggct tccttattca   2280
gaatgggatt cccaaatttc tacggtacgc aatagactac caaggcaatt gaatgagggg   2340
ctgggaaatc tagtcaagaa atctgtttct tttcctgcaa aggaactgca caaattaatg   2400
aagcgctact tggaagaaaa tacaaatgat catgtagttt atgttgcctt acagccactt   2460
cttaaaatta gtgaaaggta tagcgaaggt ttagctaatc acgaatgtga aattttttta   2520
aagttgatta aaaagtatta tgctgttgag aaaatttttg aaaatcatga tatacatgaa   2580
gaaagaaact tactaaatct gcggaggaaa gaccttacaa acttaaaaga aattttgtgc   2640
ataagtttat cgcatgctaa cgtagtcgca aagaacaagt tagtaactgc aatattgcat   2700
gaatacgagc cattgtgcca ggattcctct aagatgtctt taaaattcag ggctgttata   2760
catgatttgg caagtttgga atctaagtgg gctaaggagg ttgctgtaaa ggcaagatca   2820
gtgctactca gagggatttt ccctcccata aagaaaagaa aagagcatat taaaactctc   2880
ctgcaattgc acataaagga tactggtgcc aaaaacattc acagcaggaa catatattcc   2940
tgtatgaggg attttggtaa tttaatacat tcaaatctga tacaacttca ggatttgttc   3000
tttttttttg gccatcaaga tacggctctt tccagtatag catctgaaat ttatgcaagg   3060
tatgcctacg gcaattatca attaaaaagt attaagattc acaaaggagc gcctgattta   3120
ctaatgtcat ggcaattcag ctcattaaga aattatttag tcaatcctga tggtgagagt   3180
gatgagttta caaaactttc taaacctccc tcaacatcag gtaagagctc agcaaatagt   3240
tttggtcttc ttgtcaacat gcgtgcgctt gaatctctgg aaaagacatt agacgaggta   3300
tacgaacaaa ttcatattcc tgaggaaaga ctttccagcg gagagaactc tcttattgtt   3360
```

```
aatattttat ctcctattcg ttacagaagt gaaaatgatc taattaaaac tttaaaaatt   3420
aaacttcatg aaaatgagag aggtctatcc aagctcaagg ttaatcgtat tacatttgca   3480
tttatcgccg cgaatgcgcc cactgttaaa ttttactcct ttgatggaac tacgtacgat   3540
gaaatctctc aaataagaaa tatggatcca tcctatgaag caccgttaga gttaggaaaa   3600
atgtcgaact ataaaatcag atcactacct acatacgata gtagtatacg catttttgaa   3660
ggtattagca aatttacgcc gctagataaa aggttctttg tcaggaaaat cataaattcc   3720
ttcatgtata atgatcaaaa aacaaccgaa gaaaacttga aagcggaaat caatgctcaa   3780
gtggtttata tgttagaaca tctaggagca gttgacacct caaattcaga cttgaatcat   3840
atttttttaa gtttcaatac agttcttaac ataccagtac atcgtctcga ggaaattgtg   3900
agtacaattc taaagactca cgaaaccaga ttgtttcaag aaagaatcac agatgtagaa   3960
atttgcatct ctgttgagtg cctagaaaca aagaagccag ccccgcttag attacttatt   4020
tctaataaat ctgggtatgt ggtaaaaatt gagacatatt acgaaaagat agggaaaaat   4080
gggaatctga ttttggaacc gtgtagtgag cagagccatt atagccagaa atctctctct   4140
cttccttact cggtcaagga ttggctacaa cctaaaagat acaaagctca attcatgggt   4200
acaacatatg tgtacgattt cccaggtctg tttcatcaag ctgcaatcca acagtggaaa   4260
aggtattttc caaaacataa gctgaatgac agttttttta gttgggttga attgatagaa   4320
caaaacggta atttgataaa agtaaacagg gagccaggcc ttaataatat agggatggtt   4380
gcttttgaga ttatggttca gacacctgaa tatcctgaag ggcgtaacat gatcgtgatt   4440
tctaatgata ttacctacaa tattggatct tttggaccga gagaagattt gttttttgat   4500
agggtcacaa attatgcaag agagagaggg atcccgagga tatacttggc ggcgaattca   4560
ggagctaaat tgggtatagc cgaagagctg atccctctat ttcgtgtagc atggaatgac   4620
ccctctgatc caacaaaggg tttccagtac ttatacttag ctccaaaaga catgcagcta   4680
ctgaaagatt ctgggaaagg aaattcggtt gttgttgaac acaagatggt atacggtgaa   4740
gagagatata ttattaaagc aatagtcgga ttcgaagagg gtttaggtgt tgaatgttta   4800
cagggctcag gtttaattgc tggtgccact tcgaaagcgt atagagacat tttcactatt   4860
actgctgtta cttgtcggtc cgttggtata ggttcctatc tggtcagact aggacaacgt   4920
actattcagg tggaggataa gcctatcata ctgacgggtg catcggcgat taataaagtt   4980
ttgggtaccg atatctatac atctaaccta caaattggcg gaacccaaat catgtataaa   5040
aacggaatag cgcatttaac agccagtaat gatatgaaag ccatcgaaaa aataatgaca   5100
tggttatcat atgtcccggc gaaaagagat atgagtcctc cacttcttga aactatggat   5160
agatgggata gggatgtaga cttcaaacct gccaagcaag tgccatatga ggcaaggtgg   5220
ttgatagagg gtaaatggga ctcaaataac aacttccagt caggcctatt tgataaggat   5280
tcgtttttttg agacattatc tggatgggcc aaaggtgtaa tagttggaag agcacgtctt   5340
ggaggtattc ccgtaggtgt tattgcggta gaaactaaga ctatcgaaga aacaatcccc   5400
gctgacccag ctaatctgga ttcttcagag ttttccgtta aagaagcagg acaggtgtgg   5460
tatccaaatt ccgcgttcaa aacagctcaa actataaatg attttaacta tggtgagcaa   5520
ttaccattga ttatcttagc caattggagg ggattttctg gcggtcaaag ggatatgtac   5580
aatgaagtac taaagtacgg gtcttttatt gttgacgctc tggttgacta caaacaaccc   5640
atactgatat acattccgcc ctttggtgaa ttaaggggcg gatcatgggt tgttatagat   5700
```

-continued

```
ccaactatta atcctgaaca aatggaaatg tatgccgatg ttgaatctag gggaggtgtg   5760

ttagaacctg acggagtagt tagcataaaa taccgtaagg agaaaatgat agagacgatg   5820

attcgattag actccacata tggacatttg agaagaacgt tgacagaaaa aaagttatct   5880

ttggaaaaac aaaatgatct tacgaagaga ttgaaaataa gagagagaca gttgatacca   5940

atttataatc aaatcagcat acagtttgca gatttacatg atagatcgac taggatgcta   6000

gttaaaggag taatccgaaa ggagttggaa tggaaaaagt cacgcagatt tttatattgg   6060

agactgagaa ggaggttgaa cgagggacaa gtgatcaaaa gactgcaaaa aaaaacatgt   6120

gataacaaaa cgaaaatgaa atacgacgac ctgttgaaaa tagttcagtc atggtataac   6180

gatctggatg ttaatgatga cagagcagta gtggagttca tagaaagaaa ttcgaaaaaa   6240

attgacaaga acattgaaga gtttgagatc tcgctgttga tcgatgagct taagaaaaaa   6300

tttgaagaca gaaggggaaa cattgtcctt gaagagctaa ctaggttggt ggacagtaag   6360

cgaaagagat ag                                                        6372
```

```
<210> SEQ ID NO 193
<211> LENGTH: 272
<212> TYPE: DNA
<213> ORGANISM: Yarrowia lipolytica

<400> SEQUENCE: 193

aataaggatc tcgaaccttg tgcgatgaca acagcatgtg aataaggatc tcgaaccttg     60

tgcgatgaca acagcatgtg aataaggatc tcgaaccttg tgcgatgaca acagcatgtg    120

aataaggatc tcgaaccatt gatatttaag ttaataaacg gtcttcaatt tctcaagttt    180

cagtttcatt tttcttgttc tattacaact ttttttactt cttgctcatt agaaagaaag    240

catagcaatc taatctaagt tttaattaca aa                                   272
```

```
<210> SEQ ID NO 194
<211> LENGTH: 492
<212> TYPE: DNA
<213> ORGANISM: Yarrowia lipolytica

<400> SEQUENCE: 194

cacacaccat agcttcaaaa tgtttctact cctttttttac tcttccagat tttctcggac     60

tccgcgcatc gccgtaccac ttcaaaacac ccaagcacag catactaaat ttcccctctt    120

tcttcctcta gggtgtcgtt aattacccgt actaaaggtt tggaaaagaa aaaagagacc    180

gcctcgtttc tttttcttcg tcgaaaaagg caataaaaat ttttatcacg tttctttttc    240

ttgaaaattt ttttttttga ttttttttctc tttcgatgac ctcccattga tatttaagtt    300

aataaacggt cttcaatttc tcaagtttca gtttcatttt tcttgttcct tgtgcgatga    360

caacagcatg tgtattacaa cttttttttac ttcttcttgt gcgatgacaa cagcatgtgg    420

ctcattagaa acttgtgcga tgacaacagc atgtggaaag catagcaatc taatctaagt    480

tttaattaca aa                                                         492
```